(12) United States Patent
Jong et al.

(10) Patent No.: US 8,399,502 B2
(45) Date of Patent: *Mar. 19, 2013

(54) ANALOGS OF INDOLE-3-CARBINOL AND THEIR USE AS AGENTS AGAINST INFECTION

(75) Inventors: Ling Jong, Sunnyvale, CA (US);
Faming Jiang, Castro Valley, CA (US);
Gaoquan Li, Mountain View, CA (US);
Kristien Mortelmans, Los Altos Hills, CA (US)

(73) Assignee: SRI International, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/533,910

(22) Filed: Jun. 26, 2012

(65) Prior Publication Data

US 2012/0283240 A1 Nov. 8, 2012

Related U.S. Application Data

(62) Division of application No. 12/561,656, filed on Sep. 17, 2009, now Pat. No. 8,278,341.

(60) Provisional application No. 61/097,816, filed on Sep. 17, 2008.

(51) Int. Cl.
*A61K 31/40* (2006.01)
*A61K 31/33* (2006.01)
*A61K 31/00* (2006.01)
*A61K 31/445* (2006.01)
*A61K 31/44* (2006.01)
*A61K 31/41* (2006.01)

(52) U.S. Cl. .................. 514/410; 514/183; 514/210.21; 514/322; 514/281; 514/383; 514/385

(58) Field of Classification Search .................. 514/410, 514/183, 210.21, 322, 281, 383, 385
See application file for complete search history.

(56) References Cited

U.S. PATENT DOCUMENTS 6,800,655 B2 * 10/2004 Jong et al. ..................... 514/410
8,278,341 B2 * 10/2012 Jong et al. ..................... 514/410

OTHER PUBLICATIONS

Sung et al. "In vitro antimicrobial activity and the mode of action of indole-3-carbinol against human pathogenic microorgasims" Biol. PHarm. Bull., Oct. 2007, vol. 30, No. 10, pp. 1865-1869.*

* cited by examiner

*Primary Examiner* — Shengjun Wang
(74) *Attorney, Agent, or Firm* — Richard Aron Osman; Isaac Rutenberg

(57) ABSTRACT

Compounds useful as antibacterial agents are provided. The compounds are analogs of indole-3-carbinol and have a backbone selected from dihydroindolo[2,3-b]carbazole, 2,2'-diindolylmethane, 2',3-diindolylmethane, and 3,3'-diindolylmethane. The compounds are useful therapeutic and prophylactic treatment of bacterial infections in mammals. Methods of synthesis of the compounds are provided, as are pharmaceutical compositions containing the compounds.

20 Claims, No Drawings

ANALOGS OF INDOLE-3-CARBINOL AND THEIR USE AS AGENTS AGAINST INFECTION

CROSS-REFERENCE TO RELATED APPLICATIONS

This application is a divisional of Ser No. 12/561,656, filed Sep. 17, 2009 now U.S. Pat. No. 8,278,341, which claims priority under 35 U.S.C. 119(e) to U.S. Provisional Application Ser. No. 61/097,816, filed Sep. 17, 2008, the disclosure of which is incorporated herein by reference.

GOVERNMENT RIGHTS

This invention was made in part with government support under grant number HDTRA1-08-C-0050 awarded by the Defense Threat Reduction Agency. The government has certain rights in this invention.

TECHNICAL FIELD

This invention relates generally to compounds and compositions for the treatment of bacterial infection. More particularly, the invention pertains to novel indole analogs that are useful in treating a range of infections, including Gram positive bacterial infections and Gram negative bacterial infections.

BACKGROUND

For patients who have a bacterial infection, the most common cure is administration of antibacterial drugs. Bacterial resistance to such drugs is unfortunately a common development due, for example, to drug overuse and misuse. When patients stop taking antibacterial drugs too early, any remaining bacteria are likely to have increased resistant to the antibacterial drug. Recently, there has been a dramatic increase in the occurrence of bacteria that are resistant to many or all of the commonly used antibacterial drugs. Because multiple drug resistance is a growing problem, physicians are now confronted with infections for which there is no effective therapy.

Strategies to address these issues emphasize enhanced surveillance of drug resistance, increased monitoring and improved usage of antimicrobial drugs, professional and public education, development of new drugs, and assessment of alternative therapeutic modalities. Alternative and improved agents are needed for the treatment of bacterial infections, particularly for the treatment of infections caused by resistant strains of bacteria, e.g., penicillin-resistant, methicillin-resistant, ciprofloxacin-resistant, and/or vancomycin-resistant strains.

Accordingly, there is a need for improved, broad-spectrum antibiotic agents that are effective against both Gram-positive and Gram-negative bacteria, and are also effective against antibiotic-resistant bacteria. Ideally, such agents would show low toxicity to the patient, would be inexpensive and readily synthesized from commonly available starting materials, would exhibit high levels of oral bioavailability, and/or would exhibit high levels of efficacy at relatively low doses.

SUMMARY OF THE INVENTION

The present invention is directed to the aforementioned need in the art, and provides novel indole analogs that are potent antibacterial agents. The compounds display considerable advantages relative to existing antibacterial agents. For example, the present compounds have significant antibacterial activity, are effective against Gram positive, Gram negative, drug-resistant bacteria, and exhibit prophylactic as well as therapeutic utility. Furthermore, many of the compounds have good oral bioavailability and have a very broad therapeutic window, in turn meaning that no toxicity will be seen even at high doses. From a safety standpoint, then, the compounds are optimal. Furthermore, the compounds have fairly simple molecular structures, and may be readily synthesized using straightforward synthetic techniques.

The invention also provides a method for preventing or treating a bacterial infection in a mammalian individual by administration of an antibacterial agent as provided herein. Generally, in chemoprevention, the patient will have been identified as being at an elevated risk of developing a bacterial infection. Such patients include, for example, those commonly exposed to one or more types of harmful bacteria, those expecting to be exposed to one or more types of harmful bacteria during a particular event such as a surgical procedure, and those have weakened or depressed immunity.

In a first embodiment, the disclosure provides a method for preventing or treating a bacterial infection in a mammalian individual by administration of a therapeutically effective amount of a compound having the structure of formula (I)

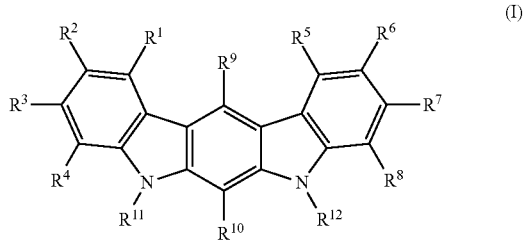

wherein: $R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonyl, $C_6$-$C_{20}$ arylcarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, dihydroxyboryl, di-($C_1$-$C_{24}$)-alkoxyboryl, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents selected from $R^1$, $R^2$, $R^3$, $R^4$, $R^5$, $R^6$, $R^7$, and $R^8$ may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, formyl, $C_1$-$C_{24}$ alkyl, $C_6$-$C_{24}$ aralkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl) amino-substituted $C_1$-$C_{24}$ alkyl, and nitrogen protecting groups.

In another embodiment, the above-described method for treatment or prevention of a bacterial infection involves administration of a compound having the structure of formula (II)

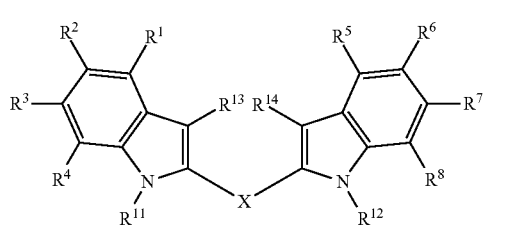

(II)

wherein:

$R^1$, $R^2$, $R^3$, $R^4$, $R^5$, $R^6$, $R^7$, and $R^8$ are independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl;

$R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$.

In a still further embodiment, the above-described method for the treatment or prevention of cancer involves administration of a novel compound having the structure of formula (III)

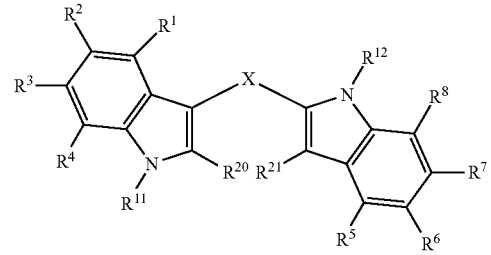

(III)

wherein:

$R^1$, $R^2$, $R^3$, $R^4$, $R^5$, $R^6$, $R^7$, $R^8$, $R^{11}$, $R^{12}$, and X are as defined for compounds having the structure of formula (II); and $R^{20}$ and $R^{21}$ are defined as for $R^1$, $R^2$, $R^3$, $R^4$, $R^5$, $R^6$, $R^7$, and $R^8$.

Additional compounds of the invention, also useful in conjunction with the above-described therapeutic and prophylactic methods, have the structure of formula (IV)

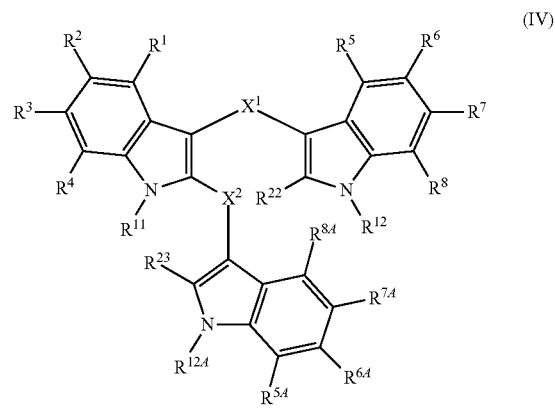

(IV)

wherein:

$R^1$, $R^2$, $R^3$, $R^4$, $R^5$, $R^6$, $R^7$, $R^8$, $R^{11}$, and $R^{12}$ are defined as for compounds having the structure of formula (II);

$R^{5A}$, $R^{6A}$, $R^{7A}$, $R^{8A}$, and $R^{12A}$ are defined as for $R^5$, $R^6$, $R^7$, $R^8$, and $R^{12}$, respectively;

$R^{22}$ and $R^{23}$ are defined as for $R^{20}$ and $R^{21}$ in the structure of formula (III); and $X^1$ and $X^2$ are independently selected from O, S, arylene, heteroarylene, $CR^{15}R^{16}$ and $NR^{17}$, or together form $=CR^{18}R^{19}$ wherein $R^{15}$, $R^{16}$, $R^{17}$, $R^{18}$, and $R^{19}$ are as defined previously with respect to compounds of formulae (II), with the proviso that at least one of $R^1$, $R^2$, $R^3$, $R^4$, $R^5$, $R^6$, $R^7$, $R^8$, $R^{5A}$, $R^{6A}$, $R^{7A}$, $R^{8A}$, $R^{11}$, $R^{12}$, $R^{22}$ and $R^{23}$ is other than hydrogen.

In a further embodiment, the invention provides a method for reducing a population of bacteria, comprising administering a compound having the structure of formula (I), (II), (III), or (IV), or a combination thereof.

In another embodiment, the invention encompasses pharmaceutical compositions containing a compound as provided herein in combination with a pharmaceutically acceptable carrier. Preferably, although not necessarily, such compositions are oral dosage forms and thus contain a carrier suitable for oral drug administration.

In a further embodiment, the invention provides compounds having the structure of formula (I), wherein $R^1$, $R^2$, $R^3$, $R^4$, $R^5$, $R^6$, $R^7$, $R^8$, $R^9$, and $R^{10}$ are as defined herein.

In a further embodiment, methods are provided for synthesizing the compounds of the invention.

DETAILED DESCRIPTION OF THE PREFERRED EMBODIMENTS

I. Definitions and Nomenclature:

Unless otherwise indicated, the invention is not limited to specific synthetic methods, analogs, substituents, pharmaceutical formulations, formulation components, modes of administration, or the like, as such may vary. It is also to be understood that the terminology used herein is for the purpose of describing particular embodiments only and is not intended to be limiting.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, norbornyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred substituents identified as "$C_1$-$C_6$ alkyl" or "lower alkyl" contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom. If not otherwise indicated, the term "aryl" includes unsubstituted, substituted, and/or heteroaryl.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic. When multicyclic, such groups may include fused rings and/or non-fused rings (i.e., rings that are substituents bonded to rings).

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, heteroatoms such as nitrogen, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkyl-sulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{20}$ aryl (preferably $C_5$-$C_{14}$ aryl), $C_6$-$C_{24}$ alkaryl (preferably $C_6$-$C_{18}$ alkaryl), and $C_6$-$C_{24}$ aralkyl (preferably $C_6$-$C_{18}$ aralkyl).

In addition, the aforementioned functional groups may, if a particular group permits, be further substituted with one or more additional functional groups or with one or more hydrocarbyl moieties such as those specifically enumerated above. In particular, any of the above-mentioned groups may, where permitted, be halogenated (including perhalogenated) or contain halogenated substituents. Representative examples include perhalogenated $C_2$-$C_{24}$ alkylcarbonyl or acyloxy groups.

Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

It will be appreciated that the aforementioned groups are not necessarily mutually exclusive, and that any given group may fall within more than one definition. For example, a benzyl group (i.e., —CH$_2$—C$_6$H$_5$) can be classified as an aralkyl group and as a substituted alkyl group. Throughout this specification, and unless specified otherwise, recitation of one definition (e.g., "alkyl") and non-recitation of an overlapping definition(s) (e.g., "aralkyl") is not intended to exclude those groups that fall within both definitions. For example, for a substituent R$^x$ defined as "H or alkyl," such definition should be interpreted to include alkyl groups that may also fall within other classifying terms (e.g., benzyl).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Also disclosed are pharmaceutically acceptable, pharmacologically active analogs of the compounds, including, but not limited to, salts, esters, amides, prodrugs, and conjugates.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. For example, treatment of a patient by administration of an anti-bacterial agent of the invention encompasses prophylactic treatment in a patient susceptible to developing a bacterial infection (e.g., at a higher risk, as a result of genetic predisposition, environmental factors, or the like), as well as therapeutic treatment of a patient having a bacterial infection.

By the terms "effective amount" and "therapeutically effective amount" of a compound of the invention is meant a nontoxic but sufficient amount of the drug or agent to provide the desired effect.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

II. Indole Analogs of the Invention and Synthesis Thereof:

The compounds of the invention are indole analogs. In a first embodiment, the compounds have the structure of formula (I)

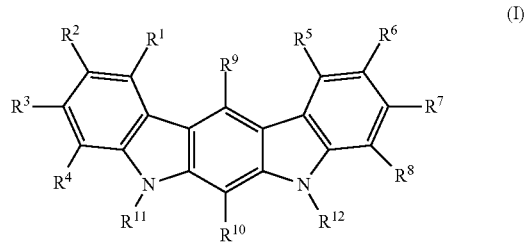

wherein:

$R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonyl, $C_6$-$C_{20}$ arylcarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, dihydroxyboryl, di-($C_1$-$C_{24}$)-alkoxyboryl, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents selected from $R^1$, $R^2$, $R^3$, $R^4$, $R^5$, $R^6$, $R^7$, and $R^8$ may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, formyl, $C_1$-$C_{24}$ alkyl, $C_6$-$C_{24}$ aralkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl) amino-substituted $C_1$-$C_{24}$ alkyl, and nitrogen protecting groups.

In some embodiments, $R^1$, $R^3$, $R^4$, $R^5$, $R^7$, and $R^8$ in formula (I) are selected from hydrogen and halo. In some preferred embodiments, $R^3$ and $R^7$ are the same, and in other preferred embodiments, $R^3$ and $R^7$ are different. In some preferred embodiments, $R^1$ and $R^5$ are the same, and in other preferred embodiments, $R^1$ and $R^5$ are different. In some preferred embodiments, $R^4$ and $R^8$ are the same, and in other preferred embodiments, $R^4$ and $R^8$ are different.

In some embodiments, $R^2$ and $R^6$ in formula (I) are independently selected from hydrogen, halo, formyl, cyano, $C_1$-$C_{24}$ alkyl (including substituted $C_1$-$C_{24}$ alkyl such as perhalogenated, ether-substituted, and amino-substituted $C_1$-$C_{24}$ alkyl, and heteroatom-containing $C_1$-$C_{24}$ alkyl), $C_2$-$C_{24}$ alkenyl, $C_1$-$C_{24}$ alkoxy (including heteroatom-containing $C_1$-$C_{24}$ alkoxy), $C_5$-$C_{20}$ aryloxy, carbamoyl (including unsubstituted carbamoyl (i.e., —(CO)—NH$_2$), mono-($C_1$-$C_{12}$ alkyl)-substituted carbamoyl, di-($C_1$-$C_{12}$ alkyl)-substituted carbamoyl, and heteroatom-containing $C_1$-$C_{12}$ alkyl substituted carbamoyl), $C_2$-$C_{24}$ alkoxycarbonyl, and amino (including mono- and di-($C_1$-$C_{12}$ alkyl)-substituted amino, $C_3$-$C_{12}$ cyclic amino, heteroatom-containing $C_2$-$C_{12}$ cyclic amino, and salts thereof). In some preferred embodiments, $R^2$ and $R^6$ are independently selected from hydrogen, halo, formyl, $C_1$-$C_{24}$ alkyl (including perhalogenated alkyl), and $C_2$-$C_{24}$ alkyloxycarbonyl (including perhalogenated alkyloxycarbonyl). In some preferred embodiments, $R^2$ and/ or $R^6$ is alkyl which may be unsubstituted or substituted with one or more substituents as described herein. Such substituents include, for example, halo, hydroxyl, alkoxy (including substituted alkoxy such as polyethers), aryloxy, and amines (including mono-alkyl-substituted amines, di-alkyl-substituted amines, cyclic amines, substituted cyclic amines, and heteroatom-containing cyclic amines). In some preferred embodiments, $R^2$ and $R^6$ are independently selected from electron withdrawing groups. As will be appreciated by the skilled artisan, the term "electron withdrawing" refers to a group that is more electronegative than a reference group, i.e., a hydrogen atom. Examples of electron withdrawing groups include halo, carbonyl groups (e.g., $C_2$-$C_{24}$ alkoxycarbonyl, $C_2$-$C_{24}$ alkylcarbonyl, and formyl), cyano, nitro, and halogenated alkyl. In some preferred embodiments, $R^2$ and $R^6$ are the same, and in other preferred embodiments, $R^2$ and $R^6$ are different.

In some embodiments, $R^9$ in formula (I) is selected from hydrogen, halo, cyano, $C_1$-$C_{24}$ alkyl (including substituted and unsubstituted $C_1$-$C_{24}$ alkyl, heteroatom-containing $C_1$-$C_{24}$ alkyl, and $C_3$-$C_{12}$ cycloalkyl), $C_2$-$C_{24}$ alkenyl (including substituted, unsubstituted, and heteroatom-containing $C_2$-$C_{24}$ alkenyl), and amino (including mono- and di-($C_1$-$C_{12}$ alkyl)-substituted amino, $C_3$-$C_{12}$ cyclic amino, heteroatom-containing $C_1$-$C_{12}$ amino, and heteroatom-containing $C_2$-$C_{12}$ cyclic amino). For example, in some preferred embodiments, $R^9$ is selected from hydrogen, halo, unsubstituted $C_1$-$C_{12}$ alkyl, $C_3$-$C_{12}$ cycloalkyl, $C_2$-$C_{12}$ alkenyl (including alkenyl substituted with a group selected from amines, amides, and esters), and —NR$^{d1}$R$^{d2}$, wherein R$^{d1}$ and R$^{d2}$ are independently selected from hydrogen, unsubstituted $C_1$-$C_{12}$ alkyl, and substituted $C_1$-$C_{12}$ alkyl, or wherein $R^{d1}$ and $R^{d2}$ are taken together to form a 5-, 6-, or 7-member cycle that may further include one or more heteroatoms, one or more substituents, or a combination thereof.

In some embodiments, $R^{10}$ in formula (I) is selected from $C_1$-$C_{24}$ alkyl, $C_2$-$C_{24}$ alkenyl, $C_2$-$C_{24}$ alkynyl, and $C_1$-$C_{24}$ alkoxy. For example, in some embodiments $R^{10}$ is selected from unsubstituted $C_1$-$C_{24}$ alkyl, substituted $C_1$-$C_{24}$ alkyl (including fluorinated and perfluorinated $C_1$-$C_{24}$ alkyl), heteroatom containing $C_1$-$C_{24}$ alkyl, unsubstituted $C_2$-$C_{24}$ alkenyl, substituted $C_2$-$C_{24}$ alkenyl, heteroatom containing $C_2$-$C_{24}$ alkenyl, unsubstituted $C_2$-$C_{24}$ alkynyl, substituted $C_2$-$C_{24}$ alkynyl, heteroatom containing $C_2$-$C_{24}$ alkynyl, unsubstituted $C_1$-$C_{24}$ alkoxy, substituted $C_1$-$C_{24}$ alkoxy, and heteroatom containing $C_1$-$C_{24}$ alkoxy. For example, in some embodiments, $R^{10}$ is —O-$L_1$-$CHR^{x1}R^{x2}$, —O-L-N($R^{y1}$)($R^{y2}$)($R^{y3}$)$_{n2}$(X)$_{n3}$, —O-L-$SR^{z1}$, or has the structure

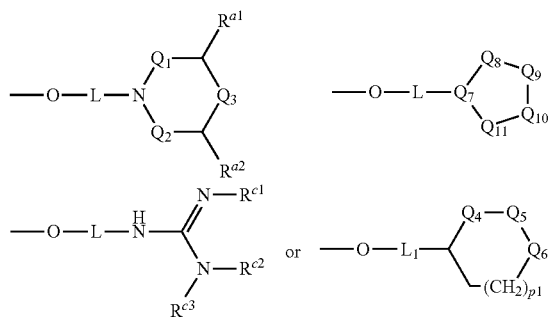

wherein:

L is a linker selected from a $C_1$-$C_{12}$ straight chain, $C_2$-$C_{12}$ branched, or $C_3$-$C_{12}$ cyclic alkylene group that may be substituted, unsubstituted, heteroatom containing, or a combination thereof, and an alkylene oxide oligomer (such as, for example, (—CH2-CH2-O—)$_{n1}$, where n1 is in the range 2-12);

$L_1$ is a linker selected from a bond, a $C_1$-$C_{12}$ straight chain, $C_2$-$C_{12}$ branched, or $C_3$-$C_{12}$ cyclic alkylene group that may be substituted, unsubstituted, heteroatom containing, or a combination thereof, and an alkylene oxide oligomer (such as, for example, (—CH2-CH2-O—)$_{n1}$, where n1 is in the range 2-12);

$R^{y1}$ and $R^{y2}$ are independently selected from hydrogen, $C_1$-$C_{24}$ alkyl, $C_2$-$C_{24}$ alkenyl, $C_5$-$C_{20}$ aryl, $C_6$-$C_{24}$ alkaryl, $C_6$-$C_{24}$ aralkyl, amino (including substituted amino), imino (including nitrogen substituted imino such that Q1 is a guanidine, substituted guanidine, or cyclic guanidine group), $C_1$-$C_{24}$ alkylsulfonyl (including halogenated alkylsulfonyl), and $C_5$-$C_{20}$ arylsulfonyl, any of which may be further substituted and/or heteroatom-containing where such groups permit, or wherein $R^{y1}$ and $R^{y2}$ are taken together to form a cyclic or polycyclic group that may be unsubstituted, substituted, and/or further heteroatom-containing;

$R^{y3}$ is selected from hydrogen and $C_1$-$C_{12}$ alkyl;

n2 and n3 are the same and are selected from 0 and 1;

X is a negatively charged counterion;

$R^{x1}$ and $R^{x2}$ are independently selected from hydrogen, $C_1$-$C_{24}$ alkyl, $C_2$-$C_{24}$ alkenyl, $C_5$-$C_{20}$ aryl, $C_6$-$C_{24}$ alkaryl, $C_6$-$C_{24}$ aralkyl, any of which may be further substituted and/or heteroatom-containing where such groups permit, or wherein $R^{x1}$ and $R^{x2}$ are taken together to form a cyclic or polycyclic group that may be unsubstituted, substituted, and/or further heteroatom-containing; and $R^{z1}$ is selected from $C_1$-$C_{24}$ alkyl, $C_2$-$C_{24}$ alkenyl, $C_5$-$C_{20}$ aryl, $C_6$-$C_{24}$ alkaryl, and $C_6$-$C_{24}$ aralkyl, any of which may be further substituted and/or heteroatom-containing where such groups permit, $Q_1$ and $Q_2$ are selected from a bond and —$CH_2$—;

$Q_3$ is selected from a bond, —CH($R^{a3}$)—, —O—, and —$NR^{a4}$—, provided that $Q_3$ is not a bond when both $Q_1$ and $Q_2$ are bonds;

$R^{a1}$ and $R^{a2}$ are independently selected from hydrogen, hydroxyl, amino, $C_1$-$C_{12}$ alkyl-substituted amino, and $C_1$-$C_{12}$ alkyl;

$R^{a3}$ and $R^{a4}$ are independently selected from hydrogen, $C_1$-$C_{12}$ alkyl, unsubstituted amino, and mono- or di-($C_1$-$C_{12}$ alkyl)-substituted amino;

$Q_4$, $Q_5$, and $Q_6$ are selected from —$CHR^{b1}$— and —$NR^{b1}$—, where $R^{b1}$ is selected from hydrogen, hydroxyl, amino, $C_1$-$C_{12}$ alkyl-substituted amino, and $C_1$-$C_{12}$ alkyl;

p1 is an integer in the range of 0-2;

$Q^7$ is selected from —CH< and —N<;

$Q^8$, $Q^9$, $Q^{10}$, and $Q^{11}$ are independently selected from —CH—, =C($R^{e1}$)—, —$NR^{e1}$—, and —N=, where $R^{e1}$ is selected from hydrogen, hydroxyl, amino, $C_1$-$C_{12}$ alkyl-substituted amino, and $C_1$-$C_{12}$ alkyl, provided that: (1) any two of $Q^8$, $Q^9$, $Q^{10}$, and $Q^{11}$ that are adjacent each other may be linked by a double bond, with the proviso that no more than two double bonds are present, and, when two double bonds are present, a single bond is present between them; and (2) any two adjacent $R^{e1}$ groups (i.e., $R^{e1}$ groups that are attached to adjacent atoms in the ring) may be taken together to form a 5- or 6-membered ring that may be further substituted and may have one or more heteroatoms;

$R^{c1}$, $R^{c2}$, and $R^{c3}$ are independently selected from hydrogen, $C_1$-$C_{24}$ alkyl, and $C_5$-$C_{20}$ aryl, any of which may be further substituted and/or heteroatom-containing where such groups permit, provided that and two of $R^{c1}$, $R^{c2}$, and $R^{c3}$ may be taken together to form a cyclic or polycyclic group that may be unsubstituted, substituted, and/or further heteroatom-containing.

For example, in some embodiments, L is —(CH$_2$)$_m$—, where m is an integer from 1 to 6. Also for example, in some embodiments, X is halo, such as F$^-$, Cl$^-$, Br$^-$, or I$^-$.

In some embodiments, $R^{11}$ and $R^{12}$ in formula (I) are independently selected from hydrogen, formyl, $C_1$-$C_{24}$ alkyl (including substituted $C_1$-$C_{24}$ alkyl and heteroatom-containing $C_1$-$C_{24}$ alkyl such as ether-substituted and amino-substituted $C_1$-$C_{24}$ alkyl), $C_6$-$C_{24}$ aralkyl, and amine protecting groups. Examples of amine protecting groups include carbamates such as Fmoc and Boc. Additional amine protecting group examples can be found in the pertinent literature (e.g., Greene et al., *Protective Groups in Organic Synthesis*, 3$^{rd}$ Ed. (New York: Wiley, 1999). In some preferred embodiments, $R^{11}$ and $R^{12}$ are the same, and in other preferred embodiments, $R^{11}$ and $R^{12}$ are different. For example, in some preferred embodiments, $R^{11}$ and $R^{12}$ are independently selected from hydrogen, formyl, $C_1$-$C_{12}$ alkoxycarbonyl, unsubstituted $C_1$-$C_{24}$ alkyl, and $C_1$-$C_{24}$ alkyl substituted with a group selected from cyano, $C_5$-$C_{20}$ aryl, and —$NR^{z1}R^{z2}$, wherein $R^{z1}$ and $R^{z2}$ are independently selected from hydrogen, unsubstituted $C_1$-$C_{12}$ alkyl, and substituted $C_1$-$C_{12}$ alkyl, or wherein $R^{z1}$ and $R^{z2}$ are taken together to form a 5-, 6-, or 7-member cycle that may further include one or more heteroatoms, one or more substituents, or a combination thereof.

In some preferred embodiments of formula (I), $R^1$, $R^4$, $R^5$, and $R^8$, are hydrogen. These compounds have the structure of formula (Ia)

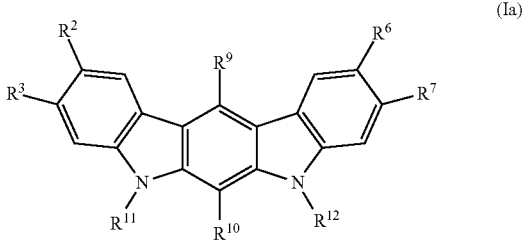

(Ia)

wherein $R^2$, $R^6$, $R^9$, $R^{10}$, $R^{11}$, and $R^{12}$ are as defined above.

In some embodiments, one of $R^{11}$ and $R^{12}$ is a group having the formula of structure (I), attached through one of $R^1$, $R^2$, $R^3$, $R^4$, $R^5$, $R^6$, $R^7$, or $R^8$. For example, when $R^{12}$ is a group having the formula of structure (I), and when the attachment point is through $R^2$, the compound will have the structure of formula (Ib):

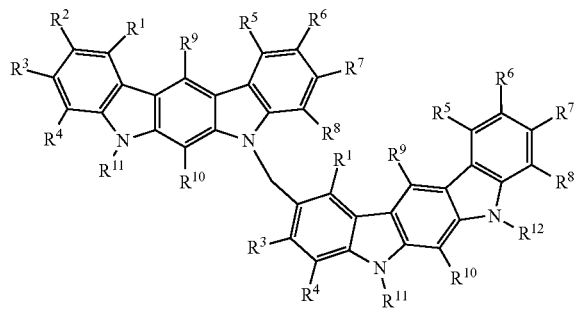

(Ib)

Other compounds useful in the methods of the invention have the structure of formula (II)

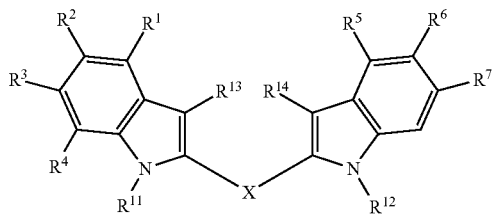

(II)

wherein:

$R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl;

$R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$.

In preferred compounds of formula (II), $R^1$, $R^3$, $R^4$, $R^5$, $R^7$, and $R^8$ are hydrogen, and X is $CR^{15}R^{16}$, such that the compounds have the structure of formula (IIa)

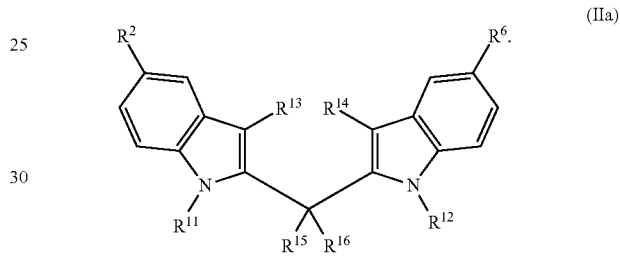

(IIa)

Preferred $R^2$ and $R^6$ moieties in structures (II) and (IIa) include, without limitation, hydrogen, halo, hydroxyl, sulfhydryl, $C_1$-$C_{12}$ alkyl, $C_2$-$C_{12}$ alkenyl, $C_1$-$C_{12}$ alkoxy, $C_5$-$C_{20}$ aryloxy, $C_2$-$C_{12}$ alkylcarbonyl, $C_6$-$C_{20}$ arylcarbonyl, $C_2$-$C_{12}$ acyloxy, $C_2$-$C_{12}$ alkoxycarbonyl, $C_6$-$C_{20}$ aryloxycarbonyl, $C_2$-$C_{12}$ alkylcarbonato, carboxy, carbamoyl, mono-($C_1$-$C_{12}$ alkyl)-substituted carbamoyl, di-($C_1$-$C_{12}$ alkyl)-substituted carbamoyl, amino, mono- and di-($C_1$-$C_{12}$ alkyl)-substituted amino, $C_2$-$C_{12}$ alkylamido, $C_1$-$C_{12}$ alkylsulfanyl, $C_1$-$C_{12}$ alkylsulfinyl, and $C_1$-$C_{12}$ alkylsulfonyl, including substituted analogs thereof for those substituents that permit substitution (e.g., hydroxyalkyl, aminoalkyl, dialkylaminoalkyl, aminoalkylcarbonyl, dialkylaminocarbonyl, carboxy-substituted alkyl, etc.). Within the aforementioned substituents, preferred $R^2$ and $R^6$ moieties are halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono-($C_1$-$C_{12}$ alkyl)-substituted carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl. Preferred $R^{11}$ and $R^{12}$ moieties are also as given for compounds of formula (I), and thus include hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino)-substituted $C_1$-$C_{12}$ alkyl, and di-($C_1$-$C_{12}$ alkyl)amino-substituted $C_1$-$C_{12}$ alkyl.

Preferred $R^{13}$ and $R^{14}$ substituents in structures (II) and (IIa) are selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino)-substituted $C_1$-$C_{24}$ alkyl, $C_5$-$C_{20}$ aryl, $C_6$-$C_{24}$ alkaryl, and $C_6$-$C_{24}$ aralkyl, and more preferred $R^{13}$ and $R^{14}$ substituents in structures (II) and (IIa) include hydrogen, $C_1$-$C_{12}$ alkyl, $C_1$-$C_{12}$ alkoxy, and $C_2$-$C_{12}$ alkoxycarbonyl.

Preferred $R^{15}$ and $R^{16}$ substituents in structure (IIa) include hydrogen and $C_1$-$C_{12}$ alkyl, and wherein $R^{15}$ and $R^{16}$ together form $=CR^{18}R^{19}$ where $R^{18}$ and $R^{19}$ are hydrogen or $C_1$-$C_6$ alkyl.

In particularly preferred compounds of formula (IIa), $R^2$ and $R^6$ are hydrogen or $C_2$-$C_6$ alkoxycarbonyl, $R^{11}$ and $R^{12}$ are hydrogen, $C_2$-$C_6$ alkoxycarbonyl, or $C_1$-$C_6$ alkyl, $R^{13}$ and $R^{14}$ are hydrogen, $C_1$-$C_6$ alkyl, $C_1$-$C_6$ alkoxy, or $C_2$-$C_6$ alkoxycarbonyl, and $R^{15}$ and $R^{16}$ are hydrogen, $C_1$-$C_6$ alkyl, or together form $=CH_2$. Optimally, $R^2$ and $R^6$ are hydrogen or ethoxycarbonyl (—(CO)—O—$CH_2CH_3$), $R^{11}$ and $R^{12}$ are hydrogen, $R^{13}$ and $R^{14}$ are independently hydrogen, methyl, or ethoxycarbonyl, and $R^{15}$ and $R^{16}$ are hydrogen or $C_1$-$C_6$ alkyl.

Exemplary compounds encompassed by formula (II) include, without limitation: 3-Methylthio-2,2'-diindolylmethane; 3,3'-Dimethyl-2,2'-diindolylmethane; 3,3'-Dimethyl-5,5'-dicarbethoxy-2,2'-diindolylmethane; 3,3'-Dimethyl-5-carbethoxy-2,2'-diindolylmethane; 5,5'-Dicarbethoxy-2,2'-diindolylmethane; N,N'-Dimethyl-3,3'-dimethyl-2,2'-diindolylmethane; N,N'-Dimethyl-3,3'-dimethyl-5,5'-dicarbethoxy-2,2'-diindolylmethane; N-Methyl-3,3'-dimethyl-5,5'-dicarbethoxy-2,2'-diindolylmethane; N,N'-Dicarbethoxy-3,3'-dimethyl-5,5'-dicarbethoxy-2,2'-diindolylmethane; and N-Carbethoxy-3,3'-dimethyl-5,5'-dicarbethoxy-2,2'-diindolylmethane.

In a further embodiment, compounds are provided having the structure of formula (III)

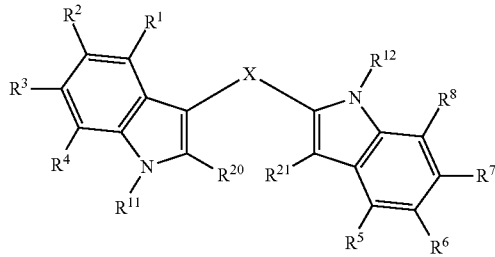

(III)

wherein:

$R^1$, $R^2$, $R^3$, $R^4$, $R^5$, $R^6$, $R^7$, $R^8$, $R^{11}$, $R^{12}$, and X are defined as for compounds of formula (II); and $R^{20}$ and $R^{21}$ are defined as for $R^1$, $R^2$, $R^3$, $R^4$, $R^5$, $R^6$, $R^7$, and $R^8$.

In preferred compounds of formula (III), $R^1$, $R^3$, $R^4$, $R^5$, $R^7$, and $R^8$ are hydrogen, and X is $CR^{15}R^{16}$, such that the compounds have the structure of formula (IIIa)

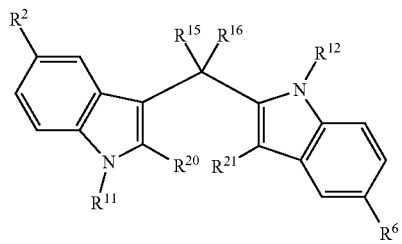

(IIIa)

Preferred $R^2$ and $R^6$ moieties in structures (III) and (IIIa) include, without limitation, hydrogen, halo, hydroxyl, sulfhydryl, $C_1$-$C_{12}$ alkyl, $C_2$-$C_{12}$ alkenyl, $C_1$-$C_{12}$ alkoxy, $C_5$-$C_{20}$ aryloxy, $C_2$-$C_{12}$ alkylcarbonyl, $C_6$-$C_{20}$ arylcarbonyl, $C_2$-$C_{12}$ acyloxy, $C_2$-$C_{12}$ alkoxycarbonyl, $C_6$-$C_{20}$ aryloxycarbonyl, $C_2$-$C_{12}$ alkylcarbonato, carboxy, carbamoyl, mono-($C_1$-$C_{12}$ alkyl)-substituted carbamoyl, di-($C_1$-$C_{12}$ alkyl)-substituted carbamoyl, amino, mono- and di-($C_1$-$C_{12}$ alkyl)-substituted amino, $C_2$-$C_{12}$ alkylamido, $C_1$-$C_{12}$ alkylsulfanyl, $C_1$-$C_{12}$ alkylsulfinyl, and $C_1$-$C_{12}$ alkylsulfonyl, including substituted analogs thereof for those substituents that permit substitution. Within the aforementioned substituents, more preferred $R^2$ and $R^6$ moieties are halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono-($C_1$-$C_{12}$ alkyl)-substituted carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl. Preferred $R^{11}$ and $R^{12}$ moieties are as given for compounds of formulae (I) and (II), and thus include hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino)-substituted $C_1$-$C_{12}$ alkyl, and di-($C_1$-$C_{12}$ alkyl)amino-substituted $C_1$-$C_{12}$ alkyl.

Preferred $R^{15}$ and $R^{16}$ substituents in structure (III) include hydrogen and $C_1$-$C_{12}$ alkyl, or wherein $R^{15}$ and $R^{16}$ together form $=CR^{18}R^{19}$ where $R^{18}$ and $R^{19}$ are hydrogen or $C_1$-$C_6$ alkyl.

Preferred $R^{20}$ and $R^{21}$ substituents in structures (III) and (IIIa) are selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino)-substituted $C_1$-$C_{24}$ alkyl, $C_5$-$C_{20}$ aryl, $C_6$-$C_{24}$ alkaryl, and $C_6$-$C_{24}$ aralkyl, and more preferred $R^{20}$ and $R^{21}$ substituents in structures (III) and (IIIa) include hydrogen, $C_1$-$C_{12}$ alkyl, $C_1$-$C_{12}$ alkoxy, and $C_2$-$C_{12}$ alkoxycarbonyl.

In particularly preferred compounds of formula (III), $R^2$ and $R^6$ are independently hydrogen or $C_2$-$C_6$ alkoxycarbonyl, $R^{11}$ and $R^{12}$ are independently hydrogen, $C_2$-$C_6$ alkoxycarbonyl, or $C_1$-$C_6$ alkyl, $R^{20}$ and $R^{21}$ are independently hydrogen, $C_1$-$C_6$ alkyl, $C_1$-$C_6$ alkoxy, or $C_2$-$C_6$ alkoxycarbonyl, and $R^{15}$ and $R^{16}$ are independently hydrogen, $C_1$-$C_6$ alkyl, or together form $=CH_2$. Optimal $R^2$ and $R^6$ substituents are hydrogen and ethoxycarbonyl (—(CO)—O—$CH_2CH_3$), optimal $R^{11}$ and $R^{12}$ substituents are hydrogen and $C_1$-$C_6$ alkyl, optimal $R^{20}$ and $R^{21}$ substituents are hydrogen, methyl, and ethoxycarbonyl, and optimal $R^{15}$ and $R^{16}$ substituents are hydrogen and $C_1$-$C_6$ alkyl.

Exemplary compounds encompassed by formula (III) include, without limitation: 2,3'-Diindolylmethane; 2,3'-Dimethyl-5,5'-dicarbethoxy-2',3-diindolylmethane; 2,3'-Dimethyl-2',3-diindolylmethane; 5,5'-Dicarbethoxy-2',3-diindolylmethane; 5-Carbethoxy-2,3'-dimethyl-2',3-diindolylmethane; N,N'-Dimethyl-2,3'-diindolylmethane; N,N'-Dimethyl-2,3'-dimethyl-2',3-diindolylmethane; N,N'-Dimethyl-2,3'-Dimethyl-5,5'-dicarbethoxy-2',3-diindolylmethane; N-Methyl-2,3'-Dimethyl-5,5'-dicarbethoxy-2',3-diindolylmethane; N,N'-Dicarbethoxy-2,3'-Dimethyl-5,5'-dicarbethoxy-2',3-diindolylmethane; and N-Carbethoxy-2,3'-Dimethyl-5,5'-dicarbethoxy-2',3-diindolylmethane.

Additional compounds of the invention have the structure of formula (IV)

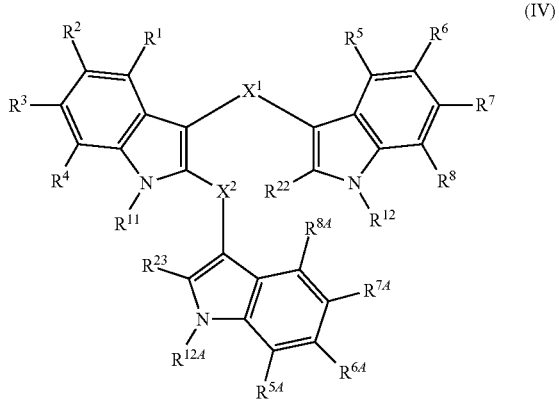

(IV)

wherein:

$R^1$, $R^2$, $R^3$, $R^4$, $R^5$, $R^6$, $R^7$, $R^8$, $R^{11}$, and $R^{12}$ are defined as for compounds having the structure of formula (II);

$R^{5A}$, $R^{6A}$, $R^{7A}$, $R^{8A}$, and $R^{12A}$ are defined as for $R^5$, $R^6$, $R^7$, $R^8$, and $R^{12}$, respectively;

$R^{22}$ and $R^{23}$ are defined as for $R^{20}$ and $R^{21}$ in the structure of formula (III); and $X^1$ and $X^2$ are independently selected from O, S, arylene, heteroarylene, $CR^{15}R^{16}$, and $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$, with the proviso that at least one of $R^1$, $R^2$, $R^3$, $R^4$, $R^5$, $R^6$, $R^7$, $R^8$, $R^{5A}$, $R^{6A}$, $R^{7A}$, $R^{8A}$, $R^{11}$, $R^{12}$, $R^{22}$ and $R^{23}$ is other than hydrogen.

In preferred compounds of formula (IV), $R^1$, $R^3$, $R^4$, $R^5$, $R^7$, $R^8$, $R^{5A}$, $R^{7A}$, and $R^{8A}$ are hydrogen, and $X^1$ and $X^2$ are $CH_2$, such that the compounds have the structure of formula (IVa)

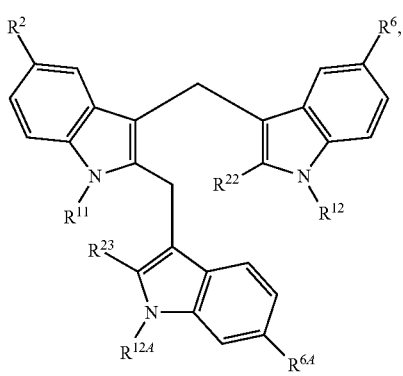

(IVa)

with the proviso that at least one of $R^2$, $R^6$, $R^{6A}$, $R^{11}$, $R^{12}$, $R^{12A}$, $R^{22}$ and $R^{23}$ is other than hydrogen.

Preferred $R^2$, $R^6$, and $R^{6A}$ moieties in structures (IVa) include, without limitation, hydrogen, halo, hydroxyl, sulfhydryl, $C_1$-$C_{12}$ alkyl, $C_2$-$C_{12}$ alkenyl, $C_1$-$C_{12}$ alkoxy, $C_5$-$C_{20}$ aryloxy, $C_2$-$C_{12}$ alkylcarbonyl, $C_6$-$C_{20}$ arylcarbonyl, $C_2$-$C_{12}$ acyloxy, $C_2$-$C_{12}$ alkoxycarbonyl, $C_6$-$C_{20}$ aryloxycarbonyl, $C_2$-$C_{12}$ alkylcarbonato, carboxy, carbamoyl, mono-($C_1$-$C_{12}$ alkyl)-substituted carbamoyl, di-($C_1$-$C_{12}$ alkyl)-substituted carbamoyl, amino, mono- and di-($C_1$-$C_{12}$ alkyl)-substituted amino, $C_2$-$C_{12}$ alkylamido, $C_1$-$C_{12}$ alkylsulfanyl, $C_1$-$C_{12}$ alkylsulfinyl, and $C_1$-$C_{12}$ alkylsulfonyl, including substituted analogs thereof for those substituents that permit substitution. Within the aforementioned substituents, preferred $R^2$, $R^6$, and $R^{6A}$ moieties are halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono-($C_1$-$C_{12}$ alkyl)-substituted carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl. In more preferred compounds, at least one of $R^2$, $R^6$, and $R^{6A}$ is $C_2$-$C_{12}$ alkoxycarbonyl or $C_2$-$C_{12}$ alkylcarbonato. Preferred $R^{11}$, $R^{12}$, and $R^{12A}$ moieties include, without limitation, hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino)-substituted $C_1$-$C_{12}$ alkyl, and di-($C_1$-$C_{12}$ alkyl) amino-substituted $C_1$-$C_{12}$ alkyl.

Preferred $R^{22}$ and $R^{23}$ substituents in structures (IV) and (IVa) are selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino)-substituted $C_1$-$C_{24}$ alkyl, $C_5$-$C_{20}$ aryl, $C_6$-$C_{24}$ alkaryl, and $C_6$-$C_{24}$ aralkyl, and more preferred $R^{22}$ and $R^{23}$ substituents in structures (II) and (IIa) include hydrogen, $C_1$-$C_{12}$ alkyl, $C_1$-$C_{12}$ alkoxy, and $C_2$-$C_{12}$ alkoxycarbonyl.

In particularly preferred compounds of formula (IVa), $R^2$, $R^6$, $R^{6A}$, $R^{22}$, and $R^{23}$ are independently hydrogen or $C_2$-$C_6$ alkoxycarbonyl, and $R^{11}$, $R^{12}$, and $R^{12A}$ are independently hydrogen, or $C_1$-$C_6$ alkyl. Optimally, $R^2$, $R^6$, $R^{6A}$, $R^{22}$, and $R^{23}$ are hydrogen or ethoxycarbonyl (—(CO)—O—$CH_2CH_3$).

Examples of specific compounds encompassed by formula (IV) include, without limitation: 2-(2-Carbethoxy-indol-3-ylmethyl)-2'-carbethoxy-3,3'-diindolylmethane; 2-(5-Bromo-indol-3-ylmethyl)-5,5'-dibromo-3,3'-diindolylmethane; and 2-(5-Carbethoxy-indol-3-ylmethyl)-5,5'-dicarbethoxy-3,3'-diindolylmethane.

Where compounds having the structure of formula (I), (II), (III), or (IV) comprise one or more stereocenters, the invention encompasses all stereoisomers of such compounds. For example, where a compound of the invention may exist as one of two enantiomers, both enantiomers are within the scope of the invention. Furthermore, a composition containing such a compound may contain a mixture of enantiomers (e.g., a racemic mixture) or a single enantiomer (to the extent that such is possible given the methods of synthesis of the particular compound). Similarly, where a compound may exist as a plurality of diastereomers, the invention includes all such diastereomers and compositions may include one or more diastereomer in any proportion.

A compound of the invention may be administered in the form of a salt, ester, amide, prodrug, active metabolite, analog, or the like, provided that the salt, ester, amide, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992).

For example, acid addition salts may be prepared from a free base (e.g., a compound containing a primary amino group) using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of any acidic moieties that may be present may be carried out in a similar manner using a pharmaceutically acceptable base such as sodium hydroxide, potassium hydroxide, ammonium hydroxide, calcium hydroxide, trimethylamine, or the like. Preparation of esters involves reaction of a hydroxyl group with an esterification reagent such as an acid chloride. Amides may be prepared from esters, using suitable amine reactants, or they may be prepared from an anhydride or an acid chloride by reaction with ammonia or a lower alkyl amine. Prodrugs, conjugates, and active metabolites may also be prepared using techniques known to those skilled in the art or described in the pertinent literature. Prodrugs and conjugates are typically prepared by covalent attachment of a moiety that results in a compound that is therapeutically inactive until modified by an individual's metabolic system.

In addition, those compounds containing one or more chiral centers can be in the form of a single stereoisomer such as a single diastereomer or enantiomer or as a mixture such as a racemic mixture of enantiomers. In some cases, i.e., with regard to certain specific compounds illustrated herein, chirality (i.e., relative stereochemistry) is indicated. In other cases, it is not, and such structures are intended to encompass both the stereoisomerically pure form of the compound shown as well as a mixture of stereoisomers. Preparation of compounds in stereoisomerically pure form may be carried out using an stereoselective synthesis; alternatively, stereoisomers may be separated post-synthesis, using routine methodology.

Other derivatives and analogs of the active agents may be prepared using standard techniques known to those skilled in the art of synthetic organic chemistry, or may be deduced by reference to the pertinent literature.

The compounds of the invention may be readily synthesized using straightforward techniques, from appropriately substituted indoles that serve as starting materials (Moyer et al. (1986) *J. Org. Chem.* 51: 5106-5110). Indole precursors used to synthesize the compounds of the invention may be prepared using conventional techniques, such as by treatment of nitrotoluene (V)

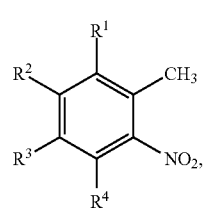

(V)

with N,N-dimethylformamide dimethyl acetal and pyrrolidine, to give the intermediate enamine (VI), which can then be cyclized by reduction with zinc in acetic acid to give the indole (VII).

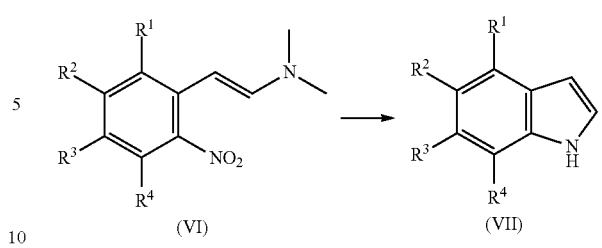

The indole precursor (VII), substituted with one or more substituents selected to result in the desired substituents on the product, is then appropriately treated to provide a reactive site capable of rendering the molecule able to self-condense. For example, precursor (VII) can be formylated (e.g., with phosphorus oxychloride and N,N-dimethylformamide) to give the aldehyde (VIII), followed by reduction with a suitable reducing agent (e.g., sodium borohydride) to the 3-hydroxymethyl-indole analog (IX), as follows:

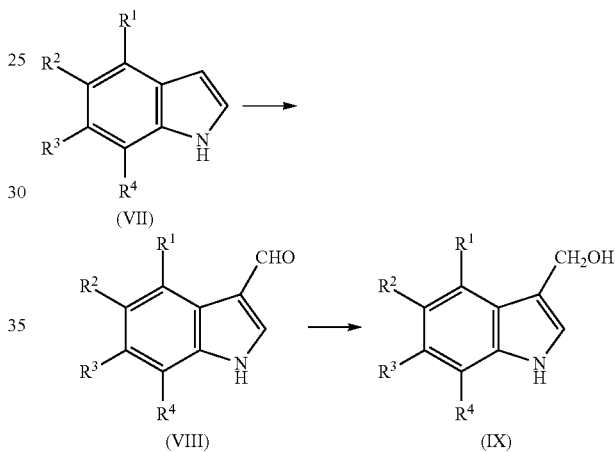

Compound (IX) will then readily self-condense under aqueous basic conditions to give the substituted 3,3'-diindolylmethane (X):

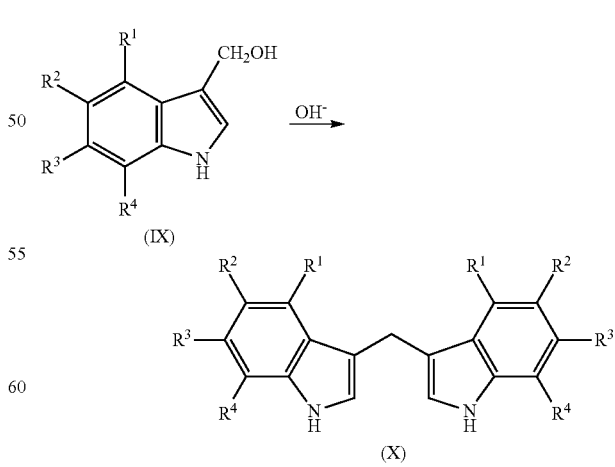

Alternatively, compound (IX) may be condensed with a differently substituted indole analog to provide the substituted 3,3'-diindolylmethane (XII):

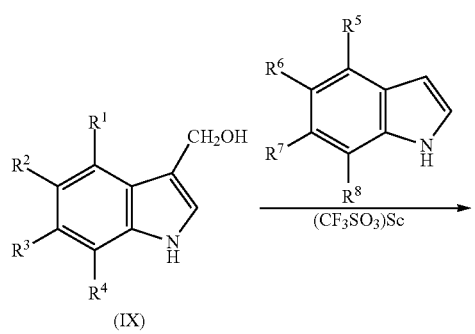

(IX)

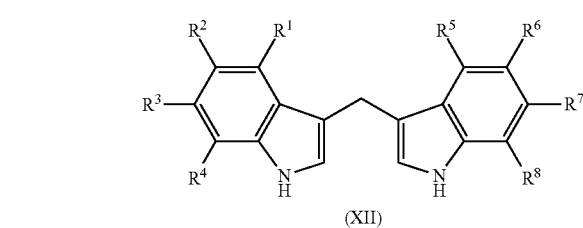

(XII)

For example, the aforementioned reaction may be carried out with 5-bromo-3-hydroxymethylindole (compound (IX), wherein $R^1$, $R^3$, and $R^4$ are hydrogen and $R^2$ is bromo) and 5-bromoindole (compound (XI), wherein $R^5$, $R^7$, and $R^8$ are hydrogen and $R^6$ is bromo), to provide the 5,5'-dibromo analog of (XII). Various reactions may then be carried out to replace the bromine substituents with other moieties, for example, with:

carboxylic ester groups, introduced by reaction of a brominated indole analog (e.g., 5,5'-dibromo-3,3'-diindolylmethane) with an alkyl, aryl, or aralkyl chloroformate (e.g., ethyl chloroformate or benzylchloroformate), during which the nitrogen atoms are protected;

carboxyl groups, prepared by basic hydrolysis of the carboxylic ester groups;

alkylsulfanyl (thioalkyl) groups, prepared by reaction of a brominated indole analog (e.g., 5,5'-dibromo-3,3'-diindolylmethane) with a disulfide, e.g., methyldisulfanyl methane;

alkylsulfonyl groups, prepared by oxidation of the alkylsulfanyl groups; and amides, by reaction of a brominated indole analog (e.g., 5,5'-dibromo-3,3'-diindolylmethane) with a carbamyl halide (e.g., dimethylcarbamyl chloride).

Alternatively, the substituted 3,3'-diindolylmethane (X) may be prepared by coupling two compounds of formula (VII) using formaldehyde in the presence of acid:

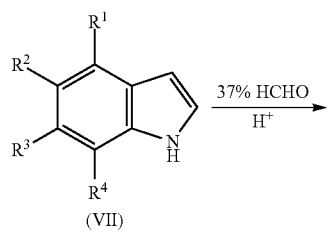

(VII)

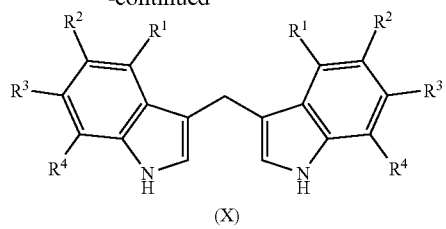

(X)

The 3,3'-diindolylmethane analogs so prepared may then be used directly in the synthesis of compounds of formula (I), i.e., 5,7-dihydro-indolo[2,3-b]carbazoles. The reaction is carried out via cyclization of a 3,3'-diindolylmethane analog of formula (XII) by: (1) protecting the indolyl nitrogen atoms of a compound (XII) with a suitable amino protecting group, to provide an N-protected intermediate (XIII); and (2) treating the protected compound so provided with an organolithium reagent LiR, optionally in conjunction with a compound selected to provide a nonhydrogen substituent $R^{10}$:

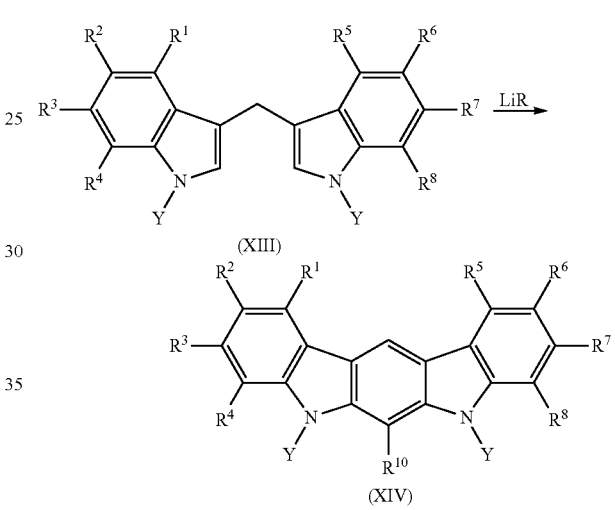

In compounds (XIII) and (XIV), Y is the amino protecting group, which may be any suitable protecting group that is inert with respect to the organolithium reagent but may be removed following synthesis of (XIV). Preferred amino protecting groups are carbamates, e.g., alkyl carbonates such as t-butyloxycarbonyl, or "BOC." Other suitable amino protecting groups will be known to those in the field of synthetic organic chemistry, and/or are described in the pertinent texts and literature. See, e.g., Greene et al., *Protective Groups in Organic Synthesis*, 3rd Ed. (New York: Wiley, 1999). The organolithium reagent LiR, as will be appreciated by those of ordinary skill in the art, may be an alkyllithium reagent such as methyl lithium, isopropyl lithium, n-butyllithium, s-butyllithium, t-butyllithium, or the like, or an aryllithium lithium reagent, e.g., phenyl lithium or p-tolyl lithium, or a lithium amide reagent, e.g., lithium 2,2,6,6-tetramethylpiperidide (LiTMP) or lithium diisopropylamide.

The optional additional reactant selected to provide a non hydrogen $R^{10}$ substituent as shown will depend, of course, on the particular $R^{10}$ substituent intended. Examples of such reactants include, without limitation, anhydrides, acyl chlorides, alkyl and aryl carbonate, and alkyl and aryl chloroformates. For example, $R^{10}$ may be —OH when an ethyl chloroformate is used as the optional additional reactant. As will be appreciated by those of skill in the art, when $R^{10}$ is —OH, a variety of modification reactions may be used to prepare compounds having any of a wide variety of groups for $R^{10}$. Examples are shown in Scheme 1.

Scheme 1

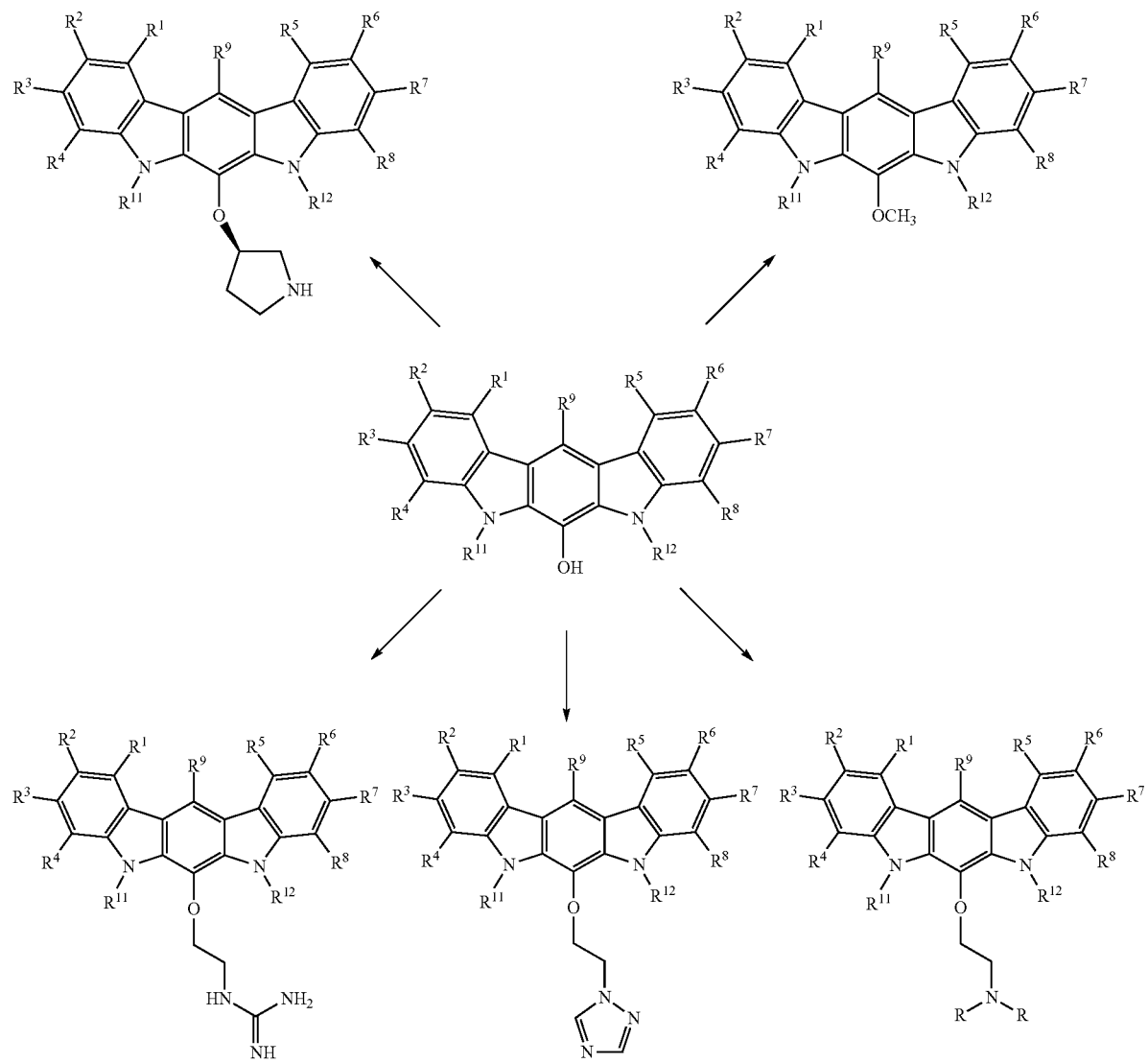

Compounds of formula (II) herein, i.e., 2,2'-diindolyl-methane analogs, are synthesized using procedures that are analogous to those described above with respect to synthesis of 3,3'-diindolylmethane analogs. However, in the synthesis of 2,2'-diindolylmethane analogs, the C3-position of the indole precursor is blocked to enable reaction at the less active (C2) site. The reaction, illustrated below with the blocking group identified as "Z," may be represented as follows:

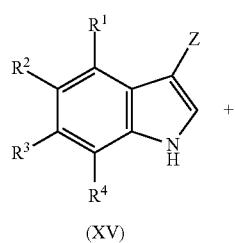

(XV)

-continued

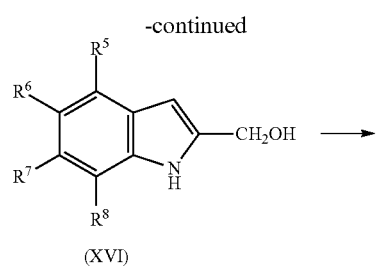

(XVI)

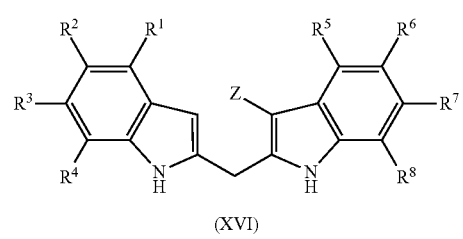

(XVI)

Z is preferably selected so as to be readily removable from the product (XVI); an ideal blocking group is methylthio or bromo, which can be removed by reductive elimination using a suitable catalyst.

Compounds of formula (III), i.e., 2,3'-diindolylmethane analogs, are also made by coupling two appropriately substituted indolyl precursors such that the linkage in the product is provided between the C3-position of one indole precursor and the C2-position of a C3-"blocked" indole precursor. Such a reaction is illustrated below in the preparation of compound (XVIII):

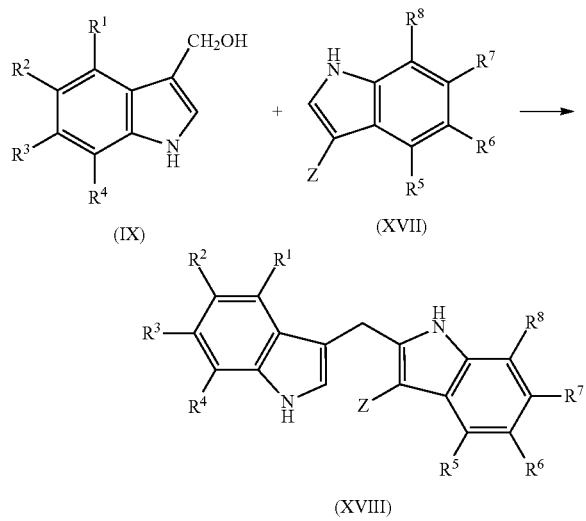

Appropriate reagents and reaction conditions are analogous to those described above with respect to synthesis of the 3,3'-diindolylmethane and 2,2'-diindolylmethane analogs.

Compounds of formula (IV) may be similarly synthesized by reaction of an indolyl precursor having the structure of formula (XIX) with a second indolyl precursor (XX) that is unsubstituted at both the C2 and C3 positions, which results in reaction at both sites. Such a reaction is illustrated below in the preparation of compound (XXI):

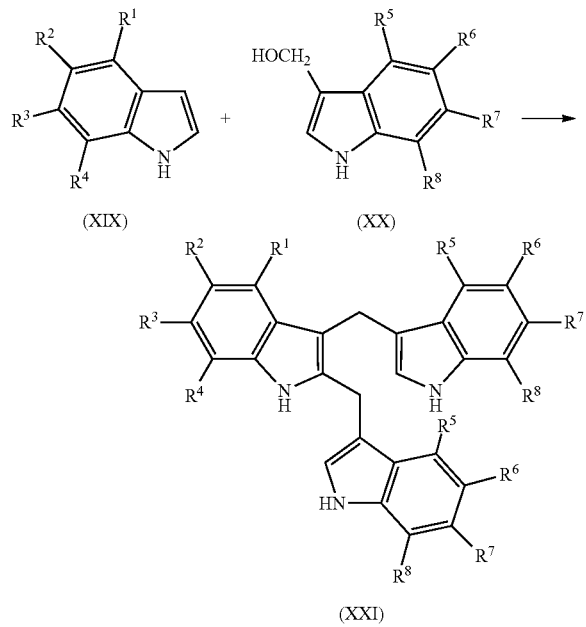

III. Pharmaceutical Formulations

The compounds of the invention are preferably administered as part of a pharmaceutical formulation. The novel compounds may be conveniently formulated into pharmaceutical formulations composed of one or more of the compounds in association with a pharmaceutically acceptable carrier, as described in more detail below. See *Remington: The Science and Practice of Pharmacy*, 19$^{th}$ Ed. (Easton, Pa.: Mack Publishing Co., 1995), which discloses typical carriers and conventional methods of preparing pharmaceutical formulations.

The pharmaceutical formulations of the invention may comprise one or more than one compound described herein. For example, the compositions may comprise 2, 3, or 4 compounds described herein in any suitable ratio.

The compounds of the present invention may also be used in combination with a known antibacterial agent. Non-limiting examples of such antibacterial agents may be selected from the following groups: (1) Macrolides or ketolides such as erythromycin, azithromycin, clarithromycin and telithromycin; (2) Beta-lactams including penicillin, cephalosporin, and carbapenems such as carbapenem, imipenem, and meropenem; (3) Monobactams such as penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmetazole, cefotaxime, ceftizoxime, ceftriaxone, cefoperazone, ceftazidime, cefixime, cefpodoxime, ceftibuten, cefdinir, cefpirome, cefepime, and astreonam; (4) Quinolones such as nalidixic acid, oxolinic acid, norfloxacin, pefloxacin, enoxacin, ofloxacin, levofloxacin, ciprofloxacin, temafloxacin, lomefloxacin, fleroxacin, grepafloxacin, sparfloxacin, trovafloxacin, clinafloxacin, gatifloxacin, moxifloxacin, sitafloxacin, ganefloxacin, gemifloxacin and pazufloxacin; (5) Antibacterial sulfonamides and antibacterial sulphanilamides, including para-aminobenzoic acid, sulfadiazine, sulfisoxazole, sulfamethoxazole and sulfathalidine; (6) Aminoglycosides such as streptomycin, neomycin, kanamycin, paromycin, gentamicin, tobramycin, amikacin, netilmicin, spectinomycin, sisomicin, dibekalin and isepamicin; (7) Tetracyclines such as tetracycline, chlortetracycline, demeclocycline, minocycline, oxytetracycline, methacycline, doxycycline; (8) Rifamycins such as rifampicin (also called rifampin), rifapentine, rifabutin, bezoxazinorifamycin and rifaximin; (9) Lincosamides such as lincomycin and clindamycin; (10) Glycopeptides such as vancomycin and teicoplanin; (11) Streptogramins such as quinupristin and daflopristin; (12) Oxazolidinones such as linezolid; (13) Polymyxin, colistin and colymycin; and (14) Trimethoprim and bacitracin.

The additional known antibacterial agent may be administered in combination with the compounds of the present inventions wherein the known antibacterial agent is administered prior to, simultaneously, or after the compound or compounds of the present invention. When simultaneous administration of a compound of the invention with a known agent is desired and the route of administration is the same, then a compound of the invention may be formulated with a known agent into the same dosage form.

The pharmaceutical formulations of the invention may further comprise one or more additional active agents (i.e., other than an antibacterial agent). Examples of such active agents include analgesics, antifungal agents, antiviral agents, and the like.

The pharmaceutical formulations of the invention may further comprise one or more excipients/carriers such as antiadherents, binders, coatings, disintegrants, fillers, diluents, flavorings, colorants, glidants, lubricants, preservatives, sorbents, and the like, some of which are described in more detail hereinbelow. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar, buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

IV. Modes of Administration

The compounds of the invention may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the compound administered will, of course, be dependent on the particular active agent, the condition or disorder being treated, the severity of the condition or disorder, the subject's weight, the mode of administration and other pertinent factors known to the prescribing physician. Generally, however, dosage will be in the range of approximately 0.001 mg/kg/day to 100 mg/kg/day, more preferably in the range of about 0.1 mg/kg/day to 10 mg/kg/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy, cited above.

For those compounds that are orally active, oral dosage forms are generally preferred, and include tablets, capsules, caplets, solutions, suspensions and syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compounds of the invention may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Compositions for rectal or vaginal administration are preferably suppositories that can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of aerosol particles. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Administration of the compositions of the invention is not limited by any particular regimen, which will typically be selected by the practitioner as appropriate. For example, the compositions may be administered on a regular schedule (e.g., once daily, twice daily, once weekly, etc.) for long periods of time when administered prophylactically, or regularly for a shorter period of time (e.g., for one, two, or three days, or one or two weeks, or one month) when administered therapeutically.

IV. Utility

The compounds of the invention are useful in the prevention and treatment of many different bacterial infections, including infections with Gram-positive, Gram-negative, and drug-resistant bacteria. For example, the present compounds exhibit efficacy with respect to the treatment of infections with *Francisella tularensis* (FT; Gram-negative); *Bacillus anthracis* (BA; Gram-positive); *Yersinia pestis* (YP; Gram-negative); *Brucella abortus* (BAB; Gram-negative); *Burkholderia mallei* (BM; Gram-negative); *Burkholderia pseudomallei* (BP; Gram-negative); *Acinetobacter baumannii* (AB; Gram-negative); *Listeria monocytogenes* (LM; Gram-positive); *Shigella dysenteriae* (SD; Gram-negative); *Enterococcus faecalis* (Gram-positive), Vancomycin-resistant enterococci (VRE) and Vancomycin-sensitive enterococci (VSE); methicillin-susceptible *Staphylococcus aureus* (MSSA); methicillin-resistant *Staphylococcus aureus* (MRSA); penicillin-susceptible *S. pneumoniae* (PSSP); and penicillin-resistant *S. pneumoniae* (PRSP); *Mycobacterium tuberculosis; Mycobacterium bovis; Mycobacterium africanum; Mycobacterium canetti; Mycobacterium microti*; etc.

Other bacterial infections that may be treated or prevented using the compounds of the invention include infections resulting from bacteria of the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, Bordetella, Burkholderia, Acinetobacter, Enterococcus*, and *Francisella*. Other examples, as well as examples of the foregoing include *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter calcoaceticus, Alcaligenes xylosoxidans, Flavobacterium meningosepticum, Providencia stuartii* and *Citrobacter freundi*, community lung infections such as those caused by *Haemophilus Influenzae, Legionella* species, *Moraxella catarrhalis, Branhamella catarrhalis, Enterobacter* species, *Acinetobacter* species, *Klebsiella* species, and *Proteus* species, and infections caused by other bacterial species such as *Neisseria* species, *Shigella* species, *Salmonella* species, *Helicobacter pylori*, Vibrionaceae and *Bordetella* species as well as the infections is caused by a *Brucella* species.

Accordingly, the invention provides methods for treating a patient (typically, although not necessarily, a human patient) in need of such treatment. The methods involve administration of one or more compounds described herein. Typically, the compound is administered in the form of a composition as described herein. The methods include therapeutic treatment of a patient having a bacterial infection, as well as prophylactic treatment of a patient (i.e., a patient not having a bacterial infection). For example, the methods include treatment of a patient having *Tuberculosis*.

Furthermore, the invention provides methods for reducing the number of bacteria in a patient by administration of the compounds described herein. The invention further provides methods for eliminating a colony of bacteria from a patient using the compound disclosed herein. The invention further provides methods for killing and/or disrupting the growth of bacteria using the compounds disclosed herein.

Generally, in prophylactic use, the patient will have been identified as being at an elevated risk of developing a bacterial infection. Such patients include, for example, those expecting to be exposed to an environment with an increased level of bacteria present. Commonly, such patients include those undergoing surgery or other procedures in hospitals. Other examples include armed-service personnel who may be exposed to bacteria as part of routine operations, or individuals (military or civilian) who are at increased risk of exposure to bacteria as a result of an attack with biological weapons.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

All patents, patent applications, journal articles, and other reference cited herein are incorporated by reference in their entireties.

EXPERIMENTAL $^1$H and $^{13}$C NMR spectra were recorded on a Varian Gemini 300 or 400 MHz spectrometer and are internally referenced depending on the deuterated NMR solvents used. Data for $^1$H NMR are reported as follows: chemical shift (δ ppm), multiplicity (s=singlet, d=doublet, t=triplet, q=quartet, m=multiplet), coupling constant (Hz), integration, and assignment. Data for $^{13}$C are reported in terms of chemical shift. IR spectra were recorded on a Perkin-Elmer 1610 spectrometer and are reported in terms of frequency of absorption (cm$^{-1}$). Mass spectra were obtained using a ThermoFinnigan LCQ Duo LC/MS/MS instrument and an electrospray ionization probe. Thin-layer chromoatgraphy was run on Analtech Uniplate silica gel TLC plates.

Example 1

2-(2,10-difluoro-5,7-dihydroindolo[2,3-b]carbazol-6-yloxy)-N,N-dimethylethanamine

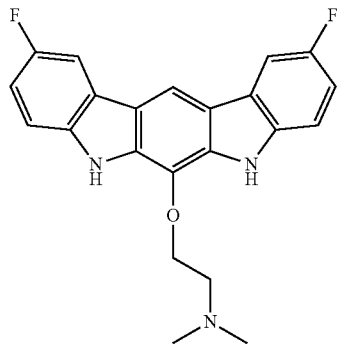 [SMILES: CN(C)CCOc1c2[nH]c3ccc(F)cc3c2cc2c1[nH]c1ccc(F)cc12]

1. To a solution of 5-fluoroindole (100 g, 750 mmol) in THF (750 mL) was added trifluoroacetic acid (9 mL) and 37% formaldehyde solution (91 mL, 1220 mmol) and stirred at 40° C. for 16 hours. The reaction mixture was cooled to room temperature and washed with water (300 mL) and 10% sodium hydroxide solution (150 mL). The organic layer was then stirred with 40% sodium hydroxide solution (150 mL) for 6 hours. Hexane (100 mL) was added and the reaction mixture washed with brine until the washings were neutral (4×500 mL). The organic layer was evaporated and the residue azeotroped with toluene (3×200 mL). The residue was chromatographed on silica gel eluting with hexane/dichloromethane (30:70) and the pure fractions evaporated to give 3,3'-di(5-fluoroindoyl)methane (43-46 g, 41-45% yield) as a white solid. $^1$H NMR (300 MHz) (CDCl$_3$) δ 7.88 (2H, br-s, —NH), 7.18-7.25 (4H, m, arom), 6.89-6.99 (4H, m, arom) and 4.13 ppm (2H, s, —CH$_2$—).

2. To a solution of 3,3'-di(5-fluoroindoyl)methane (43 g, 152 mmol) in THF (350 mL) was added di-tert-butyldicarbonate (73 g, 335 mmol) and 4-(dimethylamino) pyridine (940 mg) and stirred overnight. The reaction mixture was evaporated and triturated with methanol (200 mL) and the resulting white solid filtered and dried to give 1,1'-diboc-3,3'-di(5-fluoroindoyl)methane (60.2 g, 83% yield). $^1$H NMR (300 MHz) (CDCl$_3$) δ 8.05 (2 H, br-s, =CH), 7.41 (2 H, s, arom), 7.13 (2 H, dd, J=6.6, 1.8 Hz, arom), 7.03 (2 H, dt, J=6.9, 2.4 Hz, arom), 3.99 (2 H, s, —CH$_2$—) and 1.65 ppm (18 H, s, -Boc).

3. In a 1-liter 3-necked flask equipped with cooling bath, overhead stirrer and argon inlet was placed a solution of 2,2,6,6-tetramethylpiperidine (21.9 mL, 130 mmol) in tetrahydrofuran (90 mL) which was cooled to −30° C. To this was added 2.5M n-butyllithium (69 mL, 125 mmol) dropwise over 20 minutes and the reaction mixture warmed to 0° C. and stirred for 30 minutes. The reaction was cooled to −78° C. and a solution of 1,1'-diboc-3,3'-di(5-fluoroindoyl)methane (24 g, 49.7 mmol) in tetrahydrofuran (200 mL) added dropwise over 20 minutes, making sure not to allow the temperature to rise over −65° C. The mixture was allowed to stir for 30 minutes before the addition of ethyl chloroformate (19 mL, 192 mmol) dropwise over 30 minutes and stiffing for an additional hour. The excess chloroformate was quenched by the addition of diethylamine (16.2 mL, 200 mmol) in methanol (16 mL) over 20 minutes with stirring for an additional 30 minutes. A solution of acetic acid (57 mL) in tetrahydrofuran (57 mL) was added dropwise over 15 minutes with additional stirring for 30 minutes. The reaction mixture was allowed to warm from −70° C. to room temperature and poured into water (200 mL) and ethyl acetate (200 mL). The organic layer was separated and washed with water (200 mL), brine (2×200 mL) and the solvent evaporated to give a solid, which was triturated with methanol (200 mL) and filtered. The solid was washed with ethyl acetate (100 mL) and recrystallized from dichloromethane (100 mL) and methanol (100 mL) at 40° C. to give 5,7-diBOC-2,10-difluoro-6-hydroxyindolo[2,3-b] carbazole (9.95 g, 40% yield). $^1$H NMR (300 MHz) (CDCl$_3$) δ11.25 (1 H, s, —OH), 8.04 (2 H, dd, J=9.0, 4.3 Hz, arom), 7.89 (1 H, s, arom), 7.65 (2 H, dd, J=8.7, 2.4 Hz, arom), 7.15 (2 H, dt, J=8.7, 2.4 Hz, arom) and 1.74 ppm (18 H, s, -Boc).

4. A mixture of 5,7-diBOC-2,10-difluoro-6-hydroxyindolo[2,3-b]carbazole (406.8 mg, 0.8 mmol), 2-(dimethylamino)ethyl chloride hydrochloride (126.8 mg, 0.88 mmol) and K$_2$CO$_3$ (10 equivalents) in 4A-molecular-sieve-dried acetone (40 mL) was magnetically stirred and heated to reflux under Ar. After the reaction was complete, it was cooled to room temperature. The inorganic salt was removed by filtration and washed with a small quantity of acetone. The combined acetone solution was concentrated on a rotavapor and dried under vacuum pump. The crude product was purified by flash chromatography. The resultant product 2-(2,10-difluoro-5,7-diBOC-indolo[2,3-b]carbazol-6-yloxy)-N,N-dimethylethanamine was dissolved in $CH_2Cl_2$ (40 mL), and trifluoroacetic acid (~40 equivalents) was added. The reaction was stirred at room temperature overnight, concentrated, and dried under vacuum pump. The crude compound was dissolved in ethyl acetate (40 mL), washed with saturated $NaHCO_3$ solution, dried under $Na_2SO_4$, concentrated, and flash chromatography to provide the desired product 2-(2,10-difluoro-5,7-dihydroindolo[2,3-b]carbazol-6-yloxy)-N,N-dimethylethanamine (195.9 mg, 65%). $^1$H-NMR (400 MHz, DMSO-$d_6$) δ ppm 11.40 (s, 2 H), 8.56 (s, 1 H), 7.87 (dd, J=9.2, 2.4 Hz, 2 H), 7.44 (dd, J=8.4, 4.4 Hz, 2 H), 7.20-7.11 (m, 2 H), 4.30 (t, J=5.8 Hz, 2 H), 2.72 (t, J=5.8 Hz, 2 H), 2.32 (s, 6 H); MS (ESI) m/z 378.1 (M−H)−; MS (ESI) m/z 380.1 (M+H)+

Example 2

3-(2,10-difluoro-5,7-dihydroindolo[2,3-b]carbazol-6-yloxy)-N,N-dimethylpropan-1-amine

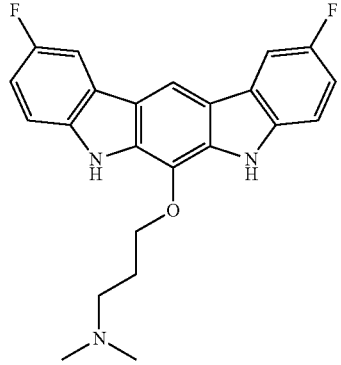 [SMILES: CN(C)CCCOc1c2[nH]c3ccc(F)cc3c2cc2c1[nH]c1ccc(F)cc12]

The title compound was prepared in a manner analogous to Example 1 except the reagent in step 4 was 3-(dimethylamino)propyl chloride hydrochloride. 1H-NMR (400 MHz, DMSO-d6) δ ppm 11.59 (s, 2 H), 8.57 (s, 1 H), 7.89 (dd, J=10.0, 2.6 Hz, 2 H), 7.44 (dd, J=8.8, 4.4 Hz, 2 H), 7.17 (td, J=9.2, 2.4 Hz, 2 H), 4.29 (t, J=6.2 Hz, 2 H), 2.62 (t, J=6.4 Hz, 2 H), 2.33 (s, 6 H), 2.10-2.00 (m, 2 H); MS (ESI) m/z 392.2 (M−H)−; MS (ESI) m/z 394.1 (M+H)+

Example 3

2,10-difluoro-6-(2-(piperidin-1-yl)ethoxy)-5,7-dihydroindolo[2,3-b]carbazole

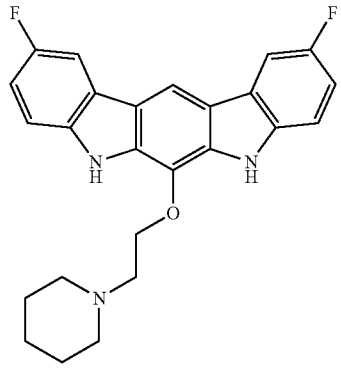 [SMILES: Fc1ccc2[nH]c3c(OCCN4CCCCC4)c4[nH]c5ccc(F)cc5c4cc3c2c1]

The title compound was prepared in a manner analogous to Example 1 except the reagent in step 4 was 1-(2-chloroethyl) piperidine hydrochloride. 1 H-NMR (400 MHz, DMSO-d6) δ ppm 11.38 (s, 2 H), 8.59 (s, 1 H), 7.90 (dd, J=9.6, 2.4 Hz, 2 H), 7.44 (dd, J=8.4, 4.4 Hz, 2 H), 7.24-7.14 (m, 2 H), 4.36 (t, J=5.6 Hz, 2 H), 2.73 (t, J=5.2 Hz, 2 H), 2.60-2.40 (m, 4 H), 1.61 (t, J=5.6 Hz, 4 H), 1.51-1.39 (m, 2 H); MS (ESI) m/z 418.2 (M−H)−; MS (ESI) m/z 420.2 (M+H)+

Example 4

2-(2,10-difluoro-5,7-dihydroindolo[2,3-b]carbazol-6-yloxy)-N,N-diethylethanamine

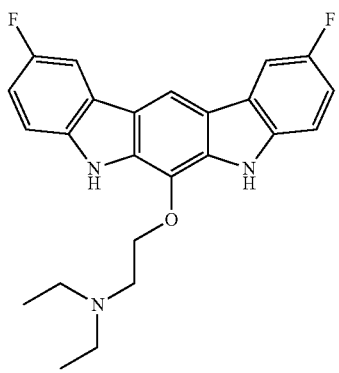 [SMILES: CCN(CC)CCOc1c2[nH]c3ccc(F)cc3c2cc2c1[nH]c1ccc(F)cc12]

The title compound was prepared in a manner analogous to Example 1 except the reagent in step 4 was 2-(diethylamino)ethyl chloride hydrochloride. 1H-NMR (400 MHz, DMSO-d6) δ ppm 11.52 (s, 2 H), 8.58 (s, 1 H), 7.90 (dd, J=9.2, 2.4 Hz, 2 H), 7.44 (dd, J=8.8, 4.8 Hz, 2 H), 7.18 (td, J=J=9.6, 2.4 Hz, 2 H), 4.31 (t, J=5.6 Hz, 2 H), 2.91 (t, J=5.6 Hz, 2 H), 2.67 (q, J=7.2 Hz, 4 H), 1.05 (t, J=7.2 Hz, 6 H)

Example 5

N-(2-(2,10-difluoro-5,7-dihydroindolo[2,3-b]carbazol-6-yloxy)ethyl)-N-methylbutan-1-amine

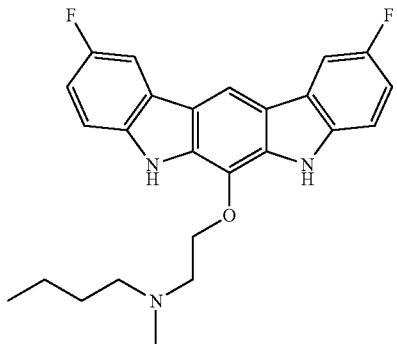 [SMILES: CCCCN(C)CCOc1c2[nH]c3ccc(F)cc3c2cc2c1[nH]c1ccc(F)cc12]

The title compound was prepared in a manner analogous to Example 1 except the reagent in step 4 was 2-(N-methyl-N-butylamino)ethyl chloride hydrochloride. $^1$H-NMR (400 MHz, DMSO-$d_6$) δ ppm 11.43 (s, 2 H), 8.58 (s, 1 H), 7.89 (dd, J=9.2, 2.4 Hz, 2 H), 7.44 (dd, J=8.4, 4.4 Hz, 2 H), 7.18 (td, J=9.2, 2.4 Hz, 2 H), 4.33 (t, J=6.0 Hz, 2 H), 2.82 (t, J=6.0 Hz, 2 H), 2.48 (t, J=5.2 Hz, 2 H), 2.31 (s, 3 H), 1.56-1.43 (m, 2 H), 1.35-1.22 (m, 2 H), 0.85 (t, J=7.2 Hz, 3 H)

Example 6

2,10-difluoro-6-(2-(pyrrolidin-1-yl)ethoxy)-5,7-dihydroindolo[2,3-b]carbazole

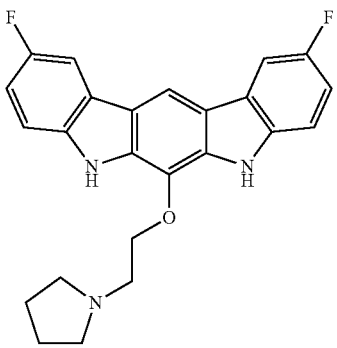 [SMILES: Fc1ccc2[nH]c3c(OCCN4CCCC4)c4[nH]c5ccc(F)cc5c4cc3c2c1]

The title compound was prepared in a manner analogous to Example 1 except the reagent in step 4 was 1-(2-chloroethyl)pyrrolidine hydrochloride. ¹H-NMR (400 MHz, DMSO-d₆) δ ppm 11.42 (s, 2 H), 8.59 (s, 1 H), 7.90 (dd, J=9.2, 2.0 Hz, 2 H), 7.43 (dd, J=8.8, 4.4 Hz, 2 H), 7.23-7.14 (m, 2 H), 4.35 (t, J=5.6 Hz, 2 H), 2.89 (t, J=5.6 Hz, 2 H), 2.67-2.54 (m, 4 H), 1.87-1.75 (m, 4 H); MS (ESI) m/z 404.2 (M–H)⁻; MS (ESI) m/z 406.1 (M+H)⁺

Example 7

2-(2,10-difluoro-5,7-dihydroindolo[2,3-b]carbazol-6-yloxy)ethanamine

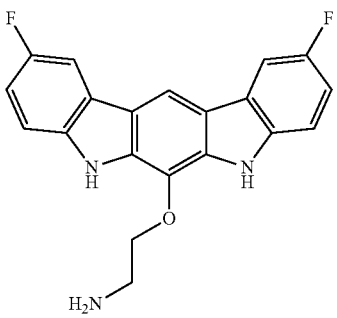 [SMILES: NCCOc1c2[nH]c3ccc(F)cc3c2cc2c1[nH]c1ccc(F)cc12]

The title compound was prepared in a manner analogous to Example 1 except the reagent in step 4 was 2-(Boc-amino)ethyl Bromide. 1 H-NMR (400 MHz, CD3OD) δ ppm 8.51 (s, 1 H), 7.85 (dd, J=5.2, 2.8 Hz, 2 H), 7.43 (dd, J=4.8, 4.0 Hz, 2 H), 7.12 (td, J=9.2, 2.8 Hz, 2 H), 4.49 (t, J=5.0 Hz, 2H), 3.55 (t, J=5.0 Hz, 2 H); MS (ESI) m/z 350.1 (M–H)–.

Example 8

3-(2,10-difluoro-5,7-dihydroindolo[2,3-b]carbazol-6-yloxy)propan-1-amine

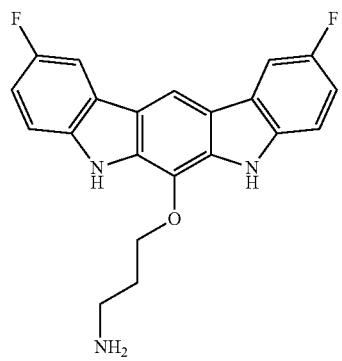 [SMILES: NCCCOc1c2[nH]c3ccc(F)cc3c2cc2c1[nH]c1ccc(F)cc12]

A mixture of 5,7-diBOC-2,10-difluoro-6-hydroxyindolo[2,3-b]carbazole (4.03 g, 8.0 mmol), tert-butyl 3-bromopropylcarbamate (2.20 g, 9.2 mmol), and Cs₂CO₃ (10.0 g, 31 mmol), and anhydrous MeCN (120 mL) was heated at 100° C. under Ar until the starting material disappeared (~2 h). After cooled to RT, the inorganic salt was removed by filtration, washed with dichloromethane, and the combined filtrate was concentrated. The resulting residue 3-(2,10-difluoro-5,7-diBOC-indolo[2,3-b]carbazol-6-yloxy)propan-1-amine was dissolved in CH₂Cl₂ (100 mL). TFA (10 mL) was added and the solution was stirred at RT overnight. After evaporation, the residue was subjected to chromatography on silica gel, eluting with ethyl acetate/hexane/MeOH (10% cNH₃.H₂O) (50/50/10-100/0/10), giving 2.35 g (82%) of 3-(2,10-difluoro-5,7-dihydroindolo[2,3-b]carbazol-6-yloxy)propan-1-amine. ¹H NMR (400 MHz, DMSO-d₆) δ 11.8 (br s, 2H), 8.56 (s, 1H), 7.89 (dd, J=9.4, 2.6 Hz, 2H), 7.44 (dd, J=8.6, 4.6 Hz, 2H), 7.17 (td, J=9.2, 2.4 Hz, 2H), 4.36 (t, J=6.2 Hz, 2H), 2.97 (t, J=6.2 Hz, 2H), 1.98 (pentalet, J=6.2 Hz, 2H).

Example 9

2,10-difluoro-6-methoxy-5,7-dihydro-indolo[2,3-b]carbazole

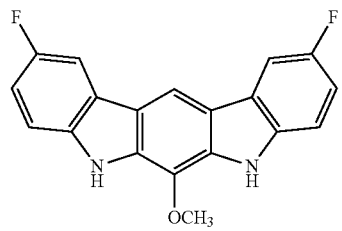 [SMILES: COc1c2[nH]c3ccc(F)cc3c2cc2c1[nH]c1ccc(F)cc12]

To a suspension of 5,7-diBOC-2,10-difluoro-6-hydroxyindolo[2,3-b]carbazole (3.0 g, 5.9 mmol) in anhydrous THF-DMF (80-50 mL) at 0-5° C. (with an ice-water cooling bath), was added NaH (320 mg, 60% in mineral oil, 8 mmol). The mixture was stirred at the same temperature for 10 to 15 min and a brownish solution resulted. MeI (1.0 mL) was then added and the resultant mixture stirred while slowly warmed up to RT and at RT for 2 hours. The reaction mixture was treated with water, extracted with ethyl acetate twice. The combined extract was washed with brine three times, dried over sodium sulfate, and evaporated to dryness to give 3.13 g of yellowish crude product 2,10-difluoro-6-methoxy-5,7-diBOC-indolo[2,3-b]carbazole, which was then dissolved in DCM (100 mL) and TFA (10 mL) added. The solution was stirred at RT overnight. All volatiles were removed on a rotary-evaporator; the residue was treated with sat. NaHCO$_3$, and extracted with ethyl acetate twice. The combined extract was washed with brine, dried over sodium sulfate, and evaporated to dryness. The residue was subjected to chromatography on silica gel, eluting with mixture solvent of hexane/dichloromethane (1/1-1/2). The desired compound was recrystallized once from DCM/Hexane to give pure desired product 2,10-difluoro-6-methoxy-5,7-dihydro-indolo[2,3-b]carbazole (1.57 g, 83%). $^1$H NMR (400 MHz, DMSO-d$_6$) δ 11.24 (s, 2H), 8.69 (s, 1H), 7.89 (dd, J=9.2, 2.8 Hz, 2H), 7.43 (dd, J=8.8, 4.4 Hz, 2H), 7.54 (td, J=9.2, 2.4 Hz, 2H), 4.08 (s, 3H).

Example 10

2-(2,10-dichloro-5,7-dihydroindolo[2,3-b]carbazol-6-yloxy)-N,N-dimethylethanamine

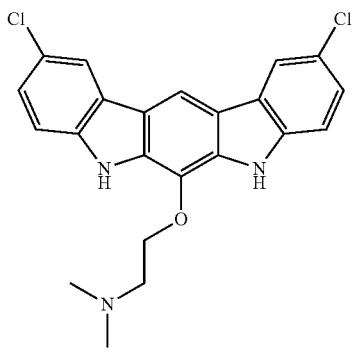 [SMILES: CN(C)CCOc1c2[nH]c3ccc(Cl)cc3c2cc2c1[nH]c1ccc(Cl)cc12]

The title compound was prepared in a manner analogous to Example 1 except the starting indole in step 1 was 5-chloroindole. $^1$H-NMR (400 MHz, DMSO-d$_6$) δ ppm 11.61 (br s, 2 H), 8.66 (s, 1H), 8.15 (d, J=1.2 Hz, 2 H), 7.50 (d, J=8.8 Hz, 2 H), 7.35 (dd, J=8.4, 1.6 Hz, 2 H), 4.33 (t, J=5.6 Hz, 2 H), 2.74 (t, J=5.2 Hz, 2 H), 2.34 (s, 6 H); MS (ESI) m/z 410.1 (M−H)$^-$; MS (ESI) m/z 412.0 (M+H)$^+$.

Example 11

2-(2,10-dichloro-5,7-dihydroindolo[2,3-b]carbazol-6-yloxy)ethanamine

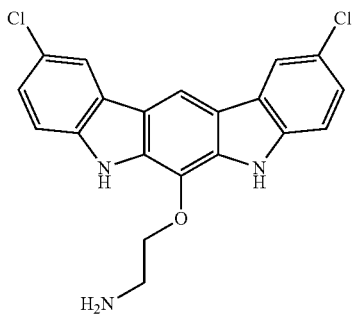 [SMILES: NCCOc1c2[nH]c3ccc(Cl)cc3c2cc2c1[nH]c1ccc(Cl)cc12]

The title compound was prepared in a manner analogous to Example 7 except the starting indole was 5-chloroindole. 1 H-NMR (400 MHz, CD3OD) δ ppm 8.54 (s, 1 H), 8.15 (dd, J=2.0, 0.4 Hz, 2 H), 7.44 (dd, J=8.4, 0.4 Hz, 2 H), 7.34 (dd, J=8.4, 2.0 Hz, 2 H), 4.49 (t, J=5.0 Hz, 2 H), 3.55 (t, J=5.2 Hz, 2 H); MS (ESI) m/z 380.5 (M−H)−; MS (ESI) m/z 382.1 (M+H)+.

Example 12

3-(2,10-dichloro-5,7-dihydroindolo[2,3-b]carbazol-6-yloxy)propan-1-amine

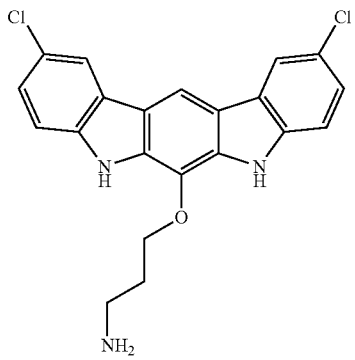 [SMILES: NCCCOc1c2[nH]c3ccc(Cl)cc3c2cc2c1[nH]c1ccc(Cl)cc12]

The title compound was prepared in a manner analogous to Example 8 except the starting indole was 5-chloroindole. $^1$H NMR (400 MHz, DMSO-d$_6$) δ 8.64 (s, 1H), 8.14 (d, T=2.4 Hz, 2H), 7.47 (d, J=9.2 Hz, 2H), 7.34 (dd, J=8.6, 2.2 Hz, 2H), 4.37 (t, J=6.0 Hz, 2H), 2.98 (t, J=6.4 Hz, 2H), 1.99 (pentalet, J=6.4 Hz, 2H).

Example 13

2-(2,10-dichloro-5,7-dihydroindolo[2,3-b]carbazol-6-yloxy)-N,N-diethylethanamine

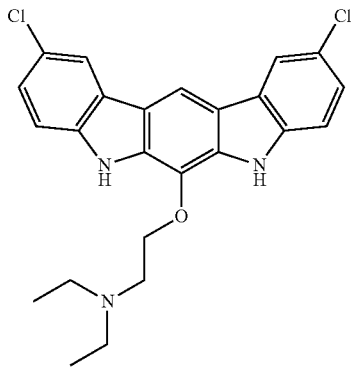 [SMILES: CCN(CC)CCOc1c2[nH]c3ccc(Cl)cc3c2cc2c1[nH]c1ccc(Cl)cc12]

The title compound was prepared in a manner analogous to Example 4 except the starting indole was 5-chloroindole. $^1$H-NMR (400 MHz, DMSO-d$_6$) δ ppm 11.71 (br s, 2 H), 8.65 (s, 1 H), 8.15 (d, J=2.0 Hz, 2 H), 7.47 (d, J=8.8 Hz, 2 H), 7.35 (dd, J=8.4, 2.2 Hz, 2 H), 4.32 (t, J=5.8 Hz, 2 H), 2.91 (t, J=5.8 Hz, 2 H), 2.67 (q, J=7.2 Hz, 4 H), 1.04 (t, J=6.8 Hz, 6 H); MS (ESI) m/z 438.2 (M−H)$^-$; MS (ESI) m/z 440.1 (M+H)$^+$.

Example 14

2,10-dichloro-6-(2-(pyrrolidin-1-yl)ethoxy)-5,7-dihydroindolo[2,3-b]carbazole

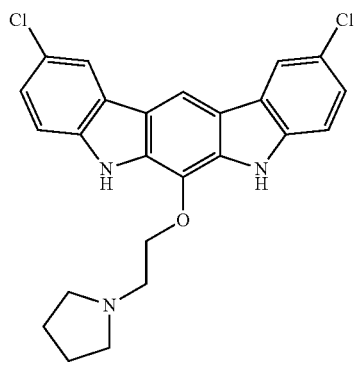 [SMILES: Clc1ccc2[nH]c3c(OCCN4CCCC4)c4[nH]c5ccc(Cl)cc5c4cc3c2c1]

The title compound was prepared in a manner analogous to Example 6 except the starting indole was 5-chloroindole. $^1$H-NMR (400 MHz, CDCl$_3$) δ ppm 10.14 (br s, 2 H), 8.38 (s, 1 H), 8.09 (dd, J=1.6, 0.8 Hz, 2 H), 7.37-7.28 (m, 4 H), 4.42 (t, J=4.4 Hz, 2 H), 3.04-2.76 (m, 6 H), 2.10-2.00 (m, 4H); MS (ESI) m/z 436.1 (M−H)$^-$; MS (ESI) m/z 438.1 (M+H)$^+$.

Example 15

3-(2,10-dichloro-5,7-dihydroindolo[2,3-b]carbazol-6-yloxy)-N,N-dimethylpropan-1-amine

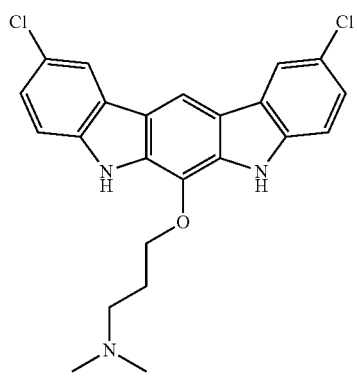 [SMILES: CN(C)CCCOc1c2[nH]c3ccc(Cl)cc3c2cc2c1[nH]c1ccc(Cl)cc12]

The title compound was prepared in a manner analogous to Example 2 except the starting indole was 5-chloroindole. $^1$H-NMR (400 MHz, DMSO-d$_6$) δ ppm 11.77 (s, 2 H), 8.65 (s, 1 H), 8.15 (d, J=2.0 Hz, 2 H), 7.47 (d, J=8.8 Hz, 2 H), 7.35 (dd, J=8.6, 1.8 Hz, 2 H), 4.30 (t, J=6.0 Hz, 2 H), 2.62 (t, J=6.4 Hz, 2 H), 2.33 (s, 6 H), 2.11-2.01 (m, 2 H); MS (ESI) m/z 424.1 (M−H)$^-$; MS (ESI) m/z 426.1 (M+H)$^+$.

Example 16

2,10-dichloro-6-(2-(piperidin-1-yl)ethoxy)-5,7-dihydroindolo[2,3-b]carbazole

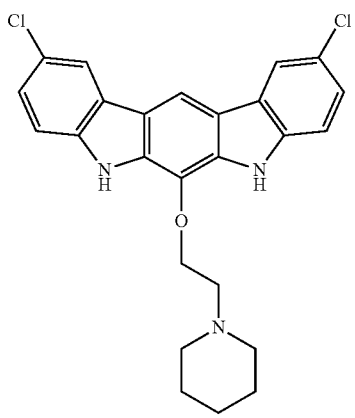 [SMILES: Clc1ccc2[nH]c3c(OCCN4CCCCC4)c4[nH]c5ccc(Cl)cc5c4cc3c2c1]

The title compound was prepared in a manner analogous to Example 3 except the starting indole was 5-chloroindole. $^1$H-NMR (400 MHz, DMSO-d$_6$) δ ppm 11.55 (br s, 2 H), 8.66 (s, 1 H), 8.16 (d, J=2.4 Hz, 2 H), 7.47 (d, J=8.4 Hz, 2 H), 7.36 (dd, J=8.4, 2.0 Hz, 2 H), 4.37 (t, J=5.6 Hz, 2 H), 2.74 (t, J=5.6 Hz, 2 H), 2.63-2.50 (m, 4 H), 1.77-1.60 (m, 4 H), 1.51-1.33 (m, 2 H). MS (ESI) m/z 450.1 (M−H)$^-$; MS (ESI) m/z 452.1 (M+H)$^+$.

Example 17

2-(2,10-difluoro-5,7-dihydroindolo[2,3-b]carbazol-6-yloxy)-N,N,N-trimethylethanaminium iodide

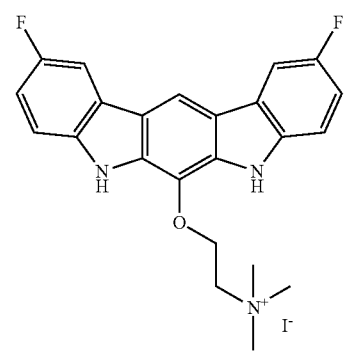 [SMILES: C[N+](C)(C)CCOc1c2[nH]c3ccc(F)cc3c2cc2c1[nH]c1ccc(F)cc12 ; [I-]]

To a solution of 2-(2,10-difluoro-5,7-dihydroindolo[2,3-b]carbazol-6-yloxy)-N,N-dimethylethanamine (14 mg) in dichloromethane (8 mL) was added MeI (1.0 mL) at RT under Ar. The resultant solution was stirred overnight and the solid formed. The solid was collected by filtration and washed once with dichloromethane and dried under vacuum to give the title compound (12 mg, 62%). $^1$H NMR (400 MHz, CD$_3$OD) δ ppm 8.51 (s, 1H), 7.84 (dd, T=9.2, 2.8 Hz, 2H), 7.44 (dd, T=8.8, 4.0 Hz, 2H), 7.12 (ddd, J=9.2, 9.6, 2.4 Hz, 2H), 4.75-4.68 (m, 2H), 4.12-4.07 (m, 2H), 3.46 (s, 9H); MS (ESI) e/z 394 (M-I)$^+$.

Example 18

2-(2,10-dibromo-5,7-dihydroindolo[2,3-b]carbazol-6-yloxy)-N,N-dimethylethanamine

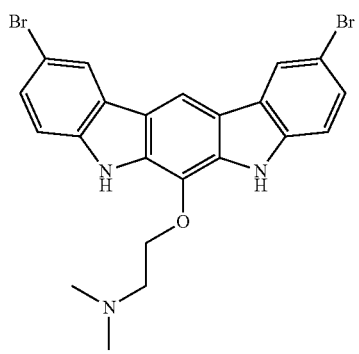 [SMILES: CN(C)CCOc1c2[nH]c3ccc(Br)cc3c2cc2c1[nH]c1ccc(Br)cc12]

The title compound was prepared in a manner analogous to Example 1 except the starting indole in step 1 was 5-bromoindole. $^1$H-NMR (400 MHz, DMSO-d$_6$) δ ppm 11.64 (s, 2 H), 8.67 (s, 1 H), 8.28 (d, J=0.8 Hz, 2 H), 7.50-7.41 (m, 4 H), 4.33 (t, J=5.6 Hz, 2 H), 2.74 (t, J=5.6 Hz, 2 H), 2.34 (s, 6 H); MS (ESI) m/z 500.0 (M−H)$^-$; MS (ESI) m/z 501.9 (M+H)$^+$.

Example 19

2-(2,10-dibromo-5,7-dihydroindolo[2,3-b]carbazol-6-yloxy)-N,N-diethylethanamine

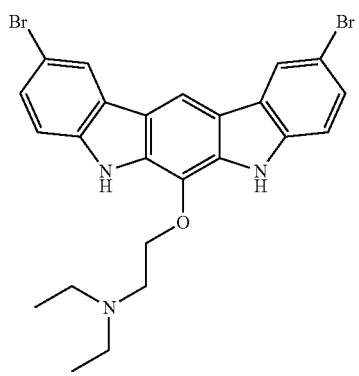 [SMILES: CCN(CC)CCOc1c2[nH]c3ccc(Br)cc3c2cc2c1[nH]c1ccc(Br)cc12]

The title compound was prepared in a manner analogous to Example 4 except the starting indole in step 1 was 5-bromoindole. $^1$H-NMR (400 MHz, DMSO-d$_6$) δ ppm 11.73 (s, 2 H), 8.67 (s, 1 H), 8.28 (d, J=2.0, 2 H), 7.50-7.39 (m, 4 H), 4.31 (t, J=4.4 Hz, 2 H), 2.91 (t, J=4.4 Hz, 2 H), 2.67 (q, J=7.2 Hz, 4 H), 1.04 (t, J=7.2 Hz, 6 H); MS (ESI) m/z 528.1 (M−H)$^-$.

Example 20

2,10-dibromo-6-(2-(piperidin-1-yl)ethoxy)-5,7-dihydroindolo[2,3-b]carbazole

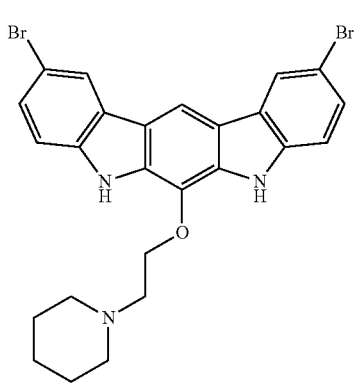

The title compound was prepared in a manner analogous to Example 3 except the starting indole in step 1 was 5-bromoindole. $^1$H-NMR (400 MHz, CD$_3$OD) δ ppm 8.45 (s, 1 H), 8.27 (d, J=2.0 Hz, 2 H), 7.43 (dd, J=8.4, 1.6 Hz, 2 H), 7.37 (d, J=8.4 Hz, 2 H), 4.40 (t, J=5.2 Hz, 2 H), 2.86 (t, J=5.2 Hz, 2 H), 2.73-2.56 (m, 4 H), 1.83-1.70 (m, 4 H), 1.64-1.52 (m, 2 H) MS (ESI) m/z 540.1 (M−H)$^-$; MS (ESI) m/z 541.9 (M+H)$^+$.

Example 21

3-(2,10-dibromo-5,7-dihydroindolo[2,3-b]carbazol-6-yloxy)-N,N-dimethylpropan-1-amine

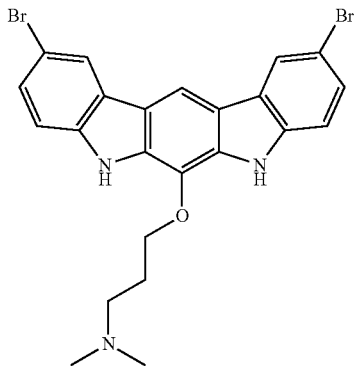 [SMILES: CN(C)CCCOc1c2[nH]c3ccc(Br)cc3c2cc2c1[nH]c1ccc(Br)cc12]

The title compound was prepared in a manner analogous to Example 2 except the starting indole in step 1 was 5-bromoindole. $^1$H-NMR (400 MHz, DMSO-d$_6$) δ ppm 11.78 (s, 2 H), 8.64 (s, 1 H), 8.26 (d, J=2.0 Hz, 2 H), 7.48-7.36 (m, 4 H), 4.27 (t, J=6.0 Hz, 2 H), 2.95 (t, J=5.2 Hz, 2 H), 2.30 (s, 6H), 2.08-1.98 (m, 2 H); MS (ESI) m/z 514.1 (M−H)$^-$; MS (ESI) m/z 515.9 (M+H)$^+$.

Example 22

2,10-dibromo-6-(2-(piperazin-1-yl)ethoxy)-5,7-dihydroindolo[2,3-b]carbazole

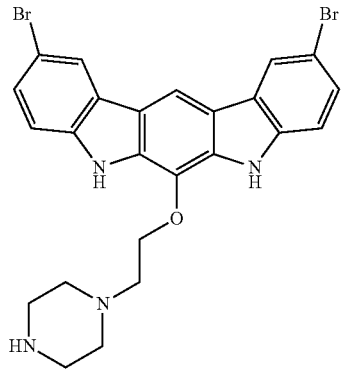 [SMILES: Brc1ccc2[nH]c3c(OCCN4CCNCC4)c4[nH]c5ccc(Br)cc5c4cc3c2c1]

The title compound was prepared in a manner analogous to Example 1 except the starting indole in step 1 was 5-bromoindole, and the reagent in step 4 is 3-(dimethylamino)propyl chloride hydrochloride. 1 H-NMR (400 MHz, CD3OD) δ ppm 8.42 (s, 1 H), 8.25 (d, J=2.0 Hz, 2 H), 7.42 (dd, J=8.4, 2.0 Hz, 2H), 7.36 (d, J=8.4 Hz, 2 H), 4.37 (t, J=5.2 Hz, 2 H), 2.95 (t, J=5.2 Hz, 4 H), 2.84 (t, J=5.2 Hz, 2 H), 2.72-2.52 (m, 4 H); MS (ESI) m/z 541.1 (M−H)−; MS (ESI) m/z 542.9 (M+H)+.

Example 23

2,10-dibromo-6-(2-(4-sec-butylpiperazin-1-yl)ethoxy)-5,7-dihydroindolo[2,3-b]carbazole

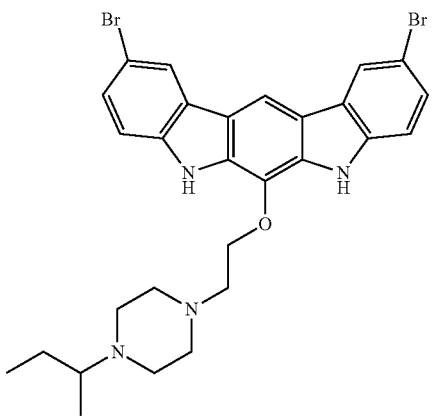 [SMILES: CCC(C)N1CCN(CCOc2c3[nH]c4ccc(Br)cc4c3cc3c2[nH]c2ccc(Br)cc23)CC1]

The title compound was prepared in a manner analogous to Example 1 except the starting indole in step 1 was 5-bromoindole, and the reagent in step 4 is 1-sec-butyl-4-(2-chloroethyl)piperazine hydrochloride. $^1$H-NMR (400 MHz, DMSO-$d_6$) δ ppm 11.42 (s, 2H), 8.65 (s, 1 H), 8.26 (d, J=2.0 Hz, 2H), 7.48-7.37 (m, 4 H), 4.36 (t, J=5.6 Hz, 2 H), 2.73 9t, J=5.6 Hz, 2 H), 2.66-2.15 (m, 9 H), 1.27-1.10 (m, 2 H), 0.87 (d, J=6.8 Hz, 3 H), 0.79 (t, J=2.8 Hz, 3 H); MS (ESI) m/z 597.1 (M−H)−; MS (ESI) m/z 599.0 (M+H)+.

Example 24

N-(2-(2,10-dibromo-5,7-dihydroindolo[2,3-b]carbazol-6-yloxy)ethyl)-N-methylbutan-1-amine

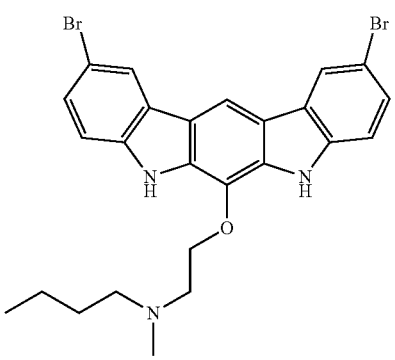 [SMILES: CCCCN(C)CCOc1c2[nH]c3ccc(Br)cc3c2cc2c1[nH]c1ccc(Br)cc12]

The title compound was prepared in a manner analogous to Example 5 except the starting indole in step 1 was 5-bromoindole. $^1$H-NMR (400 MHz, DMSO-$d_6$) δ ppm 11.62 (s, 2H), 8.67 (s, 1H), 8.26 (d, J=1.6 Hz, 2 H), 7.47-7.36 (m, 4 H), 4.32 (t, J=6.0 Hz, 2 H), 2.80 (t, J=6.0 Hz, 2 H), 2.46 (t, J=6.0 Hz, 2 H), 2.28 (s, 3 H), 1.51-1.42 (m, 2 H), 1.30-1.17 (m, 2 H), 0.82 (t, J=7.2 Hz, 3 H); MS (ESI) m/z 542.1 (M−H)−; MS (ESI) m/z 544.0 (M+H)+.

Example 25

2,10-dibromo-6-(3-(pyrrolidin-1-yl)propoxy)-5,7-dihydroindolo[2,3-b]carbazole

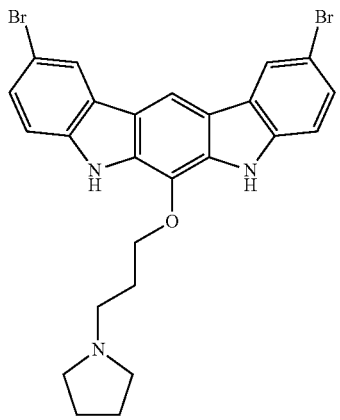 [SMILES: Brc1ccc2[nH]c3c(OCCCN4CCCC4)c4[nH]c5ccc(Br)cc5c4cc3c2c1]

The title compound was prepared in a manner analogous to Example 1 except the starting indole in step 1 was 5-bromoindole, and the reagent in step 4 is 1-(3-bromopropyl)-pyrroline hydrobromide. $^1$ H-NMR (400 MHz, DMSO-$d_6$) δ ppm 11.55 (s, 2 H), 8.66 (s, 1 H), 8.28 (d, J=2.0 Hz, 2 H), 7.47 (dd, J=8.8, 6.4 Hz, 2 H), 7.40 (d, J=8.8 Hz, 2 H), 4.31 (t, J=6.0 Hz, 2 H), 2.73 (t, J=6.6 Hz, 2 H), 2.68-2.53 (m, 4 H), 2.15-2.02 (m, 2 H), 1.88-1.78 (m, 4 H); MS (ESI) m/z 540.1 (M−H)−; MS (ESI) m/z 542.0 (M+H)+.

Example 26

2-(3,9-difluoro-5,7-dihydroindolo[2,3-b]carbazol-6-yloxy)-N,N-dimethylethanamine

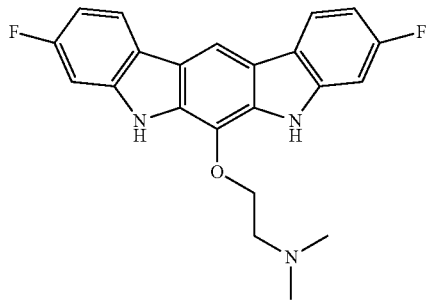 [SMILES: CN(C)CCOc1c2[nH]c3cc(F)ccc3c2cc2c1[nH]c1cc(F)ccc12]

The title compound was prepared in a manner analogous to Example 1 except the starting indole in step 1 was 6-fluoroindole. ¹H-NMR (400 MHz, DMSO-d$_6$) δ ppm 11.56 (s, 1 H), 8.52 (s, 1 H), 8.10 (dd, J=8.4, 5.6 Hz, 2 H), 7.25 (dd, J=10.0, 2.0 Hz, 2 H), 6.92-7.01 (m, 2 H), 4.33 (t, J=5.6 Hz), 2.73 (t, J=6.0 Hz, 2 H), 2.35 (s, 3 H); MS (ESI) m/z 378.2 (M−H)⁻; MS (ESI) m/z 380.1 (M+H)⁺.

Example 27

3,9-difluoro-6-methoxy-5,7-dihydroindolo[2,3-b]carbazole

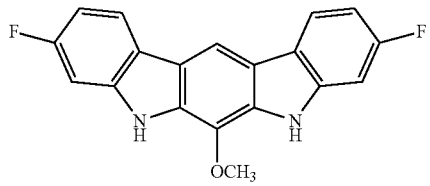 [SMILES: COc1c2[nH]c3cc(F)ccc3c2cc2c1[nH]c1cc(F)ccc12]

The title compound was prepared in a manner analogous to Example 9 except the starting indole in step 1 was 6-fluoroindole. ¹H-NMR (400 MHz, DMSO-d$_6$) δ ppm 11.35 (s, 2 H), 8.51 (s, 1 H), 8.11 (dd, J=8.4, 5.6 Hz, 2 H), 7.19 (dd, J=10.0, 2.4 Hz, 2 H), 6.91-7.00 (m, 2 H), 4.07 (s, 3 H); MS (ESI) m/z 321.2 (M−H)⁻.

Example 28

2-(2,10-difluoro-5,7-dihydroindolo[2,3-b]carbazol-6-yloxy)-N-methylethanamine

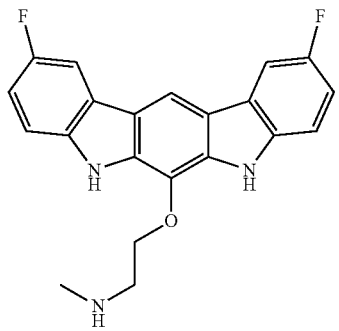 [SMILES: CNCCOc1c2[nH]c3ccc(F)cc3c2cc2c1[nH]c1ccc(F)cc12]

A mixture of 2-(N-methyl-N-Boc-amino)ethanol (215.3 mg, 1.2285 mmol), 3.0 mmol/g triphenylphosphine polymer bound (0.512 g, 1.54 mmol) and di-tert-butyl azodicarboxylate (215.3 mg, 1.23 mmol) in anhydrous THF (40 mL) was stirred for 10 minutes. 5,7-diBOC-2,10-difluoro-6-hydroxyindolo[2,3-b]carbazole (520.6 mg, 1.02 mmol) was added to the mixture and the reaction mixture was stirred at room temperature overnight. The resin was filtered and washed with a small volume of THF. The combined solution was concentrated and flash chromatography to provide the corresponding Boc protected intermediate, which was deprotected under TFA/CH$_2$Cl$_2$ to offer the desired product 2-(2,10-difluoro-5,7-dihydroindolo[2,3-b]carbazol-6-yloxy)-N-methylethanamine (102.6 mg, 27%). ¹H-NMR (400 MHz, DMSO-d$_6$) δ ppm 8.58 (s, 1 H), 7.89 (dd, J=9.2, 2.8 Hz, 2 H), 7.44 (dd, J=8.8, 4.4 Hz, 2 H), 7.22-7.13 (m, 2 H), 4.32 (t, J=5.2 Hz, 2 H), 2.90 (t, J=5.2 Hz, 2 H), 2.41 (s, 3 H); MS (ESI) m/z 364.2 (M−H)⁻; MS (ESI) m/z 366.1 (M+H)⁺.

Example 29

4-(2-(2,10-difluoro-5,7-dihydroindolo[2,3-b]carbazol-6-yloxy)ethyl)morpholine

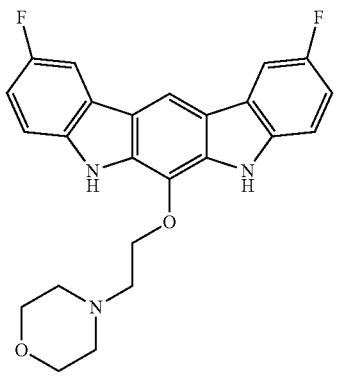 [SMILES: Fc1ccc2[nH]c3c(OCCN4CCOCC4)c4[nH]c5ccc(F)cc5c4cc3c2c1]

The title compound was prepared in a manner analogous to Example 28 except the reagent is 4-(2-Hydroxyethyl)morpholine. ¹H-NMR (400 MHz, DMSO-d$_6$) δ ppm 11.18 (s, 2 H), 8.59 (s, 1 H), 7.90 (dd, J=9.2, 2.4 Hz, 2 H), 7.46 (dd, J=8.8, 4.4 Hz, 2 H), 7.18 (td, J=9.6, 2.8 Hz, 2 H), 4.38 (t, J=6.0 Hz, 2 H), 3.61 (t, J=4.6 Hz, 4 H), 3.32 (t, J=4.8 Hz, 4 H), 2.80 (t, J=6.0 Hz, 2 H); MS (ESI) m/z 420.2 (M−H)⁻.

Example 30

2,10-difluoro-6-(2-methoxyethoxy)-5,7-dihydroindolo[2,3-b]carbazole

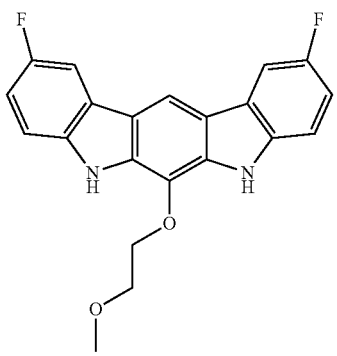 [SMILES: COCCOc1c2[nH]c3ccc(F)cc3c2cc2c1[nH]c1ccc(F)cc12]

The title compound was prepared in a manner analogous to Example 28 except the reagent is 2-methoxyethanol.

1H-NMR (400 MHz, DMSO-d6) δ ppm 11.02 (s, 2 H), 8.59 (s, 1 H), 7.89 (dd, J=9.6, 2.8 Hz, 2 H), 7.46 (dd, J=8.8, 4.4 Hz, 2 H), 7.18 (td, J=9.2, 2.4 Hz, 2 H), 4.38 (t, J=4.4 Hz, 2 H), 3.80 (t, J=4.4 Hz, 2 H), 3.07 (s, 3 H).

Example 31

1-(3-(2,10-difluoro-5,7-dihydroindolo[2,3-b]carbazol-6-yloxy)propyl)piperidin-4-amine

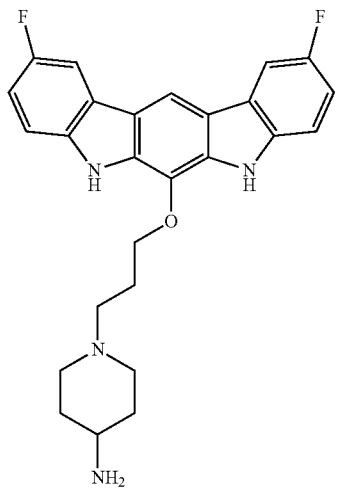 [SMILES: NC1CCN(CCCOc2c3[nH]c4ccc(F)cc4c3cc3c2[nH]c2ccc(F)cc23)CC1]

The title compound was prepared in a manner analogous to Example 28 except the reagent is tert-butyl 1-(3-hydroxypropyl)piperidin-4-ylcarbamate. $^1$H-NMR (400 MHz, DMSO-d$_6$) δ ppm 11.12 (br s, 2 H), 8.55 (s, 1 H), 7.87 (dd, J=9.2, 2.8 Hz, 2 H), 7.46 (dd, J=8.8, 4.0 Hz, 2 H), 7.15 (td, J=9.2, 2.4 Hz, 2 H), 4.25 (t, J=7.0 Hz, 2 H), 2.90-2.80 (m, 2 H), 2.62-2.50 (m, 3 H), 2.09-1.87 (m, 4 H), 1.73-1.60 (m, 2 H), 1.32-1.17 (m, 2 H); MS (ESI) m/z 447.2 (M−H)$^−$; MS (ESI) m/z 449.1 (M+H)$^+$.

Example 32

(S)-1-(3-(2,10-difluoro-5,7-dihydroindolo[2,3-b]carbazol-6-yloxy)propyl)pyrrolidin-3-amine

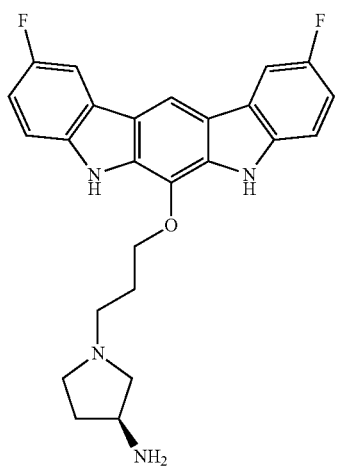 [SMILES: N[C@H]1CCN(CCCOc2c3[nH]c4ccc(F)cc4c3cc3c2[nH]c2ccc(F)cc23)C1]

The title compound was prepared in a manner analogous to Example 28 except the reagent is (S)-tert-butyl 1-(3-hydroxypropyl)pyrrolidin-3-ylcarbamate. $^1$H-NMR (400 MHz, DMSO-d$_6$) δ ppm 11.30 (br s, 2 H), 8.57 (s, 1 H), 7.89 (dd, J=9.4, 2.4 Hz, 2 H), 7.45 (dd, J=8.8, 4.4 Hz, 2 H), 7.18 (td, J=9.6, 2.4 Hz, 2 H), 4.30 (t, J=6.6 Hz, 2 H), 3.90-3.80 (m, 1 H), 3.79-3.58 (m, 5 H), 2.28-2.18 (m, 1 H), 2.13-1.98 (m, 3 H), 1.51-1.39 (m, 1 H); MS (ESI) m/z 433.2 (M−H)$^−$; MS (ESI) m/z 435.1 (M+H)$^+$.

Example 33

2,10-difluoro-6-(2-(piperazin-1-yl)ethoxy)-5,7-dihydroindolo[2,3-b]carbazole

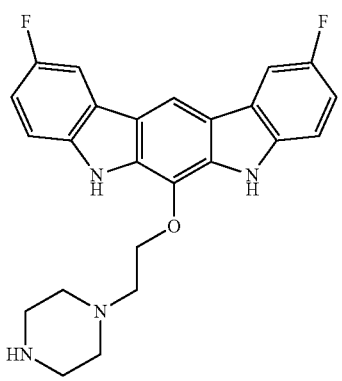 [SMILES: Fc1ccc2[nH]c3c(OCCN4CCNCC4)c4[nH]c5ccc(F)cc5c4cc3c2c1]

The title compound was prepared in a manner analogous to Example 28 except the reagent is tert-butyl 4-(2-hydroxyethyl)piperazine-1-carboxylate. $^1$H-NMR (400 MHz, CD3OD) δ ppm 8.42 (s, 1 H), 7.80 (dd, J=9.2, 2.4 Hz, 2 H), 7.39 (dd, J=8.6, 4.0 Hz, 2 H), 7.11-7.03 (m, 2 H), 4.40 (t, J=5.2 Hz, 2 H), 2.96 (t, J=5.2 Hz, 4 H), 2.85 (t, J=5.2 Hz, 2 H), 2.75-2.56 (m, 4 H); MS (ESI) m/z 419.2 (M−H)$^−$.

Example 34

6-(2-(3,5-dimethylpiperazin-1-yl)ethoxy)-2,10-difluoro-5,7-dihydroindolo[2,3-b]carbazole

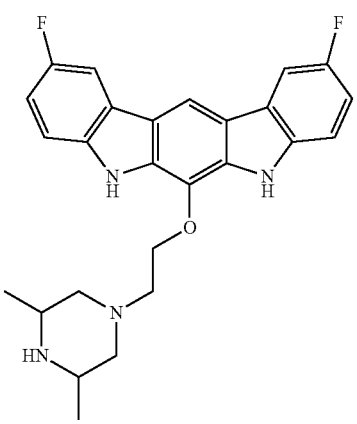 [SMILES: CC1CN(CCOc2c3[nH]c4ccc(F)cc4c3cc3c2[nH]c2ccc(F)cc23)CC(C)N1]

The title compound was prepared in a manner analogous to Example 28 except the reagent is tert-butyl 4-(2-hydroxyethyl)-2,6-dimethylpiperazine-1-carboxylate. $^1$H-NMR (400 MHz, DMSO-d$_6$) δ ppm 11.33 (s, 2 H), 8.59 (s, 1 H), 7.90 (dd, J=9.4, 2.8 Hz, 2 H), 7.44 (dd, J=8.8, 4.4 Hz, 2 H), 7.19 (td, J=9.4, 2.8 Hz, 2 H), 4.37 (t, J=5.6 Hz, 2 H), 2.94-2.80 (m, 4

H), 2.75-2.68 (m, 2 H), 1.64 (t, J=10.4 Hz, 2 H), 0.93 (d, J=6.4 Hz, 6 H); MS (ESI) m/z 447.2 (M−H)−; MS (ESI) m/z 449.1 (M+H)+.

Example 35

2,10-difluoro-6-(2-(3-methylpiperazin-1-yl)ethoxy)-5,7-dihydroindolo[2,3-b]carbazole

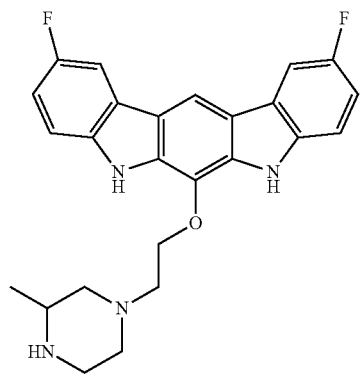 [SMILES: CC1CN(CCOc2c3[nH]c4ccc(F)cc4c3cc3c2[nH]c2ccc(F)cc23)CCN1]

The title compound was prepared in a manner analogous to Example 28 except the reagent is tert-butyl 4-(2-hydroxyethyl)-2-methylpiperazine-1-carboxylate. ¹H-NMR (400 MHz, DMSO-d₆) δ ppm 11.32 (s, 2 H), 8.59 (s, 1 H), 7.90 (dd, J=9.2, 2.4 Hz, 2 H), 7.44 (dd, J=8.8, 4.4 Hz, 2 H), 7.18 (td, J=9.2, 2.8 Hz, 2 H), 4.37 (t, J=5.6 Hz, 2 H), 2.90-2.68 (m, 7 H), 2.07-1.96 (m, 1 H), 1.74-1.65 (m, 1 H), 0.92 (d, J=6.4 Hz, 3 H); MS (ESI) m/z 433.2 (M−H)−.

Example 36

2-(2,10-difluoro-5,7-dihydroindolo[2,3-b]carbazol-6-yloxy)-N,N-dimethylpropan-1-amine

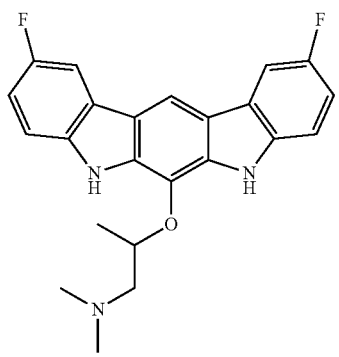 [SMILES: CC(CN(C)C)Oc1c2[nH]c3ccc(F)cc3c2cc2c1[nH]c1ccc(F)cc12]

The title compound was prepared in a manner analogous to Example 28 except the reagent is 1-(dimethylamino)propan-2-ol. ¹H-NMR (400 MHz, DMSO-d₆) δ ppm 11.58 (s, 2 H), 8.57 (s, 1 H), 7.89 (dd, J=9.2, 2.4 Hz, 2 H), 7.47 (dd, J=8.4, 4.4 Hz, 2 H), 7.17 (td, J=9.2, 2.8 Hz, 2 H), 4.50-4.42 (m, 1H), 3.63-3.55 (m, 1 H), 2.82 (dd, J=13.2, 8.0 Hz, 1 H), 2.38 (s, 6 H), 1.40 (d, J=6.0 Hz, 3 H); MS (ESI) m/z 392.2 (M−H)−.

Example 37

2,10-difluoro-6-(piperidin-4-yloxy)-5,7-dihydroindolo[2,3-b]carbazole

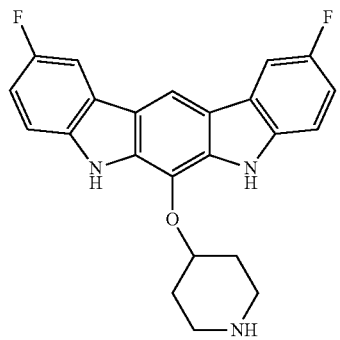 [SMILES: Fc1ccc2[nH]c3c(OC4CCNCC4)c4[nH]c5ccc(F)cc5c4cc3c2c1]

The title compound was prepared in a manner analogous to Example 28 except the reagent is tert-butyl 4-hydroxypiperidine-1-carboxylate. 1H-NMR (400 MHz, CD3OD) δ ppm 8.44 (s, 1 H), 7.81 (dd, J=9.2, 2.8 Hz, 2 H), 7.40 (dd. J=8.4, 4.0 Hz, 2 H), 7.08 (td, J=9.6, 2.8 Hz, 2 H), 4.63-4.50 (m, 1H), 3.24-3.13 (m, 2 H), 2.72-2.60 (m, 2 H), 2.18-2.05 (m, 2 H), 1.96-1.82 (m, 2 H); MS (ESI) m/z 390.2 (M−H)−; MS (ESI) m/z 392.0 (M+H)+.

Example 38

2,10-difluoro-6-(piperidin-3-yloxy)-5,7-dihydroindolo[2,3-b]carbazole

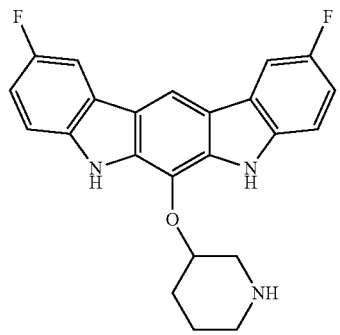 [SMILES: Fc1ccc2[nH]c3c(OC4CCCNC4)c4[nH]c5ccc(F)cc5c4cc3c2c1]

The title compound was prepared in a manner analogous to Example 28 except the reagent is tert-butyl 3-hydroxypiperidine-1-carboxylate. ¹H-NMR (400 MHz, CD₃OD) δ ppm 8.43 (s, 1 H), 7.81 (dd, J=9.2, 2.0 Hz, 2 H), 7.40 (dd, J=8.8, 4.4 Hz, 2 H), 7.12-7.03 (m, 2 H), 4.63-4.54 (m, 1 H), 3.18-3.20 (m, 1 H), 3.04 (dd, J=12.6, 6.6 Hz, 1 H), 2.88-2.74 (m, 2 H), 2.11-2.02 (m, 1 H), 2.00-1.86 (m, 2H), 1.55-1.43 (m, 1 H); MS (ESI) m/z 390.3 (M−H)−; MS (ESI) m/z 392.1 (M+H)+.

Example 39

(1S,4S)-4-(2,10-difluoro-5,7-dihydroindolo[2,3-b]carbazol-6-yloxy)cyclohexanamine

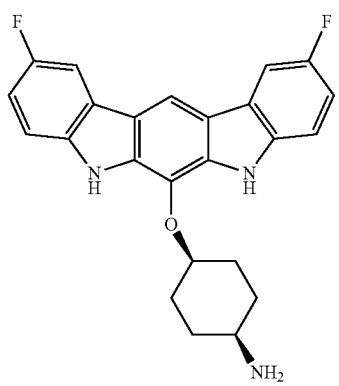 [SMILES: N[C@H]1CC[C@@H](Oc2c3[nH]c4ccc(F)cc4c3cc3c2[nH]c2ccc(F)cc23)CC1]

The title compound was prepared in a manner analogous to Example 28 except the reagent is tert-butyl (1R,4R)-4-hydroxycyclohexylcarbamate. 1H-NMR (400 MHz, CD3OD) δ ppm 8.42 (s, 1 H), 7.81 (dd, J=9.2, 2.4 Hz, 2 H), 7.42 (dd, J=8.6, 4.6 Hz, 2 H), 7.08 (td, J=9.2, 2.4 Hz, 2 H), 4.82-4.73 (m, 1 H), 2.98-2.90 (m, 1 H), 2.14-2.04 (m, 2 H), 2.00-1.88 (m, 2 H), 1.82-1.68 (m, 4 H); MS (ESI) m/z 404.1 (M−H)−; MS (ESI) m/z 406.1 (M+H)+

Example 40

2,10-difluoro-6-(pyrrolidin-3-yloxy)-5,7-dihydroindolo[2,3-b]carbazole

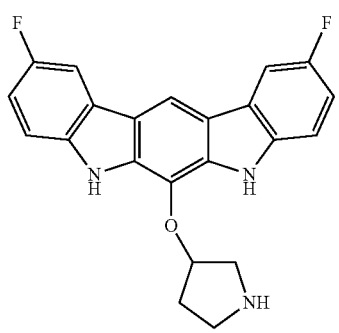 [SMILES: Fc1ccc2[nH]c3c(OC4CCNC4)c4[nH]c5ccc(F)cc5c4cc3c2c1]

The title compound was prepared in a manner analogous to Example 28 except the reagent is N-Boc-3-pyrrolidinol. 1H-NMR (400 MHz, CDCl3) δ ppm 9.12 (br s, 2 H), 8.36 (s, 1 H), 7.78 (dd, J=9.2, 2.4 Hz, 2 H), 7.35 (dd, J=8.8, 4.4 Hz, 2 H), 7.12 (td, J=9.2, 2.4 Hz, 2 H), 5.12 (t, J=4.4 Hz, 1 H), 3.54-3.46 (m, 1 H), 3.30 (d, J=12.0 Hz, 1 H), 3.14 (td, J=10.0, 4.8 Hz, 1 H), 2.83 (dd, J=11.6, 3.6 Hz, 1 H), 2.38-2.27 (m, 1 H), 2.22-2.11 (m, 1 H); MS (ESI) m/z 376.2 (M−H)−; MS (ESI) m/z 378.1 (M+H)+

Example 41

(R)-2,10-difluoro-6-(pyrrolidin-3-yloxy)-5,7-dihydroindolo[2,3-b]carbazole

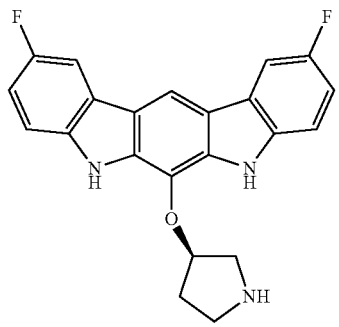 [SMILES: Fc1ccc2[nH]c3c(O[C@@H]4CCNC4)c4[nH]c5ccc(F)cc5c4cc3c2c1]

The title compound was prepared in a manner analogous to Example 28 except the reagent is (S)-(+)-N-Boc-3-pyrrolidinol. 1H-NMR (400 MHz, CDCl3) δ ppm 9.12 (br s, 2 H), 8.35 (s, 1 H), 7.77 (dd, J=9.2, 2.4 Hz, 2 H), 7.35 (dd, J=8.8, 4.4 Hz, 2 H), 7.11 (td, J=9.2, 2.4 Hz, 2 H), 5.12 (t, J=4.0 Hz, 1 H), 3.56-3.47 (m, 1 H), 3.33 (d, J=11.6 Hz, 1 H), 3.16 (td, J=10.0, 4.8 Hz, 1 H), 2.86 (dd, J=11.6, 3.6 Hz, 1 H), 2.38-2.27 (m, 1 H), 2.21-2.10 (m, 1 H); MS (ESI) m/z 376.2 (M−H)−; MS (ESI) m/z 378.1 (M+H)+

Example 42

(S)-2,10-difluoro-6-(pyrrolidin-3-yloxy)-5,7-dihydroindolo[2,3-b]carbazole

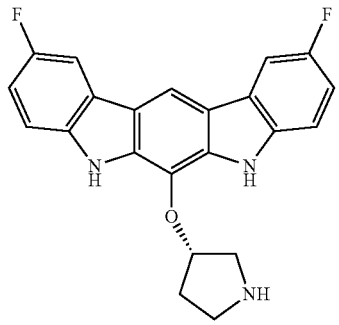 [SMILES: Fc1ccc2[nH]c3c(O[C@H]4CCNC4)c4[nH]c5ccc(F)cc5c4cc3c2c1]

The title compound was prepared in a manner analogous to Example 28 except the reagent is (R)-(+)-N-Boc-3-pyrrolidinol. 1H-NMR (400 MHz, CDCl3) δ ppm 9.12 (br s, 2 H), 8.35 (s, 1 H), 7.77 (dd, J=8.8, 2.4 Hz, 2 H), 7.35 (dd, J=8.8, 4.4 Hz, 2 H), 7.11 (td, J=9.2, 2.4 Hz, 2 H), 5.12 (t, J=4.0 Hz, 1 H), 3.57-3.47 (m, 1 H), 3.35 (d, J=11.2 Hz, 1 H), 3.17 (td, J=10.0, 4.8 Hz, 1 H), 2.87 (dd, J=12.0, 3.6 Hz, 1 H), 2.38-2.27 (m, 1 H), 2.21-2.10 (m, 1 H); MS (ESI) m/z 376.2 (M−H)−; MS (ESI) m/z 378.1 (M+H)+

Example 43

2,10-dichloro-6-(pyrrolidin-3-yloxy)-5,7-dihydroindolo[2,3-b]carbazole

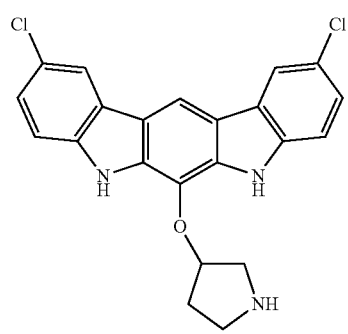

The title compound was prepared in a manner analogous to Example 28 except the starting indole is 5,7-diBOC-2,10-dichloro-6-hydroxyindolo[2,3-b]carbazole and the reagent is tert-butyl 3-hydroxypyrrolidine-1-carboxylate. $^1$H-NMR (400 MHz, CDCl$_3$) δ ppm 9.26 (br s, 2 H), 8.35 (s, 1 H), 8.06 (d, J=1.2 Hz, 2 H), 7.39-7.29 (m, 4 H), 5.11 (t, J=3.8 Hz, 1 H), 3.60-3.50 (m, 1 H), 3.34 (d, J=11.6 Hz, 1 H), 3.20 (td, J=10.2, 4.0 Hz, 1 H), 2.88 (dd, J=12.2, 3.2 Hz, 1 H), 2.40-2.30 (m, 1 H), 2.22-2.10 (m, 1 H); MS (ESI) m/z 408.1 (M−H)$^-$; MS (ESI) m/z 410.0 (M+H)$^+$

Example 44

(R)-2,10-dichloro-6-(pyrrolidin-3-yloxy)-5,7-dihydroindolo[2,3-b]carbazole

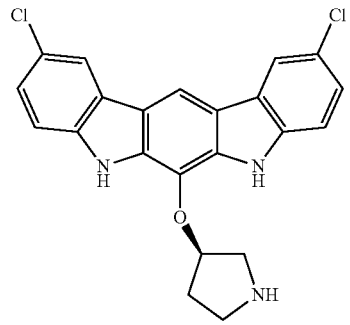 [SMILES: Clc1ccc2[nH]c3c(O[C@@H]4CCNC4)c4[nH]c5ccc(Cl)cc5c4cc3c2c1]

The title compound was prepared in a manner analogous to Example 28 except the starting indole is 5,7-diBOC-2,10-dichloro-6-hydroxyindolo[2,3-b]carbazole and the reagent is (R)-tert-butyl 3-hydroxypyrrolidine-1-carboxylate. $^1$H-NMR (400 MHz, CD3OD) δ ppm 8.51 (s, 1 H), 8.14-8.11 (m, 2H), 7.44 (dd, J=8.4, 0.6 Hz, 2 H), 7.31 (dd, J=8.4, 2.2 Hz, 2 H), 5.41 (t, J=4.6 Hz, 1 H), 3.91-3.72 (m, 2 H), 3.56-3.45 (m, 2 H), 2.48-2.40 (m, 1 H), 1.28-1.16 (m, 1 H); MS (ESI) m/z 408.2 (M−H)$^-$; MS (ESI) m/z 410.1 (M+H)$^+$

Example 45

(S)-2,10-dichloro-6-(pyrrolidin-3-yloxy)-5,7-dihydroindolo[2,3-b]carbazole

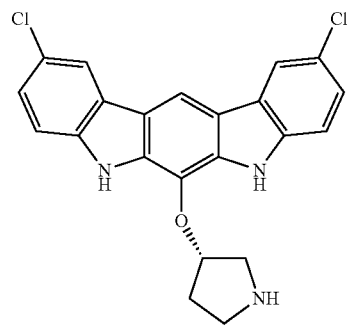 [SMILES: Clc1ccc2[nH]c3c(O[C@H]4CCNC4)c4[nH]c5ccc(Cl)cc5c4cc3c2c1]

The title compound was prepared in a manner analogous to Example 28 except the starting indole is 5,7-diBOC-2,10-dichloro-6-hydroxyindolo[2,3-b]carbazole and the reagent is (S)-tert-butyl 3-hydroxypyrrolidine-1-carboxylate. $^1$H-NMR (400 MHz, CDCl$_3$) δ ppm 9.27 (br s, 2 H), 8.35 (s, 1 H), 8.07 (s, 2 H), 7.38-7.30 (m, 4 H), 5.09 (t, J=4.0 Hz, 1 H), 3.55-3.46 (m, 2 H), 3.29 (d, J=12.0 Hz, 1 H), 3.15 (td, J=10.0, 4.8 Hz, 1 H), 2.83 (dd, J=11.6, 3.6 Hz, 1 H), 2.38-2.28 (m, 1 H), 2.21-2.10 (m, 1 H); MS (ESI) m/z 408.2 (M−H)$^-$; MS (ESI) m/z 410.1 (M+H)$^+$

Example 46

2,10-dichloro-6-(piperidin-4-ylmethoxy)-5,7-dihydroindolo[2,3-b]carbazole

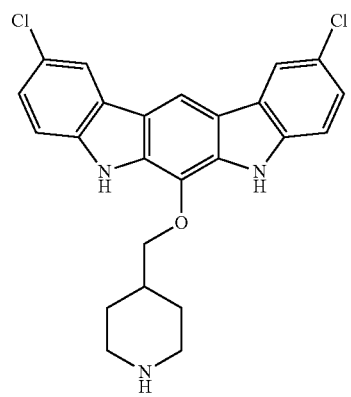 [SMILES: Clc1ccc2[nH]c3c(OCC4CCNCC4)c4[nH]c5ccc(Cl)cc5c4cc3c2c1]

The title compound was prepared in a manner analogous to Example 28 except the starting indole is 5,7-diBOC-2,10-dichloro-6-hydroxyindolo[2,3-b]carbazole and the reagent is N-Boc-4-piperidinemethanol. $^1$H-NMR (400 MHz, CD3OD) δ ppm 8.43 (s, 1H), 8.11 (d, J=2.0 Hz, 2 H), 7.43 (d, J=8.8 Hz, 2 H), 7.29 (dd, J=8.4, 2.0 Hz, 2 H), 4.16 (d, J=6.4 Hz, 2 H), 3.18-3.08 (m, 2 H), 2.70 (td, J=12.4, 2.4 Hz, 2 H), 2.22-2.10 (m, 1 H), 2.09-1.98 (m, 2 H), 1.50-1.38 (m, 2 H); MS (ESI) m/z 436.2 (M−H)$^-$; MS (ESI) m/z 438.1 (M+H)+

Example 47

(S)-2,10-dichloro-6-(pyrrolidin-2-ylmethoxy)-5,7-dihydroindolo[2,3-b]carbazole

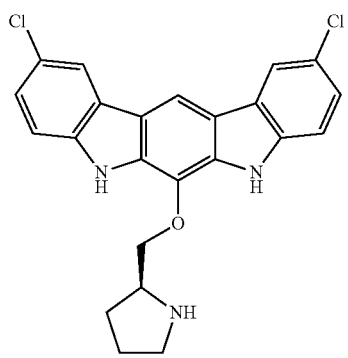 [SMILES: Clc1ccc2[nH]c3c(OC[C@@H]4CCCN4)c4[nH]c5ccc(Cl)cc5c4cc3c2c1]

The title compound was prepared in a manner analogous to Example 28 except the starting indole is 5,7-diBOC-2,10-dichloro-6-hydroxyindolo[2,3-b]carbazole and the reagent is (S)-(+)-1-(tert-butoxycarbonyl)-2-pyrrolidinemethanol.
$^1$H-NMR (400 MHz, CD3OD) δ ppm 8.46 (s, 1 H), 8.11 (d, J=2.4 Hz, 2 H), 7.41 (d, J=8.4 Hz, 2 H), 7.30 (dd, J=8.4, 2.4 Hz, 2 H), 4.33 (dd, J=10.0, 3.2 Hz, 1 H), 4.11 (dd, J=10.0, 8.4 Hz, 1 H), 3.91-3.82 (m, 1 H), 3.16 (t, J=7.2 Hz, 2 H), 2.16-2.05 (m, 1 H), 2.03-1.84 (m, 2 H), 1.72-1.62 (m, 1 H); MS (ESI) m/z 422.2 (M−H)$^−$; MS (ESI) m/z 424.0 (M+H)$^+$

Example 48

2,10-dichloro-6-(2-(piperidin-4-yl)ethoxy)-5,7-dihydroindolo[2,3-b]carbazole

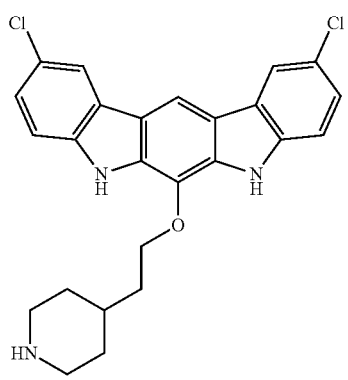 [SMILES: Clc1ccc2[nH]c3c(OCCC4CCNCC4)c4[nH]c5ccc(Cl)cc5c4cc3c2c1]

The title compound was prepared in a manner analogous to Example 28 except the starting indole is 5,7-diBOC-2,10-dichloro-6-hydroxyindolo[2,3-b]carbazole and the reagent is (S)-(+)-1-(tert-butoxycarbonyl)-2-pyrrolidinemethanol.
1H-NMR (400 MHz, CD3OD) δ ppm 8.44 (s, 1 H), 8.11 (d, J=2.0 Hz, 2 H), 7.41 (d, J=8.4 Hz, 2 H), 7.29 (dd, J=8.4, 2.4 Hz, 2 H), 4.36 (t, J=7.2 Hz, 2 H), 3.09-3.01 (m, 2 H), 2.62 (td, J=12.4, 2.4 Hz, 2 H), 1.96-1.87 (m, 2 H), 1.83-1.70 (m, 3 H), 1.33-1.18 (m, 2 H); MS (ESI) m/z 450.2 (M−H)−; MS (ESI) m/z 452.1 (M+H)+

Example 49

1-(3-(2,10-dichloro-5,7-dihydroindolo[2,3-b]carbazol-6-yloxy)propyl)piperidin-4-amine

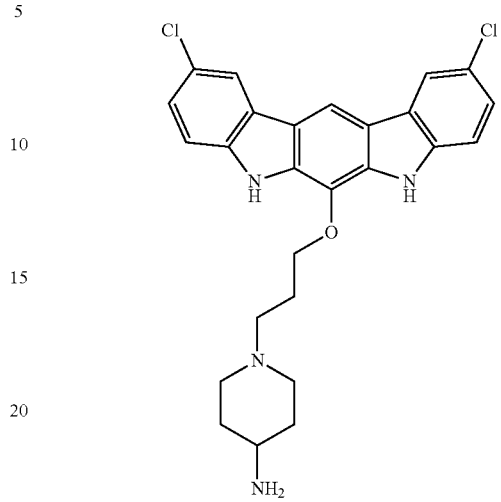

The title compound was prepared in a manner analogous to Example 28 except the starting indole is 5,7-diBOC-2,10-dichloro-6-hydroxyindolo[2,3-b]carbazole and the reagent is tert-butyl 1-(3-hydroxypropyl)piperidin-4-ylcarbamate.
$^1$H-NMR (400 MHz, CDCl$_3$) δ ppm 9.70 (s, 2 H), 8.33 (s, 1 H), 8.07 (d, J=2.0 Hz, 2 H), 7.43 (d, J=8.4 Hz, 2 H), 7.33 (dd, J=8.6, 2.2 Hz, 2 H), 4.33 (t, J=5.4 Hz, 2H), 3.24-3.13 (m, 2 H), 3.03-2.89 (m, 1 H), 2.84 (t, J=6.0 Hz, 2 H), 2.30-2.16 (m, 2 H), 2.15-2.06 (m, 2H), 2.04-1.93 (m, 2 H), 1.78-1.65 (m, 2 H); MS (ESI) m/z 479.1 (M−H)$^−$; MS (ESI) m/z 481.0 (M+H)$^+$

Example 50

1-(2-(2,10-dichloro-5,7-dihydroindolo[2,3-b]carbazol-6-yloxy)ethyl)piperidin-4-amine

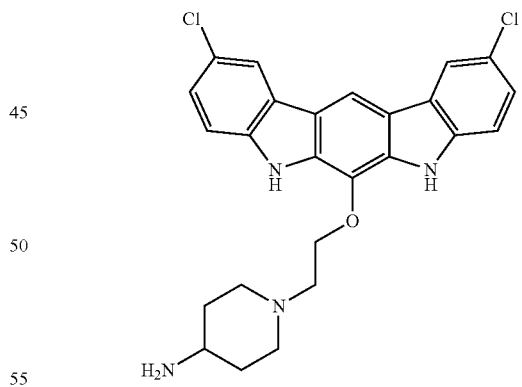

The title compound was prepared in a manner analogous to Example 28 except the starting indole is 5,7-diBOC-2,10-dichloro-6-hydroxyindolo[2,3-b]carbazole and the reagent is tert-butyl 1-(2-hydroxyethyl)piperidin-4-ylcarbamate.
$^1$H-NMR (400 MHz, CDCl$_3$) δ ppm 9.92 (s, 2 H), 8.37 (s, 1 H), 8.08 (d, J=1.6 Hz, 2 H), 7.41-7.30 (m, 4 H), 4.39 (t, J=4.6 Hz, 2 H), 3.21-3.11 (m, 2H), 2.98-2.85 (m, 1 H), 2.75 (t, J=4.6 Hz, 2 H), 2.37-2.25 (m, 2 H), 2.06-1.96 (m, 2 H), 1.78-1.65 (m, 2 H); MS (ESI) m/z 465.1 (M−H)$^−$; MS (ESI) m/z 467.1 (M+H)$^+$

Example 51

(S)-1-(2-(2,10-dichloro-5,7-dihydroindolo[2,3-b]carbazol-6-yloxy)ethyl)pyrrolidin-3-amine

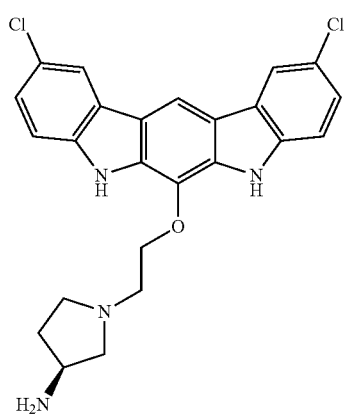 [SMILES: N[C@H]1CCN(CCOc2c3[nH]c4ccc(Cl)cc4c3cc3c2[nH]c2ccc(Cl)cc23)C1]

The title compound was prepared in a manner analogous to Example 28 except the starting indole is 5,7-diBOC-2,10-dichloro-6-hydroxyindolo[2,3-b]carbazole and the reagent is (S)-tert-butyl 1-(2-hydroxyethyl)pyrrolidin-3-ylcarbamate. $^1$H-NMR (400 MHz, CDCl$_3$) δ ppm 9.91 (s, 2 H), 8.37 (s, 1H), 8.08 (d, J=1.6 Hz, 2 H), 7.40-7.29 (m, 4 H), 4.43-4.33 (m, 2 H), 3.88-3.78 (m, 1 H), 3.09-2.96 (m, 2H), 2.95-2.74 (3 H), 2.61 (dd, J=9.6, 5.0 Hz, 1 H), 2.43-2.31 (m, 1 H), 1.79-1.68 (m, 1 H); MS (ESI) m/z 451.1 (M−H)$^-$; MS (ESI) m/z 453.0 (M+H)$^+$

Example 52

(S)-1-(3-(2,10-dichloro-5,7-dihydroindolo[2,3-b]carbazol-6-yloxy)propyl)pyrrolidin-3-amine

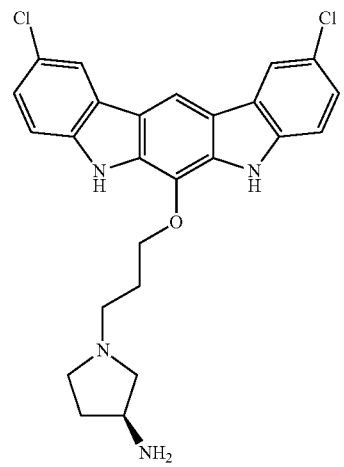 [SMILES: N[C@H]1CCN(CCCOc2c3[nH]c4ccc(Cl)cc4c3cc3c2[nH]c2ccc(Cl)cc23)C1]

The title compound was prepared in a manner analogous to Example 28 except the starting indole is 5,7-diBOC-2,10-dichloro-6-hydroxyindolo[2,3-b]carbazole and the reagent is (S)-tert-butyl 1-(3-hydroxypropyl)pyrrolidin-3-ylcarbamate. $^1$H-NMR (400 MHz, CDCl$_3$) δ ppm 9.92 (s, 2 H), 8.34 (s, 1H), 8.08 (s, 2 H), 7.39-7.29 (m, 4 H), 4.42-4.31 (m, 2 H), 3.90-3.79 (m, 1 H), 3.26 (dd, J=9.8, 6.6 Hz, 1H), 3.09-2.99 (m, 2 H), 2.98-2.86 (m, 2 H), 2.50-2.36 (m, 2 H), 2.15-2.05 (m, 2 H), 1.82-1.71 (m, 1 H); MS (ESI) m/z 465.1 (M−H)$^-$; MS (ESI) m/z 467.0 (M+H)$^+$

Example 53

N$^1$-(2-(2,10-dichloro-5,7-dihydroindolo[2,3-b]carbazol-6-yloxy)ethyl)ethane-1,2-diamine

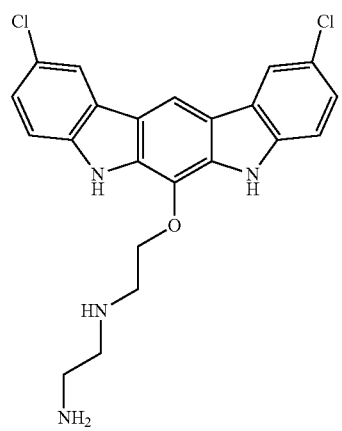 [SMILES: NCCNCCOc1c2[nH]c3ccc(Cl)cc3c2cc2c1[nH]c1ccc(Cl)cc12]

The title compound was prepared in a manner analogous to Example 28 except the starting indole is 5,7-diBOC-2,10-dichloro-6-hydroxyindolo[2,3-b]carbazole and the reagent is 2-((2-(Boc-amino)ethyl)-N-Boc-amino))ethanol. $^1$H-NMR (400 MHz, CD$_3$CN) δ ppm 8.51 (s, 1 H), 8.10 (d, J=2.0 Hz, 2 H), 7.48 (d, J=8.4 Hz, 2 H), 7.34 (dd, J=8.6, 2.0 Hz, 2 H), 4.36 (t, J=4.8 Hz, 2 H), 3.01 (t, J=4.8 Hz, 2 H), 2.94 (t, J=5.8 Hz, 2 H), 2.80 (t, J=5.6 Hz, 2 H); MS (ESI) m/z 425.1 (M−H)$^-$; MS (ESI) m/z 427.0 (M+H)$^+$

Example 54

6-(2,10-dichloro-5,7-dihydroindolo[2,3-b]carbazol-6-yloxy)-N,N-dimethylhexan-1-amine

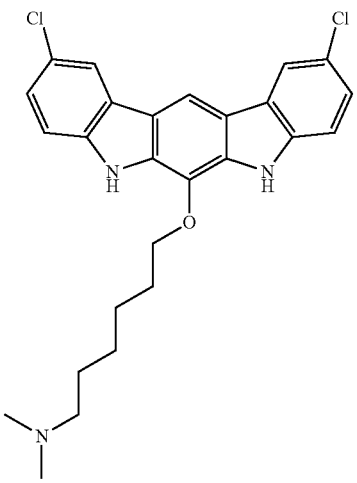 [SMILES: CN(C)CCCCCCOc1c2[nH]c3ccc(Cl)cc3c2cc2c1[nH]c1ccc(Cl)cc12]

The title compound was prepared in a manner analogous to Example 28 except the starting indole is 5,7-diBOC-2,10- dichloro-6-hydroxyindolo[2,3-b]carbazole and the reagent is 6-dimethylamino-1-hexanol. $^1$H-NMR (400 MHz, CDCl$_3$) δ ppm 8.35 (s, 1 H), 8.20 (s, 2 H), 8.08 (s, 2 H), 7.41-7.32 (m, 4 H), 4.28 (t, J=6.4 Hz, 2 H), 2.31 (t, J=7.2 Hz, 2 H), 2.23 (s, 6 H), 2.00-1.90 (m, 2 H), 1.65-1.42 (m, 6 H); MS (ESI) m/z 466.2 (M–H)$^-$; MS (ESI) m/z 468.1 (M+H)$^+$ Example 55

4-(2-(2,10-dibromo-5,7-dihydroindolo[2,3-b]carbazol-6-yloxy)ethyl)morpholine

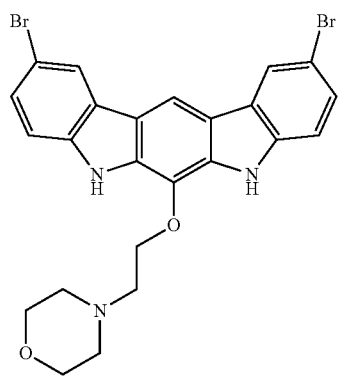

The title compound was prepared in a manner analogous to Example 28 except the starting indole is 5,7-diBOC-2,10-dibromo-6-hydroxyindolo[2,3-b]carbazole and the reagent is 4-(2-Hydroxyethyl)morpholine. $^1$H-NMR (400 MHz, CD$_3$OD) δ ppm 8.44 (s, 1 H), 8.25 (d, J=2.0 Hz, 2 H), 7.42 (dd, J=8.4, 1.6 Hz, 2 H), 7.41 (d, J=2.0 Hz, 2 H), 4.42 (t, J=5.2 Hz, 2 H), 3.81 (t, J=4.8 Hz, 4H), 2.87 (t, J=5.2 Hz, 2 H), 2.70-2.60 (m, 4 H); MS (ESI) m/z 542.1 (M–H)$^-$ Example 56

2-(2,10-dibromo-5,7-dihydroindolo[2,3-b]carbazol-6-yloxy)-N-methylethanamine

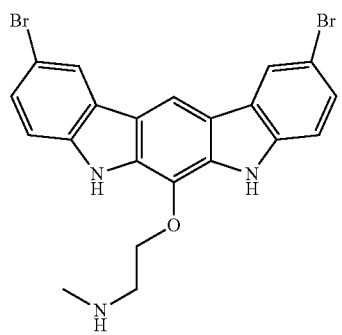

The title compound was prepared in a manner analogous to Example 28 except the starting indole is 5,7-diBOC-2,10-dibromo-6-hydroxyindolo[2,3-b]carbazole. $^1$H-NMR (400 MHz, DMSO-d$_6$) δ ppm 8.65 (s, 1 H), 8.26 (d, J=1.2 Hz, 2 H), 7.47-7.37 (m, 4 H), 4.31 (t, J=5.2 Hz, 2 H), 2.88 (t, J=5.2 Hz, 2 H), 2.39 (s, 3 H); MS (ESI) m/z 486.0 (M–H)$^-$; MS (ESI) m/z 487.9 (M+H)$^+$ Example 57

2,10-dibromo-6-(2-(2-methoxyethoxy)ethoxy)-5,7-dihydroindolo[2,3-b]carbazole

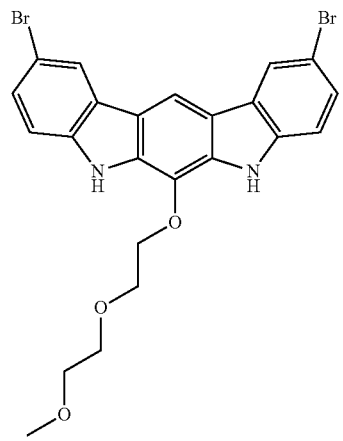 [SMILES: COCCOCCOc1c2[nH]c3ccc(Br)cc3c2cc2c1[nH]c1ccc(Br)cc12]

The title compound was prepared in a manner analogous to Example 28 except the starting indole is 5,7-diBOC-2,10-dibromo-6-hydroxyindolo[2,3-b]carbazole and the reagent is diethylene glycol monomethyl ether. 1H-NMR (400 MHz, CDCl3) δ ppm 8.74 (s, 1 H), 8.21 (d, J=2.0 Hz, 2 H), 7.50-7.26 (m, 4 H), 4.50-4.38 (m, 2 H), 3.88-3.73 (m, 6 H), 3.55 (s, 3 H); MS (ESI) m/z 531.0 (M–H)–

Example 58

2,10-dibromo-6-(2-methoxyethoxy)-5,7-dihydroindolo[2,3-b]carbazole

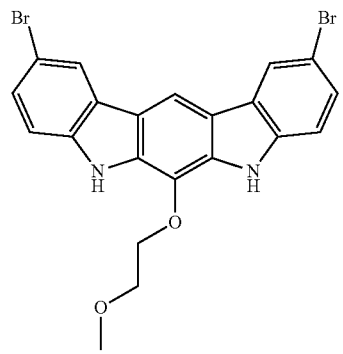

The title compound was prepared in a manner analogous to Example 28 except the starting indole is 5,7-diBOC-2,10-dibromo-6-hydroxyindolo[2,3-b]carbazole and the reagent is 2-methoxyethanol. $^1$H-NMR (400 MHz, CDCl$_3$) δ ppm 8.75 (s, 1 H), 8.21 (s, 2 H), 7.45 (d, J=6.8 Hz, 2H), 7.32-7.24 (m, 2 H), 4.43 (t, J=4.4 Hz, 2 H), 3.85 (t, J=4.4 Hz, 2 H), 3.65 (s, 3H); MS (ESI) m/z 487.0 (M−H)⁻

Example 59

2-(5,7-dihydroindolo[2,3-b]carbazol-6-yloxy)-N,N-diethylethanamine

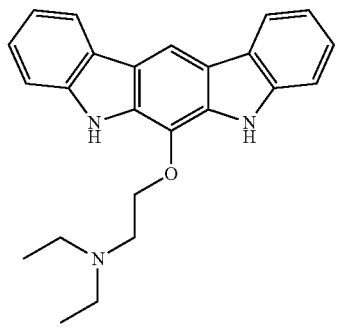 [SMILES: CCN(CC)CCOc1c2[nH]c3ccccc3c2cc2c1[nH]c1ccccc12]

A mixture of 2-(2,10-dibromo-5,7-dihydroindolo[2,3-b]carbazol-6-yloxy)-N,N-diethylethanamine (133.0 mg, 0.2513 mmol) and 10% Pd/C (0.05 equivalent) in DMF (8 mL) in a hydrogenation flask was filled with $H_2$ and then evacuated with house vacuum for three times, and then filled with $H_2$ (30–40 psi). The reaction was stirred at room temperature overnight. When TLC and MS showed the reaction was complete, the DMF solvent was removed under vacuum pump. The residue was dissolved in methanol and filtered through celite. The crude product was purified by flash chromatography to provide the desired product 2-(5,7-dihydroindolo[2,3-b]carbazol-6-yloxy)-N,N-diethylethanamine (59.3 mg, 64%). ¹H-NMR (400 MHz, CD₃OD) δ ppm 8.47 (s, 1 H), 8.09 (d, J=7.6 Hz, 2 H), 7.49 (d, J=8.0 Hz, 2 H), 7.33 (t, J=8.0 Hz, 2 H), 7.16 (t, J=7.6 Hz, 2 H), 4.57 (t, J=5.0 Hz, 2 H), 3.79 (t, J=5.0 Hz, 2 H), 3.49 (q, J=7.6 Hz, 4 H), 1.45 (t, J=7.6 Hz, 6 H); MS (ESI) m/z 370.3 (M−H)⁻; MS (ESI) m/z 372.1 (M+H)⁺

Example 60

6-(2-(piperidin-1-yl)ethoxy)-5,7-dihydroindolo[2,3-b]carbazole

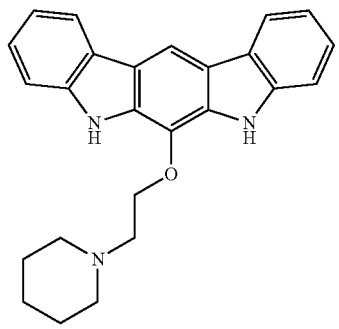 [SMILES: c1ccc2c(c1)[nH]c1c(OCCN3CCCCC3)c3[nH]c4ccccc4c3cc12]

The title compound was prepared in a manner analogous to Example 59 from corresponding 2,10-dibromoindolo2,3-b]carbazole. ¹H-NMR (400 MHz, acetone-d₆) δ ppm 8.58 (s, 1 H), 8.21-8.10 (m, 2 H), 7.50 (d, J=8.0 Hz, 2 H), 7.38-7.28 (m, 2 H), 7.16 (td, J=7.2, 0.8 Hz, 2 H), 4.45 (t, J=4.4 Hz, 2H), 2.86-2.58 (m, 6 H), 1.90-1.79 9m, 4 H), 1.60-1.45 (m, 2 H); MS (ESI) m/z 384.2 (M+H)⁺

Example 61

4-(2-(5,7-dihydroindolo[2,3-b]carbazol-6-yloxy)ethyl)morpholine

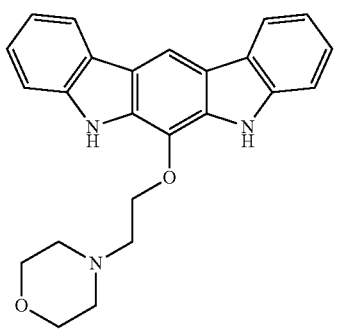 [SMILES: c1ccc2c(c1)[nH]c1c(OCCN3CCOCC3)c3[nH]c4ccccc4c3cc12]

The title compound was prepared in a manner analogous to Example 59 from corresponding 2,10-dibromoindolo[2,3-b]carbazole. ¹H-NMR (400 MHz, DMSO-d₆) δ ppm 11.13 (s, 2 H), 8.56 (s, 1 H), 8.13 (d, J=7.6 Hz, 2 H), 7.48 (d, J=7.6 Hz, 2 H), 7.38-7.26 (m, 2 H), 7.14 (t, J=7.6 Hz, 2 H), 4.40 (t, J=6.0 Hz, 2 H), 3.64 (t, J=4.6 Hz, 4 H), 2.80 (t, J=6.0 Hz, 2 H), 2.50 (t, J=7.6 Hz, 4 H); MS (ESI) m/z 386.1 (M+H)⁺

Example 62

2-(5,7-dihydroindolo[2,3-b]carbazol-6-yloxy)-N,N-dimethylethanamine

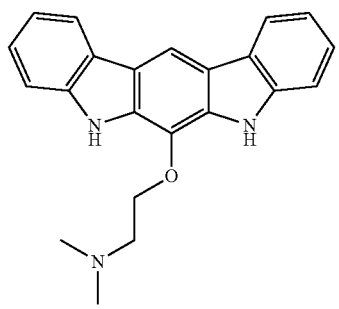

The title compound was prepared in a manner analogous to Example 59 from corresponding 2,10-dibromoindolo[2,3-b]carbazole. ¹H-NMR (400 MHz, DMSO-d₆) δ ppm 11.32 (s, 2 H), 8.54 (s, 1 H), 8.11 (d, J=7.6 Hz, 2 H), 7.46 (d, J=8.0 Hz, 2 H), 7.31 (td, J=7.2, 1.2 Hz, 2 H), 7.15-7.05 (m, 2 H), 4.32 (t, J=6.0 Hz, 2 H), 2.72 (t, J=6.0 Hz, 2 H), 2.32 (s, 6 H); MS (ESI) m/z 342.2 (M−H)⁻; MS (ESI) m/z 344.1 (M+H)⁺

Example 63

6-(2-(piperazin-1-yl)ethoxy)-5,7-dihydroindolo[2,3-b]carbazole

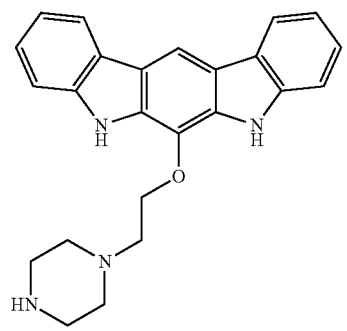 [SMILES: c1ccc2c(c1)[nH]c1c(OCCN3CCNCC3)c3[nH]c4ccccc4c3cc12]

The title compound was prepared in a manner analogous to Example 59 from corresponding 2,10-dibromoindolo[2,3-b]carbazole. $^1$H-NMR (400 MHz, DMSO-$d_6$) δ ppm 8.45 (s, 1 H), 8.10 (d, J=8.0 Hz, 2 H), 7.45 (d, J=8.0 Hz, 2 H), 7.35-7.27 (m, 2 H), 7.18-7.09 (m, 2 H), 4.42 (t, J=5.2 Hz, 2 H), 2.98 (t, J=5.2 Hz, 4 H), 2.85 (t, J=5.2 Hz, 2 H), 2.75-2.53 (m, 4 H); MS (ESI) m/z 383.3 (M−H)$^-$; MS (ESI) m/z 385.1 (M+H)$^+$

Example 64

2-(5,7-dihydroindolo[2,3-b]carbazol-6-yloxy)-N-methylethanamine

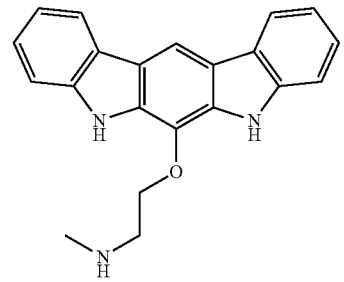 [SMILES: CNCCOc1c2[nH]c3ccccc3c2cc2c1[nH]c1ccccc12]

The title compound was prepared in a manner analogous to Example 59 from corresponding 2,10-dibromoindolo[2,3-b]carbazole. $^1$H-NMR (400 MHz, DMSO-$d_6$) δ ppm 8.55 (s, 1 H), 8.12 (t, J=7.0 Hz, 2 H), 7.46 (d, J=8.0 Hz, 2 H), 7.35-7.28 (m, 2 H), 7.18-7.10 (m, 2 H), 4.34 (t, J=5.4 Hz, 2 H), 2.91 (t, J=5.2 Hz, 2 H), 2.73 (d, J=6.4 Hz, 3 H); MS (ESI) m/z 328.2 (M−H)$^-$; MS (ESI) m/z 330.1 (M+H)$^+$

Example 65

N-(2-(5,7-dihydroindolo[2,3-b]carbazol-6-yloxy)ethyl)-N-methylbutan-1-amine

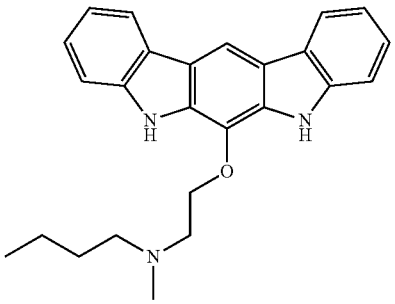 [SMILES: CCCCN(C)CCOc1c2[nH]c3ccccc3c2cc2c1[nH]c1ccccc12]

The title compound was prepared in a manner analogous to Example 59 from corresponding 2,10-dibromoindolo[2,3-b]carbazole. $^1$H-NMR (400 MHz, DMSO-$d_6$) δ ppm 11.37 (s, 2 H), 8.56 (s, 1 H), 8.13 (d, J=7.6 Hz, 2 H), 7.46 (d, J=8.0 Hz, 2 H), 7.33 (td, J=7.2, 1.2 Hz, 2 H), 7.17-7.08 (m, 2 H), 4.34 (t, J=6.0 Hz, 2 H), 2.83 (t, J=5.8 Hz, 2 H), 2.50 (t, J=4.8 Hz, 2 H), 2.32 (s, 3 H), 1.58-1.47 (m, 2H), 1.36-1.23 (m, 2 H), 0.87 (t, J=7.2 Hz, 3 H); MS (ESI) m/z 384.2 (M−H)$^-$; MS (ESI) m/z 386.1 (M+H)$^+$

Example 66

6-(3-(pyrrolidin-1-yl)propoxy)-5,7-dihydroindolo[2,3-b]carbazole

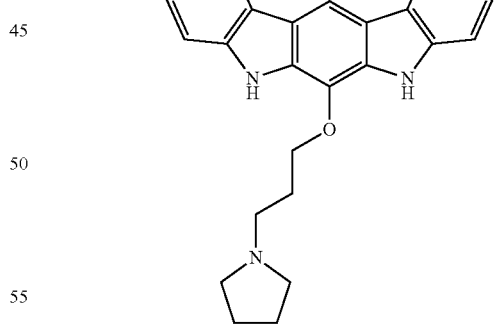

The title compound was prepared in a manner analogous to Example 59 from corresponding 2,10-dibromoindolo[2,3-b]carbazole. $^1$H-NMR (400 MHz, DMSO-$d_6$) δ ppm 11.27 (s, 2 H), 8.53 (s, 1 H), 8.11 (d, J=7.6 Hz, 2 H), 7.41 (d, J=7.6 Hz, 2 H), 7.32-7.26 (m, 2 H), 7.15-7.09 (m, 2 H), 4.30 (t, J=6.2 Hz, 2 H), 2.74 (t, J=7.6 Hz, 2 H), 2.67-2.51 (m, 4 H), 2.12-2.00 (m, 2 H), 1.88-1.73 (m, 4 H); MS (ESI) m/z 382.3 (M−H)$^-$; MS (ESI) m/z 384.2 (M+H)$^+$

Example 67

6-(2-(4-sec-butylpiperazin-1-yl)ethoxy)-5,7-dihydroindolo[2,3-b]carbazole

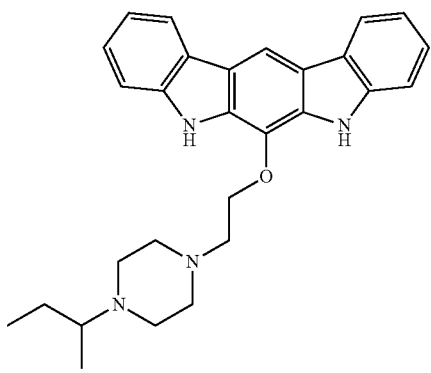 [SMILES: CCC(C)N1CCN(CCOc2c3[nH]c4ccccc4c3cc3c2[nH]c2ccccc23)CC1]

The title compound was prepared in a manner analogous to Example 59 from corresponding 2,10-dibromoindolo[2,3-b]carbazole. $^1$H-NMR (400 MHz, DMSO-d$_6$) δ ppm 11.19 (s, 2 H), 8.54 (s, 1 H), 8.11 (d, J=3.6 Hz, 2 H), 7.45 (d, J=8.0 Hz, 2 H), 7.31 (t, J=6.8 Hz, 2 H), 7.12 (t, J=6.8 Hz, 2 H), 4.36 (t, J=5.6 Hz, 2 H), 2.74 (t, J=5.6 Hz, 2 H), 2.63-2.19 (m, 9 H), 1.30-1.04 (m, 2 H), 0.91 (d, J=6.8 Hz, 3 H), 0.81 (t, J=4.0 Hz, 3 H); MS (ESI) m/z 439.3 (M−H)$^-$; MS (ESI) m/z 441.2 (M+H)$^+$

Example 68

6-(2-methoxyethoxy)-5,7-dihydroindolo[2,3-b]carbazole

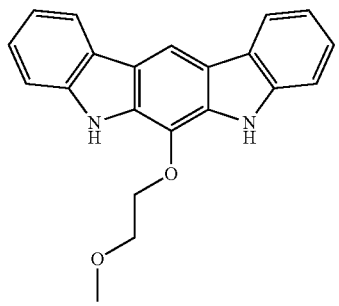 [SMILES: COCCOc1c2[nH]c3ccccc3c2cc2c1[nH]c1ccccc12]

The title compound was prepared in a manner analogous to Example 59 from corresponding 2,10-dibromoindolo[2,3-b]carbazole. $^1$H-NMR (400 MHz, DMSO-d$_6$) δ ppm 10.95 (s, 2 H), 8.56 (s, 1 H), 8.13 (d, J=7.6 Hz, 2 H), 7.49 (d, J=8.0 Hz, 2 H), 7.32 (td, J=7.2, 1.2 Hz, 2 H), 7.18-7.10 (m, 2 H), 4.39 (dd, J=6.4, 4.6 Hz, 2 H), 3.82 (dd, J=5.6, 4.4 Hz, 2 H), 3.38 (s, 3 H); MS (ESI) m/z 329.2 (M−H)$^-$

Example 69

4-(3-(5,7-dihydroindolo[2,3-b]carbazol-6-yloxy)propyl)morpholine

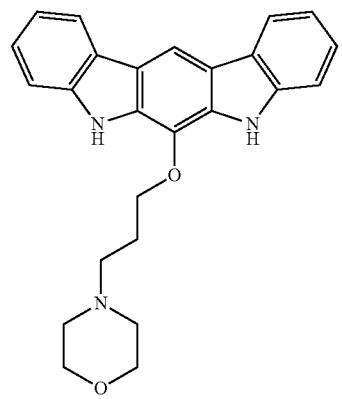 [SMILES: c1ccc2c(c1)[nH]c1c(OCCCN3CCOCC3)c3[nH]c4ccccc4c3cc12]

The title compound was prepared in a manner analogous to Example 59 from corresponding 2,10-dibromoindolo[2,3-b]carbazole. $^1$H-NMR (400 MHz, DMSO-d$_6$) δ ppm 11.03 (s, 2 H), 8.55 (s, 1 H), 8.12 (t, J=7.0 Hz, 2 H), 7.47 (d, J=8.0 Hz, 2 H), 7.37-7.29 (m, 2 H), 7.18-7.10 (m, 2 H), 4.31 (t, J=6.8 Hz, 2 H), 3.58 (t, J=4.6 Hz, 4 H), 2.55 (t, J=7.0 Hz, 2 H), 1.45-1.33 (m, 4 H), 1.13-1.03 (m, 2 H); MS (ESI) m/z 398.2 (M−H)$^-$; MS (ESI) m/z 400.1 (M+H)$^+$

Example 70

6-(2-(1,4-diazepan-1-yl)ethoxy)-2,10-difluoro-5,7-dihydroindolo[2,3-b]carbazole

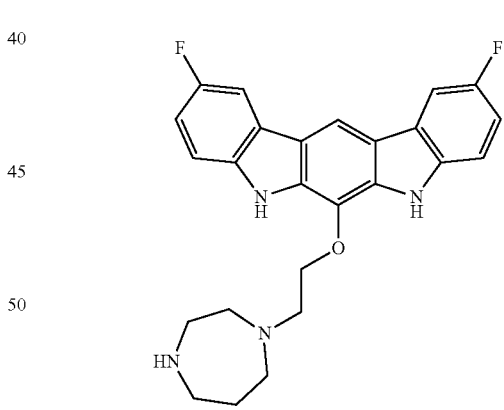

To a solution of 1,2-dibromoethane (>5 equiv) in acetonitrile was added Cs$_2$CO$_3$ (2 equiv) and 5,7-diBOC-2,10-difluoro-6-hydroxyindolo[2,3-b]carbazole (1 equiv) under argon. The suspension was refluxed and the reaction was monitored by TLC. After completion of the reaction (1-3 hours), the solid was removed by filteration and washed with dichloromethane. The combined filtrate was concentrated and the residue was subjected to chromatography on silica gel, eluting with 8% ethyl acetate in hexanes to give 5,7-diBOC-2,10-difluoro-6-(2-bromoethoxy)indolo[2,3-b]carbazole (77%). $^1$H NMR (400 MHz, CDCl$_3$) δ ppm 8.13 (s, 1H), 8.06 (dd, J=9.0, 4.2 Hz, 2H), 7.68 (dd, J=8.4, 2.8 Hz, 2H), 7.17 (td, J=9.0, 2.8 Hz, 2H), 4.21 (t, J=6.8 Hz, 2H), 3.42 (t, J=7.0 Hz, 2H), 1.74 (s, 18H).

A mixture of 5,7-diBOC-2,10-difluoro-6-(2-bromoethoxy)indolo[2,3-b]carbazole (150.0 mg, 0.24 mmol), tert-butyl 4-(2-hydroxyethyl)-1,4-diazepane-1-carboxylate (97.6 mg, 0.49 mmol), a base ($K_2CO_3$ or $Cs_2CO_3$; 2-10 equiv) and potassium iodide (0.1 equivalent) in a anhydrous solvent (DMF, MeCN or DMSO; 30 mL per mmol) was heated to 80-90° C. for 1-2 hours. The reaction was cooled to room temperature and filtered. The solution was concentrated and dried under vacuum pump. The residue was purified by flash chromatography to provide the 6-(2-(1,4-diazepan-1-yl)ethoxy)-2,10-difluoro-5,7-diBOC-indolo[2,3-b]carbazole.

The corresponding BOC-protected compound was subjected to deprotection under $TFA/CH_2Cl_2$ at room temperature or heat neatly at 180-200° C. to provide the desired compound 6-(2-(1,4-diazepan-1-yl)ethoxy)-2,10-difluoro-5,7-dihydroindolo[2,3-b]carbazole (60.2 mg, 57%). The resultant crude product purified by chromatography. In some cases, the crude product was pure enough for biology test. $^1$H-NMR (400 MHz, $CD_3OD$) δ ppm 8.42 (d, J=1.6 Hz, 1 H), 7.81 (dd, J=9.2, 2.4 Hz, 2 H), 7.40 (dd, J=8.4, 4.4 Hz, 2 H), 7.08 (td, J=8.8, 2.4 Hz, 2 H), 4.64-4.53 (m, 4 H), 3.27-3.22 (m, 2H), 2.82-2.73 (m, 2 H), 2.67-2.54 (m, 2 H), 2.43-2.28 (m, 2 H), 1.62-1.51 (m, 2 H), 1.30-1.19 (m, 2 H); MS (ESI) m/z 435.2 (M+H)$^+$ Example 71

(S)-1-(2-(2,10-difluoro-5,7-dihydroindolo[2,3-b]carbazol-6-yloxy)ethyl)pyrrolidin-3-amine

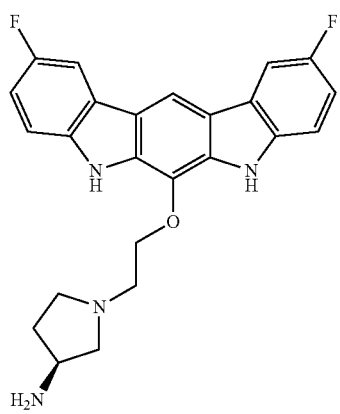 [SMILES: N[C@H]1CCN(CCOc2c3[nH]c4ccc(F)cc4c3cc3c2[nH]c2ccc(F)cc23)C1]

The title compound was prepared in a manner analogous to Example 70 except the reagent is (3S)-(−)-3-(Boc-amino) pyrrolidine. $^1$H-NMR (400 MHz, $CDCl_3$) δ ppm 9.78 (br s, 2 H), 8.36 (s, 1 H), 7.78 (dd, J=9.2, 2.4 Hz, 2 H), 7.37 (dd, J=8.8, 4.0 Hz, 2 H), 7.11 (td, J=8.8, 2.4 Hz, 2 H), 4.40 (t, J=4.0 Hz, 2 H), 3.87-3.78 (m, 1 H), 3.10-2.98 (m, 2 H), 2.98-3.76 (m, 3 H), 2.63 (dd, J=9.6, 4.4 Hz, 1 H), 2.45-2.30 (m, 1 H), 1.80-1.69 (m, 1 H); MS (ESI) m/z 419.2 (M−H)$^-$; MS (ESI) m/z 421.1 (M+H)$^+$ Example 72

1-(2-(2,10-difluoro-5,7-dihydroindolo[2,3-b]carbazol-6-yloxy)ethyl)piperidin-4-amine

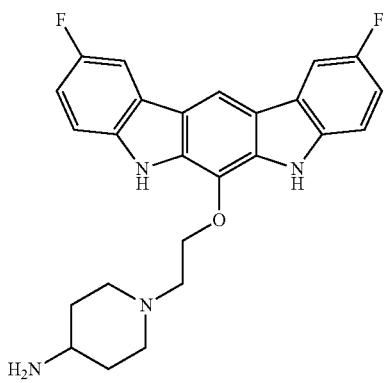 [SMILES: NC1CCN(CCOc2c3[nH]c4ccc(F)cc4c3cc3c2[nH]c2ccc(F)cc23)CC1]

The title compound was prepared in a manner analogous to Example 70 except the reagent is 4-Boc-aminopiperidine. $^1$H-NMR (400 MHz, $CDCl_3$) δ ppm 9.78 (br s, 2 H), 8.37 (s, 1 H), 7.79 (dd, J=9.2, 2.4 Hz, 2 H), 7.38 (dd, J=8.6, 4.2 Hz, 2 H), 7.12 (td, J=8.8, 2.4 Hz, 2 H), 4.41 (t, J=4.6 Hz, 2 H), 3.24-3.13 (m, 2 H), 2.97-2.85 (m, 1 H), 2.77 (t, J=4.8 Hz, 2 H), 2.40-2.25 (m, 2 H), 2.08-1.95 (m, 2 H), 1.80-1.65 (m, 2 H); MS (ESI) m/z 433.2 (M−H)$^-$; MS (ESI) m/z 435.1 (M+H)$^+$ Example 73

1-(2-(2,10-difluoro-5,7-dihydroindolo[2,3-b]carbazol-6-yloxy)ethyl)azetidin-3-ol

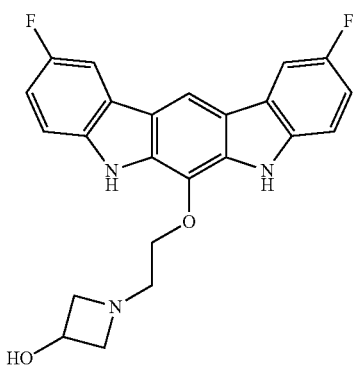 [SMILES: OC1CN(CCOc2c3[nH]c4ccc(F)cc4c3cc3c2[nH]c2ccc(F)cc23)C1]

The title compound was prepared in a manner analogous to Example 70 except the reagent is azetidin-3-ol hydrochloride (23.1 mg, 0.2109 mmol). $^1$H-NMR (400 MHz, $CDCl_3$) δ ppm 9.89 (s, 2 H), 8.36 (s, 1 H), 7.79 (dd, J=9.2, 2.8 Hz, 2 H), 7.37 (dd, J=8.6, 4.4 Hz, 2 H), 7.12 (td, J=8.8, 2.4 Hz, 2H), 4.71 (t, J=6.0 Hz, 1 H), 4.30 (t, J=4.4 Hz, 2 H), 3.91-3.83 (m, 2 H), 3.30-3.23 (m, J=2 H), 2.98 (t, J=4.4 Hz, 2 H); MS (ESI) m/z 406.2 (M−H)$^-$; MS (ESI) m/z 408.1 (M+H)$^+$

Example 74

1-(2-(2,10-difluoro-5,7-dihydroindolo[2,3-b]carbazol-6-yloxy)ethyl)piperidin-4-ol

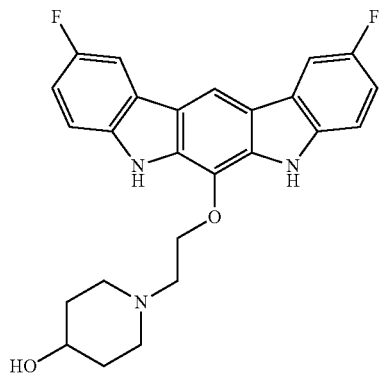 [SMILES: OC1CCN(CCOc2c3[nH]c4ccc(F)cc4c3cc3c2[nH]c2ccc(F)cc23)CC1]

The title compound was prepared in a manner analogous to Example 70 except the reagent is 4-hydroxypiperidine. 1H-NMR (400 MHz, DMSO-d6) δ ppm 11.37 (s, 2 H), 8.59 (s, 1 H), 7.90 (dd, J=9.4, 2.8 Hz, 2 H), 7.46 (dd, J=8.6, 4.8 Hz, 2 H), 7.23-7.14 (m, 2 H), 4.72 (d, J=3.6 Hz, 1 H), 4.35 (t, J=5.6 Hz, 2 H), 2.62-3.47 (m, 1 H), 2.93-2.83 (m, 2 H), 2.82-2.71 (m, 2 H), 2.30-2.15 (m, 2 H), 1.87-1.76 (m, 2 H), 1.60-1.47 (m, 2 H)

Example 75

N-(2-(2,10-difluoro-5,7-dihydroindolo[2,3-b]carbazol-6-yloxy)ethyl)-1,1,1-trifluoromethanesulfonamide

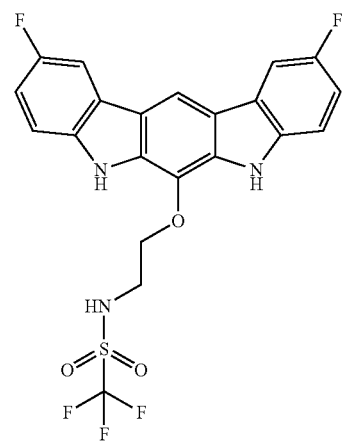 [SMILES: O=S(=O)(NCCOc1c2[nH]c3ccc(F)cc3c2cc2c1[nH]c1ccc(F)cc12)C(F)(F)F]

The title compound was prepared in a manner analogous to Example 70 except the reagent is trifluoromethanesulfonamide. $^1$H-NMR (400 MHz, DMSO-d$_6$) δ ppm 11.12 (s, 2 H), 9.68 (t, J=3.6 Hz, 1 H), 8.62 (s, 1 H), 7.92 (dd, J=9.2, 2.4 Hz, 2 H), 7.46 (dd, J=4.2, 4.8 Hz, 2 H), 7.20 (td, J=7.21 (td, J=9.2, 2.4 Hz, 2 H), 4.32 (t, J=6.0 Hz, 2 H), 3.76-3.66 (m, 2 H); MS (ESI) m/z 482.1 (M−H)$^-$; MS (ESI) m/z 484.0 (M+H)$^+$

Example 76

2-(4-(2-(2,10-difluoro-5,7-dihydroindolo[2,3-b]carbazol-6-yloxy)ethyl)piperazin-1-yl)ethanol

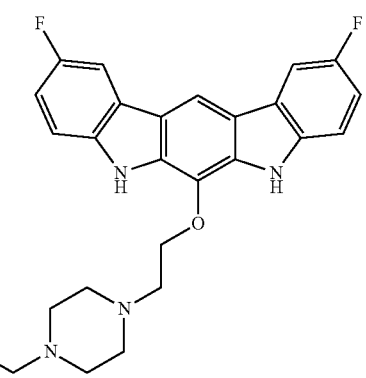

The title compound was prepared in a manner analogous to Example 70 except the reagent is 2-(piperazin-1-yl)ethanol. $^1$H-NMR (400 MHz, CD$_3$OD) δ ppm 8.42 (s, 1 H), 7.80 (dd, J=9.2, 2.8 Hz, 2H), 7.40 (dd, J=8.8, 4.4 Hz, 2 H), 7.08 (td, J=9.2, 2.4 Hz, 2 H), 4.39 (t, J=5.2 Hz, 2 H), 3.71 (t, J=6.0 Hz, 2 H), 2.87 (t, J=5.2 Hz, 2 H), 2.82-2.64 (m, 8 H), 2.61 (t, J=6.0 Hz, 2 H); MS (ESI) m/z 463.2 (M−H)$^-$; MS (ESI) m/z 465.1 (M+H)$^+$

Example 77

(S)-1-(2-(2,10-difluoro-5,7-dihydroindolo[2,3-b]carbazol-6-yloxy)ethyl)-N,N-dimethylpyrrolidin-3-amine

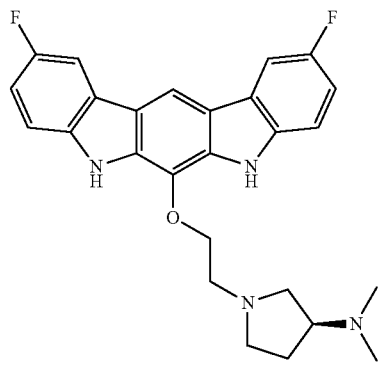 [SMILES: CN(C)[C@H]1CCN(CCOc2c3[nH]c4ccc(F)cc4c3cc3c2[nH]c2ccc(F)cc23)C1]

The title compound was prepared in a manner analogous to Example 70 except the reagent is (S)—N,N-dimethylpyrrolidin-3-amine. $^1$H-NMR (400 MHz, CD$_3$OD) δ ppm 8.43 (s, 1 H), 7.80 (dd, J=9.2, 2.4 Hz, 2 H), 7.38 (dd, J=8.8, 4.4 Hz, 2 H), 7.08 (td, J=9.2, 2.4 Hz, 2 H), 4.37 (t, J=5.6 Hz, 2 H), 3.19-3.11 (m, 1 H), 3.07-2.98 (m, 2 H), 2.97-2.88 (m, 2 H), 2.69-2.60 (m, 1 H), 2.52-2.45 (m, 1 H), 2.20-2.08 (m, 1 H), 1.93 (s, 6 H), 1.88-1.76 (m, 1 H); MS (ESI) m/z 449.1 (M−H)$^-$; MS (ESI) m/z 447.2 (M+H)$^+$

Example 78

6-(2-(4-(1,3,5-triazin-2-yl)piperazin-1-yl)ethoxy)-2,10-difluoro-5,7-dihydroindolo[2,3-b]carbazole

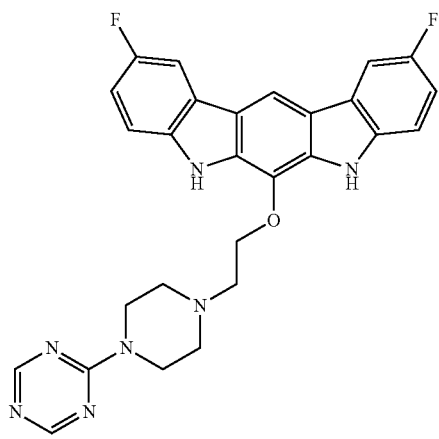 [SMILES: Fc1ccc2[nH]c3c(OCCN4CCN(c5ncncn5)CC4)c4[nH]c5ccc(F)cc5c4cc3c2c1]

The title compound was prepared in a manner analogous to Example 70 except the reagent is 1-(1,3,5-triazin-2-yl)-piperazine. 1H-NMR (400 MHz, DMSO-d6) δ ppm 11.14 (s, 2 H), 8.59 (s, 1 H), 8.56 (s, 2 H), 7.90 (dd, J=9.2, 2.4 Hz, 2 H), 7.46 (dd, J=8.8, 3.6 Hz, 2 H), 7.18 (td, J=9.2, 2.4 Hz, 2H), 4.42 (t, J=5.8 Hz, 2 H), 3.80 (t, J=4.6 Hz, 4 H), 2.86 (t, J=5.6 Hz, 2 H), 2.58 (t, J=4.6 Hz, 4 H); MS (ESI) m/z 498.3 (M–H)–; MS (ESI) m/z 500.1 (M+H)+

Example 79

2,10-difluoro-6-(2-(4-(pyrazin-2-yl)piperazin-1-yl)ethoxy)-5,7-dihydroindolo[2,3-b]carbazole

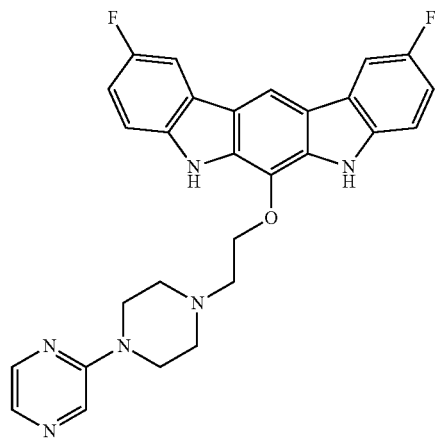 [SMILES: Fc1ccc2[nH]c3c(OCCN4CCN(c5cnccn5)CC4)c4[nH]c5ccc(F)cc5c4cc3c2c1]

The title compound was prepared in a manner analogous to Example 70 except the reagent is 1-(2-pyrazinyl)-piperazine. $^1$H-NMR (400 MHz, DMSO-d$_6$) δ ppm 11.18 (s, 2 H), 8.59 (s, 1 H), 8.32 (d, J=1.2 Hz, 1 H), 8.07 (dd, J=2.4, 1.6 Hz, 1 H), 7.90 (dd, J=9.2, 2.4 Hz, 2 H), 7.83 (d, J=2.4 Hz, 1 H), 7.45 (dd, J=8.8, 4.4 Hz, 2 H), 7.17 (td, J=9.2, 2.4 Hz, 2 H), 4.43 (t, J=5.8 Hz, 2 H), 3.59 (t, J=4.8 Hz, 4 H), 2.86 (t, J=6.0 Hz, 2 H), 2.63 (t, J=5.0 Hz, 4 H); MS (ESI) m/z 497.3 (M–H)$^-$; MS (ESI) m/z 499.1 (M+H)$^+$

Example 80

6-(2-(1H-1,2,4-triazol-1-yl)ethoxy)-2,10-difluoro-5,7-dihydroindolo[2,3-b]carbazole

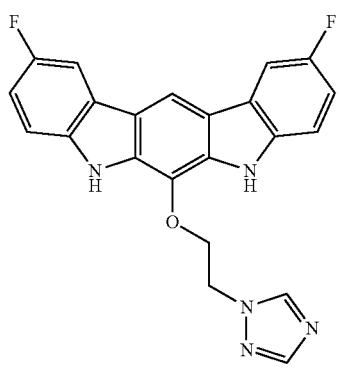 [SMILES: Fc1ccc2[nH]c3c(OCCn4cncn4)c4[nH]c5ccc(F)cc5c4cc3c2c1]

The title compound was prepared in a manner analogous to Example 70 except the reagent is 1,2,4-triazole. $^1$H NMR (400 MHz, DMSO-d$_6$) δ ppm 11.11 (s, 2H), 8.70 (s, 1H), 8.61 (s, 1H), 8.07 (s, 1H), 7.90 (dd, J=9.4, 2.6 Hz, 2H), 7.47 (dd, J=8.8, 4.4 Hz, 2H), 7.19 (td, J=9.2, 2.2 Hz, 2H), 4.75 (t, J=5.6 Hz, 2H), 4.65 (t, J=5.6 Hz, 2H), 2.41 (p, J=6.8 Hz, 2H).

Example 81

2,10-difluoro-6-(2-(5-methyl-2H-tetrazol-2-yl)ethoxy)-5,7-dihydroindolo[2,3-b]carbazole and 2,10-difluoro-6-(2-(5-methyl-1H-tetrazol-1-yl)ethoxy)-5,7-dihydroindolo[2,3-b]carbazole

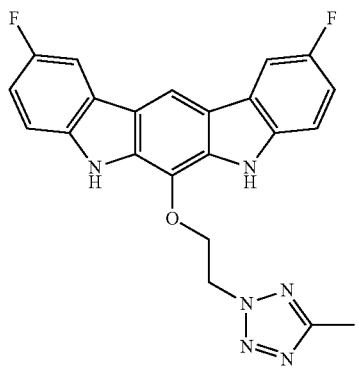

and

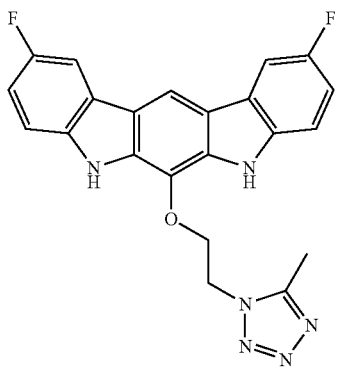

The title compounds were prepared in a manner analogous to Example 70 except the reagent is 5-methyl-tetrazole. The reaction produces a mixture of two isomers, which can be separated by chromatography. 2,10-difluoro-6-(2-(5-methyl-2H-tetrazol-2-yl)ethoxy)-5,7-dihydroindolo[2,3-b]carbazole: ¹H NMR (400 MHz, DMSO-d₆) δ ppm 11.08 (s, 2H), 8.61 (s, 1H), 7.90 (dd, J=9.2, 2.4 Hz, 2H), 7.45 (dd, J=8.8, 4.8 Hz, 2H), 7.19 (td, J=9.2, 2.6 Hz, 2H), 5.19 (t, J=5.6 Hz, 2H), 4.76 (t, J=5.6 Hz, 2H), 2.44 (s, 3H); MS (ESI) m/z 417 (M−H)⁻, 453 (M+Cl)⁻. 2,10-difluoro-6-(2-(5-methyl-1H-tetrazol-1-yl)ethoxy)-5,7-dihydroindolo[2,3-b]carbazole: ¹H NMR (400 MHz, DMSO-d₆) δ ppm 11.12 (s, 2H), 8.62 (s, 1H), 7.90 (dd, J=9.2, 2.8 Hz, 2H), 7.45 (dd, J=8.6, 4.6 Hz, 2H), 7.19 (td, J=9.2, 2.4 Hz, 2H), 4.97 (t, J=5.6 Hz, 2H), 4.61 (t, J=5.6 Hz, 2H), 2.61 (s, 3H); MS (ESI) m/z 417 (M−H)⁻, 453 (M+Cl)⁻.

Example 82

6-(2-(2H-1,2,3-triazol-2-yl)ethoxy)-2,10-dichloro-5,7-dihydroindolo[2,3-b]carbazole

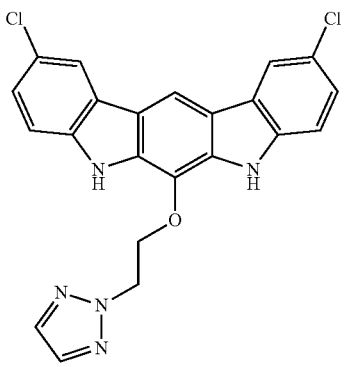 [SMILES: Clc1ccc2[nH]c3c(OCCn4nccn4)c4[nH]c5ccc(Cl)cc5c4cc3c2c1]

The title compound was prepared in a manner analogous to Example 70 except the staring material is 5,7-diBOC-2,10-dichloro-6-(2-bromoethoxy)indolo[2,3-b]carbazole and the reagent is 1,2,3-triazole. ¹H-NMR (400 MHz, DMSO-d₆) δ ppm 11.29 (s, 2 H), 8.70 (s, 1 H), 8.16 (d, J=2.0 Hz, 2 H), 7.88 (s, 2 H), 7.51 (d, J=8.8 Hz, 2 H), 7.37 (dd, J=8.4, 2.0 Hz, 2 H), 4.98 (t, J=6.4 Hz, 2 H), 4.71 (t, J=6.0 Hz, 2 H); MS (ESI) m/z 434.0 (M−H)⁻; MS (ESI) m/z 436.0 (M+H)⁺

The starting material, 5,7-diBOC-2,10-dichloro-6-(2-bromoethoxy)indolo[2,3-b]carbazole, could be prepared from 5,7-diBOC-2,10-dichloro-6-hydroxyindolo[2,3-b]carbazole and 1,2-dibromoethane in 70-75% yield. ¹H NMR (400 MHz, CDCl₃) δ ppm 8.16 (s, 1H), 8.03 (d, T=8.8 Hz, 2H), 7.99 (d, J=2.4 Hz, 2H), 7.42 (dd, J=8.8, 2.4 Hz, 2H), 4.21 (t, J=6.8 Hz, 2H), 3.41 (t, J=6.8 Hz, 2H), 1.74 (s, 18H).

Example 83

1-(2-(2,10-dichloro-5,7-dihydroindolo[2,3-b]carbazol-6-yloxy)ethyl)-1H-tetrazol-5-amine and 2-(2-(2,10-dichloro-5,7-dihydroindolo[2,3-b]carbazol-6-yloxy)ethyl)-2H-tetrazol-5-amine

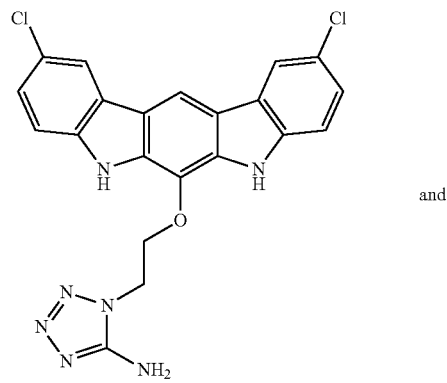

and

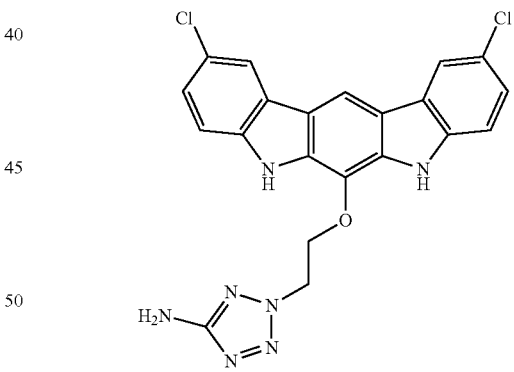

The title compounds were prepared in a manner analogous to Example 82 except the reagent is 5-amino-1(H)-tetrazole. The reaction produces a mixture of two isomers, which can be separated by chromatography. ¹H-NMR (400 MHz, DMSO-d₆) δ ppm 11.25 (s, 2 H), 8.70 (s, 1 H), 8.16 (d, J=2.0 Hz, 2 H), 7.51 (d, J=8.4 Hz, 2 H), 7.37 (dd, J=8.6, 2.4 Hz, 2 H), 6.13 (s, 2 H), 4.96 (t, J=6.0 Hz, 2 H), 4.67 (t, J=5.6 Hz, 2 H); MS (ESI) m/z 450.0 (M−H)⁻; MS (ESI) m/z 452.0 (M+H)⁺. ¹H-NMR (400 MHz, DMSO-d₆) δ ppm 11.23 (s, 2 H), 8.68 (s, 1 H), 8.14 (d, J=2.0 Hz, 2 H), 7.46, (d, J=8.4 Hz, 2 H), 7.35 (dd, J=8.4, 2.0 Hz, 2 H), 6.80 (br s, 1 H), 4.67 (t, J=6.0 Hz, 2 H), 4.10 (t, J=5.6 Hz, 2 H); MS (ESI) m/z 450.1 (M−H)⁻; MS (ESI) m/z 451.9 (M+H)⁺

Example 84

1-(3-(2,10-difluoro-5,7-dihydroindolo[2,3-b]carbazol-6-yloxy)propyl)pyrrolidin-3-ol

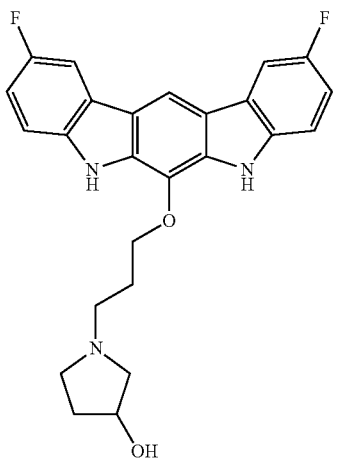 [SMILES: OC1CCN(CCCOc2c3[nH]c4ccc(F)cc4c3cc3c2[nH]c2ccc(F)cc23)C1]

The title compound was prepared in a manner analogous to Example 70 except the staring material is 5,7-diBOC-2,10-difluoro-6-(3-bromopropoxy)indolo[2,3-b]carbazole and the reagent is 3-hydroxypyrroline. The reaction can be completed at room temperature overnight. $^1$H-NMR (400 MHz, CDCl$_3$) δ ppm 9.57 (br s, 2 H), 8.27 (s, 1 H), 7.71 (dd, J=9.2, 2.4 Hz, 2 H), 7.33 (dd, J=8.8, 4.0 Hz, 2H), 7.03 (td, J=8.8, 2.4 Hz, 2 H), 4.67-4.59 (m, 1 H), 4.40-4.26 (m, 2 H), 3.80 (t, J=5.6 Hz, 1 H), 3.15-3.00 (m, 2 H), 2.96-2.80 (m, 3 H), 2.73-2.61 (m, 1 H), 2.38-2.26 (m, 1 H), 2.12-1.93 (m, 2 H), 1.79-1.70 (m, 1 H); MS (ESI) m/z 434.2 (M−H)$^-$; MS (ESI) m/z 436.1 (M+H)$^+$ The starting material, 5,7-diBOC-2,10-difluoro-6-(3-bromopropoxy)indolo[2,3-b]carbazole, could be prepared from 5,7-diBOC-2,10-difluoro-6-hydroxyindolo[2,3-b]carbazole and 1,3-dibromopropane in 90% yield. $^1$H NMR (400 MHz, CDCl$_3$) δ ppm 8.11 (s, 1H), 8.05 (dd, J=9.0, 4.6 Hz, 2H), 7.68 (dd, J=8.2, 2.6 Hz, 2H), 7.17 (td, J=9.2, 2.6 Hz, 2H), 4.05 (t, J=6.0 Hz, 2H), 3.51 (t, J=6.8 Hz, 2H), 2.14 (p, J=6.4 Hz, 2H), 1.73 (s, 18H).

Example 85

N-(3-(2,10-difluoro-5,7-dihydroindolo[2,3-b]carbazol-6-yloxy)propyl)piperidin-4-amine

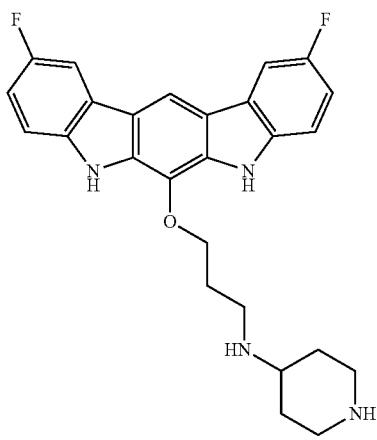 [SMILES: Fc1ccc2[nH]c3c(OCCCNC4CCNCC4)c4[nH]c5ccc(F)cc5c4cc3c2c1]

The title compound was prepared in a manner analogous to Example 84 except the reagent is 4-amino-1-Boc-piperidine. $^1$H-NMR (400 MHz, CD$_3$OD) δ ppm 8.43 (s, 1 H), 7.80 (dd, J=9.2, 2.4 Hz, 2 H), 7.41 (dd, J=8.8, 4.4 Hz, 2 H), 7.08 (td, J=9.2, 2.4 Hz, 2 H), 4.44 (t, J=6.0 Hz, 2 H), 3.52-3.32 (m, 5 H), 3.09-2.96 (m, 2 H), 2.38-2.21 (m, 4 H), 1.92-1.74 (m, 2 H); MS (ESI) m/z 447.2 (M−H)$^-$

Example 86

N-(3-(2,10-difluoro-5,7-dihydroindolo[2,3-b]carbazol-6-yloxy)propyl)-8-methyl-8-azabicyclo[3.2.1]octan-3-amine

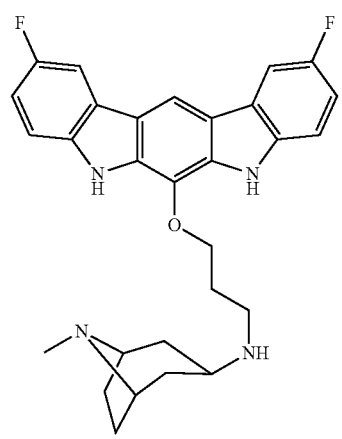 [SMILES: CN1C2CCC1CC(NCCCOc1c3[nH]c4ccc(F)cc4c3cc3c1[nH]c1ccc(F)cc13)C2]

The title compound was prepared in a manner analogous to Example 84 except the reagent is 8-methyl-8-azabicyclo[3.2.1]octan-3-amine. $^1$H NMR (400 MHz, CDCl$_3$) δ ppm 8.29 (s, 1H), 7.72 (dd, J=10.0, 2.6 Hz, 2H), 7.27 (dd, J=8.4, 4.4 Hz, 2H), 7.05 (td, J=9.0, 2.4 Hz, 2H), 4.37 (t, J=5.6 Hz, 2H), 3.40-1.40 (br m, 4H); MS (ESI) m/z 489 (M+H)$^+$.

Example 87

6-(3-(1H-1,2,4-triazol-1-yl)propoxy)-2,10-difluoro-5,7-dihydroindolo[2,3-b]carbazole and 6-(3-(4H-1,2,4-triazol-4-yl)propoxy)-2,10-difluoro-5,7-dihydroindolo[2,3-b]carbazole

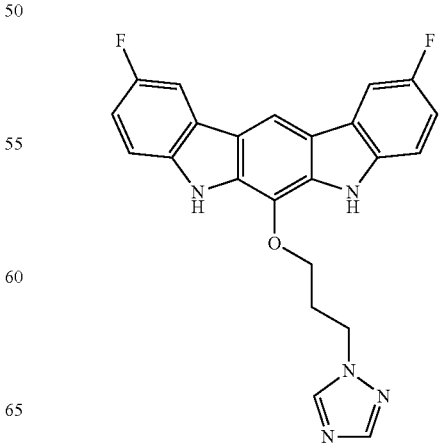

and

77

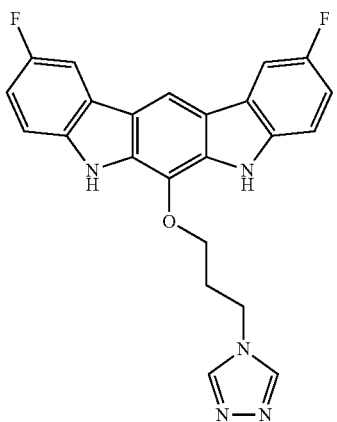

The title compounds were prepared in a manner analogous to Example 84 except the reagent is 1,2,4-triazole. The reaction produces a mixture of two isomers, which can be separated by chromatography. 6-(3-(1H-1,2,4-triazol-1-yl)propoxy)-2,10-difluoro-5,7-dihydroindolo[2,3-b]carbazole: $^{1}$H-NMR (400 MHz, DMSO-d$_{6}$) δ ppm 11.13 (s, 2 H), 8.59 (s, 1 H), 8.58 (s, 1 H), 8.02 (s, 1 H), 7.90 (dd, J=9.2, 2.8 Hz, 2 H), 7.61 (dd, J=8.8, 4.8 Hz, 2 H), 7.18 (td, J=8.8, 2.8 Hz, 2 H), 4.55 (t, J=7.2 Hz, 2H), 4.25 (t, J=6.8 Hz, 2 H), 2.43-2.32 (m, 2 H); MS (ESI) m/z 416.2 (M−H)$^{−}$; MS (ESI) m/z 418.0 (M+H)$^{+}$. 6-(3-(4H-1,2,4-triazol-4-yl)propoxy)-2,10-difluoro-5,7-dihydroindolo[2,3-b]carbazole: $^{1}$H-NMR (400 MHz, DMSO-d$_{6}$) δ ppm 11.11 (s, 2 H), 8.60 (s, 3 H), 7.91 (dd, J=9.2, 2.4 Hz, 2 H), 7.46 (dd, J=8.8, 4.8 Hz, 2 H), 7.19 (td, J=9.2, 2.4 Hz, 2 H), 4.41 (t, J=7.2 Hz, 2 H), 4.25 (t, J=6.4 Hz, 2H), 2.40-2.29 (m, 2 H); MS (ESI) m/z 416.2 (M−H)$^{−}$; MS (ESI) m/z 418.1 (M+H)$^{+}$

Example 88

2-(3-(2,10-difluoro-5,7-dihydroindolo[2,3-b]carbazol-6-yloxy)propyl)-2H-tetrazol-5-amine and 1-(3-(2,10-difluoro-5,7-dihydroindolo[2,3-b]carbazol-6-yloxy)propyl)-1H-tetrazol-5-amine

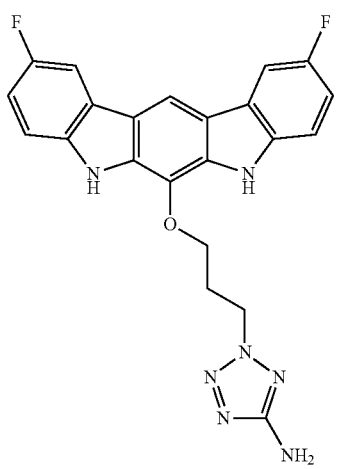

and

78

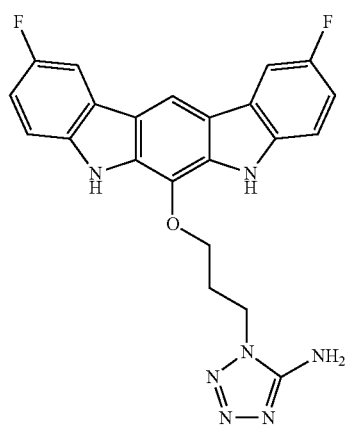

The title compounds were prepared in a manner analogous to Example 84 except the reagent is tetrazol-5-amine. The reaction produces a mixture of two isomers, which can be separated by chromatography. $^{1}$H NMR (400 MHz, DMSO-d$_{6}$) δ ppm 11.09 (s, 2H), 8.60 (s, 1H), 7.90 (dd, J=9.4, 3.0 Hz, 2H), 7.45 (dd, J=8.8, 4.4 Hz, 2H), 7.19 (td, J=9.2, 2.8 Hz, 2H), 6.02 (s, 2H), 4.77 (t, J=7.2 Hz, 2H), 4.31 (t, J=6.4 Hz, 2H), 2.46 (p, J=6.8 Hz, 2H); MS (ESI) m/z 432 (M−H)$^{−}$. $^{1}$H NMR (400 MHz, DMSO-d$_{6}$) δ ppm 11.10 (s, 2H), 8.60 (s, 1H), 7.90 (dd, J=9.2, 2.8 Hz, 2H), 7.45 (dd, J=8.6, 4.6 Hz, 2H), 7.19 (td, J=9.2, 2.4 Hz, 2H), 6.78 (s, 2H), 4.44 (t, J=7.0 Hz, 2H), 4.28 (t, J=6.4 Hz, 2H), 2.34 (p, J=6.8 Hz, 2H); MS (ESI) m/z 432 (M−H)$^{−}$.

Example 89

6-(5-(1H-1,2,4-triazol-4-yl)pentyloxy)-2,10-difluoro-5,7-dihydroindolo[2,3-b]carbazole and 6-(5-(4H-1,2,4-triazol-4-yl)pentyloxy)-2,10-difluoro-5,7-dihydroindolo[2,3-b]carbazole

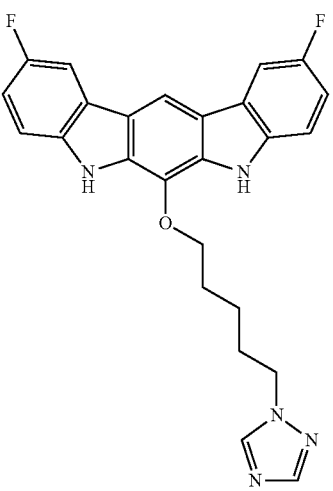

and

79
-continued

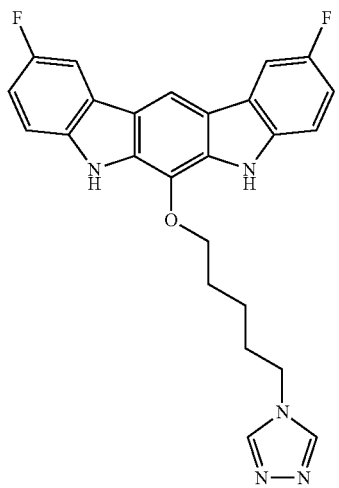

The title compounds were prepared in a manner analogous to Example 70 except the staring material is 5,7-diBOC-2,10-difluoro-6-(5-bromopentyloxy)indolo[2,3-b]carbazole and the reagent is 1,2,4-triazole. The reaction can be completed at room temperature overnight. The reaction produces a mixture of two isomers, which can be separated by chromatography. 6-(5-(1H-1,2,4-triazol-4-yl)pentyloxy)-2,10-difluoro-5,7-dihydroindolo[2,3-b]carbazole: $^1$H-NMR (400 MHz, DMSO-$d_6$) δ ppm 11.03 (s, 2 H), 8.57 (s, 1 H), 8.51 (s, 1 H), 7.94 (s, 1 H), 7.92-7.86 (m, 2 H), 7.45 (dd, J=8.8, 4.4 Hz, 2H), 7.17 (td, J=9.2, 2.8 Hz, 2 H), 4.27-4.18 (m, 4 H), 1.98-1.82 (m, 4 H), 1.49-1.38 (m, 2 H); MS (ESI) m/z 444.3 (M−H)$^-$; MS (ESI) m/z 446.1 (M+H)$^+$. 6-(5-(4 H-1,2,4-triazol-4-yl)pentyloxy)-2,10-difluoro-5,7-dihydroindolo[2,3-b]carbazole: $^1$H-NMR (400 MHz, DMSO-$d_6$) δ ppm 11.03 (s, 1 H), 8.58 (s, 1 H), 8.52 (s, 2 H), 7.89 (dd, J=9.6, 2.4 Hz, 2 H), 7.45 (dd, J=8.8, 4.4 Hz, 2 H), 7.17 (td, J=9.2, 2.4 Hz, 2H), 4.22 (t, J=7.0 Hz, 2 H), 4.06 (t, J=7.2 Hz, 2 H), 1.97-1.85 (m, 2 H), 1.85-1.73 (m, 2 H), 1.49-1.35 (m, 2 H).

The starting material, 5,7-diBOC-2,10-difluoro-6-(5-bromopentyloxy)indolo[2,3-b]carbazole, could be prepared from 5,7-diBOC-2,10-difluoro-6-hydroxyindolo[2,3-b]carbazole and 1,5-dibromopentane in 94% yield. $^1$H NMR (400 MHz, CDCl$_3$) δ ppm 8.09 (s, 1H), 8.04 (dd, J=9.0, 4.6 Hz, 2H), 7.68 (dd, J=8.2, 2.6 Hz, 2H), 7.17 (td, J=9.0, 2.6 Hz, 2H), 3.90 (t, J=6.6 Hz, 2H), 3.32 (t, J=6.8 Hz, 2H), 1.84-1.52 (m, 6H), 1.73 (s, 18H).

80
Example 90

2-(5-(2,10-difluoro-5,7-dihydroindolo[2,3-b]carbazol-6-yloxy)pentyl)-2H-tetrazol-5-amine and 1-(5-(2,10-difluoro-5,7-dihydroindolo[2,3-b]carbazol-6-yloxy)pentyl)-1H-tetrazol-5-amine

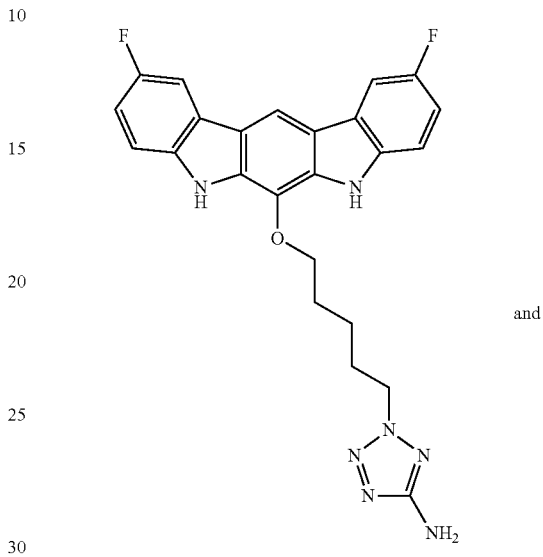

and

The title compounds were prepared in a manner analogous to Example 89 except the reagent is tetrazol-5-amine. The reaction produces a mixture of two isomers, which can be separated by chromatography. $^1$H NMR (400 MHz, DMSO-$d_6$) δ ppm 11.03 (s, 2H), 8.57 (s, 1H), 7.89 (dd, J=9.2, 2.4 Hz, 2H), 7.45 (dd, J=8.4, 4.4 Hz, 2H), 7.17 (td, J=9.2, 2.6 Hz, 2H), 5.97 (s, 2H), 4.43 (t, J=6.8 Hz, 2H), 4.22 (t, J=7.0 Hz, 2H), 2.00-1.87 (m, 4H), 1.54-1.43 (m, 2H); MS (ESI) m/z 460 (M−H)$^-$, 496 (M+Cl)$^-$. $^1$H NMR (400 MHz, DMSO-$d_6$) δ ppm 11.02 (s, 2H), 8.57 (s, 1H), 7.88 (dd, J=9.4, 2.6 Hz, 2H), 7.45 (dd, J=8.4, 4.4 Hz, 2H), 7.17 (td, J=9.2, 2.6 Hz, 2H), 6.68 (s, 2H), 4.23 (t, J=7.0 Hz, 2H), 4.12 (t, J=7.0 Hz, 2H), 2.00-1.90 (m, 2H), 1.87-1.77 (m, 2H), 1.55-1.44 (m, 2H); MS (ESI) m/z 460 (M−H)$^-$, 496 (M+Cl)$^-$.

Example 91

(1-(3-(2,10-dichloro-5,7-dihydroindolo[2,3-b]carbazol-6-yloxy)propyl)piperidin-3-yl)methanamine

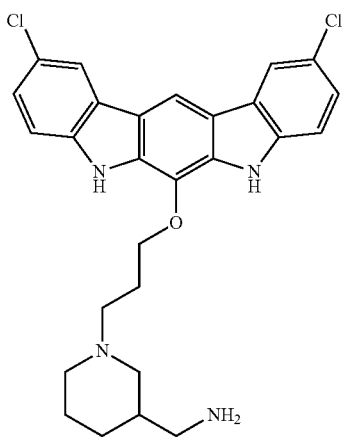 [SMILES: NCC1CCCN(CCCOc2c3[nH]c4ccc(Cl)cc4c3cc3c2[nH]c2ccc(Cl)cc23)C1]

The title compound was prepared in a manner analogous to Example 70 except the staring material is 5,7-diBOC-2,10-dichloro-6-(3-bromopropoxy)indolo[2,3-b]carbazole and the reagent is 3-(Boc-aminomethyl)piperidine. The reaction can be completed at room temperature overnight $^{1}$H-NMR (400 MHz, CDCl$_{3}$) δ ppm 9.76 (s, 2 H), 8.34 (s, 1 H), 8.08 (s, 2 H), 7.40-7.31 (m, 4 H), 4.35 (t, J=5.6 Hz, 2 H), 3.35-3.20 (m, 2 H), 2.89-2.75 (m, 2 H), 2.70-2.53 (m, 2 H), 2.18-1.71 (m, 9 H), 1.17-1.03 (m, 2 H); MS (ESI) m/z 493.2 (M–H)$^{-}$; MS (ESI) m/z 495.1 (M+H)$^{+}$ The starting material, 5,7-diBOC-2,10-dichloro-6-(3-bromopropoxy)indolo[2,3-b]carbazole, could be prepared from 5,7-diBOC-2,10-dichloro-6-hydroxyindolo[2,3-b]carbazole and 1,3-dibromopropane in 99% yield. $^{1}$H NMR (400 MHz, CDCl$_{3}$) δ ppm 8.13 (s, 1H), 8.02 (d, J=8.8 Hz, 2H), 7.99 (d, J=2.0 Hz, 2H), 7.42 (dd, J=8.8, 2.0 Hz, 2H), 4.04 (t, J=6.2 Hz, 2H), 3.51 (t, J=6.6 Hz, 2H), 2.14 (p, J=6.4 Hz, 2H), 1.73 (s, 18H).

Example 92

1-(3-(2,10-dichloro-5,7-dihydroindolo[2,3-b]carbazol-6-yloxy)propyl)piperidin-4-ol

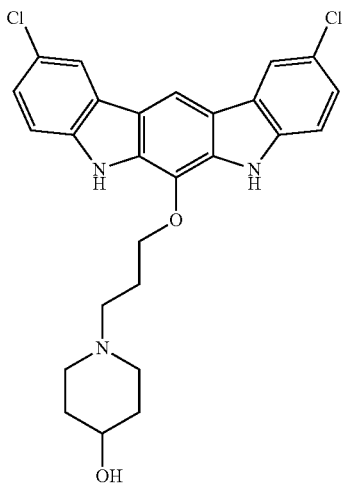 [SMILES: OC1CCN(CCCOc2c3[nH]c4ccc(Cl)cc4c3cc3c2[nH]c2ccc(Cl)cc23)CC1]

The title compound was prepared in a manner analogous to Example 91 except the reagent is 4-hydroxypiperidine. 1H-NMR (400 MHz, DMSO-d6) δ ppm 11.32 (s, 2 H), 8.65 (s, 1 H), 8.16 (d, J=2.4 Hz, 2 H), 7.49 (d, J=8.4 Hz, 2 H), 7.35 (dd, J=8.6, 2.4 Hz, 2 H), 4.63 (d, J=4.0 Hz, 1 H), 4.28 (t, J=6.4 Hz, 2 H), 3.55-3.36 (m, 1 H), 2.86-2.73 (m, 2 H), 2.53 (t, J=6.8 Hz, 2 H), 2.12-1.98 (m, 4 H), 1.79-1.68 (m, 2 H), 1.48-1.56 (m, 2 H); MS (ESI) m/z 480.1 (M–H)–; MS (ESI) m/z 482.1 (M+H)+

Example 93

1-(3-(2,10-dichloro-5,7-dihydroindolo[2,3-b]carbazol-6-yloxy)propyl)azetidin-3-ol

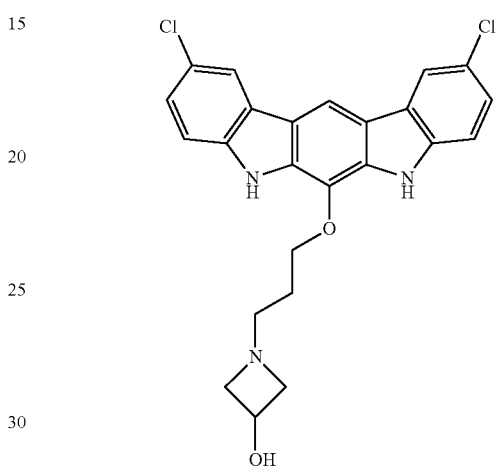

The title compound was prepared in a manner analogous to Example 91 except the reagent is azetidin-3-ol hydrochloride. $^{1}$H-NMR (400 MHz, DMSO-d$_{6}$) δ ppm 11.78 (s, 2 H), 8.65 (s, 1 H), 8.15 (d, J=2.0 Hz, 2 H), 7.50 (d, J=8.4 Hz, 2 H), 7.36 (dd, J=8.6, 2.2 Hz, 2 H), 5.52 (d, J=6.0 Hz, 1 H), 4.42-4.31 (m, 1 H), 4.26 (t, J=6.0 Hz, 2 H), 3.75-3.65 (m, 2 H), 3.0-2.88 (m, 2 H), 2.86-2.74 (m, 2 H), 1.97-1.89 (m, 2 H); MS (ESI) m/z 452.2 (M–H)$^{-}$

Example 94

1-(3-(2,10-dichloro-5,7-dihydroindolo[2,3-b]carbazol-6-yloxy)propyl)pyrrolidin-3-amine

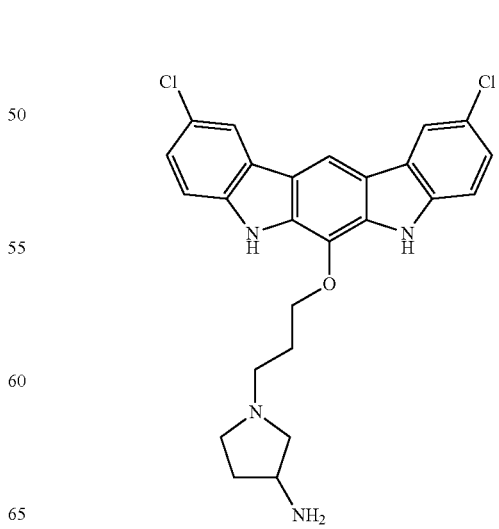

The title compound was prepared in a manner analogous to Example 91 except the reagent is 3-(tert-butoxycarbonylamino)pyrrolidine. ¹H-NMR (400 MHz, DMSO-d₆) δ ppm 11.48 (br s, 2 H), 8.65 (s, 1 H), 8.15 (d, J=2.4 Hz, 2 H), 7.48 (d, J=8.8 Hz, 2 H), 7.35 (dd, J=8.8, 2.0 Hz, 2 H), 4.30 (t, J=6.4 Hz, 2 H), 2.85 (dd, J=9.6, 6.8 Hz, 1 H), 2.78-2.58 (m, 5 H), 2.23 (dd, J=9.4, 5.6 Hz, 1 H), 2.12-1.99 (m, 3 H), 1.50-1.39 (m, 1 H); MS (ESI) m/z 465.1 (M−H)⁻; MS (ESI) m/z 467.1 (M+H)⁺

Example 95

N-(3-(2,10-dichloro-5,7-dihydroindolo[2,3-b]carbazol-6-yloxy)propyl)piperidin-4-amine

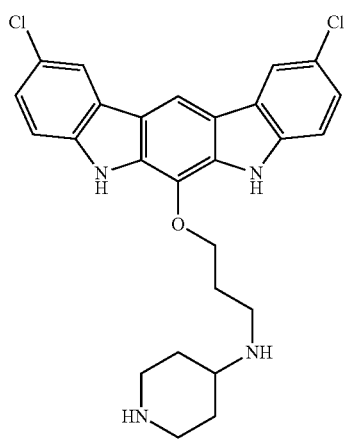 [SMILES: Clc1ccc2[nH]c3c(OCCCNC4CCNCC4)c4[nH]c5ccc(Cl)cc5c4cc3c2c1]

The title compound was prepared in a manner analogous to Example 91 except the reagent is 1-benzylpiperidin-4-amine, and the following procedure was used for debenzylation. The corresponding Boc protected product was dissolved in 1,2-dichloroethane (20 mL) and cooled at ice bath. NaHCO₃ (1.5 g) and 1-chloroethyl chloroformate (1.0 mL) were added and stirred at 0° C. for 10 min, warmed to RT for 20 min, and then refluxed for 2 h. After removed all volatiles, the residue was partitioned between ethyl acetate and water, the organic phase was separated, washed with brine, dried over anhydrous Na₂SO₄ and evaporated to dryness. The residue was dissolved in EtOH (20 mL), the solution refluxed for 2 h, and then volatiles removed to give crude debenzylated intermediate, MS (ESI) m/z 681, 683 (M+H)⁺. This crude material was further deprotected under TFA/CH₂Cl₂ to offer the title product. ¹H NMR (400 MHz, DMSO-d₆) δ ppm 11.58 (s, 2H), 8.67 (s, 1H), 8.15 (d, J=2.0 Hz, 2H), 7.53 (d, J=8.8 Hz, 2H), 7.35 (dd, J=8.6, 2.2 Hz, 2H), 4.38 (t, J=5.8 Hz, 2H), 3.49-3.25 (m, 5H), 2.93 (t, J=12.8 Hz, 2H), 2.42-2.26 (m, 4H), 2.04-1.88 (m, 2H).

Example 96

N-(3-(2,10-dichloro-5,7-dihydroindolo[2,3-b]carbazol-6-yloxy)propyl)quinuclidin-3-amine

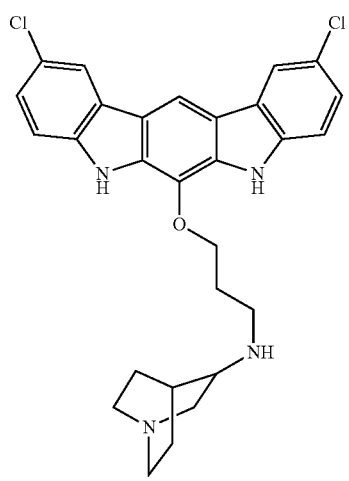 [SMILES: Clc1ccc2[nH]c3c(OCCCNC4CN5CCC4CC5)c4[nH]c5ccc(Cl)cc5c4cc3c2c1]

The title compound was prepared in a manner analogous to Example 91 except the reagent is quinuclidin-3-amine. ¹H NMR (400 MHz, DMSO-d₆) δ ppm 11.47 (s, 2H), 8.69 (s, 1H), 8.16 (d, J=2.0 Hz, 2H), 7.54 (d, J=8.8 Hz, 2H), 7.37 (dd, J=8.6, 2.2 Hz, 2H), 4.32 (t, J=5.6 Hz, 2H), 3.90 (br t, J=12.8 Hz, 1H), 3.80-3.40 (m, 8H), 2.38-1.82 (m, 7H); MS (ESI) m/z 507, 509 (M+H)⁺.

Example 97

6-(3-(1H-imidazol-1-yl)propoxy)-2,10-dichloro-5,7-dihydroindolo[2,3-b]carbazole

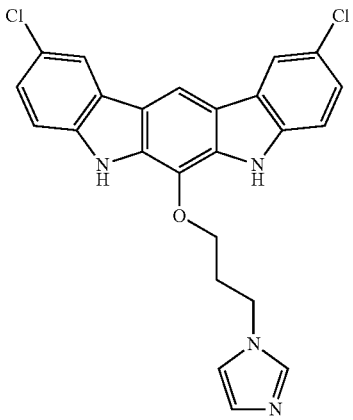 [SMILES: Clc1ccc2[nH]c3c(OCCCn4ccnc4)c4[nH]c5ccc(Cl)cc5c4cc3c2c1]

The title compound was prepared in a manner analogous to Example 91 except the reagent is 1H-imidazole. ¹H NMR (400 MHz, DMSO-d₆) δ ppm 11.26 (s, 2H), 8.68 (s, 1H), 8.16 (d, J=2.4 Hz, 2H), 7.67 (s, 1H), 7.48 (d, J=8.4 Hz, 2H), 7.36 (dd, J=8.6, 2.2 Hz, 2H), 7.21 (s, 1H), 6.88 (s, 1H), 4.32 (t, J=7.4 Hz, 2H), 4.26 (t, J=6.4 Hz, 2H), 2.31 (p, J=6.8 Hz, 2H); MS (ESI) m/z 447, 449 (M−H)⁻, 483, 485 (M+Cl)⁻.

Example 98

2,10-dichloro-6-(3-(5-methyl-2H-tetrazol-2-yl)propoxy)-5,7-dihydroindolo[2,3-b]carbazole and 2,10-dichloro-6-(3-(5-methyl-1H-tetrazol-1-yl)propoxy)-5,7-dihydroindolo[2,3-b]carbazole

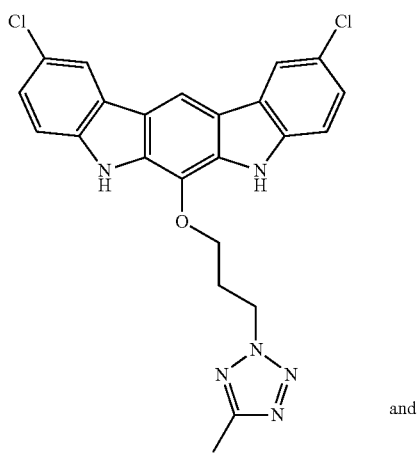

and

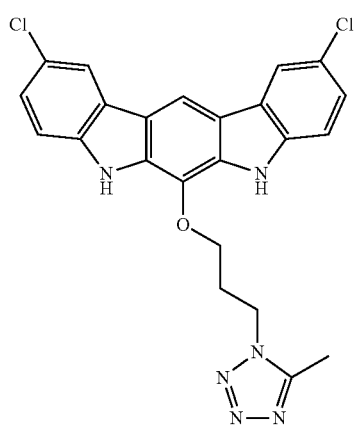

The title compounds were prepared in a manner analogous to Example 91 except the reagent is 5-methyl-tetrazole. The reaction produces a mixture of two isomers, which can be separated by chromatography. $^1$H NMR (400 MHz, DMSO-$d_6$) δ ppm 11.28 (s, 2H), 8.68 (s, 1H), 8.16 (d, J=2.0 Hz, 2H), 7.48 (d, J=8.4 Hz, 2H), 7.35 (dd, J=8.4, 2.0 Hz, 2H), 4.99 (t, J=7.4 Hz, 2H), 4.33 (t, J=6.4 Hz, 2H), 2.52-2.46 (m, 2H), 2.44 (s, 3H); MS (ESI) m/z 339, 341 (fragment), 463, 465 (M−H)$^-$, 499, 501 (M+Cl)$^-$. $^1$H NMR (400 MHz, DMSO-$d_6$) δ ppm 11.28 (s, 2H), 8.68 (s, 1H), 8.16 (d, J=2.0 Hz, 2H), 7.48 (d, J=8.4 Hz, 2H), 7.36 (dd, J=8.4, 2.4 Hz, 2H), 4.68 (t, J=7.2 Hz, 2H), 4.34 (t, J=6.4 Hz, 2H), 2.55 (s, 3H), 2.48-2.38 (m, 2H); MS (ESI) m/z 339, 341 (fragment), 463, 465 (M−H)$^-$, 499, 501 (M+Cl)$^-$.

Example 99

N-(3-(2,10-dichloro-5,7-dihydroindolo[2,3-b]carbazol-6-yloxy)propyl)-4-fluorobenzenesulfonamide

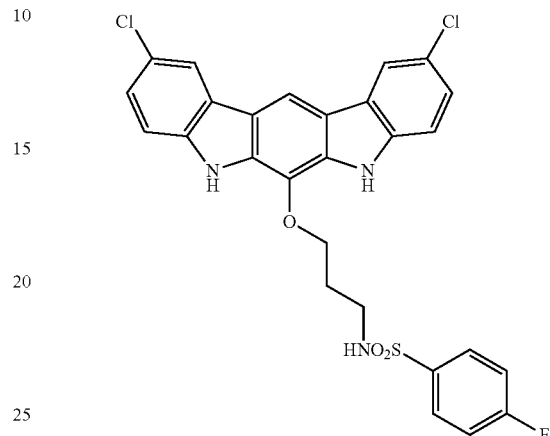

The title compound was prepared in a manner analogous to Example 91 except the reagent is 4-fluorobenzenesulfonamide and the reaction was heated at 75° C. overnight. $^1$H NMR (400 MHz, DMSO-$d_6$) δ ppm 11.18 (s, 2H), 8.65 (s, 1H), 8.14 (d, J=2.0 Hz, 2H), 7.85 (dd, J=8.8, 5.2 Hz, 2H), 7.80 (br s, 1H), 7.47 (d, J=8.4 Hz, 2H), 7.42-7.32 (m, 4H), 4.24 (t, J=6.6 Hz, 2H), 3.06 (t, J=6.6 Hz, 2H), 2.02 (p, J=6.8 Hz, 2H).

Example 100

2-(3-(2,10-dichloro-5,7-dihydroindolo[2,3-b]carbazol-6-yloxy)propyl)-2H-tetrazol-5-amine and 1-(3-(2,10-dichloro-5,7-dihydroindolo[2,3-b]carbazol-6-yloxy)propyl)-1H-tetrazol-5-amine

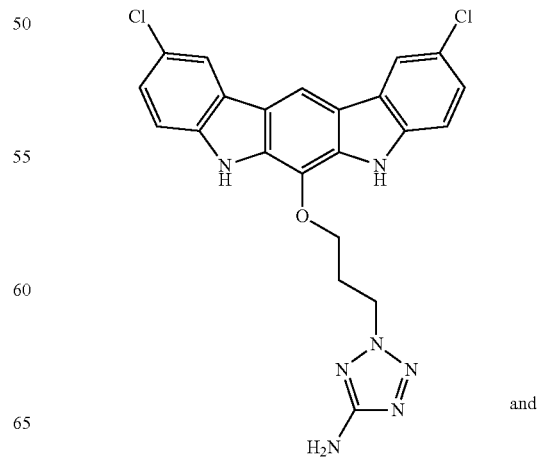

and

-continued

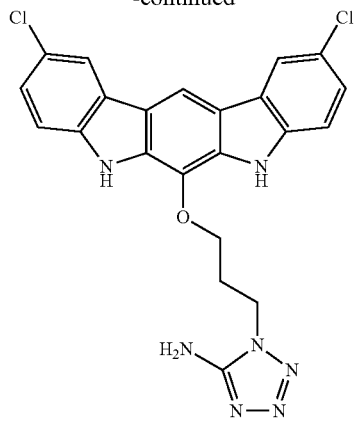

The title compounds were prepared in a manner analogous to Example 91 except the reagent is tetrazol-5-amine. The reaction produces a mixture of two isomers, which can be separated by chromatography. ¹H NMR (400 MHz, DMSO-$d_6$) δ ppm 11.27 (s, 2H), 8.67 (s, 1H), 8.16 (d, J=2.4 Hz, 2H), 7.48 (d, J=8.8 Hz, 2H), 7.36 (dd, J=8.4, 2.0 Hz, 2H), 6.02 (s, 2H), 4.77 (t, J=7.2 Hz, 2H), 4.32 (t, J=6.4 Hz, 2H), 2.50-2.40 (m, 2H); MS (ESI) m/z 339, 341 (fragment), 464, 466 (M−H)⁻, 500, 502 (M+Cl)⁻. ¹H NMR (400 MHz, DMSO-$d_6$) δ ppm 11.27 (s, 2H), 8.68 (s, 1H), 8.16 (d, J=2.0 Hz, 2H), 7.48 (d, J=8.4 Hz, 2H), 7.36 (dd, J=8.4, 2.4 Hz, 2H), 6.77 (s, 2H), 4.43 (t, J=7.0 Hz, 2H), 4.29 (t, J=6.4 Hz, 2H), 2.38 (p, J=6.8 Hz, 2H); MS (ESI) m/z 339, 341 (fragment), 464, 466 (M−H)⁻, 500, 502 (M+Cl)⁻.

Example 101

N-(3-(2,10-dichloro-5,7-dihydroindolo[2,3-b]carbazol-6-yloxy)propyl)thiazol-2-amine

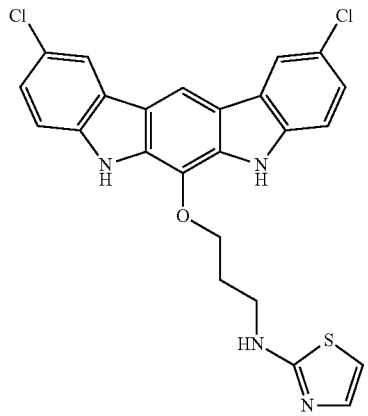 [SMILES: Clc1ccc2[nH]c3c(OCCCNc4nccs4)c4[nH]c5ccc(Cl)cc5c4cc3c2c1]

The title compound was prepared in a manner analogous to Example 91 except the reagent is thiazol-2-amine and the reaction was heated to 80° C. overnight. ¹H NMR (400 MHz, DMSO-$d_6$) δ ppm 11.25 (s, 2H), 8.67 (s, 1H), 8.16 (d, J=2.0 Hz, 2H), 7.48 (d, J=8.4 Hz, 2H), 7.36 (dd, J=8.4, 2.0 Hz, 2H), 7.20 (br s, 1H), 6.79 (br s, 1H), 4.35 (t, J=6.6 Hz, 2H), 3.58 (t, J=6.4 Hz, 2H, overlapped with H₂O), 2.21 (p, J=6.8 Hz, 2H); MS (ESI) m/z 479, 481 (M+H)⁺.

Example 102

6-(3-(1H-1,2,4-triazol-1-yl)propoxy)-2,10-dichloro-5,7-dihydroindolo[2,3-b]carbazole and 6-(3-(4H-1,2,4-triazol-4-yl)propoxy)-2,10-dichloro-5,7-dihydroindolo[2,3-b]carbazole

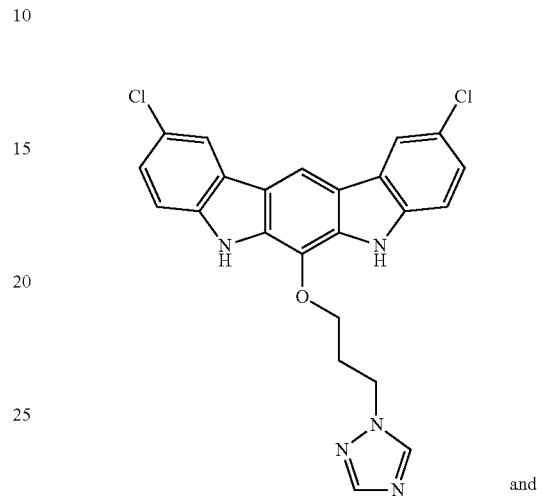

The title compounds were prepared in a manner analogous to Example 91 except the reagent is 1,2,4-triazole. The reaction produces a mixture of two isomers, which can be separated by chromatography. 6-(3-(1H-1,2,4-triazol-1-yl)propoxy)-2,10-dichloro-5,7-dihydroindolo[2,3-b]carbazole: ¹H NMR (400 MHz, DMSO-$d_6$) δ ppm 11.29 (s, 2H), 8.68 (s, 1H), 8.60 (s, 1H), 8.16 (d, J=2.4 Hz, 2H), 8.03 (s, 1H), 7.49 (d, J=8.4 Hz, 2H), 7.36 (dd, J=8.6, 2.2 Hz, 2H), 4.65 (t, J=7.2 Hz, 2H), 4.27 (t, J=6.4 Hz, 2H), 2.41 (p, J=6.8 Hz, 2H); MS (ESI) m/z 339, 341 (fragment), 448, 450 (M−H)⁻, 484, 486 (M+Cl)⁻. 6-(3-(4H-1,2,4-triazol-4-yl)propoxy)-2,10-dichloro-5,7-dihydroindolo[2,3-b]carbazole: ¹H NMR (400 MHz, DMSO-$d_6$) δ ppm 11.26 (s, 2H), 8.68 (s, 1H), 8.60 (s, 2H), 8.16 (d, J=2.0 Hz, 2H), 7.49 (d, J=8.4 Hz, 2H), 7.36 (dd, J=8.4, 2.0 Hz, 2H), 4.41 (t, J=7.4 Hz, 2H), 4.26 (t, J=6.0 Hz, 2H), 2.36 (p, J=6.8 Hz, 2H); MS (ESI) m/z 339, 341 (fragment), 448, 450 (M−H)⁻, 484, 486 (M+Cl)⁻.

Example 103

1-(3-(2,10-dichloro-5,7-dihydroindolo[2,3-b]carbazol-6-yloxy)propyl)-1H-1,2,4-triazole-3,5-diamine and 4-(3-(2,10-dichloro-5,7-dihydroindolo[2,3-b]carbazol-6-yloxy)propyl)-4H-1,2,4-triazole-3,5-diamine

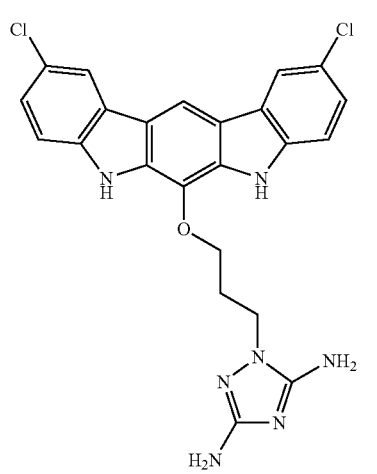

and

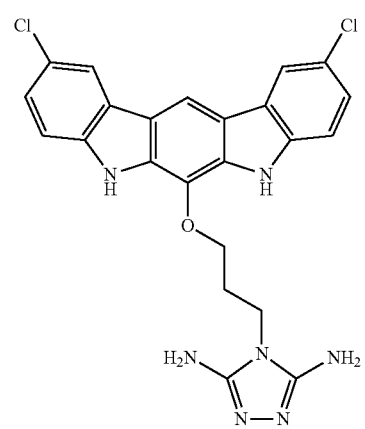

The title compounds were prepared in a manner analogous to Example 91 except the reagent is 1,2,4-triazole-3,5-diamine. The reaction produces a mixture of two isomers, which can be separated by chromatography. $^1$H NMR (400 MHz, DMSO-d$_6$) δ ppm 11.36 (s, 2H), 8.67 (s, 1H), 8.15 (d, J=2.0 Hz, 2H), 7.54 (d, J=8.4 Hz, 2H), 7.36 (dd, J=8.4, 2.0 Hz, 2H), 6.01 (s, 2H), 4.77 (s, 2H), 4.24 (t, J=6.0 Hz, 2H), 3.99 (t, J=6.4 Hz, 2H), 2.21 (p, J=6.4 Hz, 2H); MS (ESI) m/z 478, 480 (M−H)$^−$, 514, 516 (M+Cl)$^−$. $^1$H NMR (400 MHz, DMSO-d$_6$) δ ppm 11.27 (s, 2H), 8.68 (s, 1H), 8.16 (d, J=2.0 Hz, 2H), 7.50 (d, J=8.4 Hz, 2H), 7.36 (dd, J=8.6, 2.2 Hz, 2H), 6.04 (br s, 4H), 4.28 (t, J=6.8 Hz, 2H), 3.97 (t, J=7.4 Hz, 2H), 2.22 (p, J=6.8 Hz, 2H); MS (ESI) m/z 478, 480 (M−H)$^−$, 514, 516 (M+Cl)$^−$.

Example 104

7-(3-(2,10-dichloro-5,7-dihydroindolo[2,3-b]carbazol-6-yloxy)propyl)-7H-purin-6-ol and 9-(3-(2,10-dichloro-5,7-dihydroindolo[2,3-b]carbazol-6-yloxy)propyl)-9H-purin-6-ol

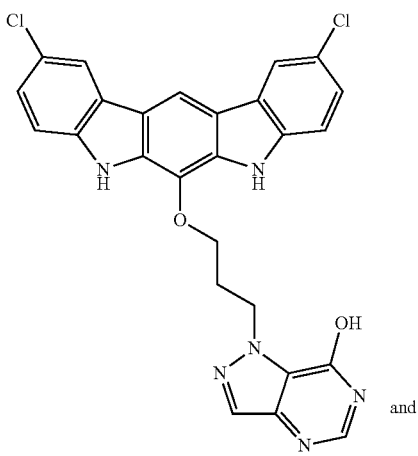

and

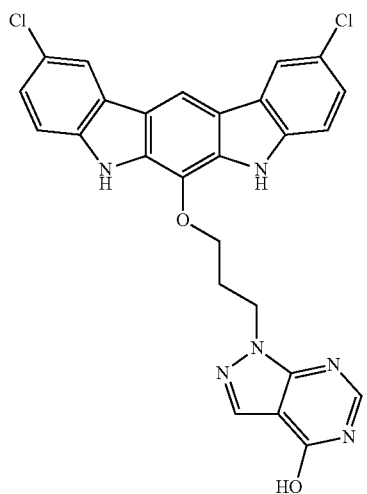

The title compounds were prepared in a manner analogous to Example 91 except the reagent is 6-chloro-purine. The reaction produces a mixture of two isomers, which can be separated by chromatography. $^1$H NMR (400 MHz, DMSO-d$_6$) δ ppm 11.27 (s, 2H), 8.68 (s, 1H), 8.16 (s, 1H), 8.15 (d, J=2.0 Hz, 2H), 8.02 (s, 1H), 7.48 (d, J=8.4 Hz, 2H), 7.36 (dd, J=8.6, 2.2 Hz, 2H), 4.50 (t, J=7.4 Hz, 2H), 4.30 (t, J=6.4 Hz, 2H), 2.44 (p, J=7.0 Hz, 2H); MS (ESI) m/z 515, 517 (M−H)$^−$. $^1$H NMR (400 MHz, DMSO-d$_6$) δ ppm 11.25 (s, 2H), 8.68 (s, 1H), 8.31 (s, 1H), 8.15 (d, J=2.0 Hz, 2H), 8.00 (s, 1H), 7.50 (d, J=8.4 Hz, 2H), 7.36 (dd, J=7.6, 2.4 Hz, 2H), 4.70 (t, J=7.4 Hz, 2H), 4.28 (t, J=6.2 Hz, 2H), 2.55-2.40 (m, 2H); MS (ESI) m/z 515, 517 (M−H)$^−$.

Example 105

8-(3-(2,10-dichloro-5,7-dihydroindolo[2,3-b]carbazol-6-yloxy)propylthio)-9H-purin-6-amine

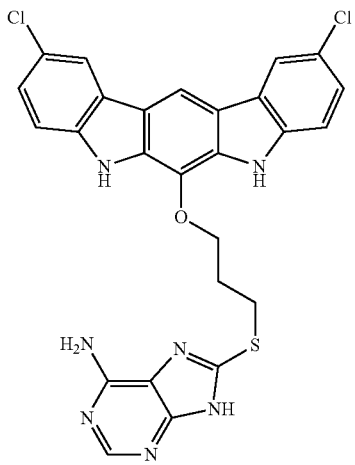 [SMILES: Nc1ncnc2[nH]c(SCCCOc3c4[nH]c5ccc(Cl)cc5c4cc4c3[nH]c3ccc(Cl)cc34)nc12]

The title compound was prepared in a manner analogous to Example 91 except the reagent is 6-amino-purine-8-thiol. $^1$H NMR (400 MHz, DMSO-d$_6$) δ ppm 11.26 (s, 2H), 8.67 (s, 1H), 8.15 (d, J=2.4 Hz, 2H), 8.03 (br s, 1H), 7.47 (d, J=8.4 Hz, 2H), 7.35 (dd, J=8.6, 2.2 Hz, 2H), 6.98 (br s, 2H), 4.39 (t, J=6.4 Hz, 2H), 3.55 (t, J=7.0 Hz, 2H), 2.33 (p, J=6.6 Hz, 2H).

Example 106

4-(2-(3-(2,10-dichloro-5,7-dihydroindolo[2,3-b]carbazol-6-yloxy)propylamino)ethyl)benzene-1,2-diol

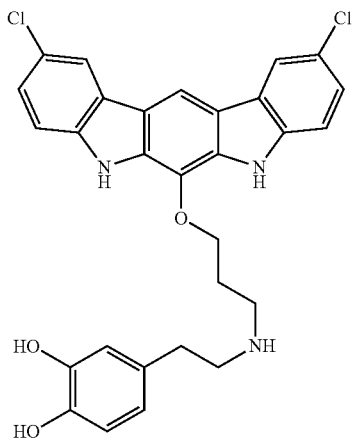 [SMILES: Oc1ccc(CCNCCCOc2c3[nH]c4ccc(Cl)cc4c3cc3c2[nH]c2ccc(Cl)cc23)cc1O]

The title compound was prepared in a manner analogous to Example 91 except the reagent is 4-(2-aminoethyl)benzene-1,2-diol hydrochloride, which was neutralized with one equivalent NaH in DMF at RT prior to reaction. $^1$H NMR (400 MHz, DMSO-d$_6$) δ ppm 11.76 (br s, 2H), 8.65 (s, 1H), 8.15 (d, J=2.4 Hz, 2H), 7.46 (d, J=8.8 Hz, 2H), 7.35 (dd, J=8.4, 2.2 Hz, 2H), 6.61 (d, J=8.0 Hz, 1H), 6.60 (d, J=2.4 Hz, 1H), 6.45 (dd, J=8.0, 2.0 Hz, 1H), 4.34 (t, J=6.2 Hz, 2H), 2.91 (t, J=6.0 Hz, 2H), 2.82 (t, J=7.6 Hz, 2H), 2.65 (t, J=7.6 Hz, 2H), 2.03 (p, J=6.4 Hz, 2H); MS (ESI) m/z 534, 536 (M+H)$^+$, 532, 534 (M–H)$^-$.

Example 107

9-(3-(2,10-dichloro-5,7-dihydroindolo[2,3-b]carbazol-6-yloxy)propyl)-9H-purin-6-amine and 7-(3-(2,10-dichloro-5,7-dihydroindolo[2,3-b]carbazol-6-yloxy)propyl)-7H-purin-6-amine

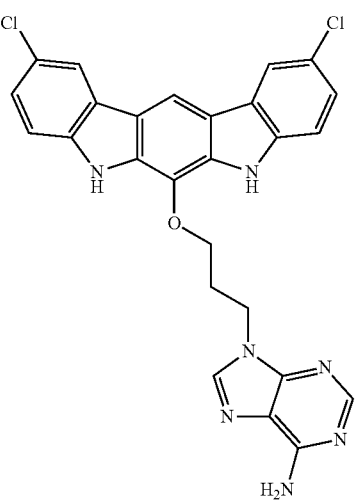 and

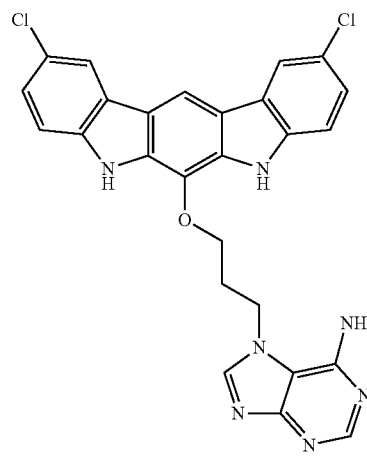

The title compounds were prepared in a manner analogous to Example 91 except the reagent is purin-6-amine. The reaction produces a mixture of two isomers, which can be separated by chromatography. $^1$H NMR (400 MHz, DMSO-d$_6$) δ ppm 11.29 (s, 2H), 8.68 (s, 1H), 8.19 (s, 1H), 8.16 (d, J=2.4 Hz, 2H), 7.48 (d, J=8.8 Hz, 2H), 7.36 (dd, J=8.6, 2.2 Hz, 2H), 7.21 (s, 2H), 4.51 (t, J=7.2 Hz, 2H), 4.29 (t, J=6.2 Hz, 2H), 2.52-2.40 (m, 2H); MS (ESI) m/z 514, 516 (M–H)$^-$, 550, 552 (M+Cl)$^-$. $^1$H NMR (400 MHz, DMSO-d$_6$) δ ppm 11.46 (s, 2H), 8.69 (s, 1H), 8.46 (s, 1H), 8.16 (d, J=2.0 Hz, 2H), 7.95 (br s, 2H), 7.89 (s, 1H), 7.51 (d, J=8.8 Hz, 2H), 7.37 (dd, J=8.4, 2.0 Hz, 2H), 4.70 (t, J=6.8 Hz, 2H), 4.31 (t, J=6.0 Hz, 2H), 2.56-2.44 (m, 2H).

Example 108

1-(3-(2,10-dichloro-5,7-dihydroindolo[2,3-b]carbazol-6-yloxy)propyl)pyrimidine-2,4(1H,3H)-dione and 3-(3-(2,10-dichloro-5,7-dihydroindolo[2,3-b]carbazol-6-yloxy)propyl)pyrimidine-2,4(1H,3H)-dione

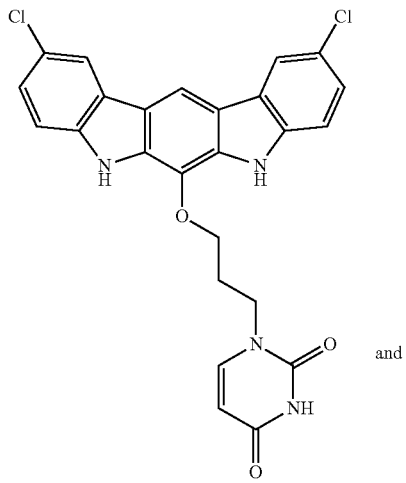

and

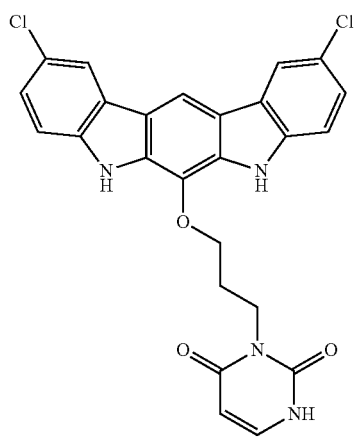

The title compounds were prepared in a manner analogous to Example 91 except the reagent is pyrimidine-2,4(1H,3H)-dione. The reaction produces a mixture of two isomers, which can be separated by chromatography. ¹H NMR (400 MHz, DMSO-d₆) δ ppm 11.22 (s, 2H), 8.66 (d, J=1.6 Hz, 1H), 8.13 (t, J=2.0 Hz, 2H), 7.84 (d, J=8.0 Hz, 1H), 7.46 (dd, J=8.6 Hz, 2H), 7.29 (ddd, J=6.4, 6.2, 2.0 Hz, 2H), 5.83 (d, J=8.0 Hz, 1H), 4.32-4.08 (m, 4H), 2.32-2.18 (m, 2H). ¹H NMR (400 MHz, DMSO-d₆) δ ppm 11.37 (br s, 1H), 11.23 (s, 2H), 8.68 (s, 1H), 8.15 (d, J=2.4 Hz, 2H), 7.74 (d, J=7.6 Hz, 1H), 7.49 (d, J=8.8 Hz, 2H), 7.36 (dd, J=8.2, 2.2 Hz, 2H), 5.59 (d, J=8.0 Hz, 1H), 4.24 (t, J=6.4 Hz, 2H), 4.03 (t, J=7.0 Hz, 2H), 2.23 (p, J=6.6 Hz, 2H).

Example 109

4-amino-1-(3-(2,10-dichloro-5,7-dihydroindolo[2,3-b]carbazol-6-yloxy)propyl)-5-fluoropyrimidin-2(1H)-one and 6-amino-1-(3-(2,10-dichloro-5,7-dihydroindolo[2,3-b]carbazol-6-yloxy)propyl)-5-fluoropyrimidin-2(1H)-one

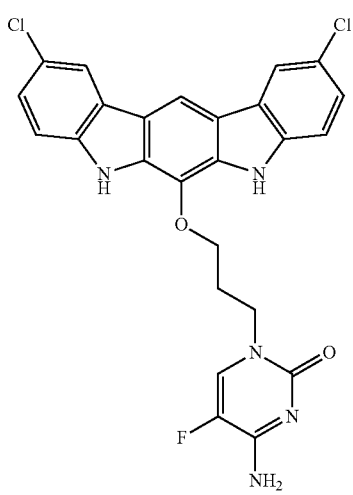

and

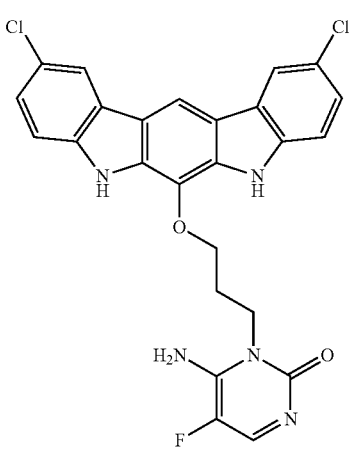

The title compounds were prepared in a manner analogous to Example 91 except the reagent is 4-amino-5-fluoropyrimidin-2(1H)-one. The reaction produces a mixture of two isomers, which can be separated by chromatography. ¹H NMR (400 MHz, DMSO-d₆) δ ppm 11.20 (s, 2H), 8.65 (d, J=1.2 Hz, 1H), 8.30 (d, J=6.8 Hz, 1H), 8.13 (t, J=2.0 Hz, 2H), 7.45 (d, J=8.0 Hz, 2H), 7.28 (td, J=8.4, 2.0 Hz, 2H), 4.32-4.06 (m, 4H), 2.32-2.18 (m, 2H). ¹H NMR (400 MHz, DMSO-d₆) δ ppm 11.23 (br s, 1H), 11.23 (s, 2H), 8.67 (s, 1H), 8.15 (d, T=2.0 Hz, 2H), 7.88 (d, T=5.2 Hz, 1H), 7.48 (d, T=8.4 Hz, 2H), 7.36 (dd, J=8.2, 2.2 Hz, 2H), 4.21 (t, J=6.4 Hz, 2H), 4.14 (t, J=7.0 Hz, 2H), 2.21 (p, J=6.8 Hz, 2H).

Example 110

4-(3-(2,10-dibromo-5,7-dihydroindolo[2,3-b]carbazol-6-yloxy)propyl)morpholine

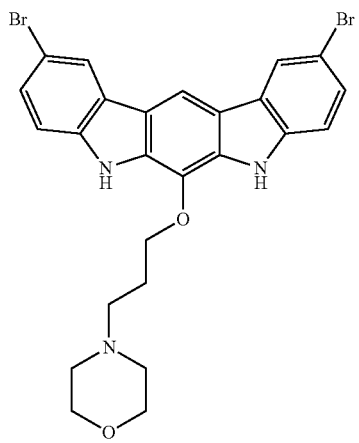 [SMILES: Brc1ccc2[nH]c3c(OCCCN4CCOCC4)c4[nH]c5ccc(Br)cc5c4cc3c2c1]

The title compound was prepared in a manner analogous to Example 70 except the starting indole is 5,7-diBOC-2,10-dibromo-6-(3-bromopropoxy)indolo[2,3-b]carbazole and the reagent is morpholine. $^1$H-NMR (400 MHz, DMSO-$d_6$) δ ppm 11.28 (s, 2 H), 8.67 (s, 1 H), 8.28 (d, J=2.0 Hz, 2H), 7.51-7.40 (m, 4 H), 4.30 (t, J=6.6 Hz, 2 H), 3.56 (t, J=4.6 Hz, 4 H), 2.52 (t, J=7.2 Hz, 2 H), 2.44-2.32 (m, 4 H), 2.11-2.00 (m, 2 H); MS (ESI) m/z 556.0 (M−H)$^−$ 5,7-diBOC-2,10-dibromo-6-(3-bromopropoxy)indolo[2,3-b]carbazole could be prepared by the Mitsunobu reaction of 3-bromopropanol and 5,7-diBOC-2,10-dibromo-6-hydroxyindolo[2,3-b]carbazole, in a manner analogous to Example 28. $^1$H-NMR (400 MHz, CDCl$_3$) δ ppm 8.90 (s, 1 H), 8.13-8.10 (m, 2 H), 7.96 (d, J=9.2 Hz, 2 H), 7.54 (dd, J=8.8, 2.0 Hz, 2 H), 4.02 9t, J=6.0 Hz, 2 H), 3.48 (t, J=6.4 Hz, 2 H), 2.15-2.06 (m, 2 H), 1.71 (s, 18 H)

Example 111

4-(4-(2,10-dibromo-5,7-dihydroindolo[2,3-b]carbazol-6-yloxy)butyl)morpholine

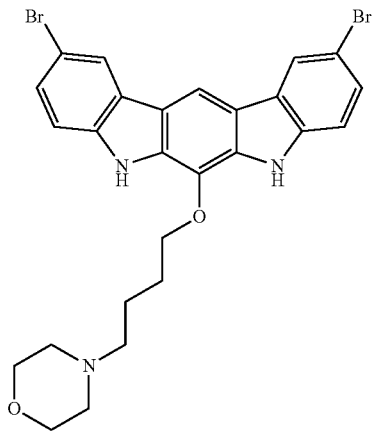 [SMILES: Brc1ccc2[nH]c3c(OCCCCN4CCOCC4)c4[nH]c5ccc(Br)cc5c4cc3c2c1]

The title compound was prepared in a manner analogous to Example 70 except the starting indole is 5,7-diBOC-2,10-dibromo-6-(4-bromobutoxy)indolo[2,3-b]carbazole and the reagent is morpholine. $^1$H-NMR (400 MHz, DMSO-$d_6$) δ ppm 11.22 (s, 2 H), 8.64 (s, 1 H), 8.25 (d, J=1.6 Hz, 2H), 7.44 (dd, J=8.4, 2.0 Hz, 2 H), 7.41 (d, J=8.4 Hz, 2 H), 4.26 (t, J=6.8 Hz, 2 H), 3.57-3.40 (m, 6 H), 2.32-2.18 (m, 4 H), 1.92-1.80 (m, 2 H), 1.65-1.50 (m, 2 H); MS (ESI) m/z 570.0 (M−H)$^−$ 5,7-diBOC-2,10-dibromo-6-(4-bromobutoxy)indolo[2,3-b]carbazole could be prepared by the Mitsunobu reaction of 4-bromobutanol and 5,7-diBOC-2,10-dibromo-6-hydroxyindolo[2,3-b]carbazole, in a manner analogous to Example 28. $^1$H-NMR (400 MHz, CDCl$_3$) δ ppm 8.79 (s, 1 H), 8.13-7.93 (m, 3 H), 7.62-7.47 (m, 3 H), 3.88 (t, J=6.4 Hz, 2 H), 3.33 (t, J=6.4 Hz, 2 H), 1.98-1.84 (m, 2 H), 1.78-1.58 9m, 20 H)

Example 112

4-(5-(2,10-dibromo-5,7-dihydroindolo[2,3-b]carbazol-6-yloxy)pentyl)morpholine

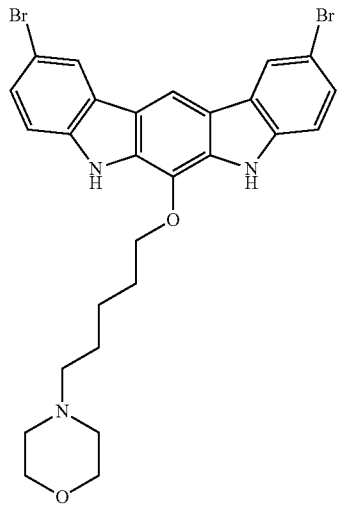 [SMILES: Brc1ccc2[nH]c3c(OCCCCCN4CCOCC4)c4[nH]c5ccc(Br)cc5c4cc3c2c1]

The title compound was prepared in a manner analogous to Example 70 except the starting indole is 5,7-diBOC-2,10-dibromo-6-(5-bromopentyloxy)indolo[2,3-b]carbazole and the reagent is morpholine. $^1$H-NMR (400 MHz, acetone-$d_6$) δ ppm 8.68 (s, 1 H), 8.32 (d, J=2.4 Hz, 2 H), 7.48-7.41 (m, 4 H), 4.34 (t, J=6.8 Hz, 2 H), 3.56 (t, J=4.8 Hz, 4 H), 2.39-2.23 (m, 6 H), 1.98-1.87 (m, 2 H), 1.60-1.44 (m, 4 H); MS (ESI) m/z 584.1 (M−H)$^−$ 5,7-diBOC-2,10-dibromo-6-(5-bromopentyloxy)indolo[2,3-b]carbazole could be prepared by the Mitsunobu reaction of 5-bromopentanol and 5,7-diBOC-2,10-dibromo-6-hydroxyindolo[2,3-b]carbazole, in a manner analogous to Example 28. $^1$H-NMR (400 MHz, CDCl$_3$) δ ppm 8.81 (s, 1 H), 8.14 (d, J=1.6 Hz, 2 H), 7.97 (d, J=8.8 Hz, 2 H), 7.55 (dd, J=8.8, 2.4 Hz, 2 H), 3.89 (t, J=6.8 Hz, 2H), 3.32 (t, J=6.8 Hz, 2 H), 1.93-1.58 (m, 24 H)

Example 113

1-(3-(2,10-difluoro-5,7-dihydroindolo[2,3-b]carbazol-6-yloxy)propyl)guanidine

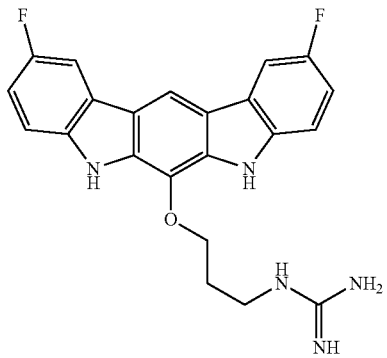 [SMILES: N=C(N)NCCCOc1c2[nH]c3ccc(F)cc3c2cc2c1[nH]c1ccc(F)cc12]

A mixture of 3-(2,10-difluoro-5,7-dihydroindolo[2,3-b]carbazol-6-yloxy)propan-1-amine (2.0 g), N,N'-Boc protected S-methylisothiourea (5.0 g), DIEA or TEA (6.0 mL) in THF/H$_2$O (70/0.6 mL) was stirred under argon at 50-90° C. overnight. After removal of all volatiles on rotary evaporator, the residue was subjected to chromatography on C18 column, eluting with H$_2$O (0.1% TFA)/MeCN (0.1% TFA) (100/0-0/100), to give the corresponding BOC-protected product. Deprotection was done under TFA (10% in volume) in DCM at RT overnight. The crude product was purified by reverse phase chromatography to give the title compound (1.6 g, 72%). $^1$H NMR (300 MHz, CD$_3$OD) δ ppm 8.42 (s, 1H), 7.80 (dd, J=9.2, 2.6 Hz, 2H), 7.41 (dd, J=8.6, 4.4 Hz, 2H), 7.09 (td, J=9.0, 2.6 Hz, 2H), 4.38 (t, J=6.6 Hz, 2H), 3.56 (t, J=7.0 Hz, 2H), 2.24 (p, J=6.8 Hz, 2H); MS (ESI) m/z 408 (M+H)$^+$.

Example 114

1-(3-(2,10-difluoro-5,7-dihydroindolo[2,3-b]carbazol-6-yloxy)propyl)-3-(3-(dimethylamino)propyl)-2-ethylguanidine

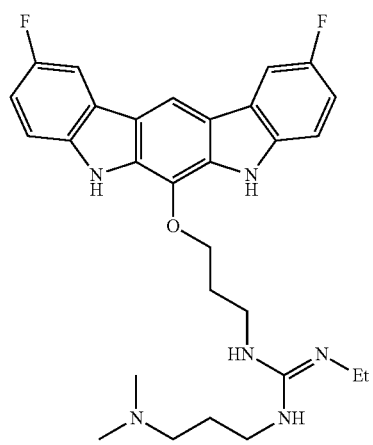 [SMILES: CC/N=C(/NCCCOc1c2[nH]c3ccc(F)cc3c2cc2c1[nH]c1ccc(F)cc12)NCCCN(C)C]

The title compound (80 mg, 47%) was obtained by heating a mixture of 3-(2,10-difluoro-5,7-dihydroindolo[2,3-b]carbazol-6-yloxy)propan-1-amine (100 mg) and 1,3-diisopropylcarbodiimide (0.2 mL) in THF (5 mL) at 80° C. overnight. $^1$H NMR (400 MHz, CD$_3$OD) δ ppm 8.47 (s, 1H), 7.83 (dd, J=9.2, 2.4 Hz, 2H), 7.42 (dd, J=8.8, 4.4 Hz, 2H), 7.11 (td, J=9.0, 2.2 Hz, 2H), 4.48 (t, J=6.2 Hz, 2H), 3.55 (t, J=6.8 Hz, 2H), 3.17-3.10 (m, 4H), 3.08-3.01 (m, 2H), 2.68 (s, 6H), 2.27 (p, J=6.6 Hz, 2H), 1.88-1.78 (m, 2H), 1.10 (t, J=7.2 Hz, 3H). MS (ESI) m/z 521 (M+H)$^+$.

Example 115

1,2-dicyclohexyl-3-(3-(2,10-difluoro-5,7-dihydroindolo[2,3-b]carbazol-6-yloxy)propyl)guanidine

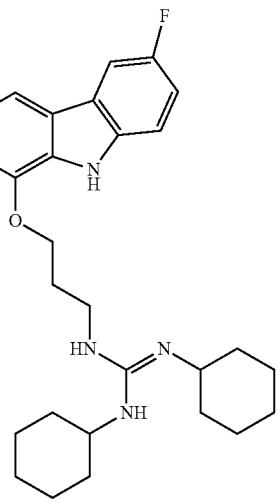

The title compound (80 mg, 38%) was obtained by heating a mixture of 3-(2,10-difluoro-5,7-dihydroindolo[2,3-b]carbazol-6-yloxy)propan-1-amine (110 mg) and 1,3-dicyclohexylcarbodiimide (70 mg) in THF (5 mL) at 85° C. overnight. $^1$H NMR (400 MHz, CD$_3$OD) δ ppm 8.46 (s, 1H), 7.82 (dd, J=9.2, 2.4 Hz, 2H), 7.40 (dd, J=8.8, 4.0 Hz, 2H), 7.10 (td, J=9.0, 2.4 Hz, 2H), 7.08 (br s, 1H), 6.61 (br d, J=7.2 Hz, 2H), 4.47 (t, J=6.6 Hz, 2H), 3.55-3.47 (m, 2H), 3.28-3.15 (m, 2H), 2.68 (s, 6H), 2.24 (p, J=6.4 Hz, 2H), 1.90-0.90 (m, 20H); MS (ESI) m/z 572 (M+H)$^+$.

Example 116

1-(3-(2,10-difluoro-5,7-dihydroindolo[2,3-b]carbazol-6-yloxy)propyl)-2,3-diisopropylguanidine

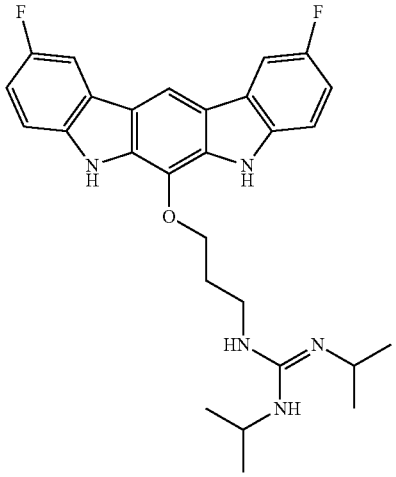 [SMILES: CC(C)/N=C(/NCCCOc1c2[nH]c3ccc(F)cc3c2cc2c1[nH]c1ccc(F)cc12)NC(C)C]

The title compound (80 mg, 47%) was obtained by heating a mixture of 3-(2,10-difluoro-5,7-dihydroindolo[2,3-b]carbazol-6-yloxy)propan-1-amine (100 mg) and 1,3-diisopropylcarbodiimide (0.2 mL) in THF (5 mL) at 80° C. overnight. $^1$H NMR (400 MHz, CD$_3$OD) δ ppm 8.45 (s, 1H), 7.82 (dd, J=9.2, 2.8 Hz, 2H), 7.40 (dd, J=8.6, 4.2 Hz, 2H), 7.13 (t, J=6.0 Hz, 1H), 7.09 (td, J=9.0, 2.6 Hz, 2H), 6.74 (br d, J=8.0 Hz, 2H), 4.44 (t, J=6.4 Hz, 2H), 3.78-3.52 (m, 4H), 2.25 (p, J=6.4 Hz, 2H), 1.11 (t, J=6.4 Hz, 12H). MS (ESI) m/z 492 (M+H)$^+$.

Example 117

N-(3-(2,10-difluoro-5,7-dihydroindolo[2,3-b]carbazol-6-yloxy)propyl)-4,5-dihydro-1H-imidazol-2-amine

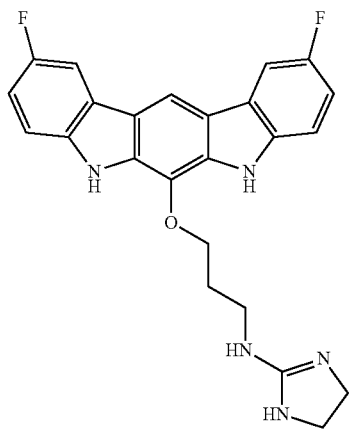 [SMILES: Fc1ccc2[nH]c3c(OCCCNC4=NCCN4)c4[nH]c5ccc(F)cc5c4cc3c2c1]

The title compound was prepared in a manner analogous to Example 113 except the reagents are 2-methylthio-2-imidazoline hydriodide and N,N-diisopropylethylamine in methanol. $^1$H-NMR (400 MHz, DMSO-d$_6$) δ ppm 11.08 (s, 2 H), 8.60 (s, 1 H), 8.30 (t, J=4.8 Hz, 1 H), 7.90 (dd, J=9.4, 2.6 Hz, 2 H), 7.45 (dd, J=8.4, 4.4 Hz, 2 H), 2.23-2.15 (m, 2 H), 4.29 (t, J=6.4 Hz, 2 H), 3.63-3.53 (m, 4 H), 3.15 (d, J=4.8 Hz, 2 H), 2.13-2.03 (m, 2 H); MS (ESI) m/z 434.2 (M+H)$^+$ Example 118

(E)-1-(3-(2,10-difluoro-5,7-dihydroindolo[2,3-b]carbazol-6-yloxy)propyl)-2-methylguanidine

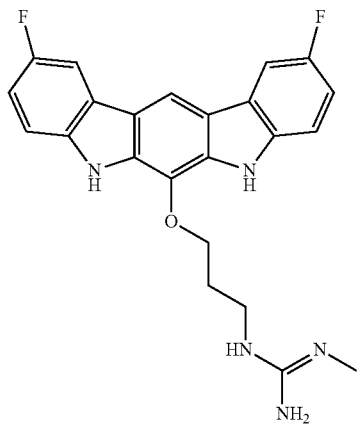 [SMILES: C/N=C(\N)NCCCOc1c2[nH]c3ccc(F)cc3c2cc2c1[nH]c1ccc(F)cc12]

The title compound was prepared in a manner analogous to Example 113 except the reagent is 1,2-dimethyl-2-thiopseudourea hydriodide. $^1$H-NMR (400 MHz, CD$_3$OD) δ ppm 8.43 (s, 1 H), 7.80 (dd, J=9.2, 2.4 Hz, 2 H), 7.43 (dd, J=8.8, 4.0 Hz, 2 H), 7.07 (td, J=9.2, 2.4 Hz, 2 H), 4.26 (t, J=6.0 Hz, 2 H), 3.62 (t, J=6.0 Hz, 2 H), 2.78 (s, 3 H), 2.13-2.04 (m, 2 H); MS (ESI) m/z 422.2 (M+H)$^+$ Example 119

1-(3-(2,10-dichloro-5,7-dihydroindolo[2,3-b]carbazol-6-yloxy)propyl)guanidine

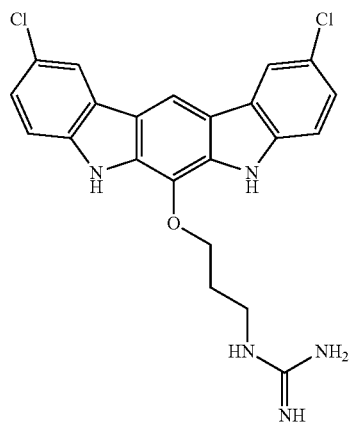 [SMILES: N=C(N)NCCCOc1c2[nH]c3ccc(Cl)cc3c2cc2c1[nH]c1ccc(Cl)cc12]

The title compound was prepared in a manner analogous to Example 113 except the starting indole is 3-(2,10-dichloro-5,7-dihydroindolo[2,3-b]carbazol-6-yloxy)propan-1-amine. $^1$H NMR (400 MHz, DMSO-d$_6$) δ ppm 11.43 (s, 2H), 8.66 (s, 1H), 8.32 (br s, 1H), 8.14 (d, J=2.0 Hz, 2H), 7.58 (d, J=8.4 Hz, 2H), 7.32 (dd, J=8.4, 2.0 Hz, 2H), 7.25 (br s, 3H), 4.29 (t, J=6.0 Hz, 2H), 2.16-2.04 (m, 2H). $^1$H NMR (400 MHz, CD$_3$OD) δ ppm 8.39 (s, 1H), 8.07 (d, J=2.0 Hz, 2H), 7.43 (d, J=8.8 Hz, 2H), 7.28 (dd, J=8.8, 2.0 Hz, 2H), 4.31 (t, J=6.2 Hz, 2H), 3.50 (t, J=6.8 Hz, 2H), 2.19 (p, J=6.4 Hz, 2H). MS (ESI) m/z 441 (M+H)$^+$.

Example 120

N-((1H-indol-3-yl)methyl)-3-(2,10-dichloro-5,7-dihydroindolo[2,3-b]carbazol-6-yloxy)propan-1-amine

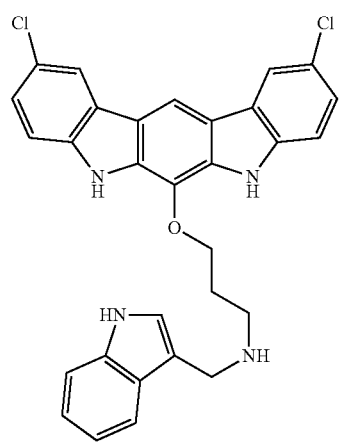 [SMILES: Clc1ccc2[nH]c3c(OCCCNCc4c[nH]c5ccccc45)c4[nH]c5ccc(Cl)cc5c4cc3c2c1]

To a solution of 3-(2,10-dichloro-5,7-dihydroindolo[2,3-b]carbazol-6-yloxy)propan-1-amine (1 equiv) in 1,2-dichloroethane (10 mL/mmol), under an atmosphere of argon, was added 1H-indole-3-carbaldehyde (1 equiv), NaBH(OAc)₃ (2 equiv), and then HOAc (2-3 equiv). The resulting mixture was stirred at RT overnight, and then partitioned between dichloromethane and 2 M Na₂CO₃. The organic layer was washed with brine, dried over Na₂SO₄, and concentrated. The residue was subjected to chromatography on silica gel, eluting with CH₂Cl₂/MeOH (10% cNH₃.H₂O) to the expected product in 50-80% yield. $^1$H NMR (400 MHz, CD₃CN) δ 11.0 (br s, 2H), 9.25 (br s, 1H), 8.31 (s, 1H), 7.99 (d, J=2.4 Hz, 2H), 7.64 (d, J=7.6 Hz, 1H), 7.44 (dt, J=8.4, 0.8 Hz, 1H), 7.21 (d, J=2.4 Hz, 1H), 7.19-7.10 (m, 3H), 7.00 (ddd, J=7.2, 6.8, 0.8 Hz, 1H), 6.93 (d, J=8.4 Hz, 1H), 4.29 (t, J=5.6 Hz, 2H), 4.09 (s, 2H), 3.07 (t, J=6.0 Hz, 2H), 2.00 (pentalet, J=5.8 Hz, 2H).

Example 121

N-((1H-pyrrol-2-yl)methyl)-3-(2,10-dichloro-5,7-dihydroindolo[2,3-b]carbazol-6-yloxy)propan-1-amine

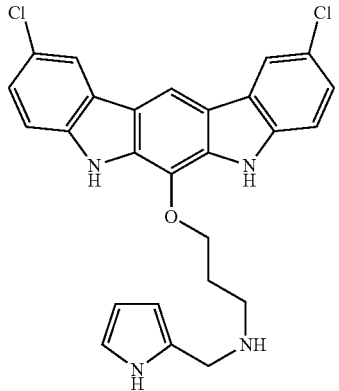 [SMILES: Clc1ccc2[nH]c3c(OCCCNCc4ccc[nH]4)c4[nH]c5ccc(Cl)cc5c4cc3c2c1]

The title compound was prepared in a manner analogous to Example 120 except the reagent is 1H-pyrrole-2-carbaldehyde. $^1$H NMR (400 MHz, CD₃CN) δ 10.7 (br s, 2H), 9.64 (br s, 1H), 8.28 (s, 1H), 7.98 (d, J=2.0 Hz, 2H), 7.30-7.15 (m, 4H), 6.72 (q, J=2.6 Hz, 1H), 6.11 (br s, 1H), 6.05 (q, J=2.8 Hz, 1H), 4.23 (t, J=5.6 Hz, 2H), 3.97 (s, 2H), 3.04 (t, J=6.2 Hz, 2H), 2.06 (pentalet, J=6.0 Hz, 2H).

Example 122

N-((1H-imidazol-2-yl)methyl)-3-(2,10-dichloro-5,7-dihydroindolo[2,3-b]carbazol-6-yloxy)propan-1-amine

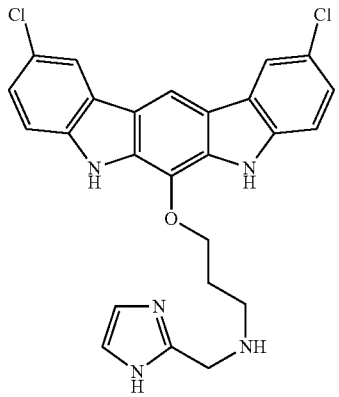 [SMILES: Clc1ccc2[nH]c3c(OCCCNCc4ncc[nH]4)c4[nH]c5ccc(Cl)cc5c4cc3c2c1]

The title compound was prepared in a manner analogous to Example 120 except the reagent is 1H-imidazole-2-carbaldehyde. $^1$H NMR (400 MHz, CD₃CN) δ 10.9 (br s, 2H), 8.47 (s, 1H), 8.07 (dd, J=2.0, 0.4 Hz, 2H), 7.35-7.20 (m, 4H), 7.02 (s, 2H), 4.36 (t, J=5.6 Hz, 2H), 4.00 (s, 2H), 3.04 (t, J=6.0 Hz, 2H), 2.07 (pentalet, J=6.2 Hz, 2H).

Example 123

3-((3-(2,10-difluoro-5,7-dihydroindolo[2,3-b]carbazol-6-yloxy)propyl)(3-(dimethylamino)propyl)amino)propanoic acid

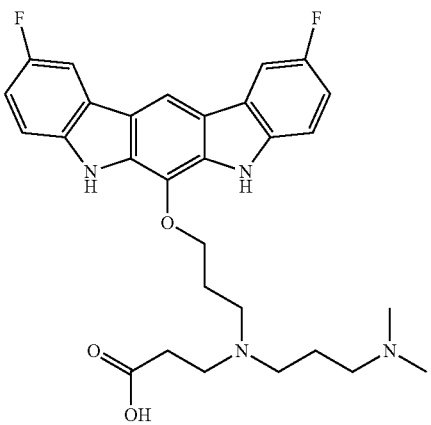 [SMILES: CN(C)CCCN(CCCOc1c2[nH]c3ccc(F)cc3c2cc2c1[nH]c1ccc(F)cc12)CCC(=O)O]

To a suspension of 3,3-dimethylaminopropyl amine (180 mg) and K₂CO₃ (280 mg) in DMF (10 mL), was added 6-(3-bromopropoxy)-2,10-difluoro-5,7-diBOC-indolo[2,3-b]carbazole (200 mg) and KI (15 mg). The mixture was stirred at 50° C. for 4 h, and then evaporated to remove DMF and excess of amine. To the residue was added DMF (10 mL), K₂CO₃ (137 mg), KI (8 mg), and benzyl 3-bromopropanoate, which was prepared from 3-bromopropanoyl chloride and benzyl alcohol. The mixture was stirred at 50° C. overnight, and partitioned between ethyl acetate and water; the organic phase was separated, washed with brine, dried over Na₂SO₄, and evaporated to dryness. The crude material was purified by chromatography on silica gel to 6-(3-((3-(benzyloxy)-3-oxopropyl)(3-(dimethylamino)propyl)amino)propoxy)-2,10-difluoro-5,7-diBOC-indolo[2,3-b]carbazole (96 mg), which was deprotected under TFA/DCM at RT overnight to give benzyl 3-((3-(2,10-difluoro-5,7-dihydroindolo[2,3-b]carbazol-6-yloxy)propyl)(3-(dimethylamino)propyl)amino)propanoate (61 mg). This resulting material was dissolved in MeOH (50 mL) follow by addition of Pd(10% on C) (40 mg). After flushed 3 times with H₂, the mixture was shaken under H₂ (40 psi) until hydrogenation was complete. After filtered through a pad of Celite, the solid was washed with ethyl acetate, DCM, and MeOH. The washings were combined to the filtrate, and the solvents were removed to give crude product (12 mg), which was purified by C18 column, giving the title product (3 mg). $^1$H NMR (400 MHz, CD₃OD) 8.43 (s, 1H), 7.80 (dd, J=9.2, 2.4 Hz, 2H), 7.42 (dd, J=8.6, 4.2 Hz, 2H), 7.09 (td, J=9.0, 2.4 Hz, 2H), 4.30 (t, J=5.4 Hz, 2H), 3.66 (t, J=5.7 Hz, 2H), 3.56 (t, J=6.0 Hz, 2H), 3.34 (t, J=5.7 Hz, 2H), 3.17 (t, J=5.7 Hz, 2H), 2.92 (t, J=5.6 Hz, 2H), 2.83 (s, 6H), 2.48-2.34 (m, 2H), 2.32-2.16 (m, 2H).

Example 124

2-(12-bromo-2,10-difluoro-5,7-dihydroindolo[2,3-b]carbazol-6-yloxy)-N,N-dimethylethanamine

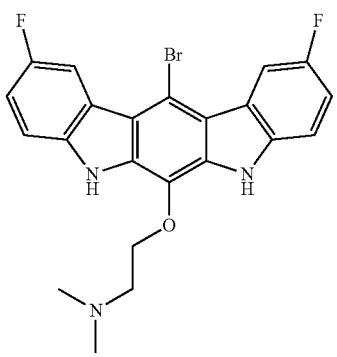 [SMILES: CN(C)CCOc1c2[nH]c3ccc(F)cc3c2c(Br)c2c1[nH]c1ccc(F)cc12]

To a solution of 2-(2,10-difluoro-5,7-dihydroindolo[2,3-b]carbazol-6-yloxy)-N,N-dimethylethanamine (213.9 mg, 0.5638 mmol) in DMF (20 mL) at 0° C. was added $Br_2$ in $CH_2Cl_2$ (50 mg/mL, 1.982 mL, 0.6201 mmol). The reaction was warmed to room temperature and stirred for two hours. DMF was removed via vacuum pump. The residue was dissolved in ethyl acetate (100 mL) and washed with saturated aq. $NaCO_3$. The organic layers was concentrated and subjected to flash chromatography to provide the title compound (188.4 mg, 73%). $^1$H-NMR (400 MHz, DMSO-$d_6$) δ ppm 11.89 (br s, 2 H), 8.39 (dd, J=10.0, 2.4 Hz, 2 H), 7.55 (dd, J=8.8, 4.4 Hz, 2 H), 7.31 (td, J=8.8, 2.4 Hz, 2 H), 4.34 (t, J=5.2 Hz, 2 H), 2.74 (t, J=5.6 Hz, 2 H), 2.36 (s, 6 H); MS (ESI) m/z 456.1 (M−H)$^-$; MS (ESI) m/z 458.0 (M+H)$^+$

Example 125

6-(2-(dimethylamino)ethoxy)-2,10-difluoro-5,7-dihydroindolo[2,3-b]carbazole-12-carbonitrile

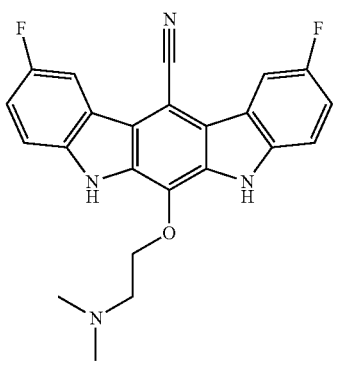 [SMILES: CN(C)CCOc1c2[nH]c3ccc(F)cc3c2c(C#N)c2c1[nH]c1ccc(F)cc12]

A mixture of 2-(12-bromo-2,10-difluoro-5,7-dihydroindolo[2,3-b]carbazol-6-yloxy)-N,N-dimethylethanamine (97.8 mg, 0.1991 mmol), zinc cyanide (233.7 mg, 1.9910 mmol) and tetrakis(triphenylphosphine)palladium (0) (23.0 mg, 0.01991 mmol) in anhydrous DMF was purged with high-purity Ar for five minutes, sealed with Teflon cap and heated to 160° C. for 12 hours. The reaction mixture was cooled down and filtered. The solvent was removed via vacuum pump. The residue was purified via flash chromatography to provide the title compound (37.3 mg, 46%). $^1$H-NMR (400 MHz, DMSO-$d_6$) δ ppm 11.90 (s, 2 H), 8.39 (dd, J=10.2, 2.8 Hz, 2 H), 7.55 (dd, 8.8, 4.4 Hz, 2 H), 7.31 (td, J=8.8, 2.4 Hz, 2 H), 4.33 (t, J=4.2 Hz, 2 H), 2.74 (t, J=4.2 Hz, 2 H), 2.35 (s, 6 H); MS (ESI) m/z 403.1 (M−H)$^-$; MS (ESI) m/z 405.0 (M+H)$^+$

Example 126

2-(2,10-difluoro-12-(pyrrolidin-1-yl)-5,7-dihydroindolo[2,3-b]carbazol-6-yloxy)-N,N-dimethylethanamine

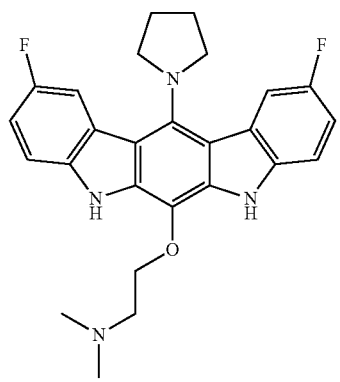 [SMILES: CN(C)CCOc1c2[nH]c3ccc(F)cc3c2c(N2CCCC2)c2c1[nH]c1ccc(F)cc12]

A mixture of 2-(12-bromo-2,10-difluoro-5,7-dihydroindolo[2,3-b]carbazol-6-yloxy)-N,N-dimethylethanamine (35.2 mg, 0.07681 mmol), pyrrolidine (19.1 µL, 0.2304 mmol), Pd(OAc)$_2$ (5.2 mg, 0.02304 mmol), BINAP (14.3 mg, 0.02304 mmol) and sodium tert-butoxide (22.1 mg, 0.2304 mmol) in toluene (5 mL) was purged with high-purity Ar for five minutes and sealed with Teflon cap. The reaction tube was heated to 200° C. in a Smith Microwave Reactor for 10 minutes. The solvents were removed via vacuum pump. The residue was subjected to flash chromatography to provide the title compound (5.2 mg, 15%). $^1$H-NMR (400 MHz, DMSO-$d_6$) δ ppm 11.53 (s, 2 H), 7.70 (dd, J=10.0, 2.4 Hz, 2 H), 7.47 (dd, J=8.8, 4.8 Hz, 2 H), 7.19 (td, J=9.2, 2.4 Hz, 2 H), 4.29 (t, J=5.6 Hz, 2 H), 3.52-3.45 (m, 4 H), 2.72 (t, J=5.6 Hz, 2 H), 2.40-2.39 (m, 10 H); MS (ESI) m/z 447.2 (M−H)$^-$; MS (ESI) m/z 449.0 (M+H)$^+$

Example 127

2-(12-bromo-2,10-dichloro-5,7-dihydroindolo[2,3-b]carbazol-6-yloxy)-N,N-dimethylethanamine

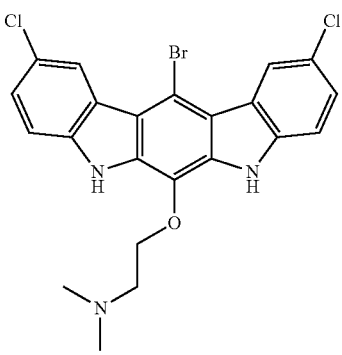 [SMILES: CN(C)CCOc1c2[nH]c3ccc(Cl)cc3c2c(Br)c2c1[nH]c1ccc(Cl)cc12]

The title compound was prepared in a manner analogous to Example 124 except the starting indole is 2-(2,10-dichloro-5,7-dihydroindolo[2,3-b]carbazol-6-yloxy)-N,N-dimethyl-ethanamine. ¹H-NMR (400 MHz, DMSO-d₆) δ ppm 12.09 (br s, 2 H), 8.66 (d, J=2.0 Hz, 2 H), 7.58 (d, J=8.4 Hz, 2 H), 7.48 (dd, J=8.8, 2.4 Hz, 2 H), 4.34 (t, J=5.6 Hz, 2 H), 2.74 (t, J=5.6 Hz, 2 H), 2.36 (s, 6 H); MS (ESI) m/z 490.0 (M−H)⁻; MS (ESI) m/z 491.9 (M+H)⁺

Example 128

2-(2,10-dichloro-12-(pyrrolidin-1-yl)-5,7-dihydroindolo[2,3-b]carbazol-6-yloxy)-N,N-dimethylethanamine

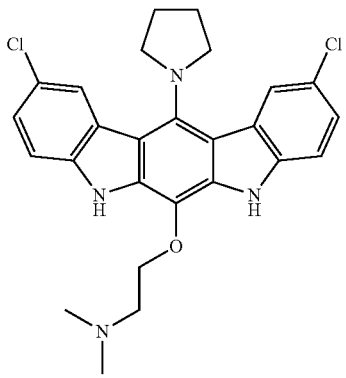 [SMILES: CN(C)CCOc1c2[nH]c3ccc(Cl)cc3c2c(N2CCCC2)c2c1[nH]c1ccc(Cl)cc12]

The title compound was prepared in a manner analogous to Example 126 except the starting indole is 2-(12-bromo-2,10-dichloro-5,7-dihydroindolo[2,3-b]carbazol-6-yloxy)-N,N-dimethylethanamine. ¹H-NMR (400 MHz, CDCl₃) δ ppm 10.14 (br s, 2 H), 8.11 (s, 2 H), 7.37-7.28 (m, 4H), 4.34 (t, J=4.4 Hz, 2 H), 2.72 (t, J=4.4 Hz, 2 H), 3.67-3.55 (m, 4 H), 2.53 (s, 6 H), 2.45-2.33 (m, 4H); MS (ESI) m/z 479.1 (M−H)⁻; MS (ESI) m/z 481.1 (M+H)⁺

Example 129

12-bromo-2,10-difluoro-6-methoxy-5,7-dihydroindolo[2,3-b]carbazole

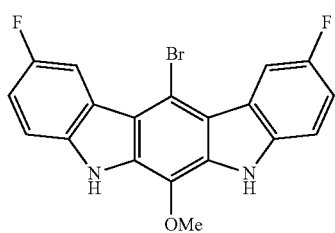 [SMILES: COc1c2[nH]c3ccc(F)cc3c2c(Br)c2c1[nH]c1ccc(F)cc12]

The title compound was prepared in a manner analogous to Example 124 except the starting indole is 2,10-difluoro-6-methoxy-5,7-dihydroindolo[2,3-b]carbazole. ¹H NMR (400 MHz, DMSO-d₆) δ 11.61 (s, 2H), 8.39 (dd, J=10.0, 2.4 Hz, 2H), 7.51 (dd, J=8.8, 4.4 Hz, 2H), 7.31 (dd, J=9.0, 2.8 Hz, 2H), 4.08 (s, 3H).

Example 130

12-cyclopropyl-2,10-difluoro-6-methoxy-5,7-dihydroindolo[2,3-b]carbazole

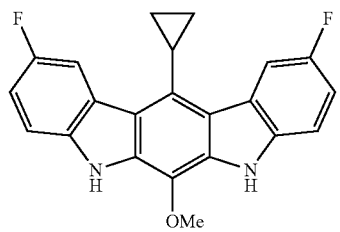 [SMILES: COc1c2[nH]c3ccc(F)cc3c2c(C2CC2)c2c1[nH]c1ccc(F)cc12]

The title compound was obtained (69% yield) by coupling of 12-bromo-2,10-difluoro-6-methoxy-5,7-dihydroindolo[2,3-b]carbazole with cyclopropyl boric acid (10 equiv) using Pd(OAc)₂ and PCy₃ as catalyst in the presence of K₃PO₄ in PhMe/H₂O (4/1) at 100° C. ¹H NMR (400 MHz, DMSO-d₆) δ ppm 11.25 (s, 2H), 8.16 (dd, J=10.6, 2.6 Hz, 2H), 7.44 (dd, J=8.8, 4.8 Hz, 2H), 7.20 (td, J=9.0, 2.8 Hz, 2H), 4.04 (s, 3H), 2.70-2.60 (m, 1H), 1.58-1.50 (m, 2H), 0.72-0.64 (m, 2H).

Example 131

2,10-difluoro-6-methoxy-12-methyl-5,7-dihydroindolo[2,3-b]carbazole

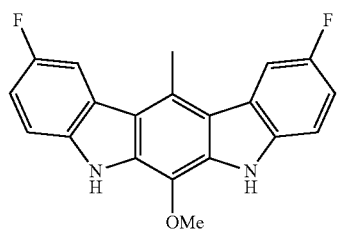 [SMILES: COc1c2[nH]c3ccc(F)cc3c2c(C)c2c1[nH]c1ccc(F)cc12]

The title compound was obtained (59% yield) by coupling of 12-bromo-2,10-difluoro-6-methoxy-5,7-dihydroindolo[2,3-b]carbazole with methyl boric acid (10 equiv) using (dppf)PdCl₂.CH₂Cl₂ as catalyst in the presence of Cs₂CO₃ and CsF in 1,4-dioxane at 100° C. ¹H NMR (400 MHz, DMSO-d₆) δ ppm 11.26 (s, 2H), 7.99 (dd, J=10.4, 2.4 Hz, 2H), 7.44 (dd, J=8.8, 4.8 Hz, 2H), 7.19 (td, J=9.2, 2.4 Hz, 2H), 4.03 (s, 3H), 3.18 (s, 3H).

Example 132

(E)-3-(2,10-difluoro-6-methoxy-5,7-dihydroindolo[2,3-b]carbazol-12-yl)acrylamide

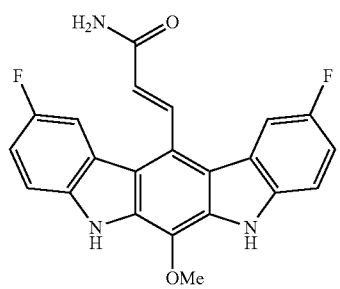 [SMILES: COc1c2[nH]c3ccc(F)cc3c2c(/C=C/C(N)=O)c2c1[nH]c1ccc(F)cc12]

The title compound was obtained (61% yield) by Heck reaction: coupling 12-bromo-2,10-difluoro-6-methoxy-5,7-dihydroindolo[2,3-b]carbazole with acrylamide (10 equiv) using Pd(OAc)$_2$ and P(o-Tol)$_3$ as catalyst in the presence of TEA in acetonitrile under reflux condition. $^1$H NMR (400 MHz, DMSO-d$_6$) δ ppm 11.43 (s, 2H), 8.37 (d, J=16.0 Hz, 2H), 7.86 (br s, 1H), 7.76 (dd, J=10.2, 2.6 Hz, 2H), 7.48 (dd, J=8.8, 4.8 Hz, 2H), 7.41 (br s, 1H), 7.20 (td, J=9.0, 2.4 Hz, 2H), 6.73 (d, J=16.0 Hz, 1H), 4.09 (s, 3H); MS (ESI) m/z 390 (M−H)$^-$, 426 (M+Cl)$^-$.

Example 133

2,10-difluoro-6-methoxy-12-(pyrrolidin-1-yl)-5,7-dihydroindolo[2,3-b]carbazole

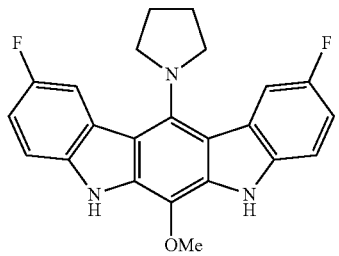 [SMILES: COc1c2[nH]c3ccc(F)cc3c2c(N2CCCC2)c2c1[nH]c1ccc(F)cc12]

The title compound was prepared by the reaction tert-butyl 12-bromo-2,10-difluoro-6-methoxyindolo[2,3-b]carbazole-5(7H)-carboxylate with pyrrolidine in the presence of Pd(OAc)$_2$, BINAP, and NaO$^t$Bu at 80° C. for 2 h, followed deprotection with TFA. $^1$H NMR (400 MHz, DMSO-d$_6$) δ ppm 11.29 (s, 2H), 7.70 (dd, J=10.0, 2.4 Hz, 2H), 7.43 (dd, J=8.8, 4.8 Hz, 2H), 7.19 (td, J=9.2, 2.4 Hz, 2H), 4.05 (s, 3H), 3.43-3.55 (m, 4H), 2.40-2.30 (m, 4H).

Example 134

2,10-difluoro-6-methoxy-N-methyl-5,7-dihydroindolo[2,3-b]carbazol-12-amine

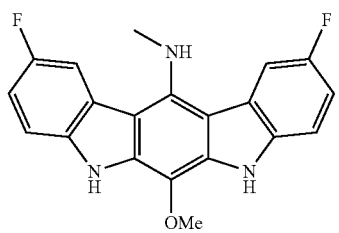 [SMILES: CNc1c2c([nH]c3ccc(F)cc32)c(OC)c2[nH]c3ccc(F)cc3c12]

The title compound was prepared in a manner analogous to Example 133. This compound was obtained by heating di-tert-butyl 12-bromo-2,10-difluoro-6-methoxyindolo[2,3-b]carbazole-5,7-dicarboxylate and MeNH$_2$ in a bomb, in the presence of Pd(OAc)$_2$, BINAP, and NaO$^t$Bu at 80° C. overnight. $^1$H NMR (400 MHz, DMSO-d$_6$) δ ppm 11.17 (s, 2H), 8.06 (dd, J=10.2, 2.6 Hz, 2H), 7.39 (dd, J=8.8, 4.4 Hz, 2H), 7.14 (td, J=9.2, 2.4 Hz, 2H), 4.77 (q, J=5.6 Hz, 1H), 4.00 (s, 3H), 3.01 (d, J=5.6 Hz, 3H).

Example 135

N1-(2,10-difluoro-6-methoxy-5,7-dihydroindolo[2,3-b]carbazol-12-yl)-N2,N2-dimethylethane-1,2-diamine

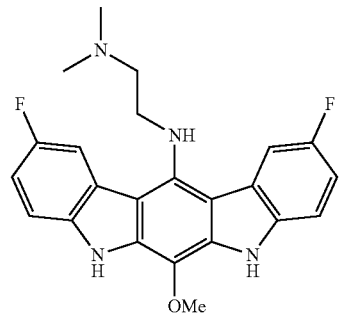 [SMILES: COc1c2[nH]c3ccc(F)cc3c2c(NCCN(C)C)c2c1[nH]c1ccc(F)cc12]

The title compound was prepared in a manner analogous to Example 133. This compound was obtained from di-tert-butyl 12-bromo-2,10-difluoro-6-methoxyindolo[2,3-b]carbazole-5,7-dicarboxylate and 2,2-dimethylaminoethyl amine. $^1$H NMR (400 MHz, CD$_3$CN) δ ppm 9.43 (s, 2H), 8.08 (dd, J=10.2, 2.6 Hz, 2H), 7.42 (dd, J=8.8, 4.4 Hz, 2H), 7.12 (td, J=9.0, 2.8 Hz, 2H), 4.02 (s, 3H), 3.41 (t, J=5.4 Hz, 2H), 2.57 (t, J=5.4 Hz, 2H), 2.35 (s, 6H). MS (ESI) m/z 409 (M+H)$^+$.

Example 136

N1-(2,10-difluoro-6-methoxy-5,7-dihydroindolo[2,3-b]carbazol-12-yl)propane-1,3-diamine

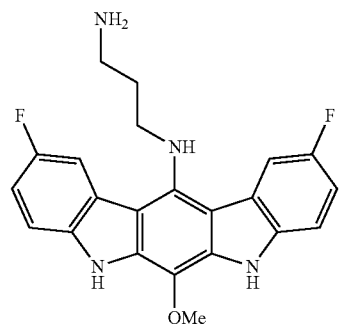 [SMILES: COc1c2[nH]c3ccc(F)cc3c2c(NCCCN)c2c1[nH]c1ccc(F)cc12]

The title compound was prepared in a manner analogous to Example 133. This compound was obtained from tert-butyl 12-bromo-2,10-difluoro-6-methoxyindolo[2,3-b]carbazole-5(7H)-carboxylate and 1,3-propanediamine under microwave for 10 min. $^1$H NMR (400 MHz, DMSO-d$_6$) δ ppm 11.16 (s, 2H), 8.06 (dd, J=10.4, 2.8 Hz, 2H), 7.39 (dd, J=8.6, 4.6 Hz, 2H), 7.13 (td, J=9.0, 2.6 Hz, 2H), 4.94 (t, J=7.0 Hz, 1H), 4.00 (s, 3H), 3.06 (td, J=5.8, 2.6 Hz, 2H), 2.61 (t, J=6.8 Hz, 2H), 1.80-1.70 (m, 2H).

Example 137

N1-(2,10-difluoro-6-methoxy-5,7-dihydroindolo[2,3-b]carbazol-12-yl)-N3,N3-dimethylpropane-1,3-diamine

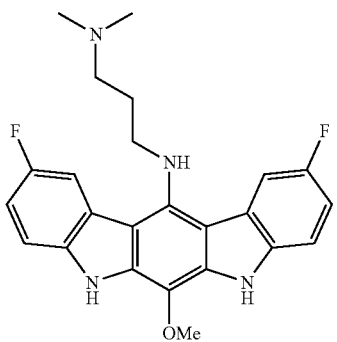 [SMILES: COc1c2[nH]c3ccc(F)cc3c2c(NCCCN(C)C)c2c1[nH]c1ccc(F)cc12]

The title compound was prepared in a manner analogous to Example 136. This compound was obtained from tert-butyl 12-bromo-2,10-difluoro-6-methoxyindolo[2,3-b]carbazole-5(7H)-carboxylate and 3,3-dimethylaminopropyl amine under microwave for 10 min. $^1$H NMR (400 MHz, DMSO-d$_6$) δ ppm 11.17 (s, 2H), 8.05 (dd, J=10.2, 2.6 Hz, 2H), 7.40 (dd, J=8.6, 4.6 Hz, 2H), 7.14 (td, J=9.2, 2.6 Hz, 2H), 5.01 (t, J=7.2 Hz, 1H), 4.00 (s, 3H), 2.40 (t, J=6.6 Hz, 2H), 2.18 (s, 6H), 1.90 (m, 2H).

Example 138

N1-(2,10-difluoro-6-methoxy-5,7-dihydroindolo[2,3-b]carbazol-12-yl)ethane-1,2-diamine

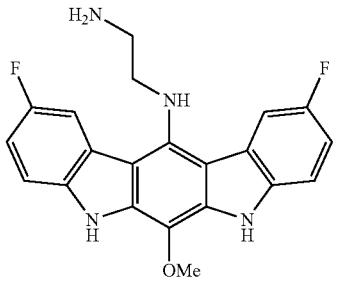 [SMILES: COc1c2[nH]c3ccc(F)cc3c2c(NCCN)c2c1[nH]c1ccc(F)cc12]

The title compound was prepared in a manner analogous to Example 136. This compound was obtained from tert-butyl 12-bromo-2,10-difluoro-6-methoxyindolo[2,3-b]carbazole-5(7H)-carboxylate and 1,2-ethylenediamine under microwave for 30 min. $^1$H NMR (400 MHz, DMSO-d$_6$) δ ppm 11.19 (s, 2H), 8.07 (dd, J=10.2, 2.6 Hz, 2H), 7.39 (dd, J=8.6, 4.6 Hz, 2H), 7.14 (td, J=9.0, 2.6 Hz, 2H), 4.97 (t, J=6.4 Hz, 1H), 4.00 (s, 3H), 3.27 (t, J=5.6 Hz, 2H), 2.85 (t, J=6.0 Hz, 2H).

Example 139

2,10-difluoro-6-methoxy-12-(piperazin-1-yl)-5,7-dihydroindolo[2,3-b]carbazole

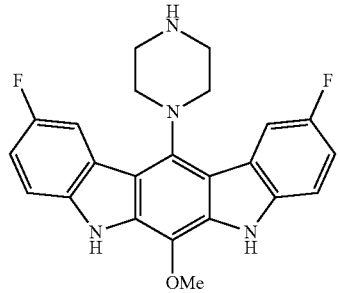 [SMILES: COc1c2[nH]c3ccc(F)cc3c2c(N2CCNCC2)c2c1[nH]c1ccc(F)cc12]

The title compound was prepared in a manner analogous to Example 126. This compound was obtained from di-tert-butyl 12-bromo-2,10-difluoro-6-methoxyindolo[2,3-b]carbazole-5,7-dicarboxylate and piperazine, followed by deprotection with TFA. $^1$H NMR (400 MHz, CD$_3$OD) δ ppm 8.38 (dd, J=10.2, 2.6 Hz, 2H), 7.41 (dd, J=8.8, 4.4 Hz, 2H), 7.11 (td, J=9.0, 2.4 Hz, 2H), 4.10 (s, 3H), 3.65-3.56 (m, 4H), 3.45-3.36 (m, 4H).

Example 140

N-butyl-2,10-difluoro-6-methoxy-5,7-dihydroindolo[2,3-b]carbazol-12-amine

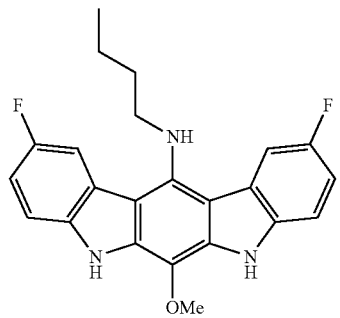 [SMILES: CCCCNc1c2c([nH]c3ccc(F)cc32)c(OC)c2[nH]c3ccc(F)cc3c12]

The title compound was prepared in a manner analogous to Example 126. This compound was obtained from di-tert-butyl 12-bromo-2,10-difluoro-6-methoxyindolo[2,3-b]carbazole-5,7-dicarboxylate and butylamine. $^1$H NMR (400 MHz, DMSO-d$_6$) δ ppm 11.17 (s, 2H), 8.01 (dd, J=10.2, 2.6 Hz, 2H), 7.39 (dd, J=8.8, 4.4 Hz, 2H), 7.13 (td, J=9.0, 2.4 Hz, 2H), 4.79 (t, J=7.0 Hz, 1H), 4.00 (s, 3H), 1.70-1.59 (m, 2H), 1.37-1.24 (m, 2H), 0.80 (t, J=7.4 Hz, 2H). MS (ESI) m/z 392 (M−H)$^-$.

Example 141

2,10-difluoro-6-methoxy-12-(4-methylpiperazin-1-yl)-5,7-dihydroindolo[2,3-b]carbazole

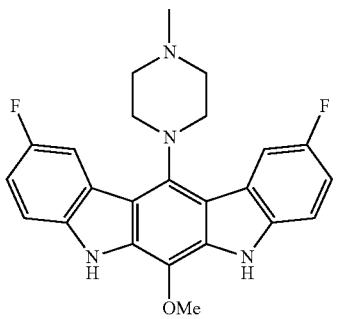 [SMILES: COc1c2[nH]c3ccc(F)cc3c2c(N2CCN(C)CC2)c2c1[nH]c1ccc(F)cc12]

The title compound was prepared in a manner analogous to Example 126. This compound was obtained from di-tert-butyl 12-bromo-2,10-difluoro-6-methoxyindolo[2,3-b]carbazole-5,7-dicarboxylate and 4-methylpiperazine. $^1$H NMR (400 MHz, DMSO-d$_6$) δ ppm 11.32 (s, 2H), 8.26 (dd, J=10.6, 2.6 Hz, 2H), 7.44 (dd, J=8.6, 4.6 Hz, 2H), 7.20 (td, J=9.0, 2.6 Hz, 2H), 4.05 (s, 3H), 3.46-3.37 (br m, 4H), 2.78-2.70 (br m, 4H), 2.42 (s, 3H); MS (ESI) m/z 421 (M+H)$^+$.

Example 142

4-(2,10-difluoro-6-methoxy-5,7-dihydroindolo[2,3-b]carbazol-12-yl)morpholine

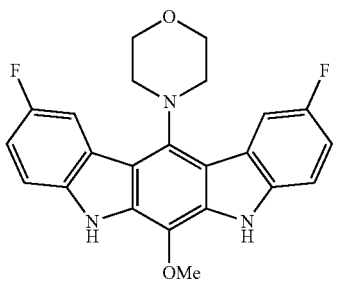 [SMILES: COc1c2[nH]c3ccc(F)cc3c2c(N2CCOCC2)c2c1[nH]c1ccc(F)cc12]

The title compound was prepared in a manner analogous to Example 126. This compound was obtained from di-tert-butyl 12-bromo-2,10-difluoro-6-methoxyindolo[2,3-b]carbazole-5,7-dicarboxylate and morpholine. $^1$H NMR (400 MHz, CD$_3$CN) δ ppm 9.50 (s, 2H), 8.32 (dd, J=10.4, 2.4 Hz, 2H), 7.46 (dd, J=8.6, 4.6 Hz, 2H), 7.18 (td, J=9.0, 2.6 Hz, 2H), 4.08 (s, 3H), 4.12-4.06 (br m, 4H), 3.48-3.43 (br m, 4H); MS (ESI) m/z 406 (M−H)$^−$.

Example 143

3-(5,7-dihydroindolo[2,3-b]carbazol-6-yl)-N,N-dimethylprop-2-yn-1-amine

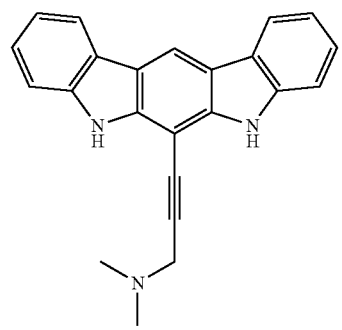 [SMILES: CN(C)CC#Cc1c2[nH]c3ccccc3c2cc2c1[nH]c1ccccc12]

To a solution of 5,7-diBOC-6-hydroxyindolo[2,3-b]carbazole (5.6043 g, 11.8603 mmol) in anhydrous THF (250 mL) was added 60% NaH (0.4744 g, 11.8603 mmol) under the protection of Ar. The solution was stirred at room temperature for 0.5 hour. Then the temperature was increased to 40° C. After half an hour, phenyltrifluoromethane-sulfonimide (5.0845 g, 14.2323 mmol) was added. The reaction was stirred at 40° C. for 3 hours under the protection of Ar. TLC showed that the reaction was complete. The reaction solution was concentrated and separated by flash chromatography to provide the 5,7-diBOC-6-(trifluoromethylsulfonyloxy)indolo[2,3-b]carbazole (6.293 g, 88%). MS (ESI) m/z 626.8 (M+Na)$^+$ A mixture of 5,7-diBOC-6-(trifluoromethylsulfonyloxy)indolo[2,3-b]carbazole (652.5 mg, 1.0792 mmol), 1-dimethylamino-2-propyne (0.5383 g, 6.4755 mmol), Copper (I) iodide (82 mg, 0.4317 mmol), triethylamine (0.9025 mL, 6.4752 mmol), tetrakis(triphenylphosphine)palladium (0) and anhydrous DMF (10 mL) was purged with high purity Ar for five minutes, sealed with a Teflon cap, and heated to 50° C. with fast stirring for 12 hours. The reaction was concentrated and dried under vacuum pump. The residue was dissolved in ethyl acetate and subjected to flash chromatography to provide 5,7-diBOC-6-(3-(dimethylamino)prop-1-ynyl)indolo[2,3-b]carbazole (0.3193 g, 55%). $^1$H-NMR (400 MHz, CDCl$_3$) δ ppm 8.54 (s, 1H), 8.11-8.01 (m, 4H), 7.50-7.37 (m, 4H), 4.15 (br s, 2H), 2.91 (s, 6H), 1.71 (s, 18 H); MS (ESI) m/z 538.0 (M+H)$^+$, 560.0 (M+Na)$^+$ 5,7-diBOC-6-(3-(dimethylamino)prop-1-ynyl)indolo[2,3-b]carbazole (165.6 mg, 0.3080 mmol) was deprotected by heating at 180° C. for 30 minutes under Ar. The crude product was purified by flash chromatography to provide 3-(5,7-dihydroindolo[2,3-b]carbazol-6-yl)-N,N-dimethylprop-2-yn-1-amine (34.7 mg, 33%). $^1$H-NMR (400 MHz, DMSO-d$_6$) δ ppm 11.51 (s, 2 H), 8.84 (s, 1 H), 8.15 (d, J=7.6 Hz, 2 H), 7.54 (d, J=8.0 Hz, 2 H), 7.39-7.31 (m, 2 H), 7.21-7.12 (m, 2 H), 3.69 (s, 2 H), 2.39 (s, 6 H); MS (ESI) m/z 334.3 (M−H)$^−$; MS (ESI) m/z 336.1 (M+H)$^+$

Example 144

3-(5,7-dihydroindolo[2,3-b]carbazol-6-yl)-N,N-dimethylpropan-1-amine

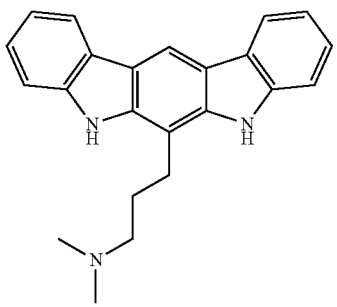 [SMILES: CN(C)CCCc1c2[nH]c3ccccc3c2cc2c1[nH]c1ccccc12]

A mixture of 3-(5,7-dihydroindolo[2,3-b]carbazol-6-yl)-N,N-dimethylprop-2-yn-1-amine (30 mg, 0.08891 mmol), 10% Pd/C (10 mg, 0.0094 mmol) and methanol (20 mL) in a 250-mL hydrogenation bottle was filled with $H_2$ and then degassed via house vacuum. This process was repeated three times. The reaction mixture was shaken at room temperature under $H_2$ (30 psi) for 12 hours. The reaction solution was filtered through celite, and concentrated. The residue was subjected to flash chromatography to provide 3-(5,7-dihydroindolo[2,3-b]carbazol-6-yl)-N,N-dimethylpropan-1-amine. (10.2 mg, 34%). $^1$H-NMR (400 MHz, DMSO-$d_6$) δ ppm 11.06 (s, 2 H), 8.64 (s, 1 H), 8.12 (d, J=7.6 Hz, 2 H), 7.46 (d, J=8.0 Hz, 2 H), 7.34-7.27 (m, 2 H), 7.17-7.08 (m, 2 H), 3.18 (t, J=7.4 Hz, 2 H), 2.31 (t, J=7.2 Hz, 2 H), 1.96-1.85 (m, 2 H); MS (ESI) m/z 340.3 (M–H)$^-$; MS (ESI) m/z 342.1 (M+H)$^+$

Example 145

3-(2,10-difluoro-5,7-dihydroindolo[2,3-b]carbazol-6-yl)-N,N-dimethylprop-2-yn-1-amine

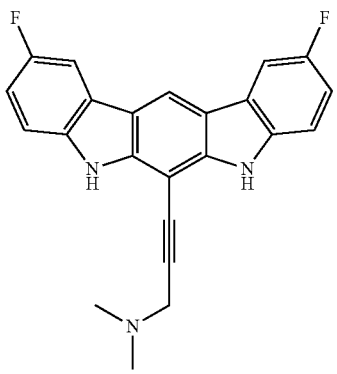 [SMILES: CN(C)CC#Cc1c2[nH]c3ccc(F)cc3c2cc2c1[nH]c1ccc(F)cc12]

The title compound was prepared in a manner analogous to Example 143 except the starting indole is 5,7-diBOC-2,10-difluoro-6-hydroxyindolo[2,3-b]carbazole in step 1. $^1$H-NMR (400 MHz, DMSO-$d_6$) δ ppm 11.22 (s, 2 H), 8.86 (s, 1 H), 7.92 (dd, J=9.2, 2.4 Hz, 2 H), 7.51 (dd, J=8.8, 4.4 Hz, 2 H), 7.20 (td, J=9.2, 2.4 Hz, 2 H), 3.69 (s, 2 H), 2.38 (s, 6 H); MS (ESI) m/z 372.2 (M–H)$^-$; MS (ESI) m/z 373.7 (M+H)$^+$

Example 146

3-(2,10-difluoro-5,7-dihydroindolo[2,3-b]carbazol-6-yl)-N,N-dimethylpropan-1-amine

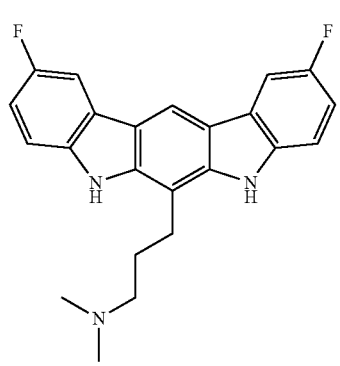 [SMILES: CN(C)CCCc1c2[nH]c3ccc(F)cc3c2cc2c1[nH]c1ccc(F)cc12]

The title compound was prepared in a manner analogous to Example 144 except the starting indole is 3-(2,10-difluoro-5,7-dihydroindolo[2,3-b]carbazol-6-yl)-N,N-dimethylprop-2-yn-1-amine. $^1$H-NMR (400 MHz, DMSO-$d_6$) δ ppm 11.13 (br s, 2 H), 8.67 (s, 1 H), 7.88 (dd, J=9.2, 2.4 Hz, 2 H), 7.44 (dd, J=8.8, 4.4 Hz, 2 H), 7.15 (td, J=9.2, 2.4 Hz, 2 H), 3.15 (t, J=5.2 Hz, 2 H), 2.29 (t, J=7.2 Hz, 2H), 2.18 (s, 6 H), 1.94-1.83 (m, 2 H); MS (ESI) m/z 376.3 (M–H)$^-$; MS (ESI) m/z 378.1 (M+H)$^+$

Example 147

2,10-Difluoro-6-methyl-5,7-dihydro-indolo[2,3-b]carbazole

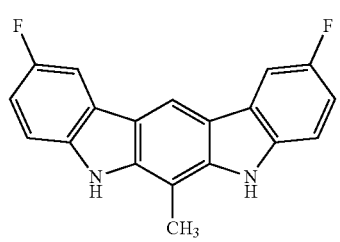 [SMILES: Cc1c2[nH]c3ccc(F)cc3c2cc2c1[nH]c1ccc(F)cc12]

In a 500 mL 3-necked flask equipped with cooling bath, overhead stirrer and argon inlet was placed a solution of 2,2,6,6-tetramethylpiperidine (17.5 mL, 104 mmol) in tetrahydrofuran (78 mL) which was cooled to –30° C. To this was added 2.5M n-butyllithium (42 mL, 104 mmol) dropwise over 20 minutes and the reaction mixture warmed to 0° C. and stirred for 30 minutes. The reaction was cooled to –78° C. and a solution of 1,1'-diboc-3,3'-di(5-fluoroindoyl)methane (20 g, 41.5 mmol) in tetrahydrofuran (140 mL) added dropwise over 20 minutes, making sure not to allow the temperature to rise over –65° C. The mixture was allowed to stir for 30 minutes before the addition of acetic anhydride (75 mL, 793 mmol) dropwise over 30 minutes. The reaction mixture was allowed to warm from –70° C. to room temperature and poured into saturated bicarbonate solution (1.5 L). The solution was extracted with ethyl acetate (1000 mL then 500 mL).

The organic layer was evaporated to give a gummy solid which was chromatographed on silica gel eluting with 5% ethyl acetate in hexane to give 5,7-diBOC-2,10-difluoro-6-methylindolo[2,3-b]carbazole (7.77 g, 37% yield).

A solution of 5,7-diBOC-2,10-difluoro-6-methylindolo[2,3-b]carbazole (4.45 g, 8.8 mmol) was stirred with a solution of 20% trifluoroacetic acid in dichloromethane (100 mL) at room temperature for two hours. The solvents were evaporated and the residue dissolved in ethyl acetate (200 mL). This was washed with saturated sodium bicarbonate solution (100 mL) and dried over magnesium sulfate. After evaporation of the solvent, the residue was chromatographed on silica gel, eluting with a gradient of dichloromethane and hexane (50% dichloromethane to 100% dichloromethane) to give 2,10-difluoro-6-methyl-5,7-dihydro-indolo[2,3-b]carbazole (2.4 g, 90% yield). $^1$H NMR (300 MHz) (DMSO-$d_6$) δ 11.05 (2H, s, —NH), 8.67 (1H, s, arom), 7.89 (2H, dd, J=9.5, 2.6 Hz, arom), 7.43 (2H, dd, J=8.9, 4.4 Hz, arom), 7.17 ppm (2H, dt, J=9.5, 2.6 Hz, arom) and 2.70 ppm (3H, s, —CH$_3$).

Example 148

2,10-Difluoro-6-trifluoromethyl-5,7-dihydro-indolo[2,3-b]carbazole

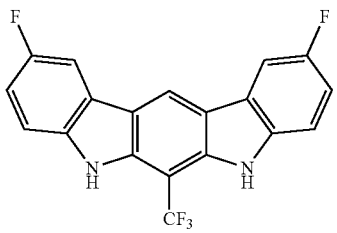 [SMILES: Fc1ccc2[nH]c3c(C(F)(F)F)c4[nH]c5ccc(F)cc5c4cc3c2c1]

The title compound was prepared in a manner analogous to Example 147 except the reagent in step 3 was trifluoroacetic anhydride. $^1$H NMR (300 MHz) (DMSO-$d_6$) δ 11.39 (2H, s, —NH), 9.18 (1H, s, arom), 7.98 (2H, dd, J=9.5, 2.6 Hz, arom), 7.58 (2H, dd, J=8.7, 4.5 Hz, arom) and 7.27 (2H, dt, J=9.5, 2.6 Hz, arom).

Example 149

6-ethyl-5,7-dihydro-indolo[2,3-b]carbazole

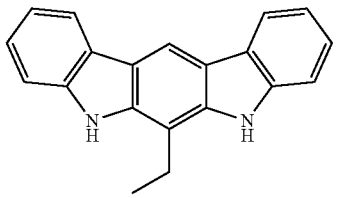 [SMILES: CCc1c2[nH]c3ccccc3c2cc2c1[nH]c1ccccc12]

The title compound was prepared in a manner analogous to Example 147 except the starting material was indole and the reagent in step 3 was propionyl chloride. (300 mg, 17% yield). $^1$H NMR (300 MHz) (DMSO-$d_6$) δ 11.01 (2H, s, —NH), 8.63 (1H, s, arom), 8.11 (2H, d, J=6.0 Hz, arom), 7.44 (2H, d, J=6.0 Hz, arom), 7.31 (2H, t, J=5.3 Hz, arom), 7.12 (2H, t, J=5.7 Hz, arom), 3.22 (2H, q, J=5.5 Hz) and 1.34 ppm (3H, t, J=5.5 Hz).

Example 150

6-trifluoromethyl-5,7-dihydro-indolo[2,3-b]carbazole

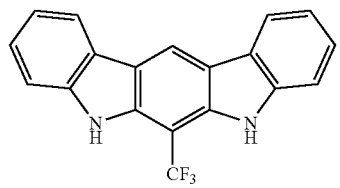

The title compound was prepared in a manner analogous to Example 147 except the starting material was indole and the reagent in step 3 was trifluoroacetic anhydride. The BOC group was removed by heating at 195° C. for 20 minutes in step 4. $^1$H NMR (300 MHz) (DMSO-$d_6$) δ11.30 (2H, s, —NH), 9.14 (1H, s, arom), 8.21 (2H, d, J=7.8 Hz, arom), 7.59 (2H, d, J=8.1 Hz, arom), 7.39 (2H, t, J=7.9 Hz, arom) and 7.22 ppm (2H, t, J=8.0 Hz, arom).

Example 151

2-(2,10-difluoro-6-methoxyindolo[2,3-b]carbazol-5(7H)-yl)-N,N-dimethylethanamine and 2,2'-(2,10-difluoro-6-methoxyindolo[2,3-b]carbazole-5,7-diyl)bis(N,N-dimethylethanamine)

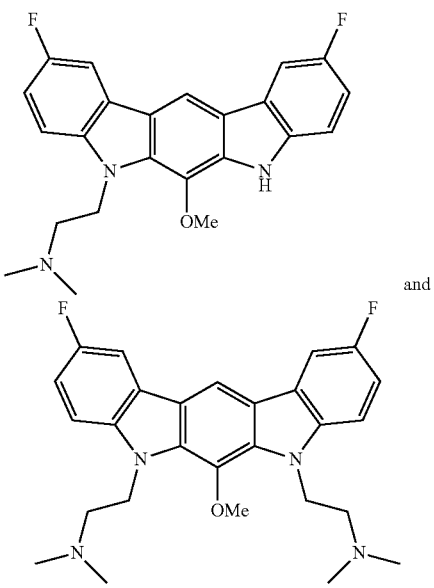

To a mixture of 2,10-difluoro-6-methoxy-5,7-dihydroindolo[2,3-b]carbazole (1 equiv) in dry DMF (10 mL/mmol), under an atmosphere of argon and at 0-5° C., was added NaH (10 equiv, 60% in mineral oil). The mixture was stirred at 0-5° C. for 30 min, and 2-dimethylaminoethyl chloride (5 equiv) was added, which was obtained by treating its hydrochloric acid salt with NaH in DMF. The resultant mixture was stirred at 0-5° C. for 1 h, and at RT for another 2 h. The reaction was quenched with cold water, extracted dichloromethane (or ethyl acetate). The extract was washed three times with brine, dried over Na$_2$SO$_4$, filtered, and concentrated. The residue was subjected to chromatography on silica gel, eluting with CH$_2$Cl$_2$/MeOH (10% cNH$_3$.H$_2$O). Two products were obtained; one is mono-alkylated and the other is di-alkylated. 2-(2,10-difluoro-6-methoxyindolo[2,3-b]carbazol-5(7H)-yl)-N,N-dimethylethanamine (63%): $^1$H NMR (400 MHz, DMSO-d$_6$) δ ppm 11.30 (s, 1H), 8.64 (s, 1H), 7.93 (dd, J=9.2, 2.8 Hz, 1H), 7.90 (dd, J=9.6, 2.8 Hz, 1H), 7.54 (dd, J=8.8, 4.4 Hz, 1H), 7.45 (dd, J=8.8, 4.4 Hz, 1H), 7.24 (td, J=9.2, 2.8 Hz, 1H), 7.20 (td, J=9.0, 2.2 Hz, 1H), 4.66 (t, T=7.4 Hz, 2H), 4.08 (s, 3H), 2.63 (t, J=7.4 Hz, 2H), 2.23 (s, 6H); MS (ESI) m/z 394 (M+H)$^+$. 2,2'-(2,10-difluoro-6-methoxyindolo[2,3-b]carbazole-5,7-diyl)bis(N,N-dimethylethanamine) (22%): $^1$H NMR (400 MHz, DMSO-d$_6$) ppm 8.69 (s, 1H), 7.93 (dd, J=9.2, 2.4 Hz, 2H), 7.62 (dd, J=9.0, 3.8 Hz, 2H), 7.26 (td, J=9.2, 2.0 Hz, 2H), 4.67 (t, J=7.0 Hz, 4H), 3.94 (s, 3H), 2.55 (t, J=6.8 Hz, 4H), 2.15 (s, 12H); MS (ESI) m/z 465 (M+H)$^+$.

Example 152

2-(2,10-difluoro-6-methylindolo[2,3-b]carbazol-5 (7H)-yl)-N,N-dimethylethanamine and 2,2'-(2,10-difluoro-6-methylindolo[2,3-b]carbazole-5,7-diyl)bis (N,N-dimethylethanamine)

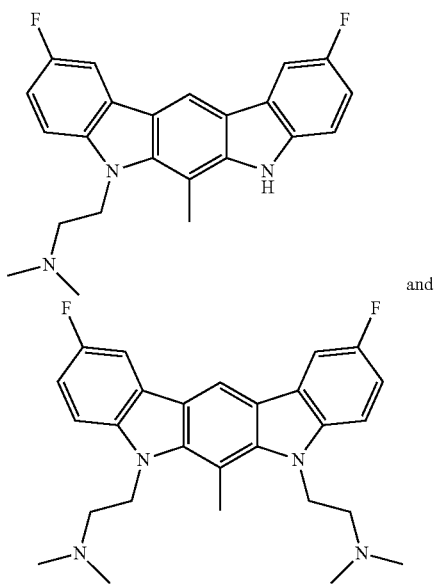

and

The title compounds were prepared in a manner analogous to Example 151 except the starting indole is 2,10-difluoro-6-methyl-5,7-dihydroindolo[2,3-b]carbazole and the base is K$_2$CO$_3$ in acetone. 2-(2,10-difluoro-6-methylindolo[2,3-b]carbazol-5(7H)-yl)-N,N-dimethylethanamine: $^1$H NMR (400 MHz, DMSO-d$_6$) δ ppm 11.11 (s, 1H), 8.72 (s, 1H), 7.92 (dd, J=9.0, 2.6 Hz, 1H), 7.88 (dd, J=9.2, 2.4 Hz, 1H), 7.52 (dd, J=8.8, 4.4 Hz, 1H), 7.44 (dd, J=8.6, 4.2 Hz, 1H), 7.22 (td, J=9.2, 2.8 Hz, 1H), 7.17 (td, J=9.2, 2.4 Hz, 1H), 4.66 (t, J=7.4 Hz, 2H), 2.92 (s, 3H), 2.62 (t, J=7.6 Hz, 2H), 2.24 (s, 6H). 2,2'-(2,10-difluoro-6-methylindolo[2,3-b]carbazole-5,7-diyl)bis(N,N-dimethylethanamine): $^1$H NMR (400 MHz, DMSO-d$_6$) δ ppm 8.74 (s, 1H), 7.90 (dd, J=9.0, 2.6 Hz, 2H), 7.58 (dd, J=8.8, 4.0 Hz, 2H), 7.24 (td, J=9.2, 2.4 Hz, 2H), 4.61 (t, J=7.4 Hz, 4H), 3.06 (s, 3H), 2.62 (t, J=7.4 Hz, 4H), 2.21 (s, 12H).

Example 153

3,3'-(2,10-difluoro-6-methylindolo[2,3-b]carbazole-5,7-diyl)bis(N,N-dimethylpropan-1-amine) (2%)

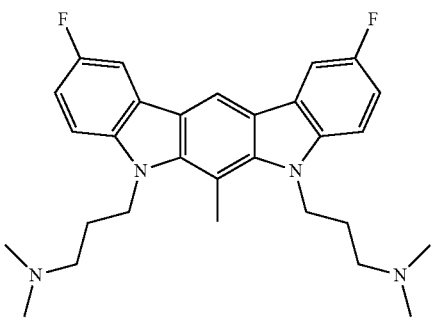

The title compound was prepared in a manner analogous to Example 152 except the reagent is 3-dimethylaminopropyl chloride. $^1$H NMR (400 MHz, DMSO-d$_6$) δ ppm 8.74 (s, 1H), 7.90 (dd, J=8.8, 2.8 Hz, 2H), 7.57 (dd, J=9.0, 4.2 Hz, 2H), 7.24 (td, J=9.2, 2.4 Hz, 2H), 4.57 (t, J=7.6 Hz, 4H), 3.05 (s, 3H), 2.15 (t, J=6.8 Hz, 4H), 2.08 (s, 12H), 1.80-1.90 (m, 4H); MS (ESI) m/z 477 (M+H)$^+$.

Example 154

2,2'-(2,10-difluoro-6-methoxyindolo[2,3-b]carbazole-5,7-diyl)diethanamine

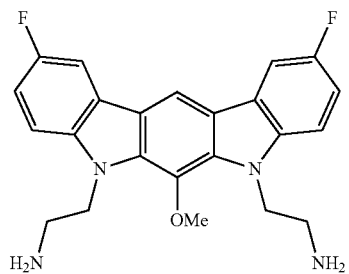 [SMILES: COc1c2c(cc3c4cc(F)ccc4n(CCN)c13)c1cc(F)ccc1n2CCN]

2,10-difluoro-6-methoxy-5,7-dihydroindolo[2,3-b]carbazole (1 equiv) in DMF (10 mL/mmol) was cooled in an ice-water bath under argon, and NaH (6 equiv, 60% in mineral oil) was added. The resultant mixture was stirred at 0-5° C. for 30 min and chloroacetonitrile was added. The cooling bath was removed and the reaction was warmed to RT and stirred for 2 h. The reaction was quenched with cold water, extracted ethyl acetate. The extract was washed three times with brine, dried over Na$_2$SO$_4$, filtered, and evaporated to give a solid, which was subjected to chromatography on silica gel. The di-nitrile substituted compound was dissolved in THF and cooled in an ice-water bath. Excess BH$_3$.SMe$_2$ was added to the solution and the resultant mixture was refluxed until reduction was complete (~3 h), and then quenched with MeOH at 0-5° C. The solvent was evaporated and the residue was subjected to chromatography on silica gel to give 2,2'-(2,10-difluoro-6-methoxyindolo[2,3-b]carbazole-5,7-diyl)diethanamine (45% yield). $^1$H NMR (400 MHz, DMSO-d$_6$) δ ppm 8.69 (s, 1H), 7.92 (dd, J=12.2, 3.4 Hz, 2H), 7.64 (dd, J=11.6, 5.6 Hz, 2H), 7.25 (td, J=12.4, 3.6 Hz, 2H), 4.55 (t, J=9.2 Hz, 4H), 3.96 (s, 3H), 2.89 (t, J=8.8 Hz, 4H); MS (ESI) m/z 409 (M+H)$^+$.

Example 155

2,2'-(2,10-dibromo-6-methoxyindolo[2,3-b]carbazole-5,7-diyl)diethanamine

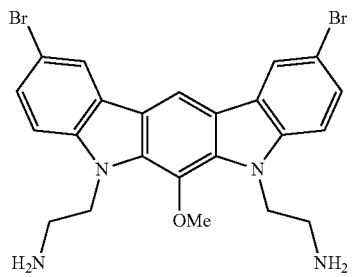 [SMILES: COc1c2c(cc3c4cc(Br)ccc4n(CCN)c13)c1cc(Br)ccc1n2CCN]

The title compound was prepared in a manner analogous to Example 154 except the starting indole is 2,10-dibromo-6-methoxy-5,7-dihydroindolo[2,3-b]carbazole. $^1$H NMR (400 MHz, DMSO-d$_6$) δ ppm 8.80 (s, 1H), 8.31 (d, J=2.0 Hz, 2H), 7.64 (d, J=8.8 Hz, 2H), 7.54 (dd, J=2.0, 8.0 Hz, 2H), 4.54 (t, J=6.8 Hz, 4H), 3.96 (s, 3H), 2.89 (t, J=6.8 Hz, 4H).

Example 156

4,4'-(2,10-dibromo-6-methoxyindolo[2,3-b]carbazole-5,7-diyl)dibutan-1-amine

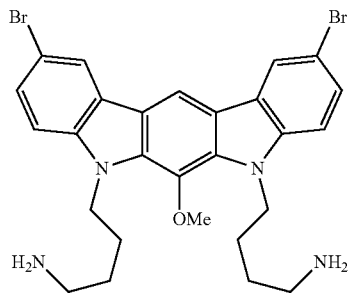 [SMILES: COc1c2c(cc3c4cc(Br)ccc4n(CCCCN)c13)c1cc(Br)ccc1n2CCCCN]

The title compound was prepared in a manner analogous to Example 155 except the reagent is 4-bromobutanenitrile. $^1$H NMR (400 MHz, DMSO-d$_6$) δ ppm 8.80 (s, 1H), 8.32 (d, J=2.0 Hz, 2H), 7.60 (d, J=8.8 Hz, 2H), 7.54 (dd, J=2.0, 8.4 Hz, 2H), 4.59 (t, J=6.8 Hz, 4H), 3.93 (s, 3H), 2.46 (t, J=7.2 Hz, 4H), 1.73 (m, 4H), 1.26 (m, 4H); MS (ESI) m/z 587 (M+H)$^+$.

Example 157

4,4'-(6-methoxyindolo[2,3-b]carbazole-5,7-diyl)dibutan-1-amine

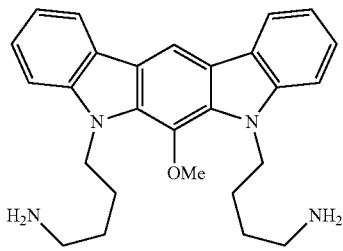 [SMILES: COc1c2c(cc3c4ccccc4n(CCCCN)c13)c1ccccc1n2CCCCN]

The title compound was prepared in a manner analogous to Example 156. 4,4'-(6-methoxyindolo[2,3-b]carbazole-5,7-diyl)dibutan-1-amine was obtained from 4,4'-(2,10-dibromo-6-methoxyindolo[2,3-b]carbazole-5,7-diyl)dibutanenitrile, which was debrominated by hydrogenation/Pd(10% on C) in THF/MeOH, and reduced with BH$_3$.SMe$_2$. $^1$H NMR (400 MHz, DMSO-d$_6$) δ ppm 8.69 (s, 1H), 8.17 (d, J=7.2 Hz, 2H), 7.61 (t, J=8.8 Hz, 2H), 7.42 (m, 2H), 7.21 (t, J=7.2 Hz, 2H), 4.70-4.50 (m, 4H), 3.94 (s, 3H), 2.69 (t, J=7.4 Hz, 2H), 2.46-2.36 (m, 2H), 1.85-1.36 (m, 8H); MS (ESI) m/z 429 (M+H)$^+$.

Example 158

2-(2,10-divinyl-5,7-dihydroindolo[2,3-b]carbazol-6-yloxy)-N,N-diethylethanamine

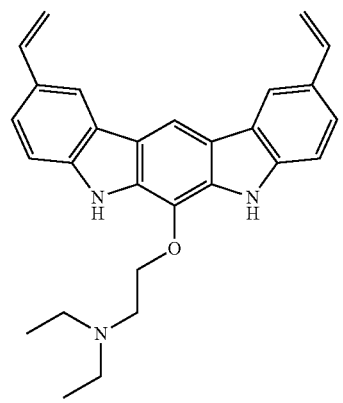 [SMILES: C=Cc1ccc2[nH]c3c(OCCN(CC)CC)c4[nH]c5ccc(C=C)cc5c4cc3c2c1]

A mixture of 2-(2,10-dibromo-5,7-dihydroindolo[2,3-b]carbazol-6-yloxy)-N,N-diethylethanamine (212.1 mg, 0.4007 mmol), tributylvinyltin (0.30 mL, 1.0274 mmol) and tetrakis(triphenylphosphine)palladium (69.5 mg, 0.06011 mmol) in anhydrous DMF (40 mL) was purged with high-purity Ar for five minutes and then heated to 80° C. and stirred overnight. The reaction mixture was concentrated. The residue was separated by flash chromatography to provide the title product (34.6 mg, 20%). $^1$H-NMR (400 MHz, DMSO-d$_6$) δ ppm 11.56 (s, 2H), 8.60 (s, 1H), 8.23 (s, 2H), 7.51-7.39 (m, 4H), 6.89 (dd, J=17.6, 10.8 Hz, 2H), 5.80 (d, J=17.2 Hz, 2H), 5.16 (d, J=11.6 Hz, 2H), 4.32 (t, J=6.0 Hz, 2H), 2.92 (t, J=5.6 Hz, 2H), 2.69 (q, J=7.2 Hz, 4H), 1.06 (t, J=7.2 Hz, 6H); MS (ESI) m/z 422.2 (M−H)$^-$; MS (ESI) m/z 424.1 (M+H)$^+$

Example 159

6-Methoxy-2,10-dimethyl-5,7-dihydroindolo[2,3-b]carbazole

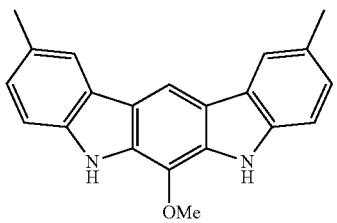 [SMILES: COc1c2[nH]c3ccc(C)cc3c2cc2c1[nH]c1ccc(C)cc12]

To a solution of diethyl 6-methoxy-5,7-dihydroindolo[2,3-b]carbazole-2,10-dicarboxylate (1.72 g, 4 mmol) in THF (40 mL), with stirring at 0-5° C. and under Ar, was slowly added a solution of LAH in THF (16 mL, 1.0 M). After addition of LAH solution, the mixture was warmed to room temperature and then refluxed 2 h. The reaction mixture was cooled in an ice-water bath and quenched by carefully adding ethyl acetate (20 mL) and water (20 mL). The resultant mixture was extracted with ethyl acetate (3×100 ml); the extracts were combined, washed with brine, dried over $Na_2SO_4$, filtered, and evaporated to dryness. The residue was subjected to chromatography on silica gel to give 6-methoxy-2,10-dimethyl-5,7-dihydroindolo[2,3-b]carbazole (180 mg, 14%), $^1$H NMR (400 MHz, DMSO-$d_6$) δ ppm 10.97 (s, 2H), 8.45 (s, 1H), 7.91 (s, 2H), 7.33 (d, J=8.0 Hz, 2H), 7.14 (dd, J=1.2, 8.0 Hz, 2H), 4.07 (s, 3H), 2.49 (s, 6H).

Example 160

Bis(2-(diethylamino)ethyl) 6-methoxy-5,7-dihydroindolo[2,3-b]carbazole-2,10-dicarboxylate

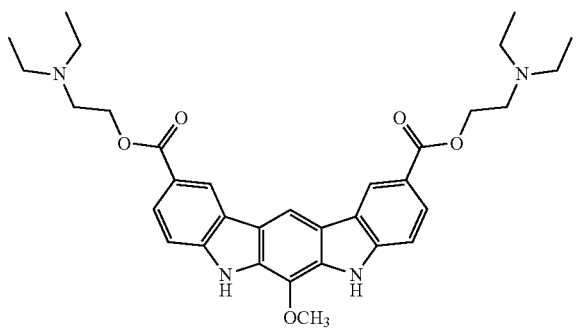 [SMILES: CCN(CC)CCOC(=O)c1ccc2[nH]c3c(OC)c4[nH]c5ccc(C(=O)OCCN(CC)CC)cc5c4cc3c2c1]

A mixture of diethyl 6-methoxy-5,7-dihydroindolo[2,3-b]carbazole-2,10-dicarboxylate (10 g, 23.23 mmol) and KOH (3.7 g) in EtOH/$H_2$O/THF(120/40/10 mL) was heated to 90-100° C. under Ar and stirred for 4-6 h until all starting material disappeared. The reaction mixture was neutralized with 1N aq. HCl. The white ppt was collected by filtration and washed with small amount of water, dried under vacuum to give 6-methoxy-5,7-dihydroindolo[2,3-b]carbazole-2,10-dicarboxylic acid (8.3 g, 95%).

A mixture of 6-methoxy-5,7-dihydroindolo[2,3-b]carbazole-2,10-dicarboxylic acid (1 g, 2.67 mmol) and 2-(diethylamino)ethyl N,N'-dicyclohexylcarbamimidate (2.6 g, 8.0 mmol) in DMF (10 mL) was stirred at room temperature for 48 h. [2-(diethylamino)ethyl N,N'-dicyclohexylcarbamimidate was prepared from DCC (1 equivalent), N,N'-diethylethanolamine (1 equivelent) and CuCl (cat.) at 135° C. under microwave for 2 h]. The reaction mixture was diluted with 50% EtOAc/Hexane and washed with water. The combined organic layer was dried ($MgSO_4$), concentrated, purified by chromatography to provide Bis(2-(diethylamino)ethyl) 6-methoxy-5,7-dihydroindolo[2,3-b]carbazole-2,10-dicarboxylate (85-90%). $^1$H NMR (300 MHz, $CD_3OD$) δ ppm 8.83 (d, J=1.4 Hz, 2H), 8.59 (s, 1H), 8.05 (dd, J=1.4, 8.5 Hz, 2H), 7.49 (d, J=8.5 Hz, 2H), 4.43 (q, J=7.3 Hz, 4H), 4.32 (m, 2H), 3.18 (m, 2H), 1.47 (t, J=7.3 Hz, 6H).

Example 161

$N^2,N^{10}$-bis(2-(dimethylamino)ethyl)-6-methoxy-5,7-dihydroindolo[2,3-b]carbazole-2,10-dicarboxamide

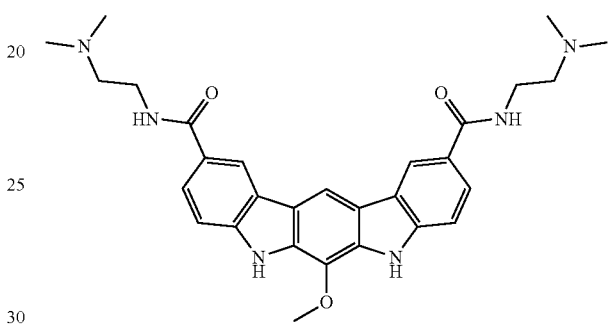

A mixture of 6-methoxy-5,7-dihydroindolo[2,3-b]carbazole-2,10-dicarboxylic acid (467.7 mg, 1.27 mmol), benzotriazol-1-yloxy-tripyrrolidinophosphonium hexafluorophosphate (1.458 g, 2.80 mmol), N,N-dimethylethylenediamine (0.31 mL, 2.80 mmol) and N,N-diisopropylethylamine (1.33 mL, 7.64 mmol) in anhydrous DMF (25 mL) was stirred at room temperature overnight. The solvent and DIEA were removed under vacuum. The residue was subjected to flash chromatography to provide the title product (0.498 g, 76%). $^1$H-NMR (400 MHz, DMSO-$d_6$) δ ppm 11.54 (s, 2 H), 8.71 (d, J=1.2 Hz, 2H), 8.62 (s, 1 H), 8.32 (t, J=6.4 Hz, 2 H), 7.88 (dd, J=8.4, 2.0 Hz, 2 H), 7.48 (d, J=8.4 Hz, 2 H), 4.12 (s, 3 H), 3.42 (q, J=6.4 Hz, 4 H), 3.05-2.96 (m, 4 H), 2.21 (s, 12 H); MS (ESI) m/z 513.3 (M−H)$^-$; MS (ESI) m/z 515.1 (M+H)$^+$

Example 162

$N^1,N^{1'}$-methoxy-5,7-dihydroindolo[2,3-b]carbazole-2,10-diyl)bis(methylene)bis($N^2,N^2$-dimethylethane-1,2-diamine)

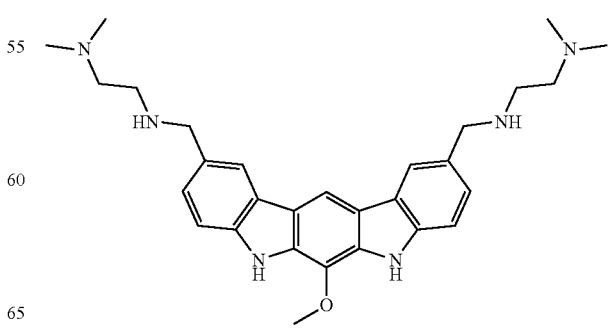

To a solution of N²,N¹⁰-bis(2-(dimethylamino)ethyl)-6-methoxy-5,7-dihydroindolo[2,3-b]carbazole-2,10-dicarboxamide (0.49 g, 0.97 mmol) in THF (100 mL) at 0° C. was added LiAlH₄ (0.784 g, 20.66 mmol) under Ar and heated to reflux. The reaction mixture was quenched by dropwise addition of water (2 mL). The solution was filtered, concentrated, and purified by flash chromatography to provide the title product (35.8 mg). ¹H-NMR (DMSO-d₆, 400 MHz) δ ppm 10.94 (s, 2 H), 8.74 (s, 1 H), 8.05 (s, 2 H), 7.36-7.22 (m, 4 H), 4.12-4.05 (m, 2 H), 3.84 (s, 3 H), 3.16 (d, J=4.4 Hz, 4 H), 2.62 (t, J=6.4 Hz, 4 H), 2.34 (t, J=6.4 Hz, 4 H), 2.10 (s, 12 H); MS (ESI) m/z 485.4 (M−H)⁻

Example 163

Diethyl 6-(2-aminoethoxy)-5,7-dihydroindolo[2,3-b]carbazole-2,10-dicarboxylate

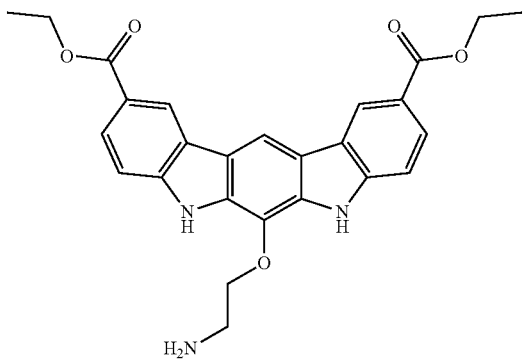 [SMILES: CCOC(=O)c1ccc2[nH]c3c(OCCN)c4[nH]c5ccc(C(=O)OCC)cc5c4cc3c2c1]

A mixture of 6-(2-(bis(tert-butoxycarbonyl)amino)ethoxy)-2,10-dibromo-5,7-diBOC-indolo[2,3-b]carbazole (1.1 g, 1.26 mmol), triethylamine (5 mL) and PdCl₂(PPh₃)₂ (0.1 g) in EtOH/DMF (50/40 mL) was heated to 60-70° C. under CO overnight. The solvent was evaporated and subjected to chromatography to give diethyl 6-(2-bis(tert-butoxycarbonyl)amino)ethoxy)-5,7-BOC-indolo[2,3-b]carbazole-2,10-dicarboxylate (70%), which was deprotected under TFA/CH₂Cl₂ to give diethyl 6-(2-aminoethoxy)-5,7-dihydroindolo[2,3-b]carbazole-2,10-dicarboxylate (92%). ¹H NMR (300 MHz, CDCl₃) δ ppm 8.84 (s, 2H), 8.49 (s, 2H), 8.47 (s, 1H), 8.10 (d, J=8.7 Hz, 2H), 7.42 (d, J=8.7 Hz, 2H), 4.49 (t, J=6.3 Hz, 4H), 4.18 (s, 3H), 2.97 (t, J=6.3 Hz, 4H), 2.72 (q, J=6.9 Hz, 8H), 1.36 (t, J=6.9 Hz, 12H).

Example 164

6-Ethoxycarbonyloxy-5,7-dihydro-indolo[2,3-b]carbazole

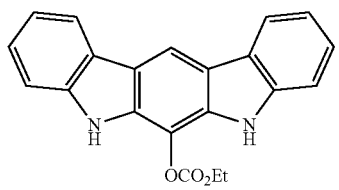

Part (a). Indole-3-carbinol (1.0 g, 6.79 mmol) in 10% aqueous NaOH solution (100 mL) was refluxed for 1 h. The solution was cooled, neutralized with carbon dioxide and the white precipitate was collected by filtration, which was then crystallized from toluene to yield 3,3'-Diindolylmethane as a white solid (0.65 g, 77%): ¹H NMR (300 MHz, CDCl₃) δ 4.26 (s, 2, CH₂), 6.94 (m, 2, PyH), 7.11 (m, 2, ArH), 7.21 (m, 2, ArH), 7.36 (m, 2, ArH), 7.64 (m, 2, ArH), 7.86 (br.s, 2, NH).

Part (b). To a solution of 3,3'-Diindolylmethane (2.0 g, 8.12 mmol) and (t-BuOOC)₂O (3.9 g, 17.87 mmol) in THF (20 mL) was added a catalytic amount of DMAP and stirred for overnight under argon. The solvent was evaporated to give a crude product. Flash chromatography (3% EtOAc/hexane) yielded 1,1'-DiBOC-3,3'-diindolylmethane as a white solid (3.44 g, 95%): ¹H NMR (300 MHz, CDCl₃) δ 1.65 (s, 18, OC(CH₃)₃), 4.09 (s, 2, CH₂), 7.21 (m, 2, ArH), 7.31 (m, 2, ArH), 7.38 (s, 2, PyH), 7.53 (m, 2, ArH), 8.12 (br.d, J=8.6 Hz, 2, ArH)

Part (c). To a solution of 2,2,6,6-tetramethylpiperidine (1.7 mL, 10 mmol) in THF (25 mL) at −78° C. under argon was added 1.6 M n-BuLi (9.4 mmol) in hexane (6.6 mL), and warmed to 0° C. for 15 min. After the reaction mixture was recooled to −78° C., 1,1'-DiBOC-3,3'-diindolylmethane (0.7 g, 1.57 mmol) in THF (5 mL) was added slowly, and stirring was continued for 30 min before ClCO₂Et (2 mL) was added. The reaction mixture was stirred for 2 h at −78° C. and poured into saturated NaHCO₃ and extracted with 50% EtOAc/hexane. The combined organic extracts were dried (MgSO₄), filtered, and concentrated to afford a crude mixture, which was then deprotected using the general procedure. Flash chromatography (20% EtOAc/hexane) yielded 6-Ethoxycarbonyloxy-5,7-dihydro-indolo[2,3-b]carbazole (0.39 g, 72%) as a white solid. ¹H NMR (300 MHz, CDCl₃) δ 1.51 (t, J=7.1 Hz, 3, CO₂CH₂CH₃), 4.49 (q, J=7.1 Hz, 2, CO₂CH₂CH₃), 7.28 (m, 2, ArH), 7.41 (m, 2, ArH), 7.46 (br.d, J=7.8 Hz, 2, ArH), 8.16 (d, J=7.7 Hz, 2, ArH), 8.21 (br.s, 2, NH), 8.60 (s, 1, ArH).

Example 165

6-Methyl-indolo[2,3-b]carbazole

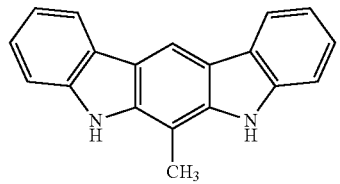

Part (a). To a solution of 2,2,6,6-tetramethylpiperidine (3.5 g, 24.8 mmol) in THF (40 mL) at −78° C. under argon was added 1.6 M n-BuLi (22.4 mmol) in hexane (14 mL), and warmed to 0° C. for 15 min. After the reaction mixture was recooled to −78° C., 1,1'-DiBOC-3,3'-diindolylmethane (1 g, 2.24 mmol) in THF (5 mL) was added slowly, and stiffing was continued for 30 min before acetic anhydride (8 mL) was added. The mixture was slowly warmed to 0° C. for 30 min. The reaction mixture was poured into saturated NaHCO₃ and extracted with 50% EtOAc/hexane. The combined organic extracts were dried (MgSO₄), filtered, and concentrated to afford a crude product. Flash chromatography (5% EtOAc/hexane) yielded 6-Methyl-5,7-diBOC-indolo[2,3-b]carbazole as a white solid (0.98 g, 93%): ¹H NMR (300 MHz, CDCl₃) δ 1.75 (s, 18, OC(CH₃)₃), 2.54 (s, 3, CH₃), 7.37 (m, 2, ArH), 7.45 (m, 2, ArH), 8.05 (dd, J=1.7, 8.0 Hz, 2, ArH), 8.11 (dd, J=1.7, 8.0 Hz, 2, ArH), 8.35 (s, 1, ArH).

Part (b). 6-Methyl-5,7-diBOC-indolo[2,3-b]carbazole (0.98 g, 2.08 mmol) was deprotected using the general procedure. Recrystallization (ethyl acetate/hexane) afforded 6-Methyl-5,7-dihydro-indolo[2,3-b]carbazole as a white solid (0.51 g, 91%): $^1$H NMR (300 MHz, CDCl$_3$) δ 2.69 (s, 3, CH$_3$), 7.26 (m, 2, ArH), 7.38 (d, J=7.7 Hz, 2, ArH), 7.44 (m, 2, ArH), 7.90 (br.s, 2, ArH), 8.16 (d, J=7.7 Hz, 2, ArH), 8.59 (s, 1, ArH).

Example 166

2,2'-Diindolylmethane

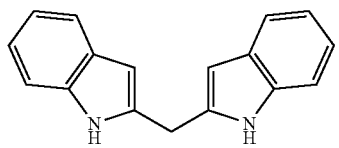 [SMILES: c1ccc2[nH]c(Cc3cc4ccccc4[nH]3)cc2c1]

Part (a). To a solution of ethyl 1H-indole-2-carboxylate (7.5 g, 39.64 mmol) in ether (100 mL) was added LiAlH$_4$ (2.3 g, 60.6 mmol) slowly at 0° C. under argon and warmed to room temperature for 1 h. The suspension was quenched slowly with water and white precipitate was removed by filtration. The filtrate was dried (MgSO$_4$) and concentrated to afford Indole-2-carbinol as a solid (5.75 g, 98%): $^1$H NMR (300 MHz, CDCl$_3$) δ 4.82 (s, 2, CH$_2$OH), 6.41 (s, 1, PyH), 7.11 (m, 1, ArH), 7.20 (m, 1, ArH), 7.35 (d, J=7.8 Hz, 1, ArH), 7.59 (d, J=7.7 Hz, 1, ArH), 8.35 (br.s, 1, NH).

Part (b). To a solution of succinimide-dimethylsulfonium chloride in CH$_2$Cl$_2$, prepared by the addition of (CH$_3$)$_2$S (1.8 mL, 23.5 mmol) to a solution of NCS (3.14 g, 23.5 mmol) in CH$_2$Cl$_2$ (60 mL) at 0° C., was added indole (2.5 g, 21.33 mmol) in CH$_2$Cl$_2$ (15 mL) at −20° C. under argon. The reaction mixture was slowly warmed to room temperature for 1 h. After removal of the solvent, 3-dimethylsulfoniumindole and succinimide were obtained quantitatively. The salt was dissolved in xylene and the mixture was heated to reflux for 30 min. Flash chromatography (10% EtOAc/hexane) yielded 3-Methylthioindole as an oil (3.2 g, 93%): $^1$H NMR (300 MHz, CDCl$_3$) δ 2.39 (s, 3, SCH$_3$), 7.22 (m, 1, PyH), 7.26 (m, 1, ArH), 7.31 (d, J=2.5 Hz, 1, ArH), 7.39 (m, 1, ArH), 7.79 (m, 1, ArH), 8.09 (br.s, 1, NH).

Part (c). To a mixture of indole-2-carbinol (0.45 g, 3.06 mmol) and 3-methylthioindole (0.5 g, 3.06 mmol) in CH$_2$Cl$_2$ (10 mL) was added (CF$_3$SO$_3$)$_3$Sc (0.2 g, 0.49 mmol) and stirred for 3 h under argon. The solvent was evaporated to give 2-((1H-indol-2-yl)methyl)-3-(methylthio)-1H-indole, which was then dissolved in EtOH (10 mL). Raney Ni was added to the solution and stirred at room temperature until no starting material was observed from TLC. The Raney Ni was removed by filtration and washed with ethyl acetate. The filtrate was dried (MgSO$_4$) and concentrated to give a solid. Flash chromatography (10% EtOAc/hexane) yielded 2,2'-Diindolylmethane as a white solid (0.49 g, 65%): $^1$H NMR (300 MHz, CDCl$_3$) δ 4.31 (s, 2, CH$_2$), 6.46 (s, 2, PyH), 7.11 (m, 2, ArH), 7.15 (m, 2, ArH), 7.25 (m, 2, ArH), 7.59 (m, 2, ArH), 7.83 (br.s, 2, NH).

Example 167

2,3'-Diindolylmethane

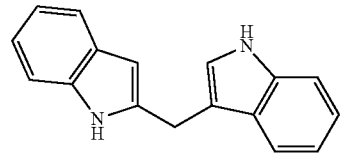 [SMILES: c1ccc2[nH]c(Cc3c[nH]c4ccccc34)cc2c1]

To a mixture of indole-2-carbinol (0.5 g, 3.4 mmol) and indole (0.4 g, 3.4 mmol) in CH$_2$Cl$_2$ (15 mL) was added (CF$_3$SO$_3$)$_3$Sc (0.17 g, 0.34 mmol) and stirred for 4 h under argon. The solvent was evaporated to give a crude product. Flash chromatography (20% EtOAc/hexane) yielded 2,3'-Diindolylmethane as a white solid (0.52 g, 63%): $^1$H NMR (300 MHz, CDCl$_3$) δ 4.30 (s, 2, CH$_2$), 6.41 (s, 2, PyH), 7.03-7.14 (m, 4, ArH, PyH), 7.17-7.26 (m, 2, ArH), 7.39 (d, J=8.2 Hz, 1, ArH), 7.55 (m, 1, ArH), 7.57 (m, 1, ArH), 7.85 (br.s, 1, NH), 7.99 (br.s, 1, NH).

Example 168

3,3'-(1H-Indole-2,3-diyl)bis(methylene)bis(1H-indole)

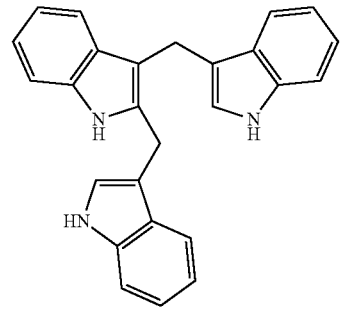 [SMILES: c1ccc2c(Cc3[nH]c4ccccc4c3Cc3c[nH]c4ccccc34)c[nH]c2c1]

To a mixture of 3-hydroxymethyl-indole (1.37 mmol) and indole (0.68 mmol) in CH$_2$Cl$_2$ (6 mL) was added (CF$_3$SO$_3$)$_3$Sc (0.05 g) and stirred for overnight under argon. The solvent was evaporated to give a crude product. Flash chromatography (30% EtOAc/hexane) yielded 3,3'-(1H-indole-2,3-diyl)bis(methylene)bis(1H-indole) as a white solid (70%).

Example 169

MIC Data for Various Compounds

Compounds according to the invention were tested against various strains of bacteria Minimum inhibitory concentrations (MICs) were determined using the following procedure. Using a 96-well microtiter plate, 2-fold dilutions of test compounds and controls were made in DMSO. The final DMSO concentration did not exhibit any cytotoxicity. A volume of 2.5 µl of each dilution of the test compounds and controls were transferred to another 96-well microtiter plate. All wells, except the sterility control wells, were inoculated with 97.5 µl of diluted bacterial suspension to give a final volume of 100 µl. (The estimated bacterial density per well was about 5×10$^5$ colony forming units (CFUs) or the equivalent of about 5×10[6] CFUs/ml.) The volume in the sterility control wells was adjusted to 100 μl with the appropriate growth medium. The microtiter plates were covered with a lid and placed, four plates in all, in a large Stratagene Big Blue Plate (Cat. #400041) lined with damped paper towels to prevent evaporation of the medium. Depending upon the organisms in the test panel, the plates were incubated for at least 24 h, and 48 h for the slower growing organisms (e.g., *F. tularensis, B. abortis*). Each well was inspected for growth. Results were scored as follows: 0=no growth; 1=faint growth; 2=some growth, but not as good as that for the negative control; and 3=the same growth as the negative control. Positive well with known antibiotics were run concurrently. The MIC (minimal inhibitory concentration) of that compound is the lowest concentration at which no growth is detected.

The bacterial strains tested were: *Francisella tularensis* (FT; Gram-negative); *Bacillus anthracis* (BA; Gram-positive); *Yersinia pestis* (YP; Gram-negative); *Brucella abortus* (BAB; Gram-negative); *Burkholderia mallei* (BM; Gram-negative); and *Burkholderia pseudomallei* (BP; Gram-negative). MIC data is provided in the following table.

TABLE 1

MIC (μg/ml) of indole analogs against bacterial threats

| Structure | FT | BA | YP | BAB | BM | BP |
|---|---|---|---|---|---|---|
| 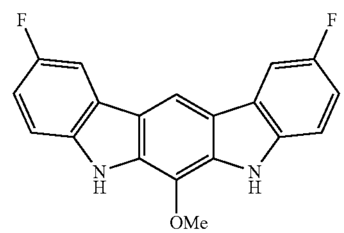 [SMILES: COc1c2[nH]c3ccc(F)cc3c2cc2c1[nH]c1ccc(F)cc12]  | 0.5 | 1 | >16 | 1 | >16 | >16 |
| 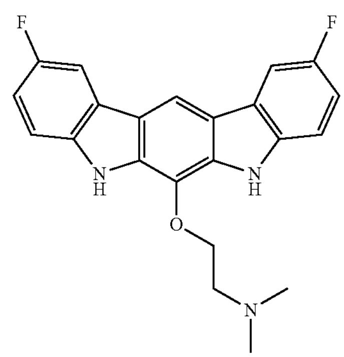 [SMILES: CN(C)CCOc1c2[nH]c3ccc(F)cc3c2cc2c1[nH]c1ccc(F)cc12]  | 0.25 | 0.5 | 8 | 0.5 | 4 | 8 |
| 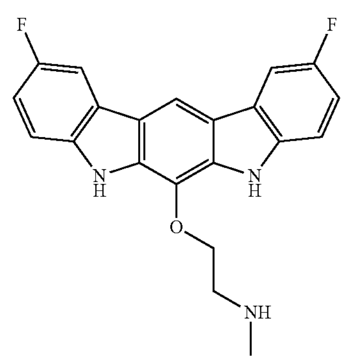 [SMILES: CNCCOc1c2[nH]c3ccc(F)cc3c2cc2c1[nH]c1ccc(F)cc12]  | 0.5 | 1 | 8 | 0.5 | 4 | 16 |
| 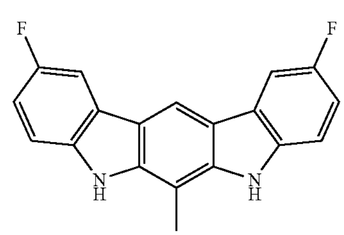 [SMILES: Cc1c2[nH]c3ccc(F)cc3c2cc2c1[nH]c1ccc(F)cc12]  | 0.5 | 0.5 | >16 | 1 | >16 | >16 |

TABLE 1-continued
MIC (μg/ml) of indole analogs against bacterial threats
| Structure | FT | BA | YP | BAB | BM | BP |
|---|---|---|---|---|---|---|
| 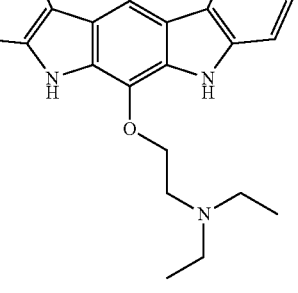 | 0.5 | 1 | >16 | 1 | ND[1] | ND |
| 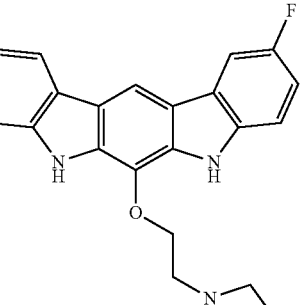 | 0.5 | 1 | 8 | 1 | >16 | >16 |
| 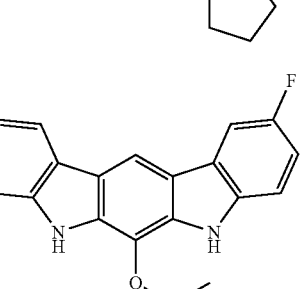 | 0.5 | 1 | 16 | 0.5 | ND | ND |
| 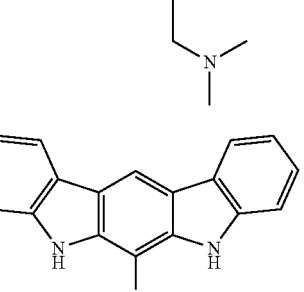 | 0.5 | 1 | >16 | 2 | >16 | >16 |
| 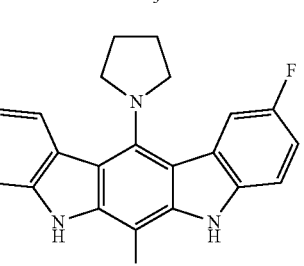 | 0.5 | 1 | >16 | 2 | >16 | >16 |

TABLE 1-continued
MIC (µg/ml) of indole analogs against bacterial threats
| Structure | FT | BA | YP | BAB | BM | BP |
|---|---|---|---|---|---|---|
| 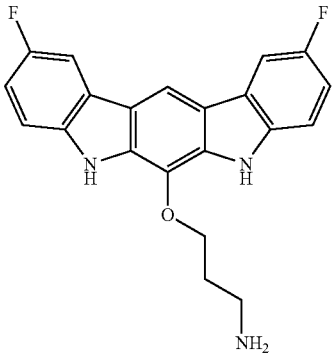 [SMILES: NCCCOc1c2[nH]c3ccc(F)cc3c2cc2c1[nH]c1ccc(F)cc12] | 0.5 | 0.5 | 2 | 0.5 | 8 | 8 |
| 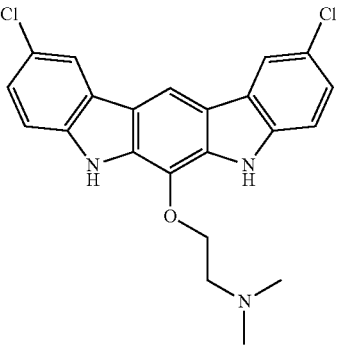 [SMILES: CN(C)CCOc1c2[nH]c3ccc(Cl)cc3c2cc2c1[nH]c1ccc(Cl)cc12] | 0.25 | 0.5-1 | 2 | 0.5 | 8 | 16 |
| 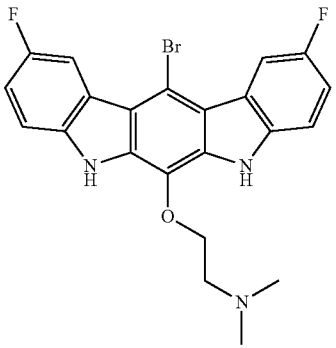 [SMILES: CN(C)CCOc1c2[nH]c3ccc(F)cc3c2c(Br)c2c1[nH]c1ccc(F)cc12] | 0.25 | 0.25 | >8 | 0.25 | >8 | >8 |
| 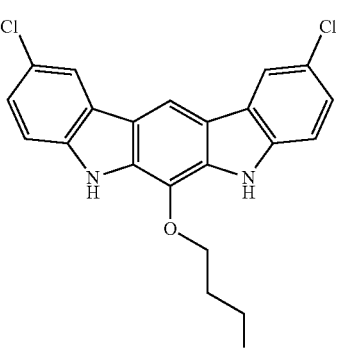 | 0.25-0.5 | 0.5 | 2 | 0.5 | 4 | 8 |

TABLE 1-continued

MIC (µg/ml) of indole analogs against bacterial threats

| Structure | FT | BA | YP | BAB | BM | BP |
|---|---|---|---|---|---|---|
| (difluoro indolocarbazole with O-propyl-piperidin-4-amine substituent) | 0.125-0.5 | 0.5 | 2 | 0.5 | ND | ND |
| (difluoro indolocarbazole with O-propyl-pyrrolidin-3-amine substituent) | 0.5 | 1 | 4 | 1 | ND | ND |
| (dichloro indolocarbazole with O-ethylamine substituent) | 0.5 | 2 | 2 | 0.5 | 4 | 8 |

TABLE 1-continued

MIC (μg/ml) of indole analogs against bacterial threats

| Structure | FT | BA | YP | BAB | BM | BP |
|---|---|---|---|---|---|---|
| (F, F difluoro indolocarbazole with propargyl dimethylamine) | 0.25 | 0.5 | 2 | 0.25 | 8 | >8 |
| (F, F difluoro indolocarbazole with propyl dimethylamine) | 1 | 1 | 8 | 1 | 16 | >16 |
| (Cl, Cl dichloro indolocarbazole with O-propyl 4-aminopiperidine) | 1 | 2 | 4 | 1 | 16 | >16 |

TABLE 1-continued

MIC (μg/ml) of indole analogs against bacterial threats

| Structure | FT | BA | YP | BAB | BM | BP |
|---|---|---|---|---|---|---|
| (dichloro indolocarbazole with O-ethyl-piperidine-NH2 substituent) | 0.5 | 2 | 16 | 1 | ND | ND |
| (difluoro indolocarbazole with O-propyl-pyrrolidine-OH substituent) | 0.5 | 0.5 | 8 | 0.251 | 8 | 8 |
| (dichloro indolocarbazole with O-propyl-NH-piperidine substituent) | 1 | 1 | 2 | 1 | 4 | 8 |

TABLE 1-continued

MIC (μg/ml) of indole analogs against bacterial threats

| Structure | FT | BA | YP | BAB | BM | BP |
|---|---|---|---|---|---|---|
| (structure: 2,10-dichloro-indolocarbazole with O-(CH₂)₃-pyrrolidin-3-amine substituent) | 0.5 | 0.5 | 2 | 0.25 | >8 | >8 |
| (structure: 2,10-dichloro-indolocarbazole with O-(CH₂)₃-guanidine substituent) | 0.25 | 0.25 | 1 | 0.25 | 1 | 2 |
| (structure: 2,10-difluoro-indolocarbazole with O-(CH₂)₂-N⁺(CH₃)₃ I⁻ substituent) | 1 | 0.5 | >8 | 2 | 8 | 8 |

TABLE 1-continued
MIC (μg/ml) of indole analogs against bacterial threats
| Structure | FT | BA | YP | BAB | BM | BP |
|---|---|---|---|---|---|---|
| 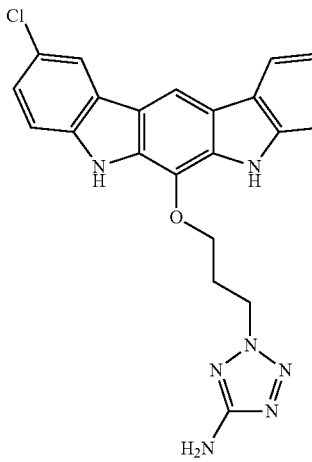 | 1 | 0.5 | >8 | 1 | >8 | >8 |
| 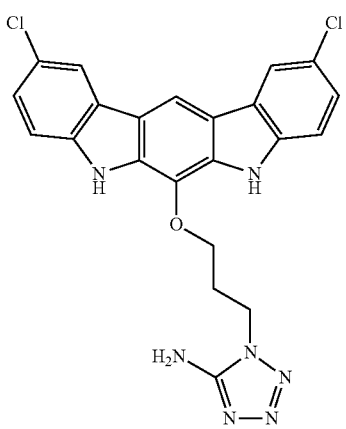 [SMILES: Nc1nnnn1CCCOc1c2[nH]c3ccc(Cl)cc3c2cc2c1[nH]c1ccc(Cl)cc12] | 1 | 0.5 | >8 | 0.5 | >8 | >8 |
| 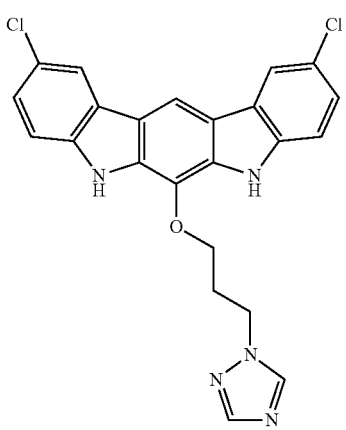 [SMILES: Clc1ccc2[nH]c3c(OCCCn4cncn4)c4[nH]c5ccc(Cl)cc5c4cc3c2c1] | 0.25 | 0.5 | ND | ND | ND | ND |

TABLE 1-continued

MIC (μg/ml) of indole analogs against bacterial threats

| Structure | FT | BA | YP | BAB | BM | BP |
|---|---|---|---|---|---|---|
| (structure) | 0.5 | 0.25 | ND | ND | ND | ND |
| (structure) | 1 | 0.5-1 | 8 | 1 | >8 | >8 |
| (structure) | 0.25-1 | 0.5-1 | 1 | 0.25 | 2 | 4 |

TABLE 1-continued
MIC (μg/ml) of indole analogs against bacterial threats
| Structure | FT | BA | YP | BAB | BM | BP |
|---|---|---|---|---|---|---|
| 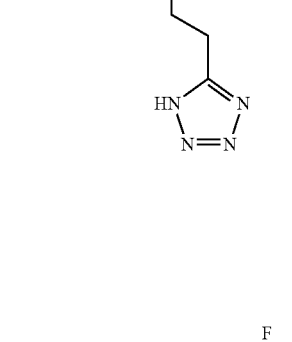 | 1 | 0.5 | >8 | 1 | >8 | >8 |
| 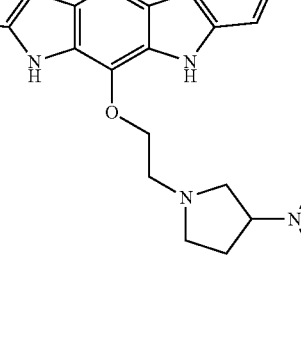 | 0.5 | 1 | >8 | 0.5 | ND | ND |
| 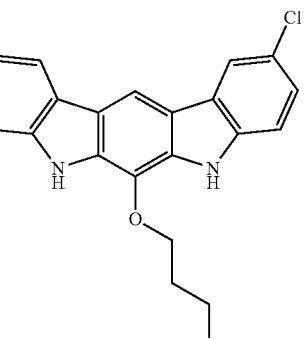 | 1 | 1 | 4 | 1 | >8 | >8 |

TABLE 1-continued
MIC (μg/ml) of indole analogs against bacterial threats
| Structure | FT | BA | YP | BAB | BM | BP |
|---|---|---|---|---|---|---|
| 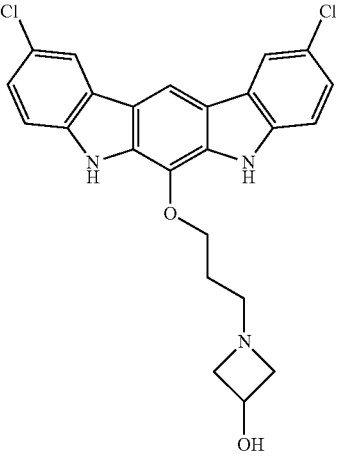 [SMILES: OC1CN(CCCOc2c3[nH]c4ccc(Cl)cc4c3cc3c2[nH]c2ccc(Cl)cc23)C1] | 0.5 | 0.5 | 4 | 1 | ND | ND |
| 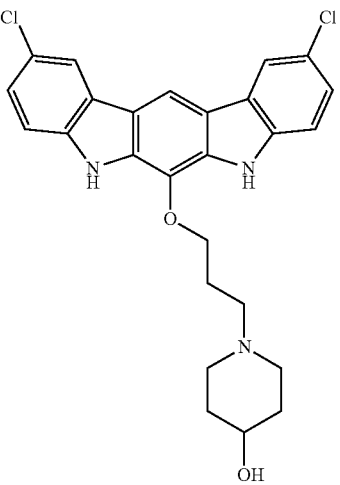 [SMILES: OC1CCN(CCCOc2c3[nH]c4ccc(Cl)cc4c3cc3c2[nH]c2ccc(Cl)cc23)CC1] | 0.25 | 0.25 | 2 | 0.25 | 8 | >8 |
| 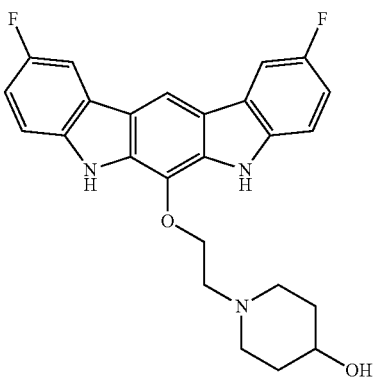 [SMILES: OC1CCN(CCOc2c3[nH]c4ccc(F)cc4c3cc3c2[nH]c2ccc(F)cc23)CC1] | 0.5 | 0.5 | 4 | 1 | 8 | >8 |

TABLE 1-continued

MIC (μg/ml) of indole analogs against bacterial threats

| Structure | FT | BA | YP | BAB | BM | BP |
|---|---|---|---|---|---|---|
| (structure) | 1 | 0.5 | >8 | 1 | >8 | >8 |
| (structure) | 1 | 0.5 | 8 | 0.25 | 2 | 4 |
| (structure) | 0.5 | 1 | >8 | 0.5 | >8 | >8 |
| (structure) | 2 | 1 | 8 | 2 | 8 | >8 |

TABLE 1-continued

MIC (μg/ml) of indole analogs against bacterial threats

| Structure | FT | BA | YP | BAB | BM | BP |
|---|---|---|---|---|---|---|
| (EtO₂C / CO₂Et disubstituted indolocarbazole with O-CH₂CH₂-NH₂ substituent) | 1 | 2 | >8 | 1 | >8 | >8 |
| (F,F-disubstituted indolocarbazole with O-piperidin-4-yl substituent) | ≦0.25 | ≦0.25 | 8 | ≦0.25 | 4 | 8 |
| (Cl,Cl-disubstituted indolocarbazole with O-CH₂-piperidin-4-yl substituent) | 0.5 | 0.5 | 2 | ≦0.25 | 8 | >8 |
| (F,F-disubstituted indolocarbazole with O-(CH₂)₃-NH-C(=NEt)-NH-(CH₂)₃-N(Me)₂ substituent) | ≦0.25 | ≦0.25 | 4 | 0.5 | 4 | 8 |

TABLE 1-continued

MIC (μg/ml) of indole analogs against bacterial threats

| Structure | FT | BA | YP | BAB | BM | BP |
|---|---|---|---|---|---|---|
| [Structure: difluoro-indolocarbazole with O-propyl-N,N'-diisopropylguanidine substituent] | 1 | 0.5 | 4 | 1 | ND | ND |
| [Structure: dichloro-indolocarbazole with O-CH2-(S)-pyrrolidine substituent] | 0.5 | 1 | 1 | 0.5 | 4 | 8 |
| [Structure: dichloro-indolocarbazole with O-propyl-N,N'-dimethylguanidine substituent] | 1 | 0.5 | 1 | 0.5 | 4 | 4 |

TABLE 1-continued

MIC (μg/ml) of indole analogs against bacterial threats

| Structure | FT | BA | YP | BAB | BM | BP |
|---|---|---|---|---|---|---|
| (structure) | 1 | ≦0.25 | 1 | 1 | 4 | 4 |
| (structure) | 0.5 | ≦0.25 | 1 | ≦0.25 | 4 | >8 |
| (structure) | 0.5 | ≦0.25 | 1 | ≦0.25 | 2 | 4 |
| (structure) | 1 | 1 | 2 | 0.5 | >8 | >8 |

TABLE 1-continued

MIC (μg/ml) of indole analogs against bacterial threats

| Structure | FT | BA | YP | BAB | BM | BP |
|---|---|---|---|---|---|---|
| (5,5'-dichloro indolocarbazole with O-propyl-NH-CH2-pyrrole) | 0.5 | 0.5 | 2 | 0.5 | >8 | >8 |
| (5,5'-dichloro indolocarbazole with O-propyl-NH-CH2-imidazole) | 1 | 1 | 2 | 0.5 | >8 | >8 |
| (5,5'-difluoro indolocarbazole with O-CH2-pyrrolidine) | 0.5 | 0.5 | 2 | 0.5 | 8 | 8 |
| (5,5'-difluoro indolocarbazole with O-piperidine) | 1 | 0.5 | 4 | 0.5 | 8 | >8 |

TABLE 1-continued

MIC (μg/ml) of indole analogs against bacterial threats

| Structure | FT | BA | YP | BAB | BM | BP |
|---|---|---|---|---|---|---|
| (F, F-substituted indolocarbazole with O-cyclohexyl-NH₂) | 1 | 0.5 | 4 | 0.5 | >8 | >8 |
| (Cl, Cl-substituted indolocarbazole with O-propyl-NH-CH₂-imidazole) | 1 | 0.5 | 4 | 0.5 | ND | ND |
| (F, F-substituted indolocarbazole with O-ethyl-NH₂) | 2 | 4 | 4 | 1 | 8 | 16 |
| (F, F-substituted indolocarbazole with O-pyrrolidine) | ≦0.25 | <0.25 | 1 | <0.25 | 2 | 4 |

TABLE 1-continued

MIC (µg/ml) of indole analogs against bacterial threats

| Structure | FT | BA | YP | BAB | BM | BP |
|---|---|---|---|---|---|---|
| [F,F-substituted indolocarbazole with pyrrolidinyloxy group] | 0.25 | 0.25 | 1 | <0.25 | 2 | 4 |
| [Cl,Cl-substituted indolocarbazole with pyrrolidinyloxy group] | ≦0.25 | ≦0.25 | 1 | ≦0.25 | 2 | >8 |
| [Cl,Cl-substituted indolocarbazole with pyrrolidinyloxy group, isomer] | ≦0.25 | ≦0.25 | 1 | ≦0.25 | 2 | >8 |

[1]ND = Not determined

Example 165

MIC Data for Various Compounds

Various compounds were tested against six bacterial strains: *Francisella tularensis* (FT; Gram-negative); *Bacillus anthracis* (BA; Gram-positive); methicillin-susceptible *Staphylococcus aureus* (MSSA); methicillin-resistant *Staphylococcus aureus* (MRSA); pen TABLE 2-continued
MIC (µg/ml) of indole analogs against bacterial threats
| | BA | FT | MSSA | MRSA | PSSP | PRSP |
|---|---|---|---|---|---|---|
| 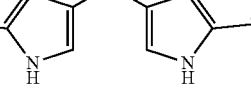 | 8 | 16 | 8 | 8 | 4 | 2 |
|  | 16 | 4 | 32 | 32 | 8 | 1 |
| 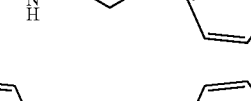 | 16 | 4 | 16 | 32 | 1 | 2 |
| 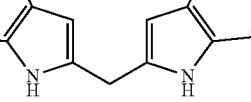 | 8 | 4 | >64 | >64 | 2 | 8 |
| 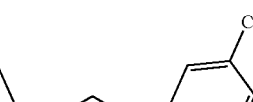 | 4 | ≦0.5 | 4 | 4 | 4 | 2 |
| 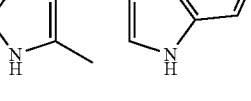 | 1 | ≦0.5 | 2 | 4 | 1 | 1 |
| 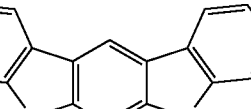 | 4 | 2 | 8 | 8 | 4 | 2 |
| Penicillin | 0.2 | >64 | ND[1] | >64 | <0.05 | >64 |
| Oxacillin | 0.8 | >64 | ND | >64 | 0.1 | ND |
[1]ND = Not determined

Example 170

MIC Data for Various Compounds

Various compounds were tested against four bacterial strains: *Acinetobacter baumannii* (AB); *Shigella dysenteriae* (SD); *Listeria monocytogenes* (LM); Vancomycin-resistant *Enterococcus faecalis* (VRE); and Vancomycin-Sensitive *Enterococcus faecalis* (VSE). MIC data is provided in the following table.

TABLE 3

MIC (μg/ml) of indole analogs against bacterial threats

| Structure | AB | LM | SD | VRE | VSE |
|---|---|---|---|---|---|
| 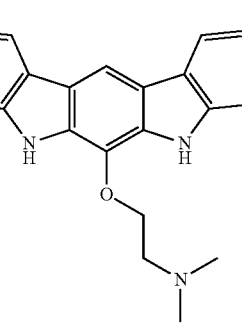 (difluoro, dimethylamino-ethoxy) | 4 | 2 | 8 | 2 | 1 |
| (dichloro, guanidino-propoxy) | 4 | 1 | 4 | 2 | 4 |
| (dichloro, 4-hydroxypiperidinyl-propoxy) | 4 | 1 | 8 | 2 | 4 |

TABLE 3-continued

MIC (μg/ml) of indole analogs against bacterial threats

| Structure | AB | LM | SD | VRE | VSE |
|---|---|---|---|---|---|
| 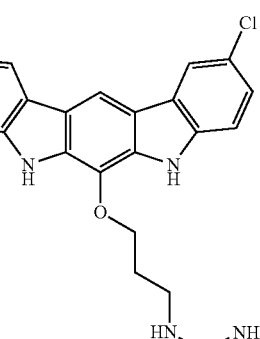 (difluoro, guanidino-propoxy) | 8 | 4 | 8 | 2 | 8 |
| (difluoro, pyrrolidinyloxy) | 4 | 2 | 4 | 1 | 2 |
| 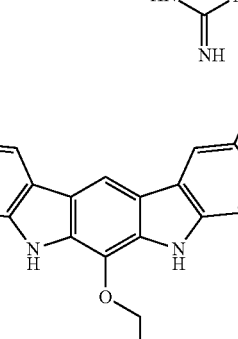 (difluoro, imidazolinyl-amino-propoxy) | 4 | 2 | 8 | 1 | 4 |

Example 171

MIC Data for Various Compounds

Various compounds were tested against Tubercule *bacillus* (i.e., for anti-mycobacterial activity).

The resazurin MIC assay, developed by Collins and Franzblau (Antimicrobial Agents and Chemotherapy, 41:1004-1009 (1997)), was used to test compounds for antimycobacterial activity. A color change from blue to pink is observed when growth occurs. Compounds are initially tested at a single point concentration of 10 μg/ml against *Mycobacteruim tuberculosis* H37Rv (H37Rv). If compounds are active at the 10 μg/ml level, they are further tested in an MIC assay at 8 concentrations in a dose range between 10 to 0.078 μg/ml.

Both visual evaluations and fluorimetric read-outs were performed. The results are expressed as μg/ml (visual evaluation) and as IC50 and IC90 (fluoremetric readout, data not shown). MIC data is provided in Table 4.

TABLE 4

MIC of indole analogs against *Tubercle bacillus*

| Structure | MIC (μg/ml) |
|---|---|
| Difluoro-indolocarbazole with OMe | >10 |
| Difluoro-indolocarbazole with O-CH₂CH₂-N(CH₃)₂ | 5 |
| Difluoro-indolocarbazole with alkyne-CH₂-N(CH₃)₂ | 10 |
| Dichloro-indolocarbazole with O-(CH₂)₃-NH-C(=NH)NH₂ (guanidine) | 10 |

TABLE 4-continued

MIC of indole analogs against *Tubercle bacillus*

| Structure | MIC (μg/ml) |
|---|---|
| Dichloro-indolocarbazole with O-(CH₂)₃-N-piperidin-4-ol | 10 |
| Difluoro-indolocarbazole with O-(CH₂)₃-1,2,4-triazole | >10 |
| Difluoro-indolocarbazole (isomer) with O-(CH₂)₃-NH-C(=NH)NH₂ (guanidine) | 10 |

TABLE 4-continued

MIC of indole analogs against *Tubercle bacillus*

| Structure | MIC (µg/ml) |
|---|---|
| (bis-fluoro indolocarbazole with O-propyl-imidazoline amine substituent) | 10 |
| (bis-fluoro indolocarbazole with O-pyrrolidine substituent) | 10 |
| (bis-fluoro indolocarbazole with O-pyrrolidine substituent, stereoisomer) | 5 |
| (indolocarbazole with CH₃ substituent) | 10 |

We claim:

1. A method for treating a bacterial infection in a mammalian individ

3. The method of claim 2, wherein:
$R^3$ and $R^7$ are independently selected from hydrogen and halo.

4. The method of claim 2, wherein $R^9$ is selected from hydrogen, halo, cyano, $C_1$-$C_{24}$ alkyl, $C_2$-$C_{24}$ alkenyl, and amino.

5. The method of claim 2, wherein $R^{10}$ is selected from methyl and substituted alkoxyl groups.

6. The method of claim 2, wherein $R^{10}$ is selected from unsubstituted $C_1$-$C_{24}$ alkoxy, substituted $C_1$-$C_{24}$ alkoxy, and heteroatom containing $C_1$-$C_{24}$ alkoxy.

7. The method of claim 2, wherein $R^{10}$ has the structure —O-L-Q1, wherein:
L is a linker selected from a bond, a $C_1$-$C_{12}$ straight chain, $C_2$-$C_{12}$ branched, or $C_3$-$C_{12}$ cyclic alkylene group that may be substituted, unsubstituted, heteroatom containing, or a combination thereof; and
Q1 is selected from hydrogen, —NR$^{y1}$R$^{y2}$(R$^{y3}$)$_{n2}$(X)n$_3$, —CHR$^{x1}$R$^{x2}$, and —SR$^{z1}$, wherein:
R$^{y1}$ and R$^{y2}$ are independently selected from hydrogen, $C_1$-$C_{24}$ alkyl, $C_2$-$C_{24}$ alkenyl, $C_5$-$C_{20}$ aryl, $C_6$-$C_{24}$ alkaryl, $C_6$-$C_{24}$ aralkyl, amino, imino, $C_1$-$C_{24}$ alkylsulfonyl, and $C_5$-$C_{20}$ arylsulfonyl, any of which may be further substituted and/or heteroatom-containing where such groups permit, or wherein R$^{y1}$ and R$^{y2}$ are taken together to form a cyclic or polycyclic group that may be unsubstituted, substituted, and/or further heteroatom-containing;
R$^{y3}$ is selected from hydrogen and $C_1$-$C_{12}$ alkyl;
n2 and n3 are the same and are selected from 0 and 1;
X is a negatively charged counterion;
R$^{x1}$ and R$^{x2}$ are independently selected from hydrogen, $C_1$-$C_{24}$ alkyl, $C_2$-$C_{24}$ alkenyl, $C_5$-$C_{20}$ aryl, $C_6$-$C_{24}$ alkaryl, $C_6$-$C_{24}$ aralkyl, any of which may be further substituted and/or heteroatom-containing where such groups permit, or wherein R$^{x1}$ and R$^{x2}$ are taken together to form a cyclic or polycyclic group that may be unsubstituted, substituted, and/or further heteroatom-containing; and
R$^{z1}$ is selected from $C_1$-$C_{24}$ alkyl, $C_2$-$C_{24}$ alkenyl, $C_5$-$C_{20}$ aryl, $C_6$-$C_{24}$ alkaryl, $C_6$-$C_{24}$ aralkyl, any of which may be further substituted and/or heteroatom-containing where such groups permit,
with the proviso that L is not a bond when Q1 is other than —CHR$^{x1}$R$^{x2}$.

8. The method of claim 2, wherein $R^{11}$ and $R^{12}$ are independently selected from hydrogen, formyl, $C_1$-$C_{24}$ alkyl, $C_6$-$C_{24}$ aralkyl, and amine protecting groups.

9. The method of claim 1, wherein the bacterial infection is by a Gram-positive bacteria.

10. The method of claim 1, wherein the bacterial infection is by a Gram-negative bacteria.

11. The method of claim 1, wherein the bacterial infection is an infection of *Francisella tularensis, Bacillus anthracis, Yersinia pestis, Brucella abortus, Burkholderia mallei, Burkholderia pseudomallei, Acinetobacter baumannii, Listeria monocytogenes, Shigella dysenteriae, Enterococcus faecalis, Mycobacterium tuberculosis, Mycobacterium bovis, Mycobacterium africanum, Mycobacterium canetti, Mycobacterium microti,* Vancomycin-resistant enterococci, Vancomycin-sensitive enterococci, methicillin-susceptible *Staphylococcus aureus*; methicillin-resistant *Staphylococcus aureus*; penicillin-susceptible *S. pneumoniae*; or penicillin-resistant *S. pneumoniae*.

12. The method of claim 1, wherein the compound is administered in the form of a composition which comprises at least two different compounds having the structure of formula (I).

13. The method of claim 1, wherein the compound is 1-(2-(2,10-dichloro-5,7-dihydroindolo[2,3-b]carbazol-6-yloxy)ethyl)-1H-tetrazol-5-amine.

14. A method for reducing a population of bacteria, comprising administering a compound having the structure of formula (I)

wherein:
$R^1$, $R^3$, $R^4$, $R^5$, $R^7$, $R^8$, and $R^9$, are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyloxy, $C_2$-$C_{24}$ alkoxycarbonyl, $C_6$-$C_{20}$ aryloxycarbonyl, $C_2$-$C_{24}$ alkylcarbonyl, $C_6$-$C_{20}$ arylcarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, dihydroxyboryl, di-($C_1$-$C_{24}$)-alkoxyboryl, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof;
$R^2$ and $R^6$ are independently halo;
$R^{10}$ is selected from unsubstituted $C_1$-$C_{24}$ alkyl, substituted $C_1$-$C_{24}$ alkyl, heteroatom containing $C_1$-$C_{24}$ alkyl, unsubstituted $C_2$-$C_{24}$ alkenyl, substituted $C_2$-$C_{24}$ alkenyl, heteroatom containing $C_2$-$C_{24}$ alkenyl, unsubstituted $C_2$-$C_{24}$ alkynyl, substituted $C_2$-$C_{24}$ alkynyl, heteroatom containing $C_2$-$C_{24}$ alkynyl, unsubstituted $C_1$-$C_{24}$ alkoxy, substituted $C_1$-$C_{24}$ alkoxy, and heteroatom containing $C_1$-$C_{24}$ alkoxy; and
$R^{11}$ and $R^{12}$ are independently selected from the group consisting of hydrogen, formyl, $C_1$-$C_{24}$ alkyl, $C_6$-$C_{24}$ aralkyl, $C_{2-24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino-substituted $C_1$-$C_{24}$ alkyl, and nitrogen protecting groups, or
a pharmaceutically acceptable salt thereof,
and detecting a resultant reduction in the population of the bacteria.

15. The method of claim 14, wherein the bacteria are Gram positive.

16. The method of claim 14, wherein the bacteria are Gram negative.

17. The method of claim 14, wherein the bacteria are of the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, Bordetella*, or *Francisella*.

18. The method of claim 17, wherein the bacteria are present in the body of a mammal.

19. The method of claim 14, wherein the compound is 1-(2-(2,10-dichloro-5,7-dihydroindolo[2,3-b]carbazol-6-yloxy)ethyl)-1H-tetrazol-5-amine.

20. A method for treating a bacterial infection in a mammalian individual in need thereof, comprising administering to the individual a therapeutically effective amount of a compound having a structure selected from the following table:

| Structure |
| --- |
| 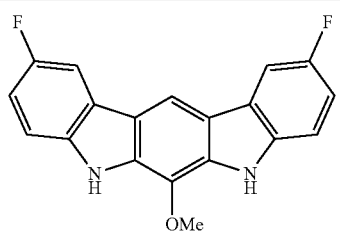 [SMILES: COc1c2[nH]c3ccc(F)cc3c2cc2c1[nH]c1ccc(F)cc12] |
| 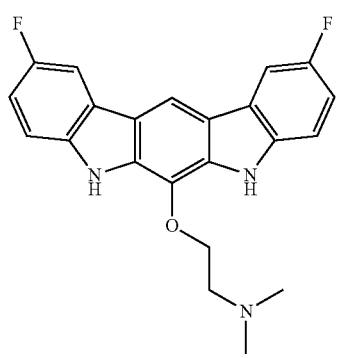 [SMILES: CN(C)CCOc1c2[nH]c3ccc(F)cc3c2cc2c1[nH]c1ccc(F)cc12] |
| 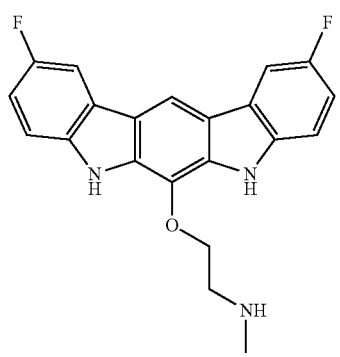 [SMILES: CNCCOc1c2[nH]c3ccc(F)cc3c2cc2c1[nH]c1ccc(F)cc12] |

-continued

| Structure |
| --- |
| 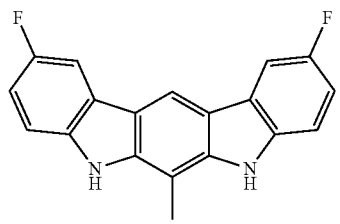 [SMILES: Cc1c2[nH]c3ccc(F)cc3c2cc2c1[nH]c1ccc(F)cc12] |
| 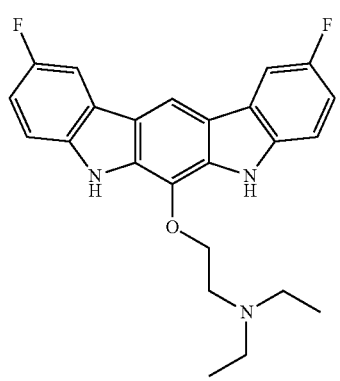 [SMILES: CCN(CC)CCOc1c2[nH]c3ccc(F)cc3c2cc2c1[nH]c1ccc(F)cc12] |
| 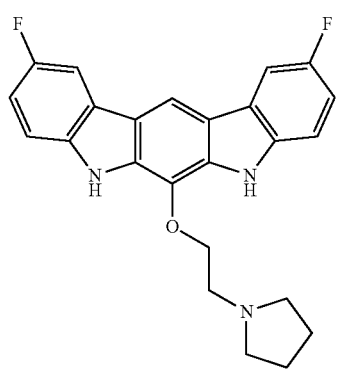 [SMILES: Fc1ccc2[nH]c3c(OCCN4CCCC4)c4[nH]c5ccc(F)cc5c4cc3c2c1] |
| 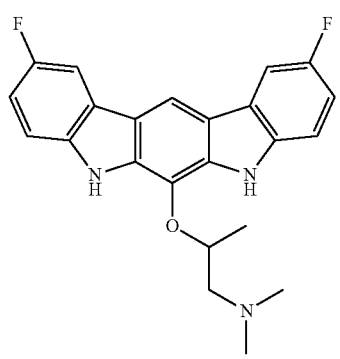 [SMILES: CC(CN(C)C)Oc1c2[nH]c3ccc(F)cc3c2cc2c1[nH]c1ccc(F)cc12] |
| 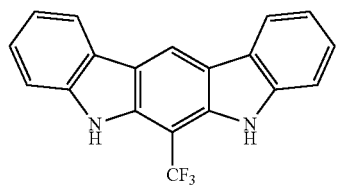 [SMILES: FC(F)(F)c1c2[nH]c3ccccc3c2cc2c1[nH]c1ccccc12] |

175
-continued
| Structure |
|---|
| 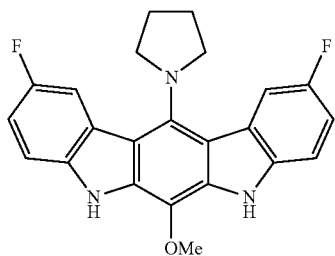 [SMILES: COc1c2[nH]c3ccc(F)cc3c2c(N2CCCC2)c2c1[nH]c1ccc(F)cc12] |
| 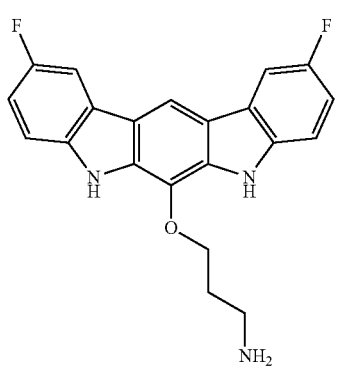 [SMILES: NCCCOc1c2[nH]c3ccc(F)cc3c2cc2c1[nH]c1ccc(F)cc12] |
| 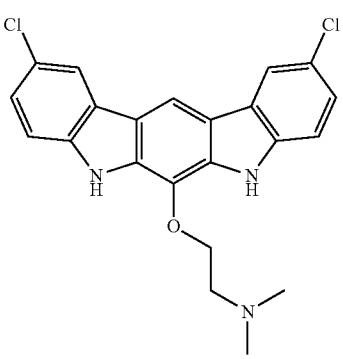 [SMILES: CN(C)CCOc1c2[nH]c3ccc(Cl)cc3c2cc2c1[nH]c1ccc(Cl)cc12] |
| 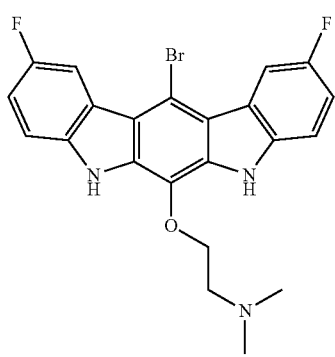 [SMILES: CN(C)CCOc1c2[nH]c3ccc(F)cc3c2c(Br)c2c1[nH]c1ccc(F)cc12] |
176
-continued
| Structure |
|---|
| 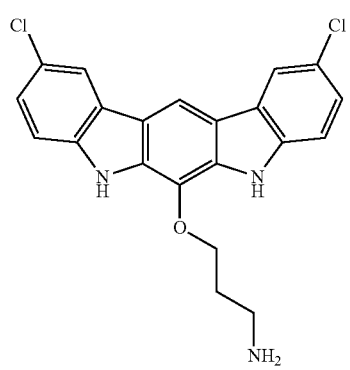 [SMILES: NCCCOc1c2[nH]c3ccc(Cl)cc3c2cc2c1[nH]c1ccc(Cl)cc12] |
| 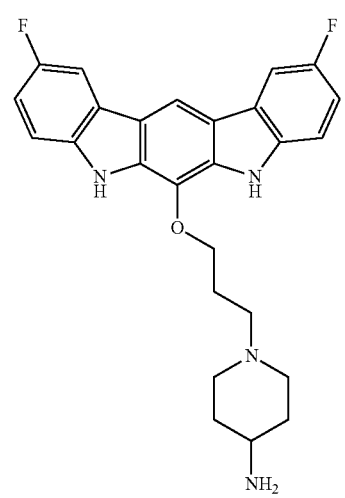 [SMILES: NC1CCN(CCCOc2c3[nH]c4ccc(F)cc4c3cc3c2[nH]c2ccc(F)cc23)CC1] |
| 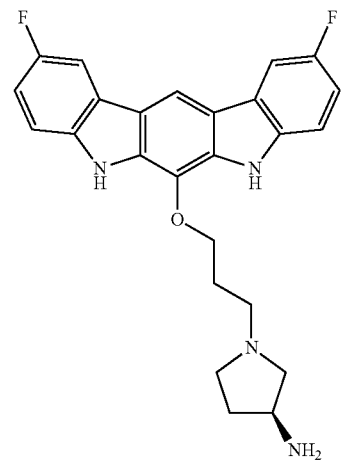 [SMILES: N[C@H]1CCN(CCCOc2c3[nH]c4ccc(F)cc4c3cc3c2[nH]c2ccc(F)cc23)C1] |

| 177 -continued | 178 -continued |
|---|---|
| Structure | Structure |
| 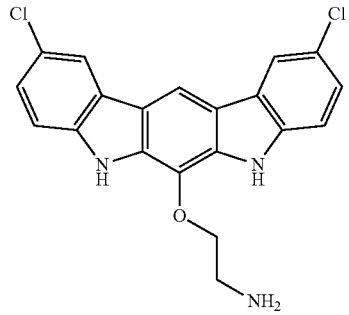 [SMILES: NCCOc1c2[nH]c3ccc(Cl)cc3c2cc2c1[nH]c1ccc(Cl)cc12] | 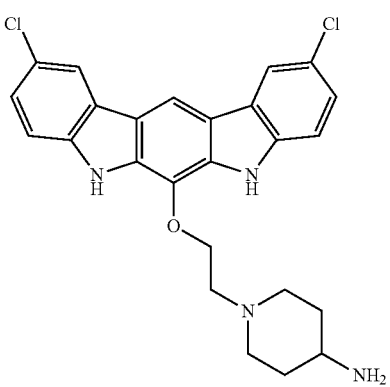 |
| 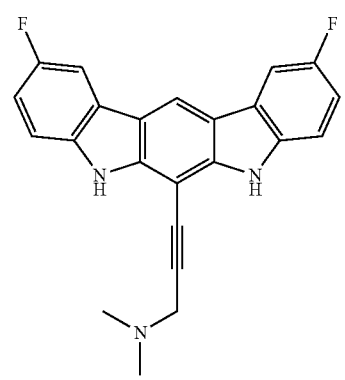 [SMILES: CN(C)CC#Cc1c2[nH]c3ccc(F)cc3c2cc2c1[nH]c1ccc(F)cc12] | 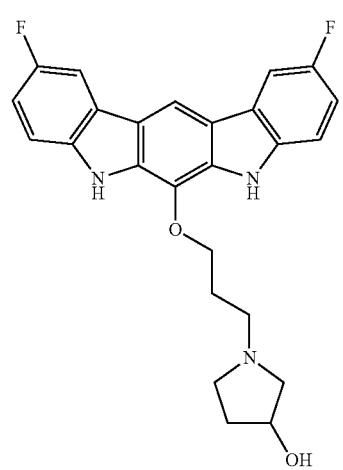 |
| 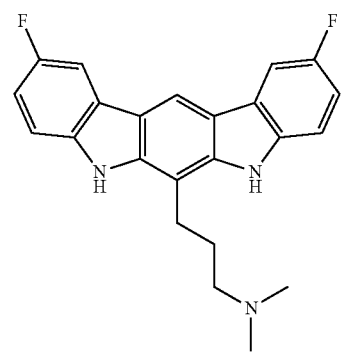 | |
| 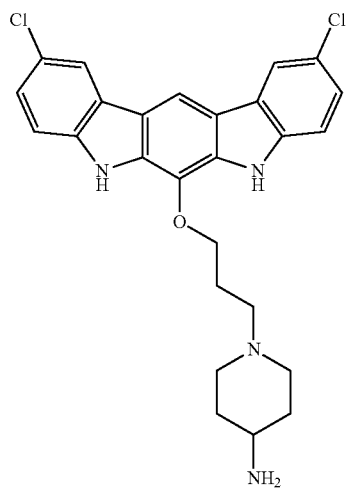 [SMILES: NC1CCN(CCCOc2c3[nH]c4ccc(Cl)cc4c3cc3c2[nH]c2ccc(Cl)cc23)CC1] | 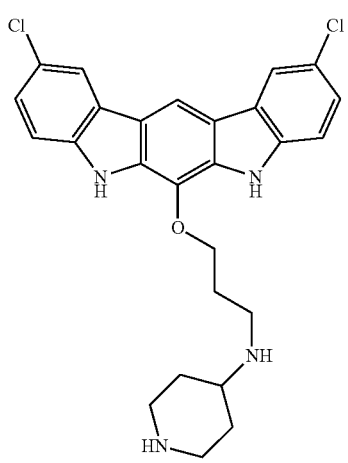 [SMILES: Clc1ccc2[nH]c3c(OCCCNC4CCNCC4)c4[nH]c5ccc(Cl)cc5c4cc3c2c1] |

| 179 -continued | 180 -continued |
|---|---|
| Structure | Structure |
| 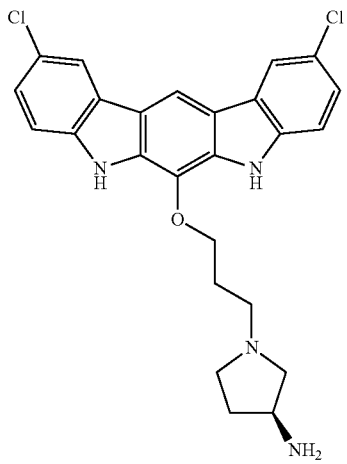 [SMILES: N[C@H]1CCN(CCCOc2c3[nH]c4ccc(Cl)cc4c3cc3c2[nH]c2ccc(Cl)cc23)C1] | 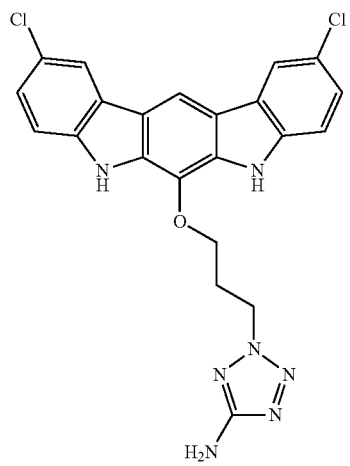 |
| 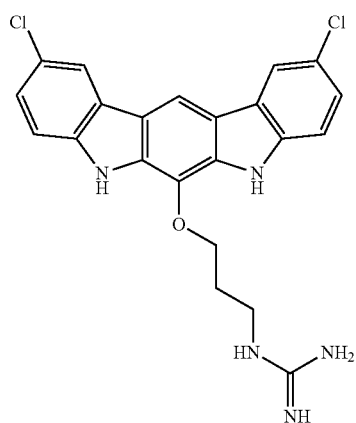 [SMILES: N=C(N)NCCCOc1c2[nH]c3ccc(Cl)cc3c2cc2c1[nH]c1ccc(Cl)cc12] | 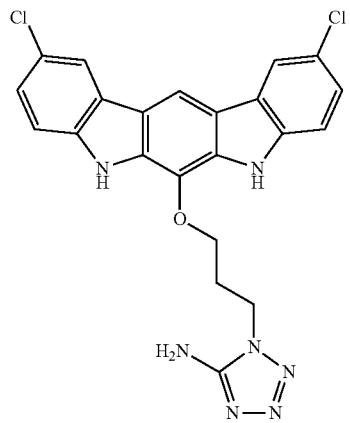 |
| 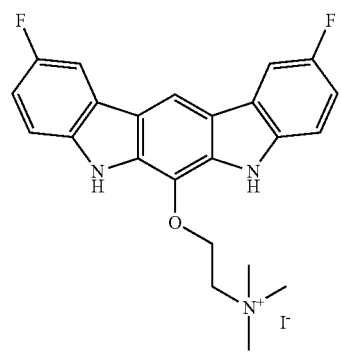 [SMILES: C[N+](C)(C)CCOc1c2[nH]c3ccc(F)cc3c2cc2c1[nH]c1ccc(F)cc12 ; [I-]] | 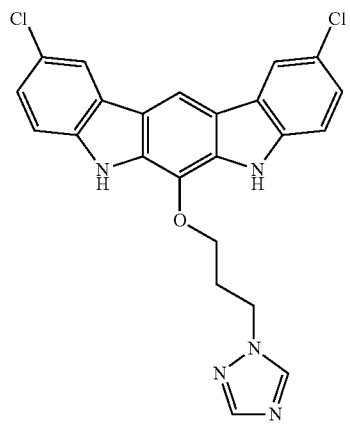 [SMILES: Clc1ccc2[nH]c3c(OCCCn4cncn4)c4[nH]c5ccc(Cl)cc5c4cc3c2c1] |

| 181 -continued | 182 -continued |
|---|---|
| Structure | Structure |
| 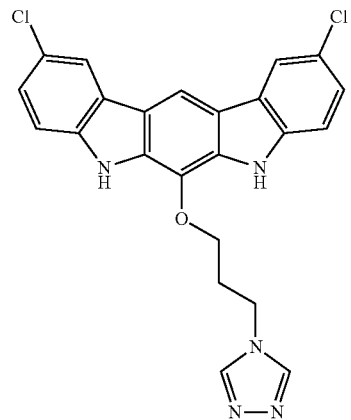 [SMILES: Clc1ccc2[nH]c3c(OCCCn4cnnc4)c4[nH]c5ccc(Cl)cc5c4cc3c2c1] | 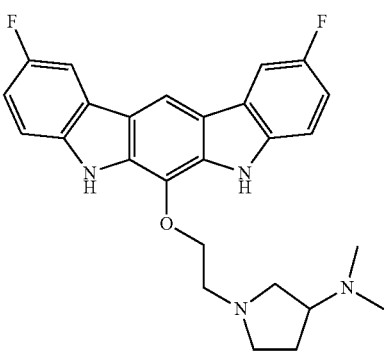 |
| 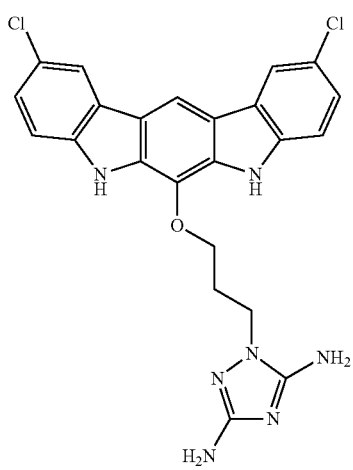 [SMILES: Nc1nc(N)n(CCCOc2c3[nH]c4ccc(Cl)cc4c3cc3c2[nH]c2ccc(Cl)cc23)n1] | 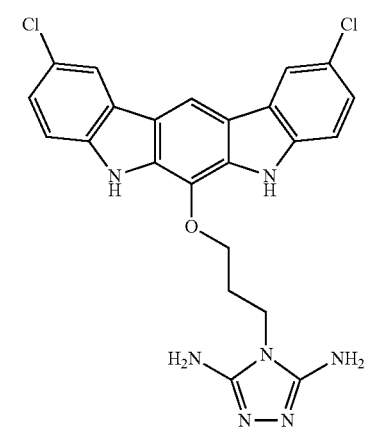 |
| 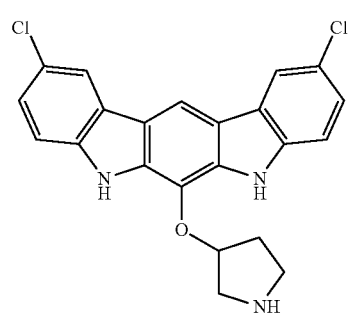 [SMILES: Clc1ccc2[nH]c3c(OC4CCNC4)c4[nH]c5ccc(Cl)cc5c4cc3c2c1] | 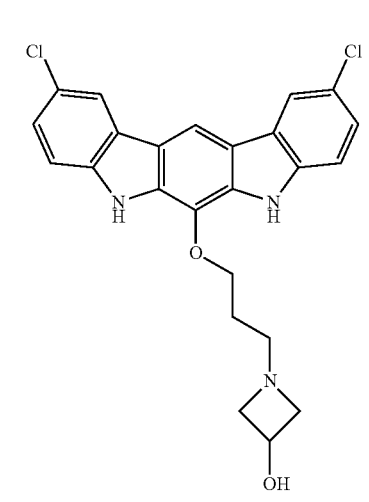 |
| 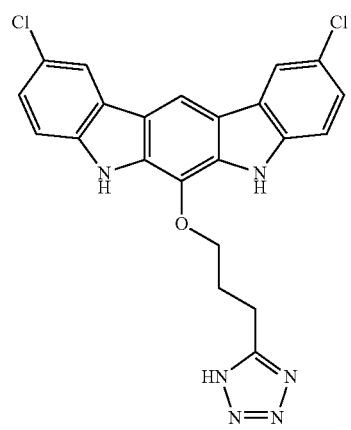 [SMILES: Clc1ccc2[nH]c3c(OCCCc4nnn[nH]4)c4[nH]c5ccc(Cl)cc5c4cc3c2c1] | |

| 183 -continued | 184 -continued |
|---|---|
| Structure | Structure |
| 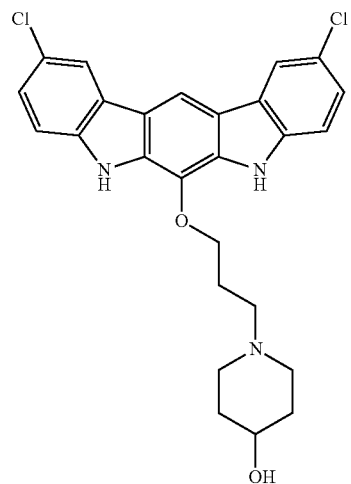 [SMILES: OC1CCN(CCCOc2c3[nH]c4ccc(Cl)cc4c3cc3c2[nH]c2ccc(Cl)cc23)CC1] | 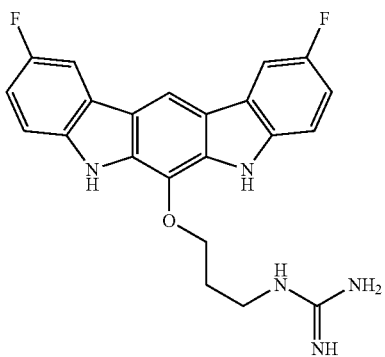 |
| 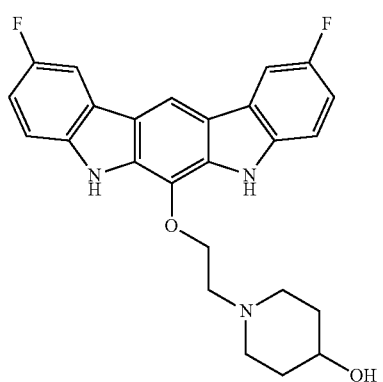 [SMILES: OC1CCN(CCOc2c3[nH]c4ccc(F)cc4c3cc3c2[nH]c2ccc(F)cc23)CC1] | 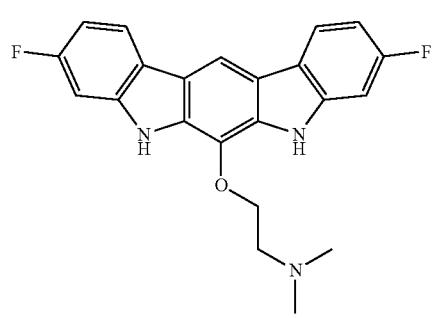 |
| 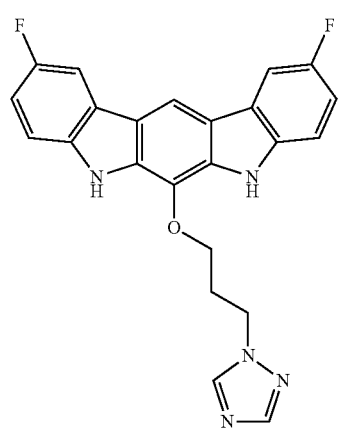 [SMILES: Fc1ccc2[nH]c3c(OCCCn4cncn4)c4[nH]c5ccc(F)cc5c4cc3c2c1] | 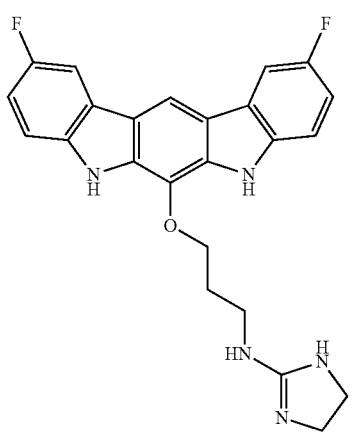 [SMILES: Fc1ccc2[nH]c3c(OCCCNC4=NCCN4)c4[nH]c5ccc(F)cc5c4cc3c2c1] |
|  | 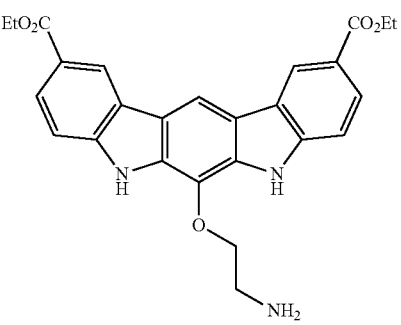 [SMILES: CCOC(=O)c1ccc2[nH]c3c(OCCN)c4[nH]c5ccc(C(=O)OCC)cc5c4cc3c2c1] |

| 185 -continued | 186 -continued |
|---|---|
| Structure | Structure |
| 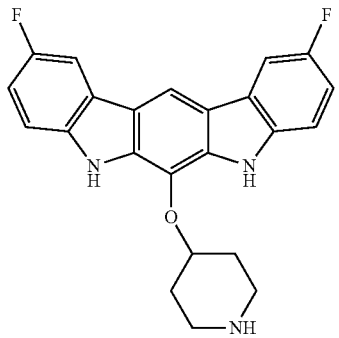 [SMILES: Fc1ccc2[nH]c3c(OC4CCNCC4)c4[nH]c5ccc(F)cc5c4cc3c2c1] | 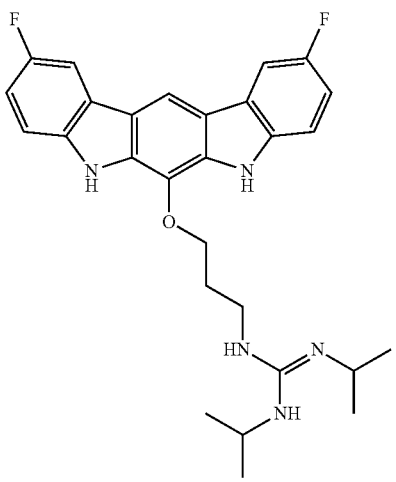 |
| 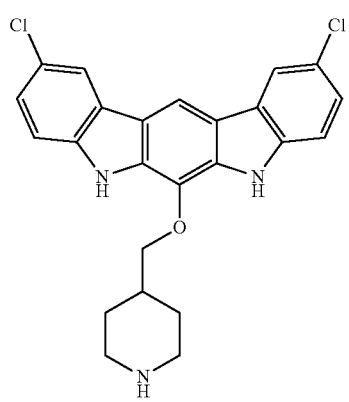 [SMILES: Clc1ccc2[nH]c3c(OCC4CCNCC4)c4[nH]c5ccc(Cl)cc5c4cc3c2c1] | 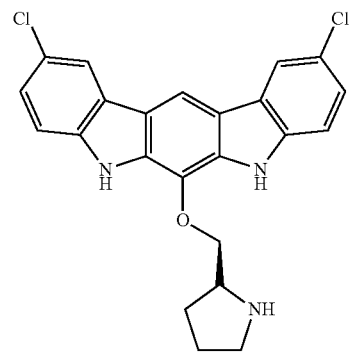 |
| 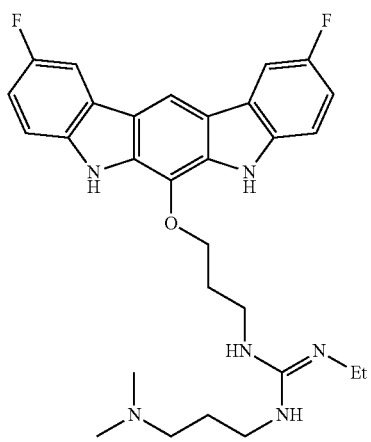 [SMILES: CC/N=C(/NCCCOc1c2[nH]c3ccc(F)cc3c2cc2c1[nH]c1ccc(F)cc12)NCCCN(C)C] | 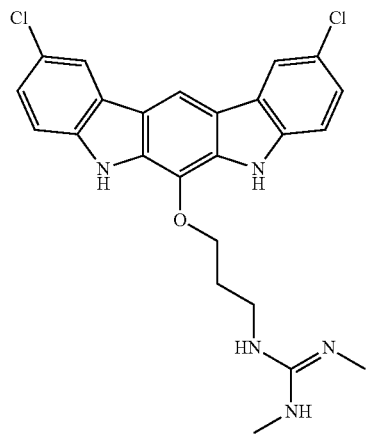 [SMILES: C/N=C(\NC)NCCCOc1c2[nH]c3ccc(Cl)cc3c2cc2c1[nH]c1ccc(Cl)cc12] |

| 187 -continued | 188 -continued |
|---|---|
| Structure | Structure |
| 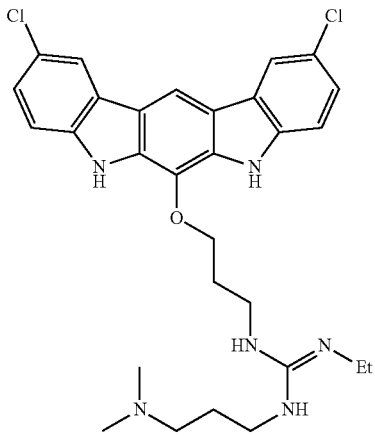 [SMILES: CC/N=C(/NCCCOc1c2[nH]c3ccc(Cl)cc3c2cc2c1[nH]c1ccc(Cl)cc12)NCCCN(C)C] | 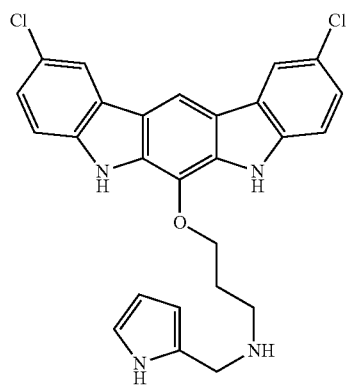 |
| 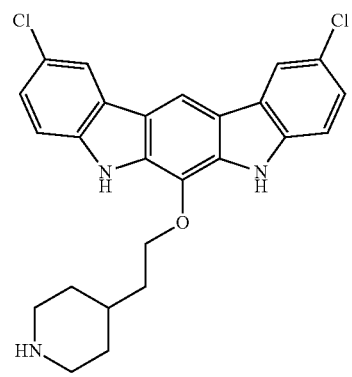 [SMILES: Clc1ccc2[nH]c3c(OCCC4CCNCC4)c4[nH]c5ccc(Cl)cc5c4cc3c2c1] | 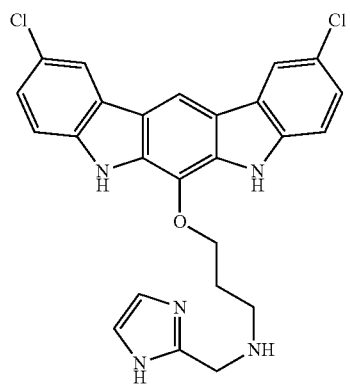 [SMILES: Clc1ccc2[nH]c3c(OCCCNCc4ncc[nH]4)c4[nH]c5ccc(Cl)cc5c4cc3c2c1] |
| 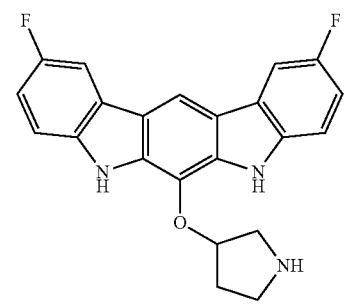 | 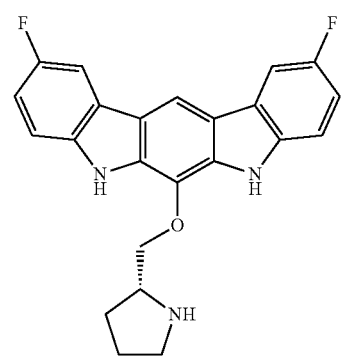 [SMILES: Fc1ccc2[nH]c3c(OC[C@H]4CCCN4)c4[nH]c5ccc(F)cc5c4cc3c2c1] |
| 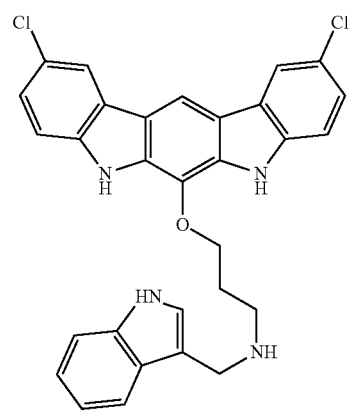 | 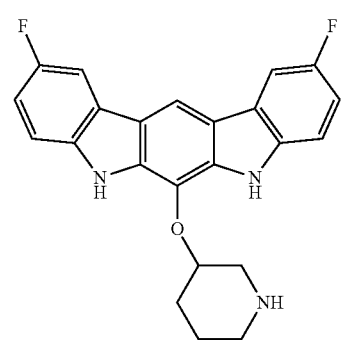 [SMILES: Fc1ccc2[nH]c3c(OC4CCCNC4)c4[nH]c5ccc(F)cc5c4cc3c2c1] |

| 189 -continued | 190 -continued |
|---|---|
| Structure | Structure |
| 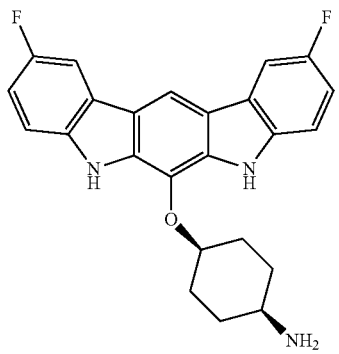 [SMILES: N[C@H]1CC[C@@H](Oc2c3[nH]c4ccc(F)cc4c3cc3c2[nH]c2ccc(F)cc23)CC1] | 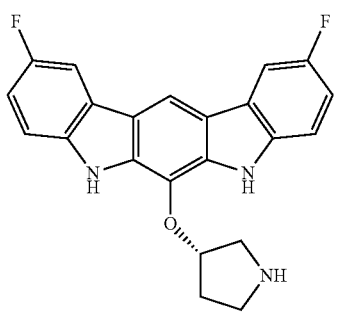 |
| 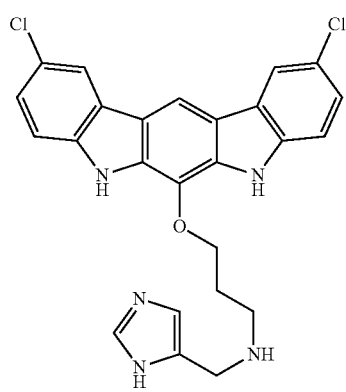 [SMILES: Clc1ccc2[nH]c3c(OCCCNCc4cnc[nH]4)c4[nH]c5ccc(Cl)cc5c4cc3c2c1] | 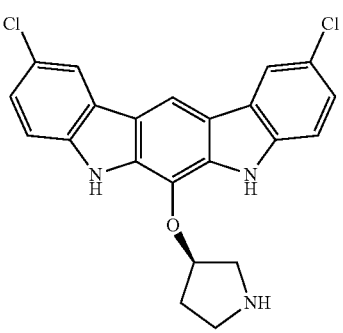 |
| 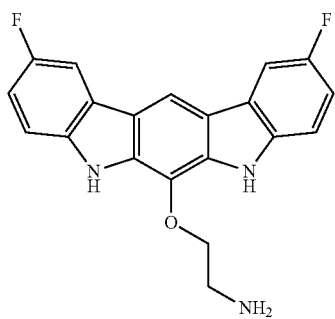 [SMILES: NCCOc1c2[nH]c3ccc(F)cc3c2cc2c1[nH]c1ccc(F)cc12] | 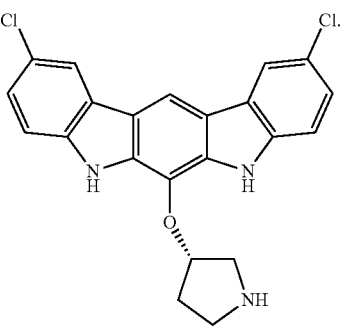 |
| 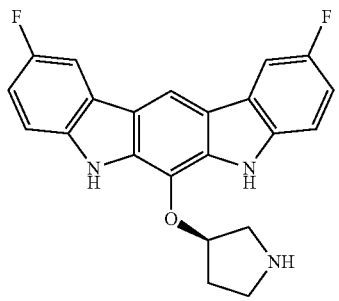 [SMILES: Fc1ccc2[nH]c3c(O[C@@H]4CCNC4)c4[nH]c5ccc(F)cc5c4cc3c2c1] | |
\* \* \* \* \*